(12) United States Patent
Thurston et al.

(10) Patent No.: US 7,067,511 B2
(45) Date of Patent: Jun. 27, 2006

(54) PYRROLOBENZODIAZEPINES

(75) Inventors: David Edwin Thurston, University Park (GB); Philip Wilson Howard, University Park (GB)

(73) Assignee: Spirogen Limited, Isle of Wight (GB)

( * ) Notice: Subject to any disclaimer, the term of this patent is extended or adjusted under 35 U.S.C. 154(b) by 504 days.

(21) Appl. No.: 10/021,213

(22) Filed: Dec. 12, 2001

(65) Prior Publication Data

US 2003/0120069 A1 Jun. 26, 2003

Related U.S. Application Data

(63) Continuation of application No. 09/763,767, filed as application No. PCT/GB99/02838 on Aug. 27, 1999.

(30) Foreign Application Priority Data

Aug. 27, 1998 (GB) ............................... 9818733
Jan. 19, 1999 (GB) ............................... 9901929

(51) Int. Cl.
A61K 31/55 (2006.01)
C07D 487/00 (2006.01)
A61P 35/00 (2006.01)

(52) U.S. Cl. ...................... 514/220; 540/496

(58) Field of Classification Search ................ 514/220; 540/496
See application file for complete search history.

(56) References Cited

U.S. PATENT DOCUMENTS

| | | | | |
|---|---|---|---|---|
| 3,523,941 A | 8/1970 | Leimgruber et al. | ..... | 260/239.3 |
| 3,524,849 A | 8/1970 | Batcho et al. | ..... | 260/239.3 |
| 4,185,016 A | 1/1980 | Takanabe et al. | ..... | 260/239.3 |
| 4,239,683 A | 12/1980 | Takanabe et al. | ..... | 260/239.3 |
| 4,309,437 A | 1/1982 | Ueda et al. | ..... | 424/274 |
| 5,143,854 A | 9/1992 | Pirrung et al. | ..... | 436/518 |
| 5,545,568 A | 8/1996 | Ellman et al. | ..... | 436/518 |
| 6,562,806 B1 | 5/2003 | Thurston et al. | ..... | 514/185 |
| 6,608,192 B1 | 8/2003 | Thurston et al. | ..... | 540/496 |
| 6,747,144 B1 | 6/2004 | Thurston et al. | ..... | 540/496 |
| 2003/0195196 A1 | 10/2003 | Thurston et al. | ..... | 514/220 |
| 2004/0092736 A1 | 5/2004 | Thurston et al. | ..... | 540/569 |

FOREIGN PATENT DOCUMENTS

| | | |
|---|---|---|
| EP | 0239400 A2 | 9/1987 |
| FR | 2027356 | 12/1969 |
| FR | 2 586 683 | 3/1987 |
| GB | 1 299 198 | 12/1972 |
| JP | 53-82792 | 7/1978 |
| JP | 57 131 791 | 8/1982 |
| JP | 58 180 487 | 10/1983 |
| WO | WO 88/07378 | 10/1988 |
| WO | WO 89/10140 | 11/1989 |
| WO | WO 92/19620 | 11/1992 |
| WO | WO 93/08288 | 4/1993 |
| WO | WO 93/18045 | 9/1993 |
| WO | WO 97/01560 | 1/1997 |
| WO | WO 00/12506 | 3/2000 |
| WO | WO 00/12507 | 3/2000 |

OTHER PUBLICATIONS

Courtney, S. M. et al., "A new convenient procedure for the synthesis of pyrrolo[2,1–c][1,4]benzodiazepines", *Tetrahedron Letters*, vol. 34, No. 33, 5327–28 (1993).

(Continued)

*Primary Examiner*—Brenda Coleman
(74) *Attorney, Agent, or Firm*—Grady J. Frenchick; Charlene L. Yager; Michael Best & Friedrich LLP

(57) ABSTRACT

Compounds of the formulae Ia and Ib:

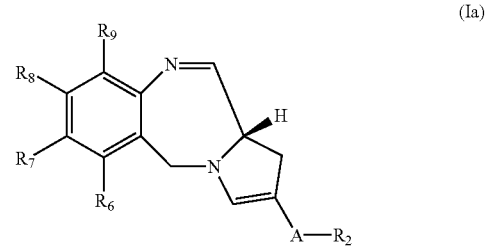

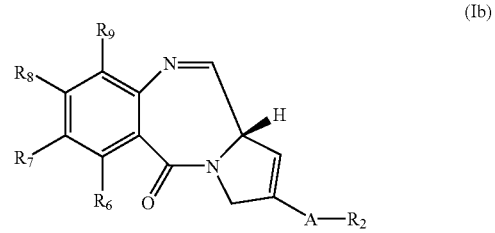

wherein:

A is $CH_2$, or a single bond;

$R_2$ is selected from: R, OH, OR, $CO_2H$, $CO_2R$, COH, COR, $SO_2R$, CN;

$R_6$, $R_7$ and $R_9$ are independently selected from H, R, OH, OR, halo, amino, NHR, nitro, $Me_3Sn$;

and $R_8$ is selected from H, R, OH, OR, halo, amino, NHR, nitro, $Me_3Sn$, where R is as defined above, or the compound is a dimer with each monomer being the same or different and being of formula Ia or Ib, where the $R_8$ groups of the monomers form together a bridge having the formula —X—R'—X— linking the monomers, where R' is an alkylene chain containing from 3 to 12 carbon atoms, which chain may be interrupted by one or more hetero-atoms and/or aromatic rings and may contain one or more carbon-carbon double or triple bonds, and each X is independently selected from O, S, or N;

except that in a compound of formula Ia when A is a single bond, then $R_2$ is not $CH=CH(CONH_2)$ or $CH=CH(CONMe_2)$. Other related compounds are also disclosed.

5 Claims, 32 Drawing Sheets

OTHER PUBLICATIONS

Chemical Abstract No. 171573p, O'Neil, "The synthesis of Functionalized Pyrrolo-[2,1-c][1,4]-Benzodiazepines", *Chemical Abstracts*, vol. 126, No. 13, 618 (1997) and entire article.

Chemical Abstract No. 4427a, Umezawa, "Mazethramycines" *Chemical Abstracts*, vol. 90, No. 1, 428 (1979).

Chemical Abstract No. 239940r, Farmer, "DNA binding properties of a new class of linked anthramycin analogs", *Chemical Abstracts*, vol. 114, No. 25, 25 (1991) and entire article.

Gregson, S. J. et al., "Synthesis of novel C2/C2'–exo unsaturated pyrrolobenzodiazepine cross–linking agent with remarkable DNA binding affinity and cytotoxicity", *Chemical Communications*, 797–798 (1999).

O'Neil, I.A. et al., "DPPE: A Convenient Replacement for Triphenylphospine in the Staudinger and Mitsunobu Reactions", *Tetrahedron Letters*, vol. 39, No. 42, 7787–7790 (1998).

Guiotto A. et al., "Synthesis of novel C7–aryl substituted pyrrolo [2,1–c] [1,4]benzodiazepines (PBDs) via Pro–N10–troc protection and suzuki coupling", *Bioorganic & Medicinal Chemistry Letters*, vol. 8, No. 21, 3017–3018 (1998).

Thurston, D. E., et al., "Effect of A–ring modifications on the DNA–binding behavior and cytotoxicity of pyrrolo[2,1–c] [1,4]benzodiazepines", *Journal of Medicinal Chemistry*, vol. 42, 1951–1964 (1999).

Chemical Abstract No. 72145x, Fujisawa, "Benzodiazepine derivatives", *Chemical Abstracts*, vol. 98, No. 9, 638 (1983).

Leimgruber et al., *J. Am. Chem. Soc.*, 87, 5793–5795 (1965).

Leimgruber et al., *J. Am. Chem. Soc.*, 87, 5791–5793 (1965).

Thurston et al., *Chem. Rev.*, 1994, 433–465 (1994).

Hochlowski et al., *J. Antibiotics*, 40, 145–148 (1987).

Konishi et al., *J. Antibiotics*, 37, 200–206 (1984).

Thurston et al., *Chem. Brit.*, 26, 767–772 (1990).

Bose et al., *Tetrahedron*, 48, 751–758 (1992).

Kunimoto et al., *J. Antibiotics*, 33, 665–667 (1980).

Takeuchi et al., *J. Antibiotics*, 29, 93–96 (1976).

Tsunakawa, et al., *J. Antibiotics*, 41, 1366–1373 (1988).

Shimizu et al., *J. Antibiotics*, 29, 2492–2503 (1982).

Langley and Thurston, *J. Org. Chem.*, 52, 91–97 (1987).

Hara et al., *J. Antibiotics*, 41, 702,704 (1988).

Itoh et al., *J. Antibiotics*, 41, 1281–1284 (1988).

Leber et al., *J. Am. Chem. Soc.*, 110, 2992–2993 (1988).

Arima et al., *J. Antibiotics*, 25, 437–444 (1972).

Kohn, *Antibiotics III*, Springer–Verlag, NY, 3–11 (1975).

Hurley and Needham–VanDevanter, *Acc. Chem. Res.*, 19, 230–237 (1986).

Leimgruber, W., Batcho, A. D., Czajkowski, R. J., *J. Am. Chem. Soc.*, 90, 5641 (1968).

Bridges, R. J., Stanley, M. S., Anderson, M. W., Cotman, C. W., Chamberlain, R. A., *J. Med. Chem.*, 34, 717 (1991).

Dangles, O., Guibé, F., Balavoine, G., Lavielle, S., Marquet, A., *J. Org. Chem.*, 52, 4948 (1987).

Althuis, T. H. and Hess, H. J., *J. Medicinal Chem.*, 20(1), 146–266 (1977).

Thurston, D.E., "Advances in the study of Pyrrolo[2,1–c] [4,1] benzodiazepine (PBD) Antitumor Antibiotics", *Molecular Aspects of Anticancer Drug–DNA interactions*, Neidle, S., Waring, M.J. eds., Macmillan Press Ltd., 1: 54–88 (1993).

Gregson, S.J., et al., "Design, Synthesis and Evaluation of a Novel Pyrrolobenzodiazepine DNA–Interactive Agent with Highly Efficient Cross–Linking Ability and Potent Cytotoxicity", *J. Med. Chem.*, 44: 737–748 (2001).

Gregson, S.J., et al., "Effect of C2–exo Unsaturation on the Cytotoxicity and DNA–Binding Reactivity of Pyrrolo[2,1–c]1,4benzodiazepines", *Bioorganic & Medicinal Chemistry Letters*, 10: 1845–1847 (2000).

Baraldi, P.G., et al., "Synthesis, in Vitro Antiproliferative Activity, and DNA–Binding Properties of Hybrid Molecules Containing Pyrrolo[2,1–c][1,4]benzodiazepine and Minor–Groove–Binding Oligopyrrole Carriers", *J. Med. Chem.*, 42: 5131–5141 (1999).

Wilson, S.C. et al., "Design, Synthesis, and Evaluation of Novel Sequence–Selective Epoxide–Containing DNA Cross–Linking Agent Based on the Pyrrolo[2,1–c][1,4]benzodiazepine System", *J. Med. Chem.* 42:4028–4041 (1999).

Thurston, D.E., et al., "Effect of A–Ring Modifications on the DNA–Binding Behavior and Cytotoxicity of Pyrrolo[2,1–c][1,4]benzodiazepines" *J. Med. Chem.*, 42: 1951–1964 (1999).

Nagasaka, T., et al., *Tetrahedron Letters*, vol. 30, No. 14, 1871–72 (1989).

Fukuyama, T., et al., *Tetrahedron Letters*, vol. 34, No. 16, 2577–2580 (1993).

Wilson, S.C., et al., *Tetrahedron Letters*, vol. 36, No. 35, 6333–6336 (1995).

Nagasaka, T., et al., *J. of Organic Chemistry*, vol. 36, No. 20, 6797–6801 (1998).

Baraldi, P.G., et al., *Bioorganic & Medicinal Chemistry Letters*, vol. 8, No. 21, 3019–3024 (1998).

Bi, Y., et al., *Bioorganic & Medicinal Chemistry Letters*, vol. 6, No. 19, 2299–2300 (1996).

Chemical Abstracts No. 139983k, Fujisawa, *Chemical Abstracts*, vol. 99, No. 17, 603 (1983).

Thurston, D.E., et al., *Chemical Communications*, 563–565 (1996).

Chemical Abstracts No. 300965y, Bi, Y., et al., *Chemical Abstracts*, vol. 125, No. 23, 1013 (1996).

Albericio, F. et al., "NPE–Resin, A New Approach to the Solid–Phase Synthesis of Protected Peptides and Oligonucleotides II. Synthesis of Protected Peptides[1,2]," *Tetrahedron Letters*, 32:1515–1518 (1991).

Albericio, F. et al., "NPE–resin, a new approach to the solid–phase synthesis of protected peptides and oligonucleotides," *Peptides* 1990, Proc. 21.sub.st Eur. Pept. Symp., 134–136 (1990).

Aristoff, J and Johnson, P., "Synthesis of CBI–PDE–I–Dimer, the Benzannelated Analogue of CC–1065," *J. Org. Chem.*, 57, 6234–6239 (1992).

Bagshawe et al., "Antibody–Enzyme Conjugates Can Generate Cytotoxic Drugs from Inactive Precursors at Tumor Sites," *Antibody, Immunoconjugates, and Radiopharmaceuticals*, 4, 915–922 (1991).

Bayley, H. et al., "Photoactivatable drugs," *TIPS*, 8, 138–143 (1987).

Berry, J. M. et al., "Solid–phase synthesis of DNA–interactive pyrrolo[2,1–c][1,4]benzodiazepines," *Tetrahedron Letters*, 41, 6171–6174 (2000).

Boger et al., "CC–1065 and the Duocarmycins: Synthetic Studies," *Chem. Rev.*, 97, 787–828 (1997).

Bose, D.S. et al., "Rational Design of a Highly Efficient Irreversible DNA Interstrand Cross–Linking Agent Based on the Pyrrolobenzodiazepine Ring System," *J. Am. Chem. Soc.*, 114, 4939–4941 (1992).

Brown, S.C. et al., "NMR Solution Structure of a Peptide Nucleic Acid Complexed with RNA," *Science*, 265, 777–780 (1994).

Bundgaard, H., "Design and Application of Prodrugs," *A Textbook of Drug Design and Development*, eds Krogsgaard–Lassen, P., and Bundgaard, H., Harwood Academic Press, 113–135 (1991).

Burgess, K. et al., "Solid Phase Synthesis of Oligoureas", *J.Ame. Chem. Soc.*, 119: 1556–1564 (1997).

Burgess, K et al., "Solid Phase Synthesis of Unnatural Biopolymers Containing Repeating Urea Units," *Agnew Chem. Int. Ed. Engl*, 34, No. 8:907–909 (1995).

Carruth, J.A.S., "Clinical applications for photodynamic therapy," *J. Photochem Photobiol.*, 9, 396–397 (1991).

Cho, C Y et al., "An Unnatural Biopolymer", *Science*, 261: 1303–1305 (1993).

Culver et al., "In Vivo Gene Transfer with Retroviral Vector–Producer Cells for Treatment of Experimental Brain Tumors," *Science*, 256, 1550–1552 (1992).

Dalton, S. and Treisman, R, "Characterization of SAP–1, a Protein Recruited by Serum Response Factor to the c–fos Serum Response Element," *Cell*, 68, 597–612 (1992).

Damayanthi, Y., et al., "Design and synthesis of novel pyrrolo [2,1–c][1,4]benzodiazepine–Lexitropsin Conjugates," *J. Org. Chem.*, 64, 290–292 (1999).

Dressman, B.A., et al., "Solid Phase Synthesis of Hydantoins Using a Carbamate Linker and a Novel Cyclization/Cleavage Step," *Tetrahedron Letters*, 37, 937–940 (1996).

Drost, K.J. and Cava, M.P., "A Photochemically Based Synthesis of the Benzannelated Analogue of the CC–1065 A Unit," *J. Org. Chem.*, 56:2240–2244 (1991).

Eashoo, M. et al., "Fibers from a Low Dielectric Constant Fluorinated Polyimide: Solution Spinning and Morphology Control," *J. Polymer Science*, 35:173–185 (1997).

Edman, P. and Begg, G., "A Protein Sequenator," *Eur. J. Biochem.*, 1, 80–91 (1967).

Egholm, M et al., "Peptide Nucleic Acids (PNA). Oligonucleotide Analogues with an Achiral Peptide Backbone," *J. Am. Chem. Soc.*, 114, 1895–1897 (1992).

Egholm, M et al., "PNA hybridizes to complementary oligonucleotides obeying the Watson–Crick hydrogen–bonding rules," *Nature*, 365, 566–568 (1993).

Englehardt et al., "Direct gene transfer of human CFTR into human bronchial epithelia of xenografts with E1–deleted adenoviruses," *Nature Genetics*, 4, 27–34 (1993).

Figliozzi, G.M. et al., "Synthesis of N–substituted Glycine Peptoid Libraries," *Methods in Enzymology*, 267: 437–447 (1996).

Foloppe, M.P. et al., "DNA–binding properties of pyrrolo [2,1–c][1,4]benzodiazephine N10–C11 amidines," *Eur. J. Med. Chem.*, 31, 407–410 (1996).

Fujisawa Pharmaceutical Co. Ltd., "Benzodiazepine derivatives," *SciFinder Scholar*, 2–3 (2002).

Furka, A. et al., "General method for rapid synthesis of multicomponent peptide mixtures," *Int. J. Peptide Protein Res.*, 37, 487–493 (1991).

Garcia–Echeverria, C., "A Base Labile Handle for Solid Phase Organic Chemistry", *Tetrahedron Letters*, 38,52, 8933–8934 (1997).

Grant, R. et al., *Grant and Hackh's Chemical Dictionary*, McGraw–Hill Book Company, 282 (1987).

Greene, T.W. and Wuts, P.G.M., *Protective Groups in Organic Synthesis*, John Wiley & Sons, $2^{nd}$ ed., Ch 7, 315–345 (1991).

Hauske, J. R. and Dorff, P., "Solid Phase CBZ Chloride Equivalent. A New Matrix Specific Linker", *Tetrahedron Letters*, 36, 10, 1589–1592 (1995).

Hocart et al., "Highly potent cyclic disulfide antagonists of somatostatin," *J. of Medicinal Chem.*, 42:11 (1999).

Holmes, C.P. and Jones, D.G., "Reagents for Combinatorial Organic Synthesis: Development of a New O–Nitrobenzyl Photolabile Linker for Solid Phase Synthesis", *J. Org. Chem.*, 60, 2318–2319 (1995).

Huber, B. et al., "Retroviral–mediated gene therapy for the treatment of hepatocellular carcinoma: An innovative approach for cancer therapy," *Proc. Natl. Acad. Sci. USA*, 88–8039–8043 (1991).

Jenkins, T.C. et al., "Structure of a Covalent DNA Minor Groove Adduct with a Pyrrolobenzodiazepine Dimer: Evidence for Sequence–Specific Interstrand Cross–Linking," *J. Med. Chem.*, 37, 4529–4537 (1994).

Jungheim, L.N. and Shepherd, T.A., "Design of Antitumor Prodrugs: Substrates for Antibody Targeted Enzymes," *Am. Chem. Soc. Chem. Rev.*, 94, 1553–1566 (1994).

Kamal, A., et al., "An Efficient Synthesis of Pyrrolo[2,1–c] [1,4] Benzodiazepine Antibiotics via Reductive Cyclization," *Bioorg. Med. Chem. Ltrs*, 7, No. 14, 1825–1828 (1997).

Kamal, A., et al., "Synthesis of Pyrrolo[2,1–c][1,4]–Benzodiazepene Antibiotics: Oxidation of Cyclic Secondary Amine with TRAP", *Tetrahedron*, v. 53, No. 9, 3223–3230 (1997).

Kapoor, T.M. et al., "Exploring the Specificity Pockets of Two Homologous SH3 Domains Using Structure–Based, Split–Pool Synthesis and Affinity–Based Selection," *J. Am. Chem. Soc.* 120:23–29 (1998).

Katritzky et al., *Heterocyclic Chemistry*, John Wiley & Sons, Inc., 247–253 (1960).

Kennedy, J.C. and Pottier, R.H., "Endogenous protoporphyrin IX, a clinical useful photosensitiser for photodynamic therapy," *J. Photochem Photobiol*, 14, 275–292 (1992).

Kunz, H. and Dombo, B., "Solid Phase Synthesis of Peptide and Glycopeptides on Polymeric Supports with Allylic Anchor Groups," *Angew Chem. Int. Ed. Engl*, 5, 711–713 (1988).

Kuzmich, S. et al., "Increased levels of glutathione S–transferase $\pi$ transcript as a mechanism of resistance to ethacrynic acid," *Journal of Biochemistry*, 281, 219–224 (1992).

Lescrinier, T. et al., "DNA–Binding Ligands from Peptide Libraries Containing Unnatural Amino Acids," *Chem. Eur. J.*, 4, 3, 425–433 (1998).

Lewis A.D. et al., "Glutathione and glutathione–dependent enzymes in ovarian adenocarcinoma cell lines derived from a patient before and after the onset of drug resistance: intrinsic differences and cell cycle effects," *Carcinogenesis*, 9, 1283–1287 (1988).

Lown et al., "Molecular Mechanism of Binding of Pyrrolo(1,4)benzodiazepine antitumor agents to deoxyribonucleic acid–anthramycin and tomaymycin," Biochem. Pharmacol. (1979), 28 (13), 2017–2026; and Abstract No. 51709.

Mizushima, S. and Nagata, S., "pEF–BOS, a powerful mammalian expression vector," *Nucl. Acids Res.*, 18, 5322 (1990).

Monks, A. et al., "Feasibility of High–Flux Anticancer Drug Screen Using a Diverse Panel of Cultured Human Tumor Cell Lines," *Journal of National Cancer Institute*, 83, 757–766 (1991).

Moran, E.J. et al., "Novel Biopolymers for Drug Discovery: Biopolymers", *Peptide Science*, John Wiley and Sons, 37:213–19 (1995).

Morgan, R.A. and Anderson, W.F., "Human Gene Therapy," *Annu. Rev. Biochem.*, 62, 191–217 (1993).

Mosmann, T., "Rapid Colorimetric Assay for Cellular Growth and Survival: Application to Proliferation and Cytotoxicity Assays," *J. Immunological Methods*, 65, 55–63 (1983).

Mullen, D.G. and Barany, G., "A New Fluoridolyzable Anchoring Linkage for Orthogonal Solid–Phase Peptide Synthesis: Design, Preparation, and Application of the N–(3 or 4)–[[4–(Hydroxymethyl)phenoxyl]–tert–butylphenylsily] phenyl Pentanedioic Acid Monoamide (Pbs) Handle", *J. Org. Chem.*, 53, 5240–5248 (1988).

Nicolaou, K.C. et al., "Designed Enediynes: A New Class of DNA–Cleaving Molecules with Potent and Selective Anticancer Activity," *Science*, 256,1172–1178 (1992).

Nielson, P.E. et al., "Sequence–Selective Recognition of DNA by Strand Displacement with a Thymine–Substituted Polyamide," *Science*, 254, 1497–1500 (1991).

O'Neil, I.A., et al., "The Synthesis of Functionalized Pyrrolo–[2,1–c][1,4]–Benzodiazepines," *Synlett*, 75–78 (1997).

Paikoff, S.J. et al., "The Solid Phase Synthesis of N–Alkylcarbamate Oligomers", *Tetrahedron Letters*, 37, No. 32: 5653–5656 (1996).

Pillai, V.N.R., "Photoremovable protecting groups in organic chemistry," *Synthesis*, 1–26 (1980).

Ram, Z. et al., "In Situ Retroviral–mediated Gene Transfer for the Treatment of Brain Tumors in Rats," *Cancer Research*, 53, 83–88 (1993).

Rawal, V.H. et al., "Photocyclization Strategy for the Synthesis of Antitumor Agent CC–1065: Synthesis of Dideoxy PDE–I and PDE–II. Synthesis of Thiopene and Furan Analogues of Dideoxy PDE–I and PDE–II," *J. Org. Chem.*, 52, 19–28 (1987).

Regula, J. et al., "Photosensitisation and photodynamic therapy of oesophagael, duodenal and colorectal tumours using 5–aminoleavulic acid induced photoporphyrin IX–a pilot study," *Gut*, 36, 67–75 (1995).

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083–2086 (2000).

Saha, A.K. et al., "Diisopropysilyl–Linked Oligonucleotide Analogs: Solid–Phase Synthesis and Physiocochemical Properties," *J. Org. Chem.*, 58, 7827–7831 (1993).

Satyam, A. et al., "Design, Synthesis, and Evaluation of Latent Alkylating Agents Activated by Glutathione S–Transferase," *J. Med. Chem.*, 39, 1736–1747 (1996).

Simon, R.J. et al., "Peptoids: A Modular Approach to Drug Discovery", *Proc. Natl. Acad. Sci. USA*,89:9367–9371 (1992).

Soth, M.J. and Nowick, J.S., "Unnatural oligomers and unnatural oligomer libraries", *Curr. Opin. Chem. Biol.*, 1:120–129 (1997).

Star, W.M., "Light delivery and light dosimetry for photodynamic therapy," *Lasers in Medical Science*, 5:107–113 (1990).

Suggs, J.W. et al., "Synthesis and structure of anthramycin analogs via hydride reduction of dilactams," *Tetrahedron Letters*, 26, No. 40, 4871–4874 (1985).

Tew, K.D. and Clapper, M.L., "Glutathione–S–transferase and anti–cancer drug resistance," *Mechanism of Drug Resistance in Neoplastic Cells*, Woolley, P.V. and Tew, K.D., Eds, Academic Press: Sand Diego, CA 141–159 (1988).

Thurston, D.E. et al., "Synthesis of Sequence–selective C8–linked Pyrrolo [2,1–c][1,4] Benzodiazepine DNA Interstrand Cross–linking Agent," *J. Org. Chem.*, 61:8141–8147 (1996).

Umezawa, H. et al., "Mazethramycins," *SciFinder Scholar*, 2–3 (2002).

Zuckerman, R.N. et al., "Discovery of Nanomolecular Ligands for 7–Transmembrane G–Protein–Coupled Receptors from a Diverse N–(Substituted) glycine Peptoid Library", *J. Med. Chem.*, 37:2678–2685 (1994).

*Dictionary of Science and Technology*, Professor P.M.B. Walker ed. Larousse plc., pp. 63, 457, 523 (1995).

PYRROLOBENZODIAZEPINES

CROSS REFERENCE TO RELATED APPLICATIONS

This patent application is a continuation of prior U.S. patent application Ser. No. 09/763,767, filed on Feb. 26, 2001 which is a filing under 35 U.S.C. 371 based upon International Application No. PCT/GB99/02838, filed on Aug. 27, 1999, which claims priority to Great Britain Application No. 9818733.9, filed on Aug. 27, 1998 and Great Britain Application No. 9901929.1, filed on Jan. 28, 1999.

BACKGROUND TO THE INVENTION

Some pyrrolobenzodiazepines (PBDS) have the ability to recognise and bond to specific sequences of DNA; the preferred sequence is PuGPu. The first PBD antitumour antibiotic, anthramycin, was discovered in 1965 (Leimgruber et al., 1965 *J. Am. Chem. Soc.*, 87, 5793–5795; Leimgruber et al., 1965 *J. Am. Chem. Soc.*, 87, 5791–5793). Since then, a number of naturally occurring PBDs have been reported, and over 10 synthetic routes have been developed to a variety of analogues (Thurston et al., 1994 *Chem. Rev.* 1994, 433–465). Family members include abbeymycin (Hochlowski et al., 1987 *J. Antibiotics*, 40, 145–148), chicamycin (Konishi et al., 1984 *J. Antibiotics*, 37, 200–206), DC-81 (Japanese Patent 58-180 487; Thurston et al., 1990, *Chem. Brit.*, 26, 767–772; Bose et al., 1992 *Tetrahedron*, 48, 751–758), mazethramycin (Kuminoto et al., 1980 *J. Antibiotics*, 33, 665–667), neothramycins A and B (Takeuchi et al., 1976 *J. Antibiotics*, 29, 93–96), porothramycin (Tsunakawa et al., 1988 *J. Antibiotics*, 41, 1366–1373), prothracarcin (Shimizu et al, 1982 *J. Antibiotics*, 29, 2492–2503; Langley and Thurston, 1987 *J. Org. Chem.*, 52, 91–97), sibanomicin (DC-102) (Hara et al., 1988 *J. Antibiotics*, 41, 702–704; Itoh et al., 1988 *J. Antibiotics*, 41, 1281–1284), sibiromycin (Leber et al., 1988 *J. Am. Chem. Soc.*, 110, 2992–2993) and tomamycin (Arima et al., 1972 *J. Antibiotics*, 25, 437–444). PBDs are of the general structure:

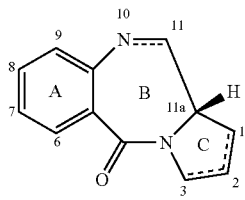

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III*. Springer-Verlag, New York, pp. 3–11; Hurley and Needham-VanDevanter, 1986 *Acc. Chem. Res.*, 19, 230–237). Their ability to form an adduct in the minor groove, enables them to interfere with DNA processing, hence their use as antitumour agents.

DISCLOSURE OF THE INVENTION

A first aspect of the present invention is a compound with the formula Ia or Ib:

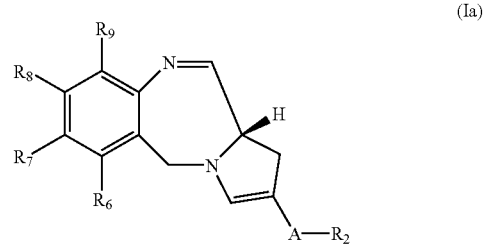

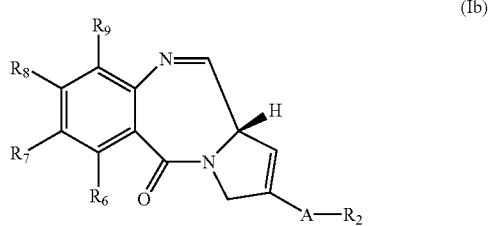

wherein:

A is $CH_2$, or a single bond;

$R_2$ is selected from: R, OH, OR, $CO_2H$, $CO_2R$, COH, COR, $SO_2R$, CN;

$R_6$, $R_7$ and $R_9$ are independently selected from H, R, OH, OR, halo, amino, NHR, nitro, $Me_3Sn$;

where R is a lower alkyl group having 1 to 10 carbon atoms, or an aralkyl group (i.e. an alkyl group with one or more aryl substituents), preferably of up to 12 carbon atoms, whereof the alkyl group optionally contains one or more carbon-carbon double or triple bonds, which may form part of a conjugated system, or an aryl group, preferably of up to 12 carbon atoms; and is optionally substituted by one or more halo, hydroxy, amino, or nitro groups, and optionally containing one or more hetero atoms which may form part of, or be, a functional group; or $R_7$ and $R_8$ together from a group —O—$(CH_2)_p$—O—, where p is 1 or 2;

and $R_8$ is selected from H, R, OH, OR, halo, amino, NHR, nitro, $Me_3Sn$, where R is as defined above, or the compound is a dimer with each monomer being the same or different and being of formula Ia or Ib, where the $R_8$ groups of the monomers form together a bridge having the formula —X—R'—X— linking the monomers, where R' is an alkylene chain containing from 3 to 12 carbon atoms, which chain may be interrupted by one or more hetero-atoms and/or aromatic rings, e.g. benzene or pyridine, and may contain one or more carbon-carbon double or triple bonds, and each X is independently selected from O, S, or N; except that in a compound of formula Ia when A is a single bond, then $R_2$ is not $CH=CH(CONH_2)$ or $CH=CH(CONMe_2)$ If A is a single bond then $R_2$ is bonded directly to the C-ring of the PBD.

If R is an aryl group, and contains a hetero atom, then R is a heterocyclic group. If R is an alkyl chain, and contains a hetero atom, the hetero atom may be located anywhere in the alkyl chain, e.g. —O—$C_2H_5$, —$CH_2$—S—$CH_3$, or may form part of or be a functional group e.g. carbonyl, hydroxy.

It is preferred that in a compound of formula Ia when A is a single bond, then $R_2$ is not $CH=CR^AR^B$, where $R^A$ and $R^B$ are independently selected from H, $R^C$, $COR^C$, $CONH_2$, $CONHR^C$, $CONR^C_2$, cyano or phosphonate, where $R^C$ is an unsubstituted alkyl group having 1 to 4 carbon atoms.

R is preferably selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R is selected from a lower alkyl group having 1 to 10 carbon atoms optionally substituted by one or more halo, hydroxy, amino, or nitro groups. It is particularly preferred that R is an unsubstituted straight or branched chain alkyl, having 1 to 10, preferably 1 to 6, and more preferably 1 to 4, carbon atoms, e.g. methyl, ethyl, n-propyl, n-butyl or t-butyl.

Alternatively, $R_6$, $R_7$, $R_9$ and, unless the compound is a dimer, $R_8$ may preferably be independently selected from R groups with the following structural characteristics:

(i) an optionally substituted phenyl group;
(ii) an optionally substituted ethenyl group;
(iii) an ethenyl group conjugated to an electron sink.

The term 'electron sink' means a moiety covalently attached to a compound which is capable of reducing electron density in other parts of the compound. Examples of electron sinks include cyano, carbonyl and ester groups.

It may be preferred that A is $CH_2$ and/or that $R_2$ is $CO_2H$, $CO_2R$, $CH_2OH$, or $CH_2OR$. It may be further preferred that $R_2$ is $CO_2Me$, $CO_2^tBu$, $CH_2OH$, or $CH_2OAc$.

$R_6$, $R_7$, and $R_9$, unless the compound is a dimer, $R_8$ are preferably selected from H and OR, and more particularly H, OMe and $OCH_2Ph$. It is further preferred that R. and, unless the compound is a dimer, $R_8$ are OR, more preferably OMe or $OCH_2Ph$, and that $R_6$ and $R_9$ are H.

If A is a single bond, then $R_2$ is preferably an aryl group, eg Ph, p-MeO—Ph, or an alkyl or alkaryl group which contains at least one double bond which forms part of a conjugated system with the double bond of the C-ring, eg $CH=CH_2$, $CH=CH—CH_3$.

Compounds of the first aspect of the invention are preferably of formula Ia.

If the compound of formula Ia or Ib is a dimer, the dimer bridge may be of the formula —O—$(CH_2)_p$—O—, where p is from 1 to 12, more preferably 3 to 9.

A second aspect of the present invention is a compound with the formula II:

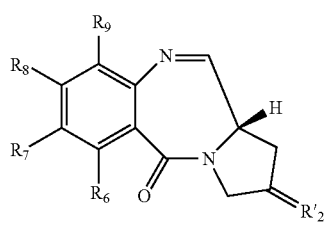

(II)

wherein:
R'$_2$ is selected from: O, CHR"$_2$, where R"$_2$ is selected from H, R, $CO_2R$, COR, CHO, $CO_2H$, halo;
$R_6$, $R_7$ and $R_9$ are independently selected from H, R, OH, OR, halo, amino, NHR, nitro, $Me_3Sn$;
where R is a lower alkyl group having 1 to 10 carbon atoms, or an aralkyl group (i.e. an alkyl group with one or more aryl substituents), preferably of up to 12 carbon atoms, whereof the alkyl group optionally contains one or more carbon-carbon double or triple bonds, which may form part of a conjugated system, or an aryl group, preferably of up to 12 carbon atoms; and is optionally substituted by one or more halo, hydroxy, amino, or nitro groups, and optionally containing one or more hetero atoms which may form part of, or be, a functional group;

and $R_8$ is selected from H, R, OH, OR, halo, amino, NHR, nitro, $Me_3Sn$, where R is as defined above or the compound is a dimer with each monomer being the same or different and being of formula II, where the $R_8$ groups of the monomers form together a bridge having the formula —X—R'—X— linking the monomers, where R' is an alkylene chain containing from 3 to 12 carbon atoms, which chain may be interrupted by one or more hetero-atoms and/or aromatic rings, e.g. benzene or pyridine, and may contain one or more carbon-carbon double or triple bonds, and each X is independently selected from O, S, or N; or $R_7$ and $R_8$ together form a group —O—$(CH_2)_p$—O—, where p is 1 or 2;

except that:
(i) when $R_{12}$ is CH—Et, and $R_6$, $R_8$ and R, are H, $R_7$ is not sibirosamine pyranoside; and
(ii) when R'$_2$ is CH—Me, and $R_6$ and $R_9$ are H, $R_7$ and $R_8$ are not both H or both Ome, or OMe and OH respectively.

If R is an aryl group, and contains a hetero atom, then R is a heterocyclic group. If R is an alkyl chain, and contains a hetero atom, the hetero atom may be located anywhere in the alkyl chain, e.g. —O—$C_2H_5$, —$CH_2$—S—$CH_3$, or may form part of or be a functional group e.g. carbonyl, hydroxy.

R is preferably selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R is selected from a lower alkyl group having 1 to 10 carbon atoms optionally substituted by one or more halo, hydroxy, amino, or nitro groups. It is particularly preferred that R is an unsubstituted straight or branched chain alkyl, having 1 to 10, preferably 1 to 6, and more preferably 1 to 4, carbon atoms, e.g. methyl, ethyl, n-propyl, n-butyl or t-butyl.

Alternatively, $R_6$, $R_7$ and $R_9$ and, unless the compound is a dimer, $R_8$ may preferably be independently selected from R groups with the following structural characteristics:

(i) an optionally substituted phenyl group;
(ii) an optionally substituted ethenyl group;
(iii) an ethenyl group conjugated to an electron sink.

R'$_2$ is preferably O, $CH_2$ or $CHCH_3$ and more preferably $CH_2$ or $CHCH_3$.

$R_6$, $R_7$, and $R_9$ and, unless the compound is a dimer, $R_8$ are preferably selected from H and OR and a halogen atom, and more particularly H, OMe and OCH,Ph, and I. It is further preferred that $R_7$ and, unless the compound is a dimer, $R_8$ are OR or a halogen atom, more preferably OMe, $OCH_2Ph$ or I, and that $R_6$ and $R_9$ are H. Most preferably $R_8$ is BnO.

If the compound of formula II is a dimer, the dimer bridge may be of the formula —O—$(CH_2)_p$—O—, where p is from 1 to 12, more preferably 3 to 9, and most preferably 3 to 5.

A third aspect of the present invention is a compound with the formula III:

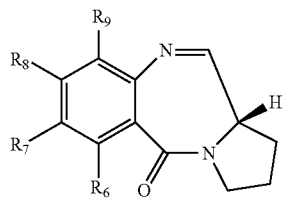
(III)

wherein:
R₆, R₇ and R₉ are independently selected from H, R, OH, OR, halo, amino, NHR, nitro, Me₃Sn;
where R is a lower alkyl group having 1 to 10 carbon atoms, or an aralkyl group (i.e. an alkyl group with one or more aryl substituents), preferably of up to 12 carbon atoms, whereof the alkyl group optionally contains one or more carbon-carbon double or triple bonds, which may form part of a conjugated system, or an aryl group, preferably of up to 12 carbon atoms;
and is optionally substituted by one or more halo, hydroxy, amino, or nitro groups, and optionally containing one or more hetero atoms which may form part of, or be, a functional group;
and R₈ is selected from H, R, OH, OR, halo, amino, NHR, nitro, Me₃Sn, where R is as defined above or the compound is a dimer with each monomer being the same or different and being of formula III, where the R₈ groups of the monomer form together a bridge having the formula —X—R'—X— linking the monomers, where R' is an alkylene chain containing from 3 to 12 carbon atoms, which chain may be interrupted by one or more hetero-atoms and/or aromatic rings, e.g. benzene or pyridine, and may contain one or more carbon-carbon double or triple bonds, and each X is independently selected from O, S, or N; or R₇ and R₈ together form a group —O—(CH₂)$_p$—O—, where p os 1 or 2;
wherein at least one of R₆, R₇, R₈ and R₉ are not H;
except that:
(i) when R₆ and R₉ are H, R₇ and R₈ are not both OMe, OMe and OBn respectively, or OMe and OH respectively;
(ii) when R₆ and R₇ are H, R₈ and R₉ are not Me and OH respectively;
(iii) when three of R₆, R₇, R₈ and R₉ are H, the other is not Me;
(iv) when R₆, R₇, and R₈ are H, R, is not OMe;
(v) when R₆, R₈ and R₉ are H, R₇ is not OMe; and
(vi) when R₆, and R₉ are H and R₇ is OMe, the compound is not a dimer.

If R is an aryl group, and contains a hetero atom, then R is a heterocyclic group. If R is an alkyl chain, and contains a hetero atom, the hetero atom may be located anywhere in the alkyl chain, e.g. —O—C₂H₅, —CH₂—S—CH₃, or may form part of or be a functional group e.g. carbonyl, hydroxy.

R is preferably selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R is selected from a lower alkyl group having 1 to 10 carbon atoms optionally substituted by one or more halo, hydroxy, amino, or nitro groups. It is particularly preferred that R is an unsubstituted straight or branched chain alkyl, having 1 to 10, preferably 1 to 6, and more preferably 1 to 4, carbon atoms, e.g. methyl, ethyl, n-propyl, n-butyl or t-butyl.

Alternatively, R₆, R₇ and R₉ and, unless the compound is a dimer, R₈, may preferably be independently selected from R groups with the following structural characteristics:

(i) an optionally substituted phenyl group;
(ii) an optionally substituted ethenyl group;
(iii) an ethenyl group conjugated to an electron sink.

It is preferred that either:

(i) only one of R₆, R₇, R₈ and R₉ is H; or
(ii) at least one of R₆, R₇, R₈, and R₉ is NH₂; or
(iii) at least one of R₆, R₇, R₈ and R₉ is an aryl group, preferably of up to 12 carbon atoms, which is optionally substituted by one or more halo, hydroxy, amino, or nitro groups, and optionally contains one or more hetero atoms which may form part of, or be, a functional group.

If only one of R₆, R₇, R₈ and R₉, it is further preferred that the A-ring substituents (i.e. those of R₆, R₇, R₉ and, unless the compound is a dimer, R₈ which are not H) are OR, and are more preferably selected from OMe, and OBn.

If at least one of R₆, R₇, R₈ and R₉ is an aryl group, preferably of up to 12 carbon atoms, which is optionally substituted by one or more halo, hydroxy, amino, or nitro groups, and optionally contains one or more hetero atoms which may form part of, or be, a functional group, it is further preferred that at least one of R₆, R₇, R₈ and R₉, is a phenyl group optionally substituted by one or more methoxy, ethoxy or nitro groups, although the nitro groups are less preferred. More preferably, the aryl group is selected from: Ph and p-MeO—Ph.

If the compound of formula III is a dimer, the dimer bridge may be of the formula —O—(CH₂)$_p$—O—, where p is from 1 to 12, more preferably 3 to 9. Also in this case, it is preferred that R₆ and R₉ are H, and R₇ is an alkoxy or aryloxy group.

A fourth aspect of the present invention provides a compound with the formula IV:

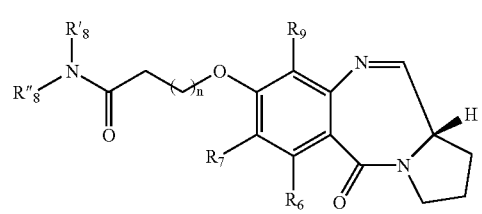
(IV)

wherein:
R₆, R₇ and R₉ are independently selected from H, R, OH, OR, halo, amino, NHR, nitro, Me₃Sn;
where R is a lower alkyl group having 1 to 10 carbon atoms, or an aralkyl group (i.e. an alkyl group with one or more aryl substituents), preferably of up to 12 carbon atoms, whereof the alkyl group optionally contains one or more carbon-carbon double or triple bonds, which may form part of a conjugated system, or an aryl group, preferably of up to 12 carbon atoms;
and is optionally substituted by one or more halo, hydroxy, amino, or nitro groups, and optionally containing one or more hetero atoms which may form part of, or be, a functional group;
R₈' and R₈" are either independently selected from H, R or together form a cyclic amine; and
n is from 1 to 7.

If $R_8'$ and $R_8''$ form a cyclic amine, then there is usually a single N atom in a ring which is otherwise carbocyclic and is preferably 5- or 6-membered and may be saturated or unsaturated. The ring may be fused to another ring system which may be aromatic, e.g. being a benzene ring. Thus for example the cyclic amine may be an indolyl or isoindolyl group. It is also possible that the cyclic amine contains one or more hetero atoms, in addition to N in the amine ring and/or in a fused ring and may also be substituted by one or more R groups.

If R is an aryl group, and contains a hetero atom, then R is a heterocyclic group. If R is an alkyl chain, and contains a hetero atom, the hetero atom may be located anywhere in the alkyl chain, e.g. $-O-C_2H_5$, $-CH_2-S-CH_3$, or may form part of or be a functional group e.g. carbonyl, hydroxy.

R is preferably selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R is selected from a lower alkyl group having 1 to 10 carbon atoms optionally substituted by one or more halo, hydroxy, amino, or nitro groups. It is particularly preferred that R is an unsubstituted straight or branched chain alkyl, having 1 to 10, preferably 1 to 6, and more preferably 1 to 4, carbon atoms, e.g. methyl, ethyl, n-propyl, n-butyl or t-butyl.

It may be preferred that one of $R'_8$ and $R''_8$ is a nitrogen protecting group, such as Fmoc.

$R_7$ is preferably an electron donating group, and is more preferably of the formula OR; particularly preferred are the groups OMe, OEt, and OBn. The term 'electron donating group' means a moiety covalently attached to a compound which is capable of increasing electron density in other parts of the compound.

In addition $R_6$ and $R_9$ are more preferably selected from H and OR; particularly preferred are Ome, OEt and OBn.

Alternatively, $R_6$, $R_7$ and $R_9$ may preferably be independently selected from R groups with the following structural characteristics:

(i) an optionally substituted phenyl group;
(ii) an optionally substituted ethenyl group;
(iii) an ethenyl group conjugated to an electron sink.

n is preferably 1 to 3, and more preferably 1.

A fifth aspect of the present invention is the use of a compound as described in the first, second, third or fourth aspects of the invention in a method of therapy. Conditions which may be treated include gene-based diseases, including, for example, neoplastic diseases and Alzheimer's Disease, and also bacterial, parasitic and viral infections. Any condition which may be treated by the regulation of gene expression may be treated using compounds of the invention. In accordance with this aspect of the present invention, the compounds provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated.

Pharmaceutical compositions according to the present invention, and for use in accordance with the present invention, may comprise, in addition to the active ingredient, i.e. a compound of formula Ia, Ib, II, III or IV, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A sixth aspect of the present invention is a pharmaceutical composition containing a compound of any one of formulae Ia, Ib, II, III, or IV as described above, and a pharmaceutically acceptable carrier or diluent. The preparation of pharmaceutical compositions is described in relation to the fifth aspect of the invention above.

A seventh aspect of the present invention provides the use of a compound of any one of formulae Ia, Ib, II, III, or IV as described above to prepare a medicament for the treatment of a gene-based disease, preferably a proliferative disease. The compound of formula Ia, Ib, II, III, or IV may be provided together with a pharmaceutically acceptable carrier or diluent. The compounds may be used for the selective killing of oxic and hypoxic tumour cells in methods for the treatment of cancers, for example leukemias and particularly solid cancers including colon, CNS, renal, and lung tumours, including small cell lung carcinoma, and melanomas. In particular, dimers of formula II may be used for the selective killing of lung, colon, and CNS tumours and melanomas. The compounds of formula III and IV may be used selectively against melanomas.

A further aspect of the present invention provides the use of a compound of any one of formulae Ia, Ib, II, III, or IV as described above to prepare a medicament for the treatment of a viral, parasitic or bacterial infection. The preparation of a medicament is described in relation to the fifth aspect of the invention above.

In further aspects, the invention provides processes for preparing compounds according to the first, second, third and fourth aspects of the present invention.

Aspects of the invention will now be further described with reference to the accompanying drawings in which:

FIGS. 1 to 6a/b are synthesis routes for compounds of formula Ia of the present invention;

Preferred General Synthetic Strategies

Figure 1:
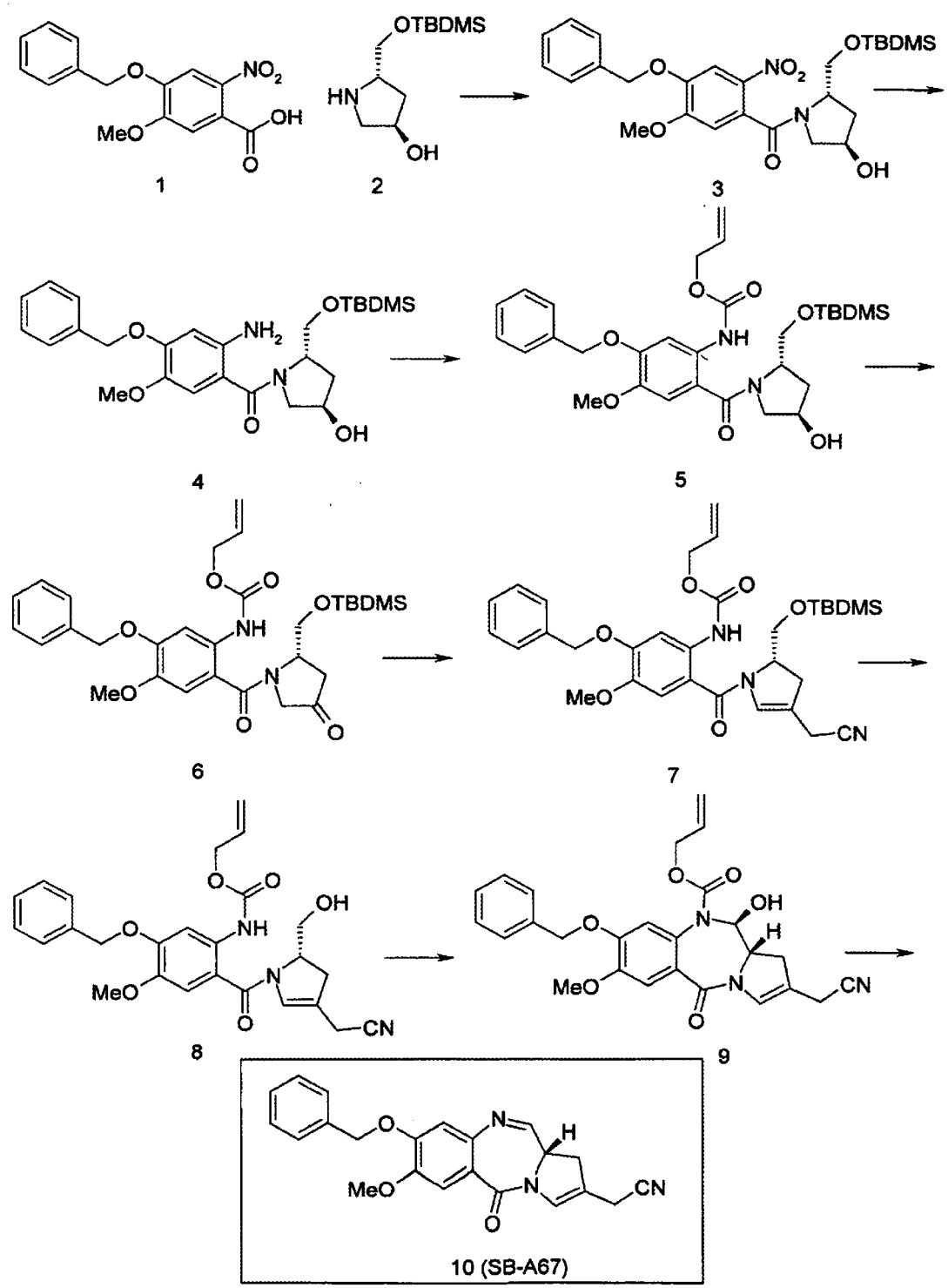

A key step in a preferred route to compounds of formula Ia, Ib, II, III or IV is a cyclisation to produce the B-ring, involving generation of an aldehyde (or functional equivalent thereof) at what will be the 11-position, and attack thereon by the Pro-N10-nitrogen:

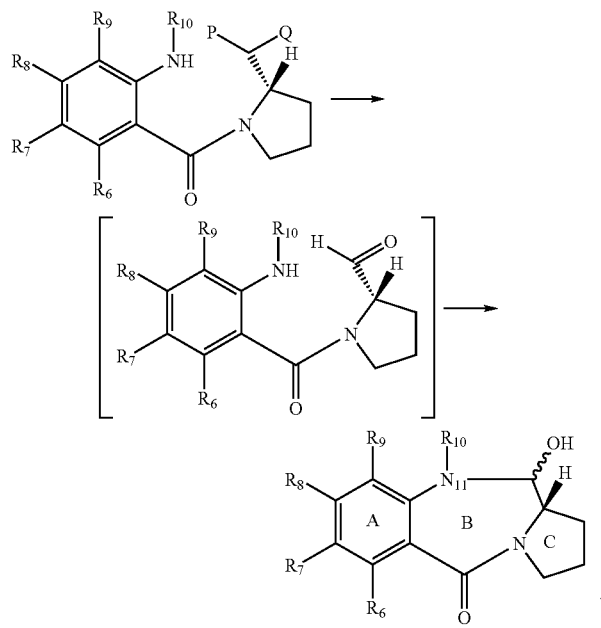

In this structure, no C-ring substitution or unsaturation is shown. $R_8$ represents $O(CH_2)_nCH_2COR'_8$ in compounds of formula IV. $R_{10}$ is a nitrogen protecting group, preferably with a carbamate functionality bonded to the nitrogen of the PBD. The "masked aldehyde" —CPQ may be an acetal or thioacetal (possibly cyclic), in which case the cyclisation involves unmasking. Alternatively, the masked aldehyde may be an aldehyde precursor, such as alcohol —CHOH, in which case the reaction involves oxidation, e.g. by means of TPAP or DMSO (Swern oxidation).

The masked aldehyde compound can be produced by condensing a corresponding 2-substituted pyrrolidine with a 2-nitrobenzoic acid:

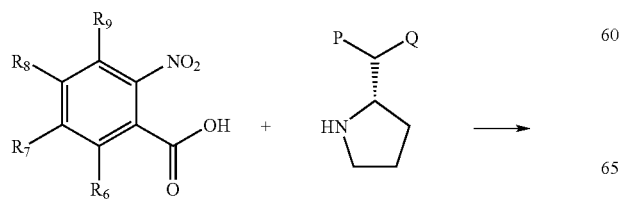

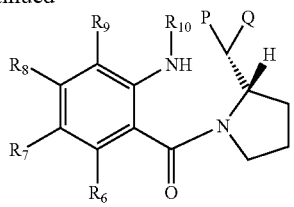

The nitro group can then be reduced to —$NH_2$ and protected by reaction with a suitable reagent, e.g. a chloroformate, which provides the removable nitrogen protecting group in the synthesis route.

A process involving the oxidation-cyclization procedure is illustrated in scheme 1 (an alternative type of cyclisation will be described later with reference to scheme 2).

Scheme 1

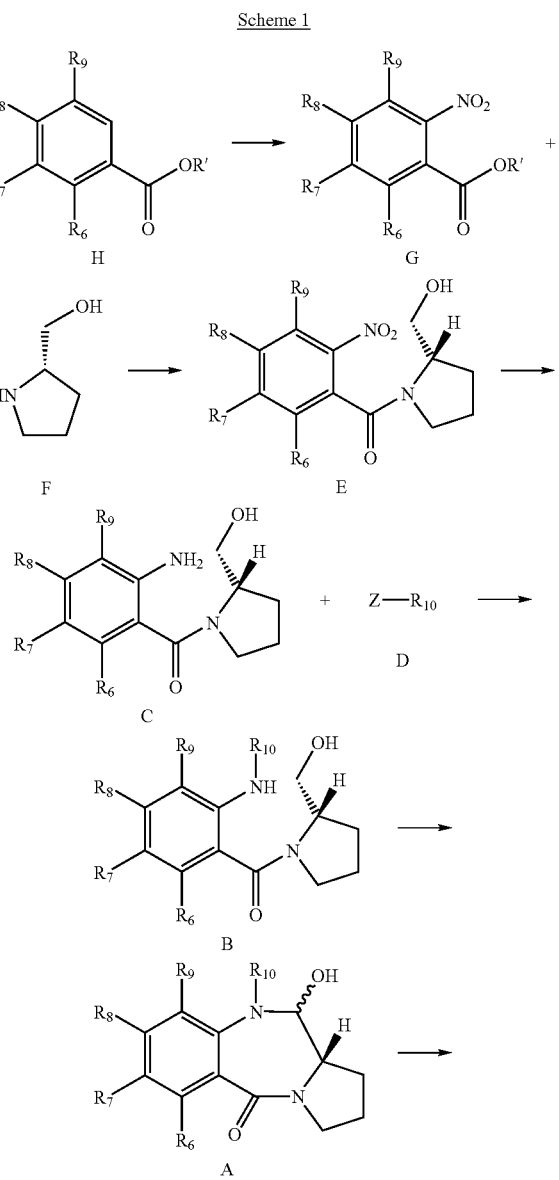

-continued

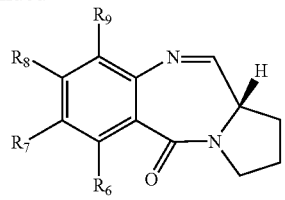

The imine/carbinolamine bond in the PBD (A) can be unprotected by standard methods to yield the desired compound, e.g. if $R_{10}$ is Alloc, then the deprotection is carried out using palladium to remove the N10 protecting group, followed by the elimination of water to give the imine.

Exposure of the alcohol (B) (in which the Pro-N10-nitrogen is generally protected as carbamate) to tetrapropylammonium perruthenate (TPAP)/N-methylmorpholine N-oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g).

The uncyclized alcohol (B) may be prepared by the reaction of a nitrogen protection reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable.

The nitro compound of formula E may be prepared by coupling the appropriate o-nitrobenzoyl chloride to a compound of formula F, e.g. in the presence of $K_2CO_3$ at −25° C. under a $N_2$ atmosphere. Compounds of formula F can be readily prepared, for example by olefination of the ketone derived from L-trans-hydroxy proline. The ketone intermediate can also be exploited by conversion to the enol triflate for use in palladium mediated coupling reactions.

The o-nitrobenzoyl chloride is synthesised from the o-nitrobenzoic acid (or alkyl ester after hydrolysis) of formula G, which itself is prepared from the vanillic acid (or alkyl ester) derivative H. Many of these are commercially available and some are disclosed in Althuis, T. H. and Hess, H. J., *J. Medicinal Chem.*, 20(1), 146–266 (1977).

Alternative Cyclisation (Scheme 2)

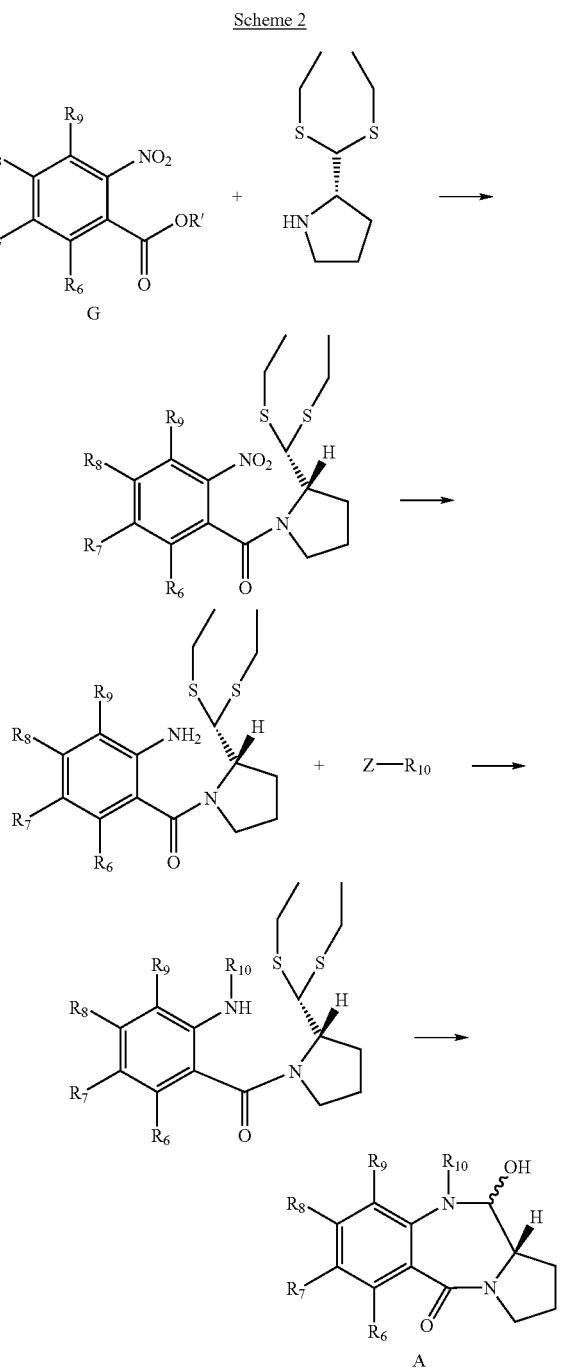

In scheme 1, the final or penultimate step was an oxidative cyclisation. An alternative, using thioacetal coupling, is shown in scheme 2. Mercury-mediated unmasking causes cyclisation to the protected PBD compound (A).

The thioacetal compound may be prepared as shown in scheme 2: the thioacetal protected C-ring [prepared via a literature method: Langley, D. R. & Thurston, D. E., *J. Organic Chemistry*, 52, 91–97 (1987)] is coupled to the o-nitrobenzoic acid (or alkyl ester after hydrolysis) (G) using a literature procedure. The resulting nitro compound cannot be reduced by hydrogenation, because of the thioacetal group, so the tin(II) chloride method is used to afford the amine. This is then N-protected, e.g., by reaction with a chloroformate or acid chloride, such as 2,2,2-trichloroethylchloroformate.

Acetal-containing C-rings can be used as an alternative in this type of route with deprotection involving other methods, including the use of acidic conditions.

Dimer Synthesis (Scheme 3)

An alternative synthesis of the bis(nitro acid) involves oxidation of the bis(nitro aldehyde), e.g. with potassium permanganate. This can be obtained in turn by direct nitration of the bis(aldehyde), e.g. with 70% $HNO_3$. Finally, the bis(aldehyde) can be obtained via the Mitsunobu etherification of two equivalents of the benzoic aldehyde with the appropriate alkanediol.

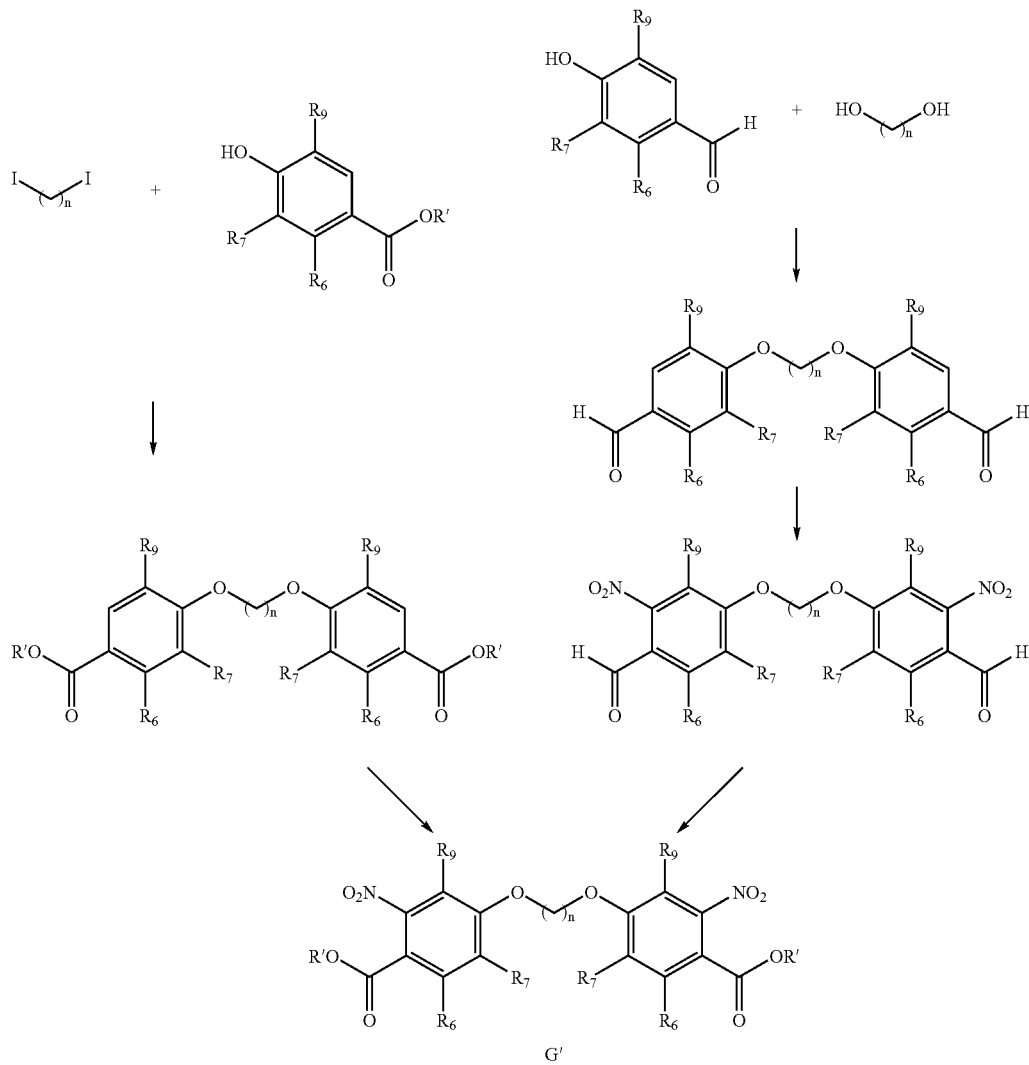

Scheme 3

PBD dimers may be synthesized using the strategy developed for the synthesis of the protected PBD monomers. The synthesis routes illustrated in scheme 3 show compounds when the dimer linkage is of the formula —O—$(CH_2)_n$—O—. The step of dimer formation is normally carried out to form a bis(nitro acid) G'. This compound can then be treated as compound G in either scheme 1 or scheme 2 above.

The bis(nitro acid) G' may be obtained by nitrating (e.g. using 70% nitric acid) the bis(carboxylic acid). This can be synthesised by alkylation of two equivalents of the relevant benzoic acid with the appropriate diiodoalkane under basic conditions. Many benzoic acids are commercially available and others can be synthesised by conventional methods. Alternatively, the relevant benzoic acid esters can be joined together by a Mitsunobo etherification with an appropriate alkanediol, followed by nitration, and then hydrolysis (not illustrated).

An alternative synthesis approach to those detailed above is to protect the pro N10 position on the component which will form the A-ring, before joining the component which will form the C-ring.

Preferred Synthetic Strategies for Compounds of Formula Ia

The synthesis route of scheme 1 is generally applicable to compounds of formula Ia.

C2/C3-endo-unsaturated PBDs of formula Ia may be synthesised from their N10-carbamate protected precursors. Typically, palladium catalysed removal of an allyl carbamate may be used to generate the N10-C11 imine without affecting the key C2-unsaturation. For example, if the N10-C11 imine/carbinolamine is protected by an Alloc group, the C2/C3-endo-unsaturation is maintained during the Alloc cleavage reaction.

The reduction of the nitro-compound E as shown in scheme 1 with tin (II) chloride in refluxing methanol leaves the C2/C3-unsaturation unaffected. The hydrazine/Raney nickel method would not be suitable due to the double bond.

The compound of formula F may be used in its TBDMS protected form, and therefore a deprotection step has to be included to produce the amino-alcohol compound E.

The TBDMS ether, which is the product of the coupling of TBDMS protected compound with the appropriate o-nitrobenzoyl chloride, can be treated with AcOH:THF:H$_2$O (3:1:1). TBAF was found to be unsuitable for this transformation due to the rapid degradation of reaction products.

A class of requisite C-ring providing compounds F can be obtained as shown in scheme 4.

converted to the C2/C3-endo compound F1(Ia) upon treatment with excess sodium hydride. Palladium-mediated cleavage of the N-alloc protecting group (Dangles 0.; Guibé, F.; Balavoine, G.; Lavielle, S.; Marquet, A.; *J. Org. Chem.* 1987, 52, 4984) yields the compound F(Ia).

Alternative Route to Compounds of Formula Ia

A more linear synthetic route to compound B of scheme 1 has been developed which enables larger scale production of the C2/C3-endo-unsaturated PBDs, and is shown in scheme 5.

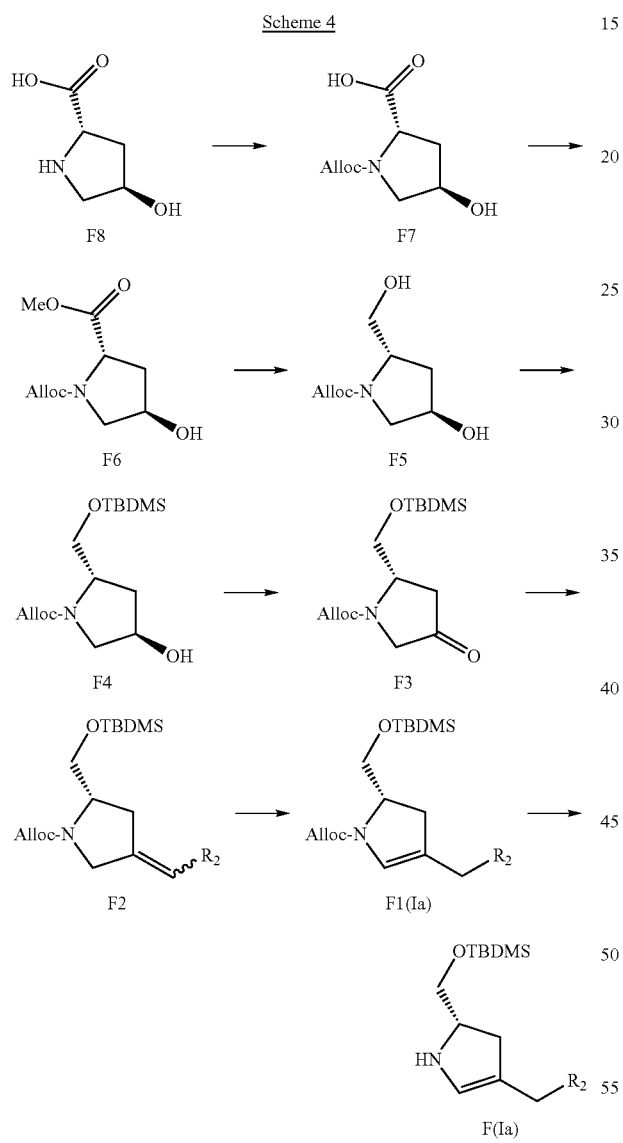

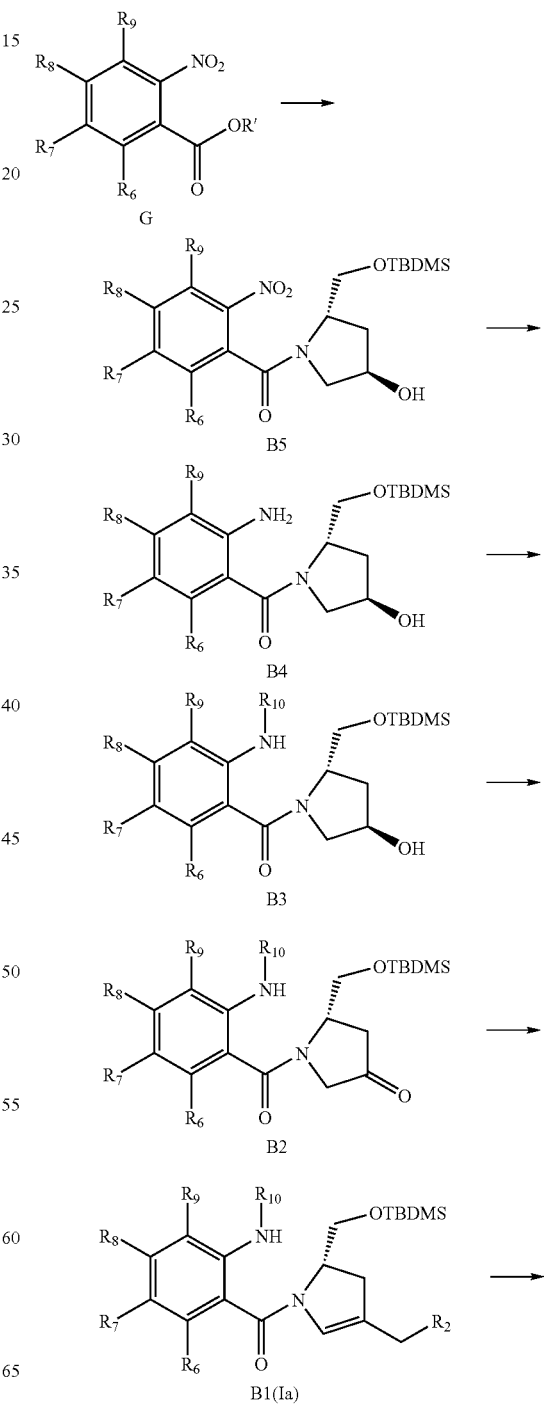

Commercially available trans-4-hydroxy-L-proline F8 can be N-alloc protected to give the allyl carbamate F7 which can then be esterified using standard conditions. Hydride reduction of the ester F6 furnishes the diol F5. Selective TBDMS protection of the diol gives a silyl ether F4, which can then be oxidised, using either Swern or TPAP oxidation, to provide the ketone F3.

The ketone F3 can then undergo a Wittig reaction to yield a mixture of the E/Z exo-esters F2 which can then be

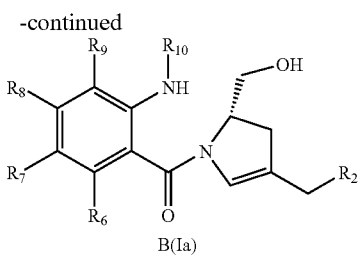

B(Ia)

The silyl protecting group may be cleaved in good yield by treating B1(Ia) with AcOH:THF:H$_2$O (3:1:1). The key C2/C3-endo-unsaturation present in B1(Ia) may be introduced directly by performing the Horner-Emmons reaction on a ketone of type B2. Unlike the previous route (Scheme 4), the addition of extra NaH to ensure double-bond migration was not necessary for this substrate. Swern oxidation of the secondary alcohol B3 may be used to furnish the ketone B2. The carbamate protected aniline B3 may be prepared from the nitro compound B5 in two steps. Firstly, the nitro group may be reduced to the aniline by employing the Raney nickel/hydrazine method because a compound of type B5 lacks C2-unsaturation. This method is more advantageous than the tin (II) chloride procedure since the product is easier to isolate. The aniline B4 may then be N-carbamate protected in high yield without significant carbonate formation at the C2 oxygen.
An amide of type B5 may be synthesised by coupling an acid chloride of type G to the key amine KEC5 (Scheme 6).

Scheme 6

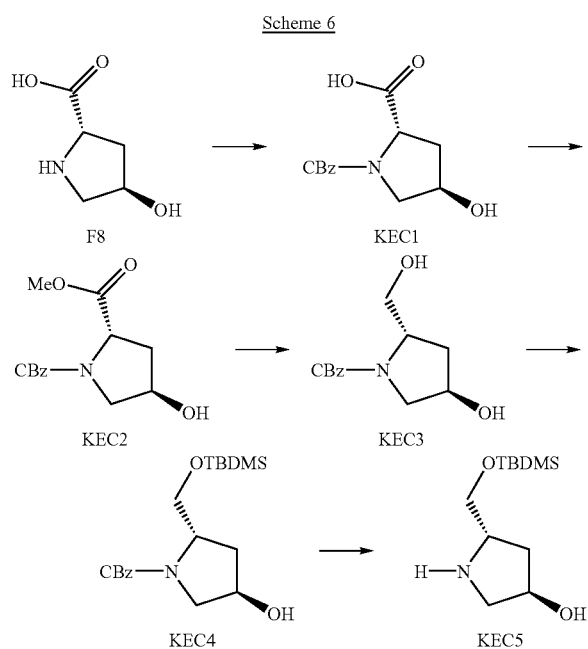

Overall, this route has several advantages over the previous route which results in the larger scale production of the C2/C3-endo-unsaturated PBDs. Firstly, catalytic hydrogenation of KEC4 allows large scale preparation of key intermediate KEC5. Secondly, this more efficient nitro reduction step may be carried out on an intermediate devoid of C2-unsaturation. Importantly, the double-bond migration observed during the Horner-Emmons reaction is spontaneous, so excess sodium hydride is not necessary. This double-bond migration has also been observed by other workers (Leimgruber, W.; Batcho, A. D.; Czajkowski, R. C. *J. Am. Chem. Soc.* 1968, 90, 5641).

Parr-hydrogenation of KEC4, in order to cleave the Cbz protecting group, allowed the large scale synthesis of the key amino intermediate KEC5. The TBDMS ether KEC4 was prepared in an analogous fashion to the corresponding Alloc protected intermediate F4 (Scheme 4). Selective silylation of the primary alcohol KEC3 was achieved using DBU as a silyl transfer agent. The diol KEC3 was obtained from hydride reduction of ester KEC2 which in turn was synthesised from carboxylic acid KEC1. N-Cbz protection of trans-4-hydroxy-L-proline (F4) was achieved by adopting a procedure reported in the literature (Bridges, R. J.; Stanley, M. S.; Anderson, M. W.; Cotman, C. W.; Chamberlain, R. A. *J. Med. Chem.* 1991, 34, 717).

Certain R$_2$ groups may require protection during the synthesis routes set out above, e.g. alcohols can be protected by using an acetate protecting group (see example 1(d))

Further Alternative Route to Compound of Formula Ia

Scheme 7

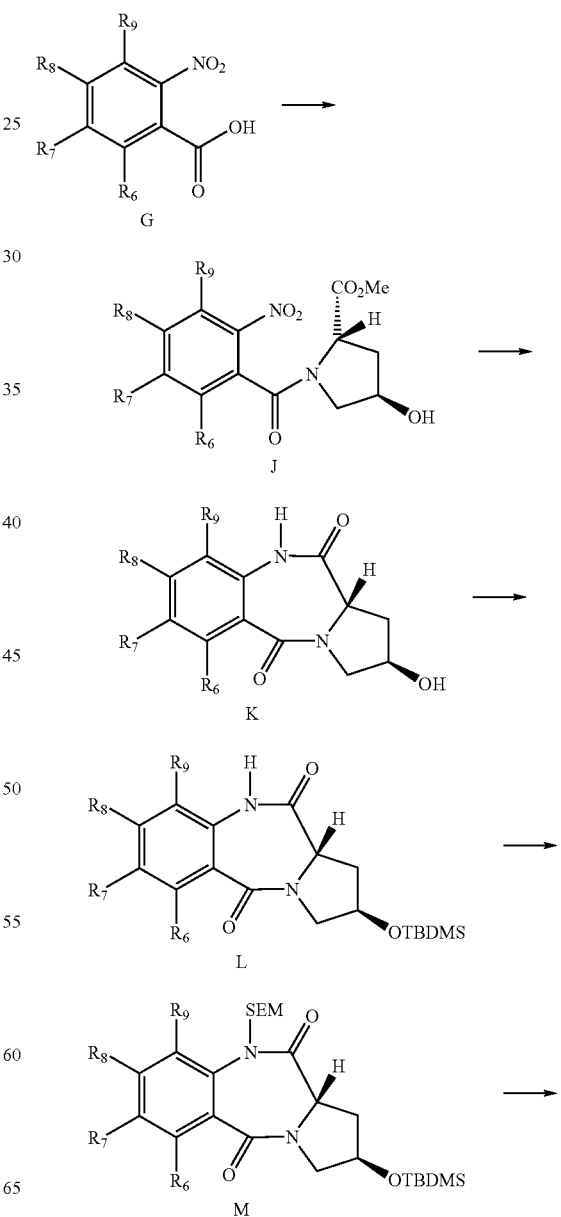

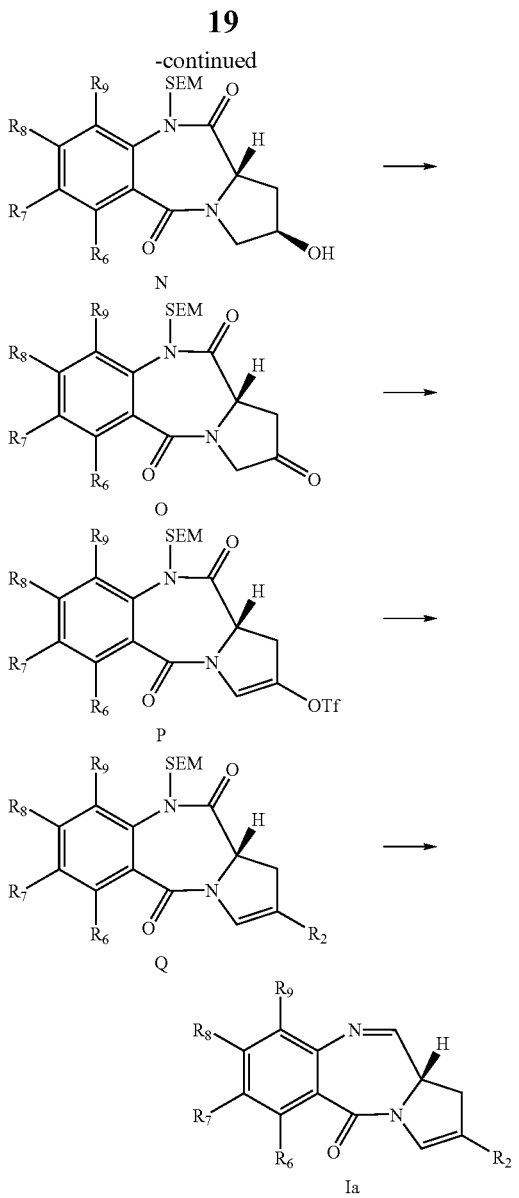

The following route is particularly suited to a compound of formula Ia where A is a single bond, and $R_2$ is an allyl group or contains a double bond which is conjugated to that in the C-ring. However, elements of the synthesis, eg the SEM protection, may be useful in a route to other compounds.

The target PBDs were prepared by reduction of the SEM protected dilactam (Q) with sodium tetraborohydride followed by treatment with silica gel. The sodium tetraborohydride, initially, converts the dilactam into a protected carbinolamine. However, this species is very unstable and treatment with silica gel is sufficient to provoke fragmentation of the SEM protecting group accompanied by imine formation.

The SEM protected dilactams (Q) were prepared by Suzuki and Stille coupling reactions on the enol triflate intermediate (P). The Suzuki reaction is particularly useful as it can be used to install both aryl and vinyl substituents at the C2 position of the PBD. In excess of 70 boronic acids are commercially available allowing great diversity to be introduced into the PBD system. Heck reactions can also be performed smoothly on the enol triflate intermediate.

The enol triflate (P) was prepared from the ketone precursor (O) using triflic anhydride in DCM in the presence of pyridine. The ketone (O) was prepared from the secondary alcohol precursor (N) by Swern oxidation. Other oxidation methods involving TPAP or the Dess Martin reagent provide the ketone in equally good yields. The secondary alcohol was obtained by selective removal of a TBDMS group of compound M in the presence of the SEM N10 protecting group. The SEM group was installed by quenching the N10 dilactam anion (from L) with SEM-Cl; this is a general method and can be used to install related protecting groups such as MOM. In order to prevent the C2 hydroxy of compound K interfering with the N10 protection step if was protected as a TBDMS ether. The 2-hydroxy dilactam (K) was formed by hydrogenating the A-ring nitro group of compound J and coupling to the C-ring methyl ester. The A-ring nitro C-ring ester compound (J) was prepared by coupling commercially available acid (G) to methyl 4-hydroxyprolinate.

The alternative synthesis routes are equally applicable to the synthesis of dimers.

Preferred Synthesis Strategies for Compounds of formula II

The synthesis route of scheme 1 is generally applicable to compounds of formula II.

C2-unsaturated PBDs of formula II may be synthesised from their N10-carbamate protected precursors. Typically, palladium catalysed removal of an allyl carbamate may be used to generate the N10-C11 imine without affecting the key C2-unsaturation. Alternatively, cadmium-lead couple may be employed to cleave an N10-2,2,2-trichloroethyl carbamate from the protected PBD.

The reduction of the nitro-compound E as shown in scheme 1 with tin (II) chloride maintains the C2-unsaturation, although isolating the aniline C from the tin salts can be problematic.

The compound of formula F may be used in its TBDMS protected form, and therefore a deprotection step has to be included to produce the amino-alcohol compound E.

The TBDMS ether of type E, which is the product of the coupling of the TBDMS protected compound with the appropriate o-nitrobenzoyl chloride, can be treated with AcOH:THF:H$_2$O (3:1:1). TBAF was found to be unsuitable for this transformation due to the rapid degradation of reaction products.

C-ring providing compounds F(II) can be obtained as shown in scheme 8.

Scheme 8

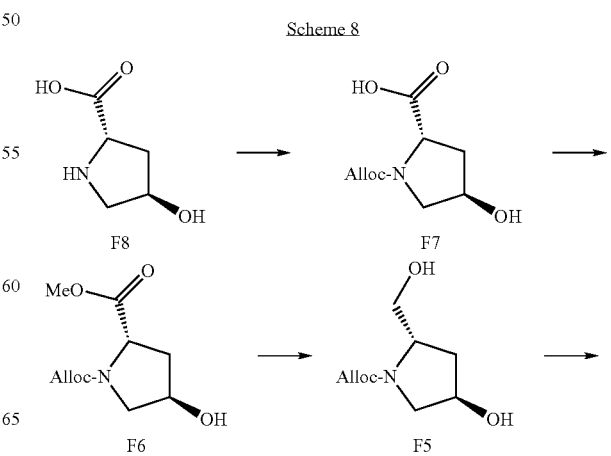

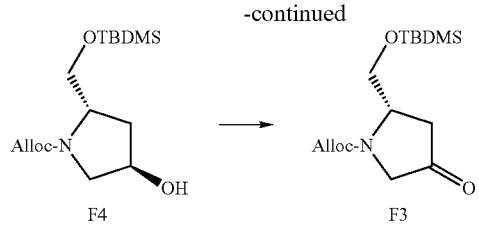

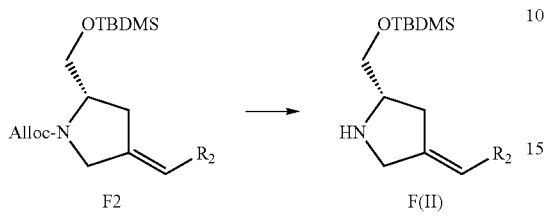

Commercially available trans-4-hydroxy-L-proline F8 can be N-alloc protected to give the allyl carbamate F7 which can then be esterified using standard conditions. Hydride reduction of the ester F6 furnishes the diol F5. Selective TBDMS protection of the diol gives a silyl ether F4, which can then be oxidised, using either Swern or TPAP oxidation, to provide the ketone F3.

The C2-olefinic functionality present in F2 may be introduced by performing the Wittig reaction on ketone F3. Palladium-mediated cleavage of the N-alloc protecting group (Dangles O.; Guibé, F.; Balavoine, G.; Lavielle, S.; Marquet, A.; *J. Org. Chem.* 1987, 52, 4984) yields compound F(II).

Alternative Route to Compound C

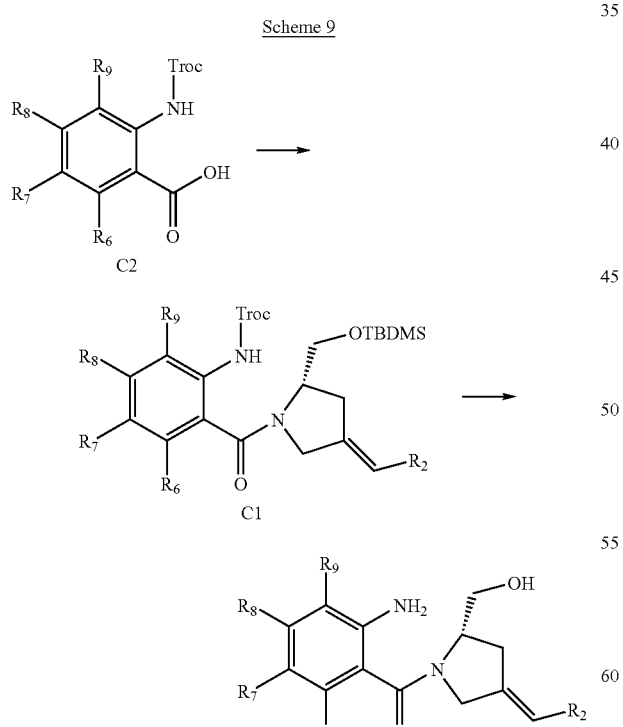

An alternative route to compound C has been developed (Scheme 9). The amide of formula C1 may be synthesised by forming the acid chloride of an N-Troc protected anthranilic acid of type C2. Interestingly, N-Troc anthranilic acids do not generate isatoic anhydrides, thus enabling amide formation reactions with amines of type F(II). Simultaneous TBAF-mediated cleavage of the 2,2,2-trichloroethyl carbamate and TBDMS groups from C1 may provide the key amino-alcohol C.

Alternative Route to Compounds of Formula II

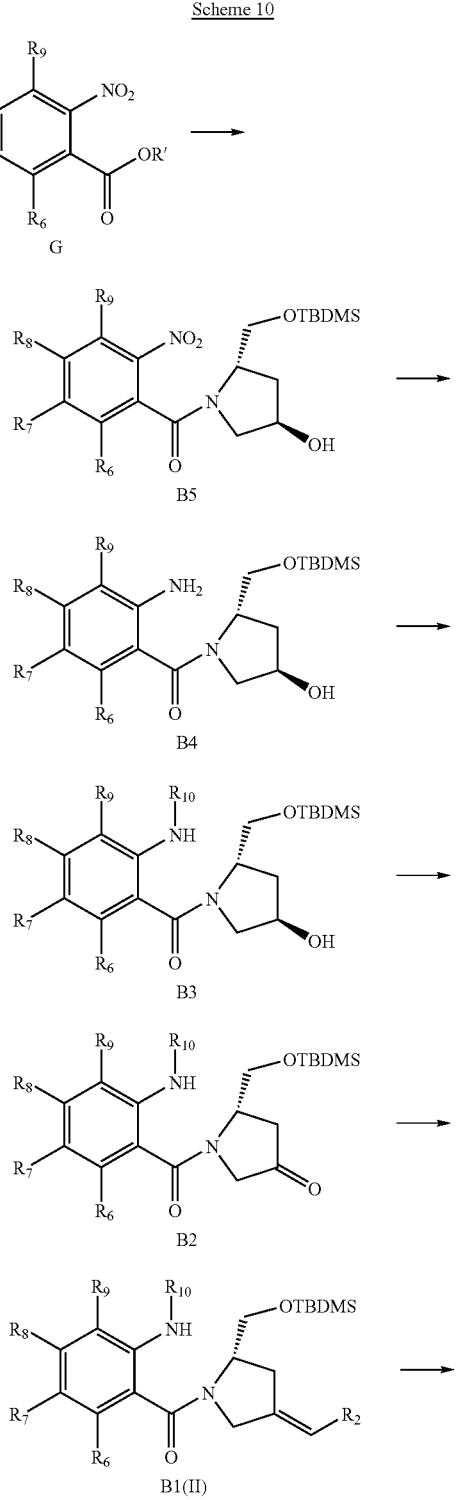

-continued

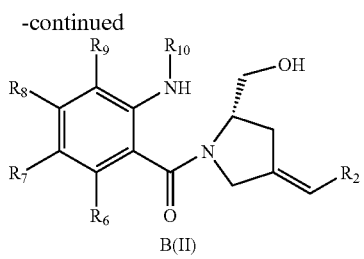

B(II)

A more linear synthetic route to compound B of scheme 1 has been developed which enables larger scale production of the C2-unsaturated PBDs, and is shown in scheme 10. TBAF-mediated cleavage of the TBDMS group may be used to produce B(II) from B1(II). The key C2-unsaturation present in B1(II) may be introduced by performing the Wittig olefination reaction on a ketone of type B2. Swern oxidation of the secondary alcohol B3 may be used to furnish the ketone B2. The carbamate protected aniline B3 may be prepared from the nitro compound B5 in two steps. Firstly, the nitro group may be reduced to the aniline by employing the Raney nickel/hydrazine method because a compound of type B5 lacks C2-unsaturation. This method is more advantageous than the tin (II) chloride procedure since the product is easier to isolate. The aniline B4 may then be N-carbamate protected in high yield without significant carbonate formation at the C2 oxygen.

An amide of type B5 may be synthesised by coupling an acid chloride of type G to the key amine KEC5 (see scheme 6). Overall, this route has several advantages over the convergent route which allow larger scale production of the C2-unsaturated PBDs. Firstly, catalytic hydrogenation of KEC4 allows large scale preparation of key intermediate KEC5. Secondly, the nitro reduction step may be carried out on an intermediate devoid of C2-unsaturation. Finally, the Wittig olefination may be performed in the latter stages of the synthetic route where large scale limitations are tolerated.

In dimer synthesis, the routes set out above may be used in preference to those set out in the overall synthetic strategies. In particular, the nitrogen-protecting group may advantageously be a carbamate, as protecting groups of this type may be removed in the final step by a variety of methods which, in general, do not affect the key C2-unsaturation.

General Experimental Methods

Melting points (mp) were determined on a Gallenkamp P1384 digital melting point apparatus and are uncorrected. Infrared (IR) spectra were recorded using a Perkin-Elmer 297 spectrophotometer. $^1$H- and $^{13}$C-NMR spectra were recorded on a Jeol GSX 270 MHZ FT-NMR spectrometer operating at 20° C.+/−1° C. Chemical shifts are reported in parts per million (δ) downfield from tetramethylsilane (TMS). Spin multiplicities are described as: s (singlet), bs (broad singlet), d (doublet), dd (doublet of doublets), t (triplet), q (quartet), p (pentuplet) or m (multiplet). Mass spectra (MS) were recorded using a Jeol JMS-DX 303 GC Mass Spectrometer (EI mode: 70 eV, source 117–147° C.). Accurate molecular masses (HRMS) were determined by peak matching using perfluorokerosene (PFK) as an internal mass marker, and FAB mass spectra were obtained from a glycerol/thioglycerol/trifluoroacetic acid (1:1:0.1) matrix with a source temperature of 180° C. Optical rotations at the Na-D line were obtained at ambient temperature using a Perkin-Elmer 141 Polarimeter. Analytical results were generally within +/−0.2% of the theoretical values. Flash chromatography was performed using Aldrich flash chromatography "Silica Gel-60" (E. Merck, 230–400 mesh). Thin-layer chromatography (TLC) was performed using $GF_{254}$ silica gel (with fluorescent indicator) on glass plates. All solvents and reagents, unless otherwise stated, were supplied by the Aldrich Chemical Company Ltd. and were used as supplied without further purification. Anhydrous solvents were prepared by distillation under a dry nitrogen atmosphere in the presence of an appropriate drying agent, and were stored over 4A molecular sieves or sodium wire. Petroleum ether refers to the fraction boiling at 40–60° C.

EXAMPLES

Example 1(a)

Synthesis of the 2-Cyanomethyl PBD (10, SB-A67) (See FIG. 1)

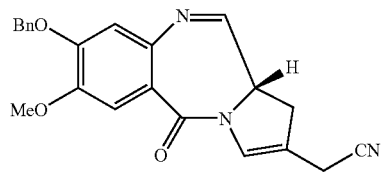

Synthesis of the Nitro Alcohol (3)

A solution of the acid 1 (3.03 g, 10 mmol, 1 equiv) in freshly distilled $CH_2Cl_2$ (50 mL) was treated with oxalyl chloride (1.05 mL, 12 mmol, 1.2 equiv) under a nitrogen atmosphere and stirred. DMF (0.1 mL) was added and the solution effervesced. The reaction was allowed to stir overnight at RT. The following day the acid chloride solution was added dropwise over 2 hours to a stirred mixture of the amine 2 (2.31 g, 10 mmol, 1 equiv) and TEA (3.48 mL, 25 mmol, 2.5 equiv) in freshly distilled $CH_2Cl_2$ (30 mL) while the temperature was kept under 0° C., under a nitrogen atmosphere. The reaction mixture was then allowed to warm to RT and stirred overnight. The solution was washed with $NaHCO_3$ (100 mL), saturated $NH_4Cl$ (100 mL), $H_2O$ (100 mL), brine (100 mL), dried ($MgSO_4$), filtered and evaporated in vacuo to give a brown oil which was purified by flash chromatography ($SiO_2$, EtOAc) and provided the coupled compound 3 (3.24 g, 6.28 mmol, 62.8%) as a yellow glass: $^1$H NMR ($CDCl_3$, 270 MHz) rotamers: δ−0.10 (s, 6H, $Si(CH_3)_2$), 0.80 (s, 9H, $SiC(CH_3)_3$), 2.04–2.55 (m, 3H, 1-H, OH), 3.05–4.60 (m, 9H, 11-H, 11a-H, OMe, 3-H, 2-H), 5.20 (br s, 2H, OBn), 6.78 and 6.85 (2×s, 1H, 6-H), 7.27–7.47 (m, 5H, Ph), 7.73 and 7.76 (2×s, 1H, 9-H); $^{13}$C NMR ($CDCl_3$, 270 MHz): δ−5.5, −5.4, 18.2, 25.7, 25.8, 36.3, 56.6, 57.2, 62.6, 70.2, 71.3, 109.0, 109.4, 127.6–128.8, 135.2, 137.3, 147.9, 154.7, 166.6; IR (neat): 3401, 3065, 3033, 2951, 2856, 2739, 2628, 1956, 1743, 1620, 1578, 1522, 1462, 1434, 1378, 1336, 1277, 1221, 1075, 1051, 1002, 914, 836, 779, 752, 697, 669, 650, 615; EIMS m/z (relative intensity) 516 ($M^+$, 0.6), 460 (29.8), 459 (92.6), 368 (7.9), 286 (49.6), 91 (100.0), 73 (9.5); FAB m/z (relative intensity) 517 ($M^+$ +1, 15.1), 385 (9.2), 286 (19.3), 92 (9.3), 91 (100.0), 75 (14.0), 73 (42.2).

Reduction to the Amino Alcohol (4)

A solution of hydrazine (3.11 mL, 100 mmol, 5 equiv) in MeOH (50 mL) was added dropwise to a refluxing solution of the nitro compound 3 (10.32 g, 20 mmol, 1 equiv), antibumping granules and Raney Ni (3.5 g) in MeOH (150 mL). After 1 hour at reflux TLC ($SiO_2$, 5% MeOH—$CHCl_3$) revealed total consumption of starting material. The mixture was then treated with sufficient Raney Ni to decompose any unreacted hydrazine. After cooling to RT the mixture was filtered through Celite and the filtrate evaporated in vacuo. The resulting residue was dissolved in $CH_2Cl_2$ (300 mL), dried ($MgSO_4$), filtered and evaporated in vacuo to provide 4 (6.80 g, 14 mmol, 70%) as a pink oil which was carried through to the next stage without purification: $^1H$ NMR ($CDCl_3$, 270 MHz) rotamers: δ−0.001 (s, 6H, $Si(CH_3)_2$), 0.88 (br s, 9H, $SiC(CH_3)_3$), 1.96–2.23 (m, 2H, 1-H), 3.44–4.48 (m, 12H, 11-H, 3-H, OMe, $NH_2$, OH, 2-H, 11a-H), 5.09 (br s, 2H, OBn), 6.25 and 6.27 (2×s, 1H, 6-H), 6.68 and 6.73 (2×s, 1H, 9-H), 7.26–7.42 (m, 5H, Ph); $^{13}C$ NMR ($CDCl_3$, 270 MHz): δ−5.4, 18.2, 25.9, 35.7, 56.9, 57.2, 70.4, 70.7, 103.2, 112.9, 113.4, 127.2, 127.4, 127.9, 128.6, 128.6, 136.7, 141.6; IR (neat): 3356.80, 2930.13, 2857.36, 2247.82, 1622.19, 1514.60, 1463.60, 1408.95, 1261.43, 1176.55, 1118.48, 1003.88, 911.00, 836.61, 778.15, 733.59, 697.72, 646.32.

Synthesis of the Alloc Pro-N10-Protected C2-Alcohol (5)

A solution of allyl chloroformate (1.54 mL, 14.48 mmol, 1.05 equiv) in freshly distilled $CH_2Cl_2$ (30 mL) was added dropwise to a stirred mixture of the amine 4 (6.70 g, 13.79 mmol, 1 equiv), pyridine (2.45 mL, 30.34 mmol, 2.2 equiv) in freshly distilled $CH_2Cl_2$ (200 mL), at 0° C. under a nitrogen atmosphere. The mixture was allowed to warm at RT and stirred overnight. The following day TLC ($SiO_2$, 5% MeOH—$CHCl_3$) revealed reaction completion. The mixture was washed with saturated $CuSO_4$ (100 mL), $H_2O$ (100 mL), brine (100 mL), dried ($MgSO_4$), filtered and evaporated in vacuo to give a dark yellow oil. Flash chromatography ($SiO_2$, 30% EtOAc-petroleum ether) afforded the pure Alloc-compound 5 (6.70 g, 11.75 mmol, 85.2%) as a yellow oil: $^1H$ NMR ($CDCl_3$, 270 MHz) rotamers: δ0.03 and 0.04 (2×s, 6H, $Si(CH_3)_2$), 0.89 (br s, 9H, $SiC(CH_3)_3$), 1.99–2.40 (m, 2H, 1-H), 3.56 (br s, 4H, 11-H, 3-H), 3.79 (s, 3H, OMe), 4.05–4.20 (m, 1H, 11a-H), 4.38 (s, 1H, 2-H), 4.58–4.62 (m, 3H, OH, Alloc), 5.16–5.37 (m, 4H, OBn, Alloc), 5.86–6.00 (m, 1H, Alloc), 6.80 (s, 1H, 6-H), 7.30–7.48 (m, 5H, Ph), 7.80 (s, 1H, 9-H), 8.86 (br s, 1H, NH); $^{13}C$ NNR ($CDCl_3$, 270 MHz): δ−5.5, −5.4, 18.1, 25.8, 35.6, 56.4, 57.2, 60.4, 65.8, 70.5, 70.7, 106.4, 111.7, 116.4, 118.0, 127.7–128.6, 132.5, 136.3, 144.3, 150.2, 153.8, 169.4; IR (neat): 3336, 3067, 2953, 2931, 2858, 1732, 1600, 1525, 1464, 1408, 1327, 1225, 1175, 1121, 1048, 1028, 1002, 937, 837, 812, 778, 744, 698, 671, 636, 608, 562; EIMS m/z (relative intensity) 570 ($M^{+\cdot}$, 35.0), 513 (27.2), 340 (19.3), 149 (24.3), 91 (24.1), 77 (16.4), 58 (33.0), 57 (100.0), 44 (27.2), 39 (39.8); $[\alpha]^{23}_D$=−55.94° (c=1.010, $CHCl_3$).

Oxidation to the C2-Ketone (6)

A solution of DMSO (2.50 mL, 35.25 mmol, 3 equiv) in freshly distilled $CH_2Cl_2$ (200 mL) was added dropwise over 1.5 hours to a stirred solution of oxalyl chloride (8.81 mL of a 2M solution in $CH_2Cl_2$, 17.62 mmol, 1.5 equiv) at −55/−60° C. (liquid nitrogen/$CHCl_3$) under a nitrogen atmosphere. After 30 minutes stirring at −55° C., a solution of the secondary alcohol 5 (6.70 g, 11.75 mmol, 1 equiv) in $CH_2Cl_2$ (150 mL) was added dropwise to the reaction mixture over 1.5 h. Following stirring at −55/−60° C. for 45 minutes the reaction was treated dropwise with a solution of TEA (11.14 mL, 79.90 mmol, 6.8 equiv) in $CH_2Cl_2$ (50 mL) over a period of 40 minutes. The mixture was stirred for a further 45 minutes at −30° C. and was then allowed to warm to RT. The reaction was then treated with brine (150 mL), cooled to 0° C. and acidified to pH=2 with concentrated HCl. The organic phase was washed with $H_2O$ (150 mL), brine (150 mL), dried ($MgSO_4$), filtered and evaporated in vacuo to give the ketone 6 as a dark orange oil (6.18 g, 10.88 mmol, 93%), sufficiently pure by TLC ($SiO_2$, 40% EtOAc-petroleum ether) to be carried through to the next stage without further purification: $^1H$ NMR ($CDCl_3$, 270 MHz) rotamers: δ0.04 and 0.05 (2×s, 6H, $Si(CH_3)_2$), 0.87 (s, 9H, $SiC(CH_3)_3$), 2.47–2.78 (m, 2H, 1-H), 3.66–4.10 (m, 8H, 3-H, OMe, 11-H, 11a-H), 4.62–4.65 (m, 2H, Alloc), 4.80–5.40 (m, 4H, OBn, Alloc), 5.88–6.03 (m, 1H, Alloc), 6.76 (s, 1H, 6-H), 7.27–7.49 (m, 5H, Ph), 7.90 (s, 1H, 9-H), 8.62 (br s, 1H, NH); $^{13}C$ NMR ($CDCl_3$, 270 MHz): δ−5.8, −5.7, 18.0, 25.6, 25.7, 56.5, 65.8, 68.0, 70.7, 106.4, 111.0, 118.2, 127.7–128.6, 132.4, 136.1, 150.6, 153.4, 208.9; IR (neat): 3510, 3332, 2957, 2870, 2740, 1959, 1771, 1738, 1633, 1537, 1428, 1274, 1233, 1120, 1029, 844, 785, 700; EIMS m/z (relative intensity) 568 ($M^{+\cdot}$, 90.6), 512 (28.7), 511 (79.8), 453 (12.1), 340 (38.6), 298 (12.7), 282 (16.9), 172 (23.9), 91 (100.0), 41 (15.1); $[\alpha]^{23}_D$=−1.98° (c=1.010, $CHCl_3$).

Insertion of the $C_2$-Cyanomethyl Group (7)

Sodium hydride (0.70 g of a 60% dispersion in minuteseral oil, 17.60 mmol, 2.5 equiv) was stirred in petroleum ether for 10 minutes. The suspension was allowed to settle and the solvent transferred under nitrogen from the flask via a double-tipped needle. The remaining residue was suspended in freshly distilled anhydrous THF (50 mL), cooled to 0° C. and treated dropwise with a solution of the diethyl cyanomethylphosphonate (11.14 mL, 79.90 mmol, 6.8 equiv) in THF (60 mL) under a nitrogen atmosphere. The mixture was allowed to warm to RT and stir for 1.5 h. After cooling to 0° C. the reaction mixture was treated dropwise with a solution of the ketone 6 (11.14 mL, 79.90 mmol, 6.8 equiv) in THF (40 mL). After stirring overnight TLC ($SiO_2$, 30% EtOAc-petroleum ether) revealed almost complete consumption of starting material. THF was evaporated in vacuo and the resulting residue treated with a saturated solution of $NaHCO_3$ (100 mL) and EtOAc (100 mL). The aqueous layer was washed with EtOAc (100 mL) and the combined organic layers were then washed with $H_2O$ (100 mL), brine (100 mL), dried ($MgSO_4$), filtered and evaporated in vacuo to give a brown glass which was subjected to flash chromatography ($SiO_2$, 30% EtOAc-petroleum ether) to provide the pure cyano compound 7 (2.6 g, 4.40 mmol, 63%) as a yellow glass: $^1H$ NMR ($CDCl_3$, 270 MHz): δ0.03–0.09 (m, 6H, $Si(CH_3)_2$), 0.88 (m, 9H, $SiC(CH_3)_3$), 2.68–2.91 (m, 2H, 1-H), 3.12–3.13 (m, 2H, 12-H), 3.72–3.76 (m, 2H, 11-H), 3.82 (s, 3H, OMe), 4.62–4.65 (m, 2H, Alloc), 4.75 (m, 1H, 11a-H), 5.19 (s, 2H, OBn), 5.22–5.39 (m, 2H, Alloc), 5.88–6.02 (m, 1H, Alloc), 6.59 (s, 1H, 3-H), 6.68 (s, 1H, 6-H), 7.32–7.50 (m, 5H, Ph), 7.95 (s, 1H, 9-H), 8.72 (s, 1H, NH); $^{13}C$ NMR ($CDCl_3$, 270 MHz): δ−5.4, 17.5, 18.1, 25.6–25.7, 34.0, 56.6, 59.8, 62.3, 65.8, 70.7, 106.1, 111.8, 114.0, 116.2, 118.1, 127.7–129.3, 132.4, 132.8, 136.1, 144.2, 150.9, 153.4, 166.1; IR (neat): 3337, 3067, 3034, 2954, 2930, 2857, 2253, 1732, 1622, 1599, 1524, 1495, 1464, 1408, 1362, 1336, 1259, 1205, 1166, 1116, 1051, 1026, 992, 914, 839, 778, 735, 698, 647; EIMS m/z (relative intensity) 591 ($M^{+\cdot}$, 20.1), 534 (15.0), 340 (67.5), 282 (20.9), 252 (25.6), 195 (32.4), 91 (100.0); HRMS m/z Calcd for 591.2765 ($C_{32}H_{41}N_3O_6Si$). Found 591.2758; $[\alpha]^{23}_D$=−83.25° (c=1.015, $CHCl_3$).

Deprotected Alcohol (8)

Glacial ACOH (15 mL) was added to a stirred solution of the silyl ether 7 (2.10 g, 3.55 mmol) in THF (10 mL) and $H_2O$ (15 mL). The reaction mixture was allowed to stir at RT and monitored every hour by TLC ($SiO_2$, 30% EtOAc-petroleum ether). Over the course of 3 hours AcOH (10 mL) was added in two further portions. The mixture was stirred for a total of 4 hours at which time the reaction had gone to completion. The mixture was then cooled to 0° C. and treated dropwise with a 10% solution of $NaHCO_3$ in $H_2O$ (50 mL). The aqueous solution was extracted with EtOAc (3×20 mL) and the combined organic layers were washed with H₂O (20 mL), brine (20 mL), dried (MgSO₄), filtered and evaporated in vacuo to give a yellow oil. Flash chromatography (SiO₂, 5% MeOH—CHCl₃) afforded the free alcohol 8 (1.40 g, 2.93 mmol, 83%) as a yellow glass: ¹H NMR (CDCl₃, 270 MHz): δ2.41–3.02 (m, 2H, 1-H), 3.13 (s, 2H, 12-H), 3.70–4.10 (m, 6H, 11-H, OMe, OH), 4.61–4.64 (m, 2H, Alloc), 4.76 (m, 1H, 11a-H), 5.16 (s, 2H, OBn), 5.23–5.28 (m, 2H, Alloc), 5.87–6.02 (m, 1H, Alloc), 6.53 (s, 1H, 3-H), 6.78 (s, 1H, 6-H), 7.27–7.48 (m, 5H, Ph), 7.75 (s, 1H, 9-H), 8.45 (s, 1H, NH); ¹³C NMR (CDCl₃, 270 MHz): δ17.4, 34.8, 56.8, 61.5, 65.1, 65.9, 70.8, 106.9, 111.8, 114.4, 116.1, 118.2, 127.7–129.1, 132.1, 132.4, 136.0, 144.8, 151.1, 153.7, 167.3; IR (neat): 3340, 3067, 2934, 2856, 2252, 1732, 1601, 1523, 1455, 1407, 1374, 1336, 1226, 1167, 1111, 1048, 1028, 996, 938, 869, 838, 768, 745, 698, 668, 636, 608; EIMS m/z (relative intensity) 477 (M⁺·, 14.6), 340 (46.9), 282 (13.0), 91 (100.0); HRMS m/z Calcd for 477.1900 (C₂₆H₂₇N₃O₆). Found 477.1962; [α]²³_D=−67.42° (c=1.068, CHCl₃).

N10-Protected Cyclized PBD (9)

A solution of DMSO (0.75 mL, 10.55 mmol, 3.6 equiv) in freshly distilled CH₂Cl₂ (40 mL) was added dropwise at a rapid rate to a stirred solution of oxalyl chloride (2.64 mL of a 2M solution in CH₂Cl₂, 5.27 mmol, 1.8 equiv) at −40/−50° C. (liquid nitrogen/chlorobenzene) under a nitrogen atmosphere. After 5 minutes stirring at −45° C., a solution of the primary alcohol 8 (1.40 g, 2.93 mmol, 1 equiv) in CH₂Cl₂ (30 mL) was added dropwise to the reaction mixture over 45 minutes. Following stirring at −45° C. for 45 minutes the reaction was treated dropwise with a solution of TEA (1.72 mL, 12.31 mmol, 4.2 equiv) in CH₂Cl₂ (20 mL) over a period of 30 minutes. The mixture was stirred for a further 40 minutes at −45° C. and was then allowed to warm to RT and diluted with 20 mL CH₂Cl₂. The reaction was then cooled to 0° C. and washed with 1N HCl (200 mL), H₂O (100 mL), brine (100 mL), dried (MgSO₄), filtered and evaporated in vacuo to give a yellow foam which was subjected to flash chromatography (SiO₂, 5% MeOH—CHCl₃) to provide the pure ring closed compound 9 (0.95 g, 2.00 mmol, 68%) as a slightly yellow glass: ¹H NMR (CDCl₃, 270 MHz): δ2.69–3.14 (m, 2H, 1-H), 3.24 (s, 2H, 12-H), 3.84–3.98 (m, 6H, 11-H, OMe, OH), 4.46 (m, 2H, Alloc), 5.07–5.18 (m, 4H, OBn, Alloc), 5.60–5.80 (m, 2H, Alloc, 11a-H), 6.74 (s, 1H, 3-H), 7.04 (s, 1H, 6-H), 7.24–7.43 (m, 6H, Ph, 9-H); ¹³C NMR (CDCl₃, 270 MHz): δ17.5, 36.5, 56.2, 59.6, 66.9, 71.1, 85.7, 111.0, 113.2, 114.7, 116.1, 118.3, 124.6, 127.3–128.7, 131.7, 136.0, 149.2, 150.6, 163.6; IR (neat): 3396, 3089, 2938, 2615, 2251, 1707, 1602, 1513, 1432, 1308, 1219, 1113, 1045, 918, 869, 790, 735, 698, 648; EIMS m/z (relative intensity) 475 (M⁺·, 34.2), 340 (25.4), 339 (35.0), 279 (10.3), 134 (10.6), 91 (100.0); HRMS m/z Calcd for 475.1743 (C₂₆H₂₅N₃O₆). Found 475.1883; [α]²³_D=+101.46° (c=1.030, CHCl₃).

C₂-Cyanomethyl PBD (10, SB-A67)

Triphenylphosphine (25 mg, 0.095 mmol, 0.05 equiv), pyrrolidine (167 μl, 2.0 mmol, 1.05 equiv) and Pd(PPh₃)₄ (56 mg, 0.048 mmol, 0.025 equiv) were added sequentially to a stirred solution of the Alloc-compound 9 (900 mg, 1.90 mmol, 1 equiv) in freshly distilled dry CH₂Cl₂ (100 mL). The reaction mixture was allowed to stir at RT under a nitrogen atmosphere for 2 hours by which time TLC (SiO₂, 1% MeOH—CHCl₃) revealed reaction completion. The mixture was evaporated in vacuo and the residue applied to a gravity chromatography column (SiO₂, 1% MeOH—CHCl₃) to isolate the PBD SB-A67 (720 mg, 1.93 mmol, 100%) as a yellow glass: ¹H NMR (CDCl₃, 270 MHz): 3.05–3.40 (m, 4H, 1-H, 12-H), 3.95 (s, 3H, OMe), 4.38 (m, 1H, 11a-H), 5.21 (s, 2H, OBn), 6.84 (s, 1H, 6-H), 7.06 (s, 1H, 3-H), 7.27–7.70 (m, 6H, Ph, 9-H), 7.80 (d, 1H, 11a-H, J=3 Hz); ¹³C NMR (CDCl₃, 270 MHz): δ17.4, 36.8, 53.9, 56.3, 70.9, 111.7, 111.9, 112.8, 116.0, 118.7, 120.7, 127.1–128.7, 132.0, 136.0, 140.2, 148.3, 151.2, 161.8; IR (neat): 3353, 2931, 2251, 2222, 1604, 1508, 1437, 1247, 1120, 1000, 913, 874, 724, 697, 542; EIMS m/z (relative intensity) 373 (M⁺·, 9.8), 371 (24.4), 280 (12.5), 91 (100.0); HRMS m/z Calcd for 373.1426 (C₂₂H₁₉N₃O₃). Found 373.1364; [α]²³_D=254.5° (c=1.045, CHCl₃).

Figure 2:
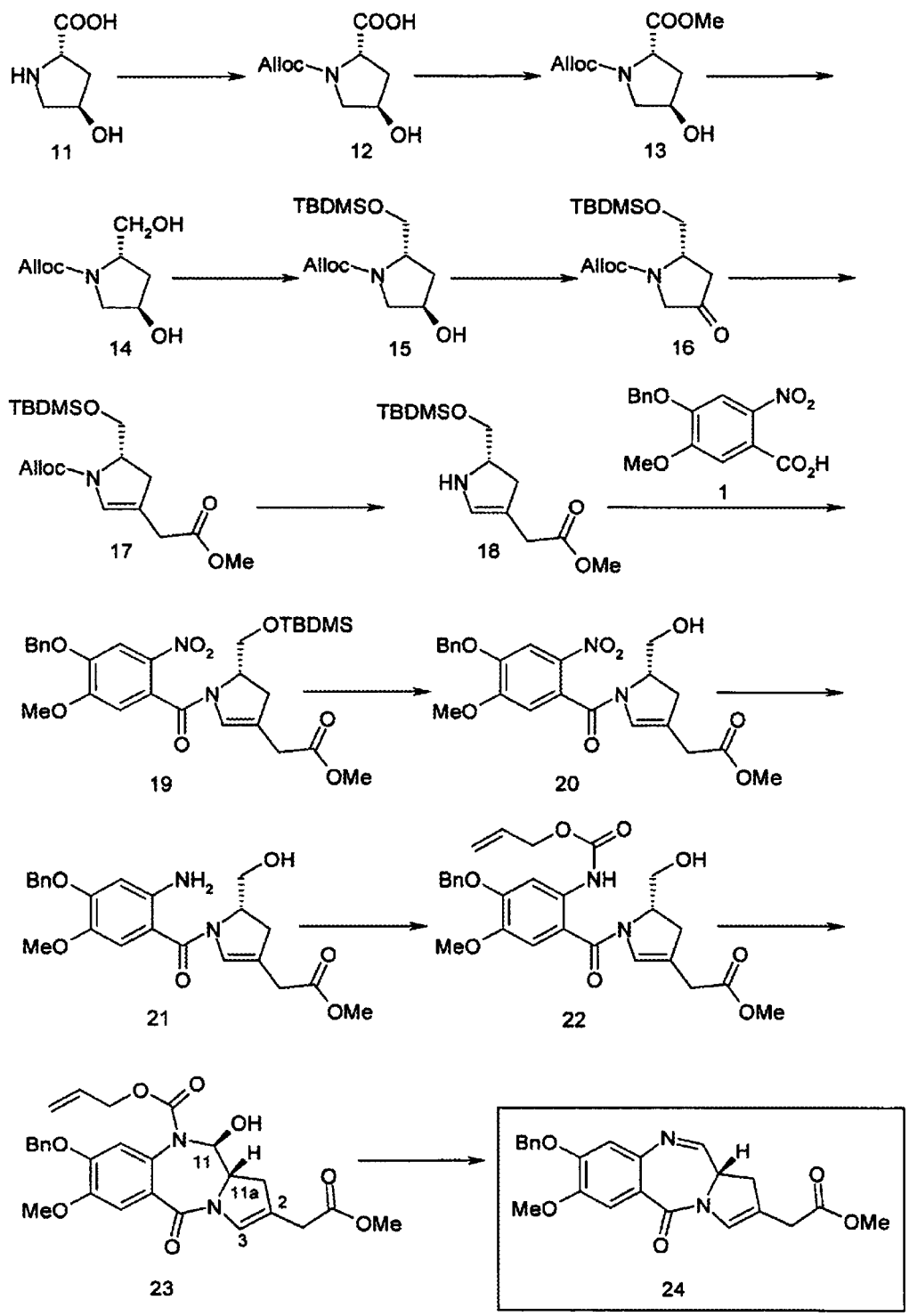

Example 1(b)
Synthesis of the 2-Methoxycarbonylmethyl PBD (24, SJG-245) (See FIG. 2)

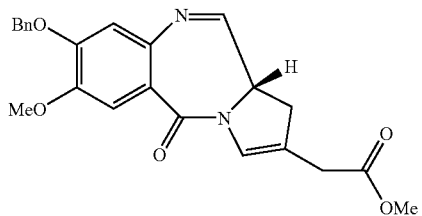

(2S,4R)-N-(Allyloxycarbonyl)-4-hydroxypyrrolidine-2-carboxylic Acid (12)

A solution of allyl chloroformate (29.2 mL, 33.2 g, 275 mmol) in THF (30 mL) was added dropwise to a suspension of trans-4-hydroxy-L-proline (11) (30 g, 229 mmol) in a mixture of THF (150 mL) and H₂O (150 mL) at 0° C. (ice/acetone), whilst maintaining the pH at 9 with 4 N NaOH. After stirring at 0° C. for 1 hour at pH 9, the aqueous layer was saturated with NaCl, and the mixture diluted with EtOAc (100 mL). The aqueous layer was separated, washed with EtOAc (100 mL) and the pH adjusted to 2 with conc. HCl. The resulting milky emulsion was extracted with EtOAc (2×100 mL), washed with brine (200 mL), dried (MgSO₄), filtered and evaporated in vacuo to give the allyl carbamate 12 as a clear viscous oil (42.6 g, 87%): [α]²⁰_D=−62.1° (c=0.69, MeOH); ¹H NMR (270 MHz, CDCl₃+DMSO-d₆) (Rotamers) δ5.98–5.81 (m, 1H, NCO₂CH₂CH═CH₂), 5.40–5.14 (m, 2H, NCO₂CH₂CH═CH₂), 4.64–4.42 (m, 4H, NCO₂CH₂CH═CH₂, NCH₂CHOHCH₂ and CHCO₂H), 3.82–3.51 (m, 2H, NCH₂CHOHCH₂), 2.34–2.08 (m, 2H, NCH₂CHOHCH₂); ¹³C NMR (67.8 MHz, CDCl₃+DMSO) (Rotamers) δ175.0 and 174.5 (CO₂H), 155.1 and 154.6 (NC═O), 132.9 and 132.8 (NCO₂CH₂CH═CH₂), 117.6 and 116.7 (NCO₂CH₂CH═CH₂), 69.5 and 68.8 (NCH₂CHOH), 65.9 and 65.8 (NCO₂CH₂CH═CH₂), 58.0 and 57.7 (CHCO₂H), 55.0 and 54.5 (NCH₂CHOH), 39.3 and 38.3 (NCH₂CHOHCH₂); MS (EI), m/z (relative intensity) 215 (M⁺·, 10) 197 (12), 170 (M—CO₂H, 100), 152 (24), 130 (M—CO₂C₃H₅, 97), 126 (34), 112 (50), 108 (58), 86 (11), 68 (86), 56 (19); IR (Neat) 3500–2100 (br, OH), 2950, 1745 and 1687 (br, C═O), 1435, 1415, 1346, 1262, 1207, 1174, 1133, 1082, 993, 771 cm⁻¹; exact mass calcd for C₉H₁₃NO₅ m/e 215.0794, obsd m/e 215.0791.

Methyl (2S,4R)-N-(Allyloxycarbonyl)-4-hydroxypyrrolidine-2-carboxylate (13)

A catalytic amount of concentrated H₂SO₄ (4.5 mL) was added to a solution of Alloc-hydroxyproline (12) (43 g, 200 mmol) in MeOH (300 mL) at 10° C. (ice) and the reaction mixture was then heated at reflux for 2 h. After cooling to room temperature the reaction mixture was treated with TEA (43 mL) and the MeOH evaporated in vacuo. The residue was dissolved in EtOAc (300 mL), washed with brine (200 mL), dried (MgSO$_4$), filtered and concentrated in vacuo to give a viscous oil. Purification by flash chromatography (40% EtOAc/Petroleum Ether) removed the high R$_f$ impurity to provide the pure ester 13 as a transparent yellow oil (19.6 g, 43%): [α]$^{23}$$_D$=79.0° (c=0.35, CHCl$_3$); $^1$H NMR (270 MHz, CDCl$_3$) (Rotamers) δ5.98–5.78 (m, 1H, NCO$_2$CH$_2$CH=CH$_2$), 5.35–5.16 (m, 2H, NCO$_2$CH$_2$CH=CH$_2$), 4.65–4.45 (m, 4H, NCO$_2$CH$_2$CH=CH$_2$, NCH$_2$CHOHCH$_2$ and NCHCO$_2$CH$_3$), 3.75 and 3.72 (s×2, 3H, OCH$_3$), 3.70–3.54 (m, 2H, NCH$_2$CHOHCH$_2$), 3.13 and 3.01 (br s×2, 1H, OH), 2.39–2.03 (m, 2H, NCH$_2$CHOHCH$_2$); $^{13}$C NMR (67.8 MHz, CDCl$_3$) (Rotamers) δ173.4 and 173.2 (CO$_2$CH$_3$), 155.0 and 154.6 (NC=O), 132.6 and 132.4 (NCO$_2$CH$_2$CH=CH$_2$), 117.6 and 117.3 (NCO$_2$CH$_2$CH=CH$_2$), 70.0 and 69.2 (NCH$_2$CHOH), 66.2 (NCO$_2$CH,CH=CH$_2$), 57.9 and 57.7 (NCHCO$_2$CH$_3$), 55.2 and 54.6 (NCH$_2$CHOH), 52.4 (OCH$_3$), 39.1 and 38.4 (NCH$_2$CHOHCH$_2$); MS (EI), m/z (relative intensity) 229 (M$^{+\cdot}$, 7), 170 (M—CO$_2$Me, 100), 144 (M—CO$_2$C$_3$H$_5$, 12), 126 (26), 108 (20), 68 (7), 56 (8); IR (Neat) 3438 (br, OH), 2954, 1750 and 1694 (br, C=O), 1435, 1413, 1345, 1278, 1206, 1130, 1086, 994, 771 cm$^{-1}$; exact mass calcd for C$_{10}$H$_{15}$NO$_5$ m/e 229.0950, obsd m/e 229.0940.

(2S,4R)-N-(Allyloxycarbonyl)-4-hydroxy-2-(hydroxymethyl)pyrrolidine (14)

A solution of the ester 13 (19.5 g, 85 mmol) in THF (326 mL) was cooled to 0° C. (ice/acetone) and treated with LiBH$_4$ (2.78 g, 128 mmol) in portions. The reaction mixture was allowed to warm to room temperature and stirred under a nitrogen atmosphere for 2.5 hours at which time TLC (50% EtOAc/Petroleum Ether) revealed complete consumption of ester 13. The mixture was cooled to 0° C. and water (108 mL) was carefully added followed by 2 N HCl (54 mL). After evaporation of the THF in vacuo, the mixture was neutralised to pH 7 with 10 N NaOH and saturated with solid NaCl. The saturated aqueous solution was then extracted with EtOAc (5×100 mL), the combined organic layers washed with brine (200 mL), dried (MgSO$_4$), filtered and evaporated in vacuo to furnish the pure diol 14 as a clear colourless oil (16.97 g, 99%): [α]$^{24}$$_D$=-57.0° (c=0.61, CHCl$_3$); $^1$H NMR (270 MHz, CDCl$_3$) δ6.01–5.87 (m, 1H, NCO$_2$CH$_2$CH=CH$_2$), 5.36–5.20 (m, 2H, NCO$_2$CH$_2$CH=CH$_2$), 4.84 (br s, 1H, NCHCH$_2$OH), 4.60 (d, 2H, J=5.31 Hz, NCO$_2$CH$_2$CH=CH$_2$), 4.39 (br s, 1H, NCHCH$_2$OH), 4.18–4.08 (m, 1H, 3.35, NCH$_2$CHOH), 3.90–3.35 (m, 4H, NCH$_2$CHOH, NCHCH$_2$OH, and OH), 3.04 (br s, 1H, OH), 2.11–2.03 (m, 1H, NCH$_2$CHOHCH$_2$), 1.78–1.69 (m, 1H, NCH$_2$CHOHCH$_2$); $^{13}$C NMR (67.8 MHz, CDCl$_3$) δ157.1 (NC=O), 132.6 (NCO$_2$CH$_2$CH=CH$_2$), 117.7 (NCO$_2$CH$_2$CH=CH$_2$), 69.2 (NCH$_2$CHOH), 66.4 and 66.2 (NCO$_2$CH$_2$CH=CH$_2$ and NCHCH$_2$OH), 59.2 (NCHCH$_2$OH), 55.5 (NCH$_2$CHOH), 37.3 (NCH$_2$CHOHCH$_2$); MS (EI), m/z (relative intensity) 201 (M$^{+\cdot}$, 2), 170 (M—CH$_2$OH, 100), 144 (M—OC$_3$H$_5$, 6), 126 (26), 108 (20), 68 (9); IR (Neat) 3394 (br, OH), 2946, 2870, 1679 (C=O), 1413, 1339, 1194, 1126, 1054, 980, 772 cm$^{-1}$; exact mass calcd for C$_9$H$_{11}$NO$_4$ m/e 201.1001, obsd m/e 201.1028.

(2S,4R)-N-(Allyloxycarbonyl)-2-(tert-butyldimethylsilyloxymethyl)-4-hydroxypyrrolidine (15)

A solution of the diol 14 (16.97 g, 84 mmol) in CH$_2$Cl$_2$ (235 mL) was treated with TEA (11.7 mL, 8.5 g, 84 mmol) and stirred for 15 minutes at room temperature. TBDMSCl (9.72 g, 64 mmol) and DBU (16.8 mmol, 2.51 mL, 2.56 g) were added and the reaction mixture stirred for a further 16 hours under a nitrogen atmosphere. The reaction mixture was diluted with EtOAc (500 mL), washed with saturated NH$_4$Cl (160 mL), brine (160 mL), dried (MgSO$_4$), filtered and evaporated in vacuo to give an oil which was a mixture of the required product (major component), unreacted diol and the presumed disilyated compound by TLC (50% EtOAc/Petroleum Ether). Flash chromatography (20–100% EtOAc/Petroleum Ether) isolated the 3 components, to provide the monosilylated compound 15 as a slightly yellow transparent oil (13.85 g, 52%): [α]$^{21}$$_D$=-58.6° (c=1.14, CHCl$_3$); $^1$H NMR (270 MHz, CDCl$_3$) (Rotamers) δ6.01–5.86 (m, 1H, NCO$_2$CH$_2$CH=CH$_2$), 5.34–5.18 (m, 2H, NCO$_2$CH$_2$CH=CH$_2$), 4.59–4.49 (m, 3H, NCO$_2$CH$_2$CH=CH$_2$ and NCHCH$_2$OTBDMS), 4.06–3.50 (m, 5H, NCH$_2$CHOH, NCH$_2$CHOH and NCHCH$_2$OTBDMS), 2.20–2.01 (m, 2H, NCH$_2$CHOHCH$_2$), 0.87 (s, 9H, SiC(CH$_3$)$_3$), 0.0 (s, 6H, Si(CH$_3$)$_2$); $^{13}$C NMR (67.8 MHz, CDCl$_3$) (Rotamers) δ155.0 (NC=O), 133.1 (NCO$_2$CH$_2$CH=CH$_2$), 117.6 and 117.1 (NCO$_2$CH$_2$CH=C—H$_2$), 70.3 and 69.7 (NCH$_2$CHOH), 65.9 and 65.6 (NCO$_2$CH$_2$CH=CH$_2$), 63.9 and 62.8 (NCHCH$_2$OTBDMS), 57.8 and 57.4 (NCHCH$_2$OTBDMS), δ55.7 and 55.2 (NCH$_2$CHOH), 37.3 and 36.6 (NCH$_2$CHOHCH$_2$), 25.9 (SiC(CH$_3$)$_3$), 18.2 (SiC(CH$_3$)$_3$), -5.5 (Si(CH$_3$)$_2$); MS (EI), m/z (relative intensity) 316 (M$^{+\cdot}$+1, 29), 315 (M$^{+\cdot}$, 4), 300 (M—CH$_3$, 26), 284 (4), 261 (8), 260 (50), 259 (100), 258 (M—OC$_3$H, or M—$^t$Bu, 100), 218 (13), 215 (10), 214 (52), 200 (12), 170 (M—CH$_2$OTBDMS, 100), 156 (40), 126 (58), 115 (33), 108 (41), 75 (35); IR (Neat) 3422 (br, OH), 2954, 2858, 1682 (C=O), 1467, 1434, 1412 (SiCH$_3$), 1358, 1330, 1255 (SiCH$_3$), 1196, 1180, 1120, 1054, 995, 919, 837, 776, 669 cm$^{-1}$; exact mass calcd for C$_{15}$H$_{29}$NO$_4$Si m/e 315.1866, obsd m/e 315.1946.

(2S)-N-(Allyloxycarbonyl)-2-(tert-butyldimethylsilyloxymethyl)-4-oxopyrrolidine (16)

Method A: A solution of DMSO (12.9 mL, 14.3 g, 183 mmol) in CH$_2$Cl$_2$ (90 mL) was added dropwise to a solution of oxalyl chloride (45.1 mL of a 2.0 M solution in CH$_2$Cl, 90.2 mmol) at -60° C. (dry ice/acetone) under a nitrogen atmosphere. After stirring at -70° C. for 30 minutes, a solution of the alcohol 15 (25.8 g, 81.9 mmol) dissolved in CH$_2$Cl$_2$ (215 mL) was added dropwise at -60° C. After 1.5 hours at -70° C., the mixture was treated dropwise with TEA (57.2 mL, 41.5 g, 410 mmol) and allowed to warm to 10° C. The reaction mixture was treated with brine (150 mL) and acidified to pH 3 with conc. HCl. The layers were separated and the organic phase washed with brine (200 mL), dried (MgSO$_4$), filtered and concentrated in vacuo to give an orange oil. Purification by flash chromatography (40% EtOAc/Petroleum Ether) furnished the ketone 16 as a pale yellow oil (24.24 g, 95%):

Method B: A solution of the alcohol 15 (4.5 g, 14.3 mmol) in CH$_2$Cl$_2$ (67.5 mL) was treated with CH$_3$CN (7.5 mL), 4 Å powdered molecular sieves (3.54 g) and NMO (2.4 g, 20.5 mmol). After 15 minutes stirring at room temperature, TPAP (0.24 g, 0.7 mmol) was added to the reaction mixture and a colour change (green→black) was observed. The reaction mixture was allowed to stir for a further 2.5 hours at which time complete consumption of starting material was observed by TLC (50% EtOAc/Petroleum ether 40°–60°). The black mixture was concentrated in vacuo and the pure ketone 16 was obtained by flash chromatography (50% EtOAc/Petroleum Ether) as a golden oil (4.1 g, 92%): [α]$^{22}$$_D$+1.25° (c=10.0, CHCl$_3$); $^1$H NMR (270 MHz, CDCl$_3$) (Rotamers) δ6.0–5.90 (m, 1H, NCO$_2$CH$_2$CH=CH$_2$), 5.35–5.22 (m, 2H, NCO$_2$CH$_2$CH=CH$_2$), 4.65–4.63 (m, 2H, $NCO_2CH_2CH=CH_2$), 4.48–4.40 (m, 1H, $NCHCH_2OTBDMS$), 4.14–3.56 (m, 4H, $NCH_2C=O$ and $NCHCH_2OTBDMS$), 2.74–2.64 (m, 1H, $NCH_2C=OCH_2$), 2.46 (d, 1H, J=18.69 Hz, $NCH_2C=OCH_2$), 0.85 (s, 9H, $SiC(CH_3)_3$), 0.0 (s, 6H, $Si(CH_3)_2$); $^{13}C$ NMR (67.8 MHz, $CDCl_3$) (Rotamers) δ210.1 (C=O), 154.1 (NC=O), 132.7 ($NCO_2CH_2CH=CH_2$), 118.0 and 117.7 ($NCO_2CH_2CH=CH_2$), 66.0 and 65.8 ($NCO_2CH_2CH=CH_2$), 65.0 ($NCHCH_2OTBDMS$), 55.7 ($NCHCH_2OTBDMS$), 53.6 ($NCH_2C=O$), 40.8 and 40.1 ($NCH_2C=OCH_2$), 25.7 ($SiC(CH_3)_3$), 18.1 ($SiC(CH_3)_3$), –5.7 and –5.8 ($Si(CH_3)_2$); MS (CI), m/z (relative intensity) 314 ($M^+$1, 100), 256 ($M-OC_3H_5$ or $M-^tBu$, 65); IR (Neat) 2930, 2858, 1767 (C=O), 1709 (NC=O), 1409 ($SiCH_3$), 1362, 1316, 1259 ($SiCH_3$), 1198, 1169, 1103, 1016, 938, 873, 837, 778, 683 cm$^{-1}$; exact mass calcd for $C_{15}H_{27}NO_4Si$ m/e 313.1710, obsd m/e 313.1714.

(2S)-N-(Allyloxycarbonyl)-2-(tert-butyldimethylsilyloxymethyl)-4-(methoxycarbonylmethyl)-2,3-dihydropyrrole (17)

Petroleum ether 40°–60° (100 mL) was added to a sample of NaH (0.80 g of a 60% dispersion in oil, 20.12 mmol) and stirred at room temperature under a nitrogen atmosphere. After 0.5 hours the mixture was allowed to settle and the Petroleum Ether was transferred from the flask via a double-tipped needle under nitrogen. THF (100 mL) was added to the remaining residue and the mixture was cooled to 0° C. (ice/acetone). The cool solution was treated dropwise with a solution of methyldiethylphosphonoacetate (3.69 mL, 4.23 g, 20.12 mmol) in THF (100 mL) under nitrogen. After 1 hour at room temperature, the mixture was cooled to 0° C. and treated dropwise with a solution of the ketone 16 (3.0 g, 9.58 mmol) in THF (30 mL) under nitrogen. After 16 hours at room temperature, TLC (50% EtOAc/Petroleum Ether) revealed the complete consumption of ketone and further TLC (5% EtOAc/Petroleum Ether) revealed the formation of mainly the exo-product. The reaction mixture was cooled to 0° C. (ice/acetone) and transferred via a double-tipped needle under nitrogen to another flask containing NaH (0.40 g of a 60% dispersion in oil, 10.1 mmol) at 0° C., freshly washed as above. The reaction mixture was maintained at 0° C., and after 40 minutes TLC revealed the almost complete conversion to endo-product. The THF was evaporated in vacuo and the mixture partitioned between saturated $NaHCO_3$ (100 mL) and EtOAc (100 mL). The layers were separated and the aqueous layer extracted with EtOAc (2×50 mL). The combined organic layers were washed with brine (100 mL), dried ($MgSO_4$), filtered and concentrated in vacuo to give an orange oil. Purification by flash chromatography (5% EtOAc/Petroleum Ether) furnished the endo-ester 17 (2.22 g, 63%): $[\alpha]^{21}_D$=–97.7° (c=2.78, $CHCl_3$); $^1H$ NMR (270 MHz, $CDCl_3$) (Rotamers) δ6.47 and 6.42 (br s×2, 1H, $NCH=CCH_2CO_2CH_3$), 5.98–5.86 (m, 1H, $NCO_2CH_2CH=CH_2$), 5.31 (d, 1H, J=16.85 Hz, $NCO_2CH_2CH=CH_2$), 5.22 (d, 1H, J=10.62 Hz, $NCO_2CH_2CH=CH_2$), 4.65–4.49 (m, 2H, $NCO_2CH_2CH=CH_2$), 4.37–4.18 (m, 1H, $NCHCH_2OTBDMS$), 3.76–3.69 (m, 5H, $NCHCH_2OTBDMS$ and $CO_2H_3$), 3.09 (br s, 2H, $NCH=CCH_2CO_2CH_3$), 2.86–2.80 (m, 1H, $NCH=CCH_2C_2OCH_3CH_2$), 2.59 (d, 1H, J=17.40 Hz, $NCH=CCH_2CO2CH_3CH_2$), 0.87 (s, 9H, $SiC(CH_3)_3$), 0.04 and 0.03 (s×2, 6H, $Si(CH_3)_2$); $^{13}C$ NMR (67.8 MHz, $CDCl_3$) (Rotamers) δ171.2 ($CO_2CH_3$), 151.9 (NC=O), 132.8 ($NCO_2CH_2CH=CH_2$), 127.1 and 126.4 ($NCH=CCH_2CO_2CH_3$), 118.0 and 117.7 ($NCO_2CH_2CH=CH_2$), 114.6 ($NCH=CCH_2CO_2H_3$), 65.9 ($NCO_2CH_2CH=CH_2$), 63.4 and 62.6 ($NCHCH_2OTBDMS$), 59.0 and 58.7 ($NCHCH_2OTBDMS$), 51.9 ($CO_2CH_3$), 36.0 and 34.8 ($NCH=CCH_2CO_2CH_3CH_2$), 34.2 and 33.9 ($NCH=CCH_2COCH_3$), 25.8 ($SiC(CH_3)_3$), 18.2 ($SiC(CH_3)_3$), –5.4 and –5.5 ($Si(CH_3)_2$); MS (EI), m/z (relative intensity) 369 ($M^{+\cdot}$, 58), 354 (28), 326 (31), 312 ($M-OC_3H$, or $M-^tBu$, 100), 268 (80), 236 (21), 227 (86), 210 (22), 192 (22), 168 (93), 152 (55), 138 (22), 120 (79), 89 (70), 73 (75); IR (NEAT) 3086, 2954, 2930, 2885, 2857, 1744, 1709, 1670, 1463, 1435, 1413, 1362, 1337, 1301, 1253, 1195, 1107, 1064, 1014, 983, 937, 887, 838, 778, 758, 680, 662 555 cm$^{-1}$; exact mass calcd for $C_{18}H_{31}NO_5Si$ m/e 369.1972, obsd m/e 369.1868.

(2S)-2-(tert-butyldimethylsilyloxymethyl)-4-(methoxycarbonylmethyl)-2,3-dihydropyrrole (18)

A catalytic amount of $PdCl_2(PPh_3)_2$ (84 mg, 0.12 mmol) was added to a stirred solution of the allyl carbamate 17 (1.10 g, 2.98 mmol) and $H_2O$ (0.32 mL, 17.8 mmol) in $CH_2Cl_2$ (36 mL) After 5 minutes stirring at room temperature, $Bu_3SnH$ (0.89 mL, 0.96 g, 3.30 mmol) was added rapidly in one portion. A slightly exothermic reaction with vigorous gas evolution immediately ensued. The mixture was stirred for 16 hours at room temperature under nitrogen at which time TLC (50% EtOAc/Petroleum Ether) revealed the formation of amine along with the complete consumption of starting material. After diluting with $CH_2Cl_2$ (30 mL), the organic solution was dried ($MgSO_4$), filtered and evaporated in vacuo to give an orange oil which was purified by flash chromatography (50% EtOAc/Petroleum Ether) to afford the enamine 18 as a slightly orange oil (0.57 g, 67%): $^1H$ NMR (270 MHz, $CDCl_3$) δ7.53 and 7.48 (br s×2, 1H, $NCH=CCH_2CO_2CH_3$), 4.35–4.13 (m, 1H, $NCHCH_2OTBDMS$), 3.82–3.17 (m, 7H, $NCH=CCH_2CO_2CH_3$, $NCHCH_2OTBDMS$ and $CO_2CH_3$), 2.64–2.04 (m, 2H, $NCH=CCH_2CO_2CH_3CH_2$), 0.90–0.88 (m, 9SiC($CH_3)_3$), 0.09–0.00 (m, 6H, $Si(CH_3)_2$); MS (EI), m/z (relative intensity) 285 ($M^{+\cdot}$, 1), 270 ($M-CH_3$, 7), 254 (6), 242 (4), 230 (6), 228 ($M-^tBu$, 100), 212 (4), 196 (3), 168 (13), 115 (3), 89 (10), 80 (4), 73 (13); MS (CI), m/z (relative intensity) 342 ($M^{+\cdot}$57, 7), 302 ($M^{+\cdot}$ +17, 7), 286 ($M^{+\cdot}$ +1, 100), 228 ($M-^tBu$, 100).

(2S)-N-(4-Benzyloxy-5-methoxy-2-nitrobenzoyl)-2-(tert-butyldimethylsilyloxymethyl)-4-(methoxycarbonylmethyl)-2,3-dihydropyrrole (19)

A catalytic amount of DMF (2 drops) was added to a stirred solution of the acid 1 (0.506 g, 1.67 mmol) and oxalyl chloride (0.17 mL, 0.25 g, 1.98 mmol) in $CH_2Cl_2$ (33 mL). After 16 hours at room temperature the acid chloride solution was added dropwise to a stirred mixture of the enamine 18 (0.524 g, 1.84 mmol) and TEA (0.47 g, 0.65 mL, 4.60 mmol) in $CH_2Cl_2$ (12 mL) at 0° C. (ice/acetone) under a nitrogen atmosphere. The reaction mixture was allowed to warm to room temperature and stirred for a further 2.5 h. The mixture was diluted with $CH_2Cl_2$ (50 mL), washed with saturated $NaHCO_3$ (50 mL), saturated $NH_4Cl$ (50 mL), $H_2O$ (50 mL), brine (50 mL), dried ($MgSO_4$), filtered and evaporated in vacuo to give the crude product as a dark orange oil. Purification by flash chromatography (25% EtOAc/Petroleum Ether) isolated the pure enamide 19 as an orange oil (0.55 g, 58%): $^1H$ NMR (270 MHz, $CDCl_3$) δ7.77 (s, 1H$_{arom}$), 7.45–7.28 (m, 5H$_{arom}$), 6.81 (s, 1H$_{arom}$), 5.80 (S, 1H, $NCH=CCH_2CO_2CH_3$), 5.22 (s, 2H, $PhCH_2O$), 4.76–4.64 (m, 1H, $NCHCH_2OTBDMS$), 3.97 (s, 3H, $OCH_3$), 3.72–3.66 (m, 5H, $NCHCH_2OTBDMS$ and $CO_2CH_3$), 3.02 (s, 2H, $NCH=CCH_2CO_2CH_3$), 3.01–2.63 (m, 2H, $NCH=CCH_2CO_2CH_3CH_2$), 0.90 (s, 9H, $SiC(CH_3)_3$), 0.11 (s, 6H, $Si(CH_3)_2$); $^{13}C$ NMR (67.8 MHz, CDCl$_3$) δ170.7 (CO$_2$CH$_3$), 154.6 (NC=O), 148.3 (C$_{arom}$), 137.6 (C$_{arom}$), 135.2 (C$_{arom}$), 128.8, 128.5 and 127.6 (BnC—H$_{arom}$), 126.7 (C$_{arom}$), 126.1 (NCH=CCH$_2$CO$_2$CH$_3$), 118.8 (NCH=CCH$_2$CO$_2$CH$_3$), 109.9 (C—H$_{arom}$), 109.0 (C—H$_{arom}$) 71.3 (PhCH$_2$O), 60.7 (NCHCH$_2$OTBDMS), 59.0 (NCHCH$_2$OTBDMS), 56.7 (OCH3), 52.0 (CO$_2$CH$_3$), 35.1 (NCH=CCH$_2$CO$_2$CH$_3$), 33.8 (NCH=CCH$_2$CO$_2$CH$_3$CH$_2$), 25.8 (SiC(CH$_3$)$_3$), 18.2 (SiC(CH$_3$)$_3$), −5.3 and −5.4 (Si(CH$_3$)$_2$).

(2S)-N-(4-Benzyloxy-5-methoxy-2-nitrobenzoyl)-2-(hydroxymethyl)-4-(methoxycarbonylmethyl)-2,3-dihydropyrrole (20)

A solution of the silyl protected compound 274 (0.45 g, 0.79 mmol) in THF (8 mL) was treated with H$_2$O (8 mL) and glacial acetic acid (24 mL). After 5 hours stirring at room temperature TLC (50% EtOAc/Petroleum Ether) showed the complete consumption of starting material. The mixture was carefully added dropwise to a stirred solution of NaHCO$_3$ (64 g) in H$_2$O (640 mL) and extracted with EtOAc (3×100 mL). The combined organic layers were washed with H$_2$O (100 mL), brine (100 mL), dried (MgSO$_4$), filtered and concentrated in vacuo to give the crude product as an orange glass. Purification by flash chromatography (80% EtOAc/Petroleum Ether) furnished the pure alcohol 20 as a light orange glass (0.35 g, 98%): $^1$H NMR (270 MHz, CDCl$_3$) δ7.78 (s, 1H$_{arom}$), 7.48–7.33 (m, 5H$_{arom}$), 6.86 (s, 1H$_{arom}$), 5.82 (s, 1H, NCH=CCH$_2$CO$_2$CH$_3$), 5.22 (s, 2H, PhCH$_2$O), 4.81–4.71 (m, 1H, NCHCH$_2$OH), 3.98–3.92 (m, 5H, NCHCH$_2$OH and OCH$_3$), 3.72 (s, 3H, CO$_2$CH$_3$), 3.10–2.22 (m, 3H, NCH=CCH$_2$CO$_2$CH$_3$ and NCH=CCH$_2$CO$_2$CH$_3$CH$_2$), 2.50–2.35 (m, 1H, NCH=CCH$_2$CO$_2$CH$_3$CH$_2$); $^{13}$C NMR (67.8 MHz, CDCl$_3$) δ170.6 (CO$_2$CH$_3$), 154.8 (NC=O), 148.5 (C$_{arom}$), 137.5 (C$_{arom}$), 135.1 (C$_{arom}$), 128.9, 128.6 and 127.6 (BnC—H$_{arom}$), 126.2 (NCH=CCH$_2$CO$_2$CH$_3$), 119.4 (NCH=CCH$_2$CO$_2$CH$_3$), 109.8 (C—H$_{arom}$), 109.0 (C—H$_{arom}$), 71.4 (PhCH$_2$O), 61.5 (NCHCH$_2$OH), 61.4 (NCHCH$_2$OH), 56.8 (OCH$_3$), 52.1 (CO$_2$CH$_3$), 35.6 (NCH=CCH$_2$CO$_2$CH$_3$), 33.5 (NCH=CCH$_2$CO$_2$CH$_3$CH$_2$); MS (EI), m/z (relative intensity) 456 (M$^{+\cdot}$, 7), 286 (M—NCHC=CH$_2$CO$_2$CH$_3$CH$_2$CHCH$_2$OH, 25), 270 (NCHC=CH$_2$CO$_2$CH$_3$CH$_2$CHCH$_2$OH, 6), 91 (PhCH$_2$, 100), 80 (6); exact mass calcd for C$_{23}$H$_{21}$N$_2$O$_8$ m/e 456.1533, obsd m/e 456.1557.

(2S)-N-(2-Amino-4-benzyloxy-5-methoxybenzoyl)-2-(hydroxymethyl)-4-(methoxycarbonylmethyl)-2,3-dihydropyrrole (21)

A solution of the nitro-alcohol 20 (0.35 g, 0.77 mmol) and SnCl$_2$/2H$_2$O (0.87 g, 3.86 mmol) in methanol (16 mL) was heated to reflux and monitored by TLC (90% CHCl$_3$/MeOH). After 1 hour the MeOH was evaporated in vacuo and the resulting residue cooled (ice), and treated carefully with saturated NaHCO$_3$ (65 mL). The mixture was diluted with EtOAc (65 mL), and after 16 hours stirring at room temperature the inorganic precipitate was removed by filtration through celite. The organic layer was separated, washed with brine (100 mL), dried (MgSO$_4$), filtered and evaporated in vacuo to give the crude amine 21 as a pale orange glass (0.29 g, 88%) which was carried through to the next step without further purification or analysis due to the instability of the amine.

(2S)-N-[(2-Allyloxycarbonylamino)-4-benzyloxy-5-methoxybenzoyl]-2-(hydroxymethyl)-4-(methoxycarbonylmethyl)-2,3-dihydropyrrole (22)

A solution of the amino-alcohol 21 (0.29 g, 0.68 mmol) in CH$_2$Cl$_2$ (12 mL) was cooled to 0° C. (ice/acetone) and treated with pyridine (0.11 mL, 0.11 g, 1.39 mmol). A solution of allyl chloroformate (79 μL, 90 mg, 0.75 mmol) in CH$_2$Cl$_2$ (10 mL) was then added dropwise to the stirred mixture. The reaction mixture was allowed to warm to room temperature and stirred for a further 2.5 h, at which point TLC (EtOAc) revealed complete consumption of the amine 21. The mixture was diluted with CH$_2$Cl$_2$ (30 mL) and washed with saturated CuSO$_4$ (20 mL), H$_2$O (20 mL), brine (20 mL), dried (MgSO$_4$), filtered and evaporated in vacuo. The crude residue was purified by flash chromatography (70% EtOAc/Petroleum Ether) to afford the pure allocamino compound 22 as a colourless glass (0.14 g, 40%): $^1$H NMR (270 MHz, CDCl$_3$) δ8.58 (br s, 1H, NH), 7.88 (br s, 1H$_{arom}$), 7.50–7.29 (m, 5H$_{arom}$), 6.83 (s, 1H$_{arom}$), 6.42 (br s, 1H, NCH=CCH$_2$CO$_2$CH$_3$), 6.03–5.89 (m, 1H, NCO$_2$CH$_2$CH=CH$_2$), 5.39–5.22 (m, 2H, NCO$_2$CH$_2$CH—CH$_2$), 5.18 (s, 2H, PhCH$_2$O), 4.77–4.73 (m, 1H, NCHCH$_2$OH), 4.65–4.62 (m, 2H, NCO$_2$CH$_2$CH=CH$_2$), 4.32–3.84 (m, 5H, NCHCH$_2$OH and OCH$_3$), 3.69 (s, 3H, CO$_2$CH$_3$), 3.09 (s, 2H, NCH=CCH$_3$CO$_2$CH$_3$), 3.05–2.95 (m, 1H, NCH=CCH$_2$CO$_2$CH$_3$CH$_2$), 2.35 (dd, 1H, J=3.76, 16.72 Hz, NCH=CCH$_2$CO$_2$CH$_3$CH$_2$); $^{13}$C NMR (67.8 MHz, CDCl$_3$) δ170.6 (CO$_2$CH$_3$), 167.4 (NC=O$_{amide}$), 153.5 (NC=O$_{carbamate}$), 151.1 (C$_{arom}$), 144.4 (C$_{arom}$), 136.1 (C$_{arom}$), 132.6 (C$_{arom}$), 132.4 (NCO$_2$CH$_2$CH=CH$_2$), 128.6, 128.1 and 127.7 (BnC—H$_{arom}$), 118.5 (NCH=CCH$_2$CO$_2$CH$_3$), 118.2 (NCO$_2$CH$_2$CH=CH$_2$), 112.1 (C—H$_{arom}$), 106.3 (C—H$_{arom}$), 70.7 (PhCH$_2$O), 66.5 (NCHCH$_2$OH), 65.9 (NCO$_2$CH$_2$CH=CH$_2$), 61.9 (NCHCH$_2$OH), 56.7 (OCH3), 52.1 (CO$_2$CH$_3$), 35.6 (NCH=CCH$_2$CO$_2$CH$_3$), 33.6 (NCH=CCH$_2$CO$_2$CH$_3$CH$_2$); MS (FAB), m/z (relative intensity) 618 (M$^{+\cdot}$+Thioglycerol, 2), 511 (M$^{+\cdot}$ +1, 5), 510 (M$^{+\cdot}$, 1), 340 (M—NCH=CCH$_2$CO$_2$CH$_3$CH$_2$CHCH$_2$OH, 20), 300 (3), 282 (14), 256 (7), 192 (6), 171 (16), 149 (22), 140 (12), 112 (4), 91 (PhCH$_2$, 100), 80 (6), 65 (1), 57 (3).

(11S,11aS)-10-Allyloxycarbonyl-8-benzyloxy-11-hydroxy-7-methoxy-2-(methoxycarbonylmethyl)-1,10,11,11a-tetrahydro-5H-pyrrolo[2,1-c][1,4]benzodiazepin-5-one (23)

A solution of the alcohol 22 (0.14 g, 0.28 mmol) in CH$_2$Cl$_2$/CH$_3$CN (12 mL, 3:1) was treated with 4 Å powdered molecular sieves (0.15 g) and NMO (49 mg, 0.42 mmol). After 15 minutes stirring at room temperature, TPAP (4.90 mg, 14 μmol) was added and stirring continued for a further 1 hour 30 minutesutes at which point TLC (80% EtOAc/Petroleum Ether) showed product formation along with some unoxidised starting material. The mixture was then treated with a further quantity of NMO (49 mg, 0.42 mmol) and TPAP (4.9 mg, 14 μmol), and allowed to stir for a further 0.5 hours when TLC revealed reaction completion. The mixture was evaporated in vacuo onto silica and subjected to flash chromatography (60% EtOAc/Petroleum Ether) to provide the protected carbinolamine 23 as a colourless glass (39 mg, 28%): $^1$H NMR (270 MHz, CDCl$_3$) δ7.43–7.25 (m, 6H$_{arom}$), 6.90 (br s, 1H$_{arom}$) 6.74 (s, 1H, NCH=CCH$_2$CO$_2$CH$_3$), 5.79–5.64 (m, 1H, NCO$_2$CH$_2$CH=CH$_2$), 5.77 (d, 1H, J=10.26 Hz, NCHCHOH), 5.19–5.06 (m, 4H, NCO$_2$CH$_2$CH=CH$_2$ and PhCH$_2$O), 4.64–4.45 (m, 2H, NCO$_2$CH$_2$CH=CH$_2$), 4.18–3.83 (m, 4H, OCH$_3$ and NCHCHOH), 3.71 (s, 3H, CO$_2$CH$_3$), 3.19 (s, 2H, NCH=CCH$_2$CO$_2$CH$_3$), 3.09 (dd, 1H, J=11.09, 16.70 Hz, NCH=CCH$_2$CO$_2$CH$_3$CH$_2$), 2.74 (d, 1H, J=17.03 Hz, NCH=CCH$_2$CO$_2$CH$_3$CH,); $^{13}$C NMR (67.8 MHz, CDCl$_3$) δ170.7 (CO$_2$CH$_3$), 163.3 (NC=O$_{amide}$) 155.9 (NC=O$_{carbamate}$), 150.3 (C$_{arom}$), 149.1 (C$_{arom}$), 136.1 (C$_{arom}$), 131.8 (NCO$_2$CH$_2$CH=CH$_2$), 128.7, 128.2 and 127.3 (BnC—H$_{arom}$), 126.2 (NCH=CCH$_2$CO$_2$CH$_3$), 125.1

($C_{arom}$), 118.1 ($NCO_2CH_2CH=CH_2$), 117.7 ($NCH=CCH_2CO_2CH_3$), 114.7 ($C-H_{arom}$), 111.0 ($C-H_{arom}$), 85.9 (NCHCHOH), 71.1 ($PhCH_2O$), 66.8 ($NCO_2CH_2CH=CH_2$), 59.5 (NCHCHOH), 56.2 ($OCH_3$), 52.1 ($CO_2CH_3$), 37.0 ($NCH=CCH_2CO_2CH_3$), 33.7 ($NCH=CCH_2CO_2CH_3CH_2$); MS (EI), m/z (relative intensity) 508 ($M^{+\cdot}$, 16), 449 (3), 422 (3), 404 (2), 368 (3), 340 (19), 324 (2), 282 (6), 255 (2), 225 (1), 206 (2), 192 (3), 169 (4), 152 (2), 140 (10), 131 (5), 108 (5), 91 ($PhCH_2$, 100), 80 (9), 57 (9), IR (NUJOL®) 3600–2500 (br, OH), 2924, 2853, 2360, 1715, 1602, 1514, 1462, 1377, 1271, 1219, 1169, 1045, 722, 699; exact mass calcd for $C_{27}H_{28}N_2O_7$ m/e 508.1846, obsd m/e 508.1791.

(11S,11aS)&(11R,11aS)-8-Benzyloxy-7,11-dimethoxy-2-(methoxycarbonylmethyl)-1,10,11,11a-tetrahydro-5H-pyrrolo[2,1-c][1,4]benzodiazepin-5-one (24, SJG-245)

A catalytic amount of tetrakis(triphenylphosphine) palladium (5.0 mg, 4.33 µmol) was added to a stirred solution of the Alloc-protected carbinolamine 23 (88 mg, 0.17 mmol), triphenylphosphine (2.27 mg, 8.65 µmol) and pyrrolidine (13 mg, 0.18 mmol) in $CH_2Cl_2$ (15 mL). After 2 hours stirring at room temperature under a nitrogen atmosphere, TLC (80% EtOAc/Petroleum Ether) revealed the complete consumption of starting material. The solvent was evaporated in vacuo and the crude residue was purified by flash chromatography (60% EtOAc/Petroleum Ether) to afford the novel PBD (SJG-245) as a colourless glass (54 mg, 77%) which was repeatedly evaporated in vacuo with $CHCl_3$ in order to provide the N10-C11 imine form 24: $^1H$ NMR (270 MHz, $CDCl_3$) (imine) δ7.80 (d, 1H, J=4.03 Hz, HC=N), 7.50 (s, $1H_{arom}$), 7.45–7.26 (m, $5H_{arom}$), 6.91 (br s, 1H, $NCH=CCH_2OC_2CH_3$), 6.83 (s, $1H_{arom}$), 5.21–5.12 (m, 2H, $PhCH_2O$), 3.94 (s, 3H, $OCH_3$), 3.73 (s, 3H, $CO_2CH_3$), 3.23 (s, 2H, $NCH=CCH_2CO_2CH_3$), 3.15 (m, 2H, $NCH=CCH_2CO_2CH_3CH_2$); $^{13}C$ NMR (67.8 MHz, $CDCl_3$) (imine) δ170.7 ($CO_2CH_3$), 162.7 (HC=N), 161.4 (NC=O), 150.9 ($C_{arom}$), 148.1 ($C_{arom}$), 140.1 ($C_{arom}$), 136.0 ($C_{arom}$), 128.7, 128.2 and 127.3 (BnC—$H_{arom}$), 127.3 ($NCH=CCH_2CO_2CH_3$), 119.2 ($C_{arom}$), 117.5 ($NCH=CCH_2CO_2CH_3$), 111.8 ($C-H_{arom}$), 111.5 ($C-H_{arom}$), 70.8 ($PhCH_2O$), 56.2 ($OCH_3$), 53.8 (NCHHC=N), 52.0 ($CO_2CH_3$), 37.4 ($NCH=CCH_2CO_2CH_3$), 33.6 ($NCH=CCH_2CO_2CH_3CH_2$)

Repeated evaporation in vacuo of 24 with $CH_3OH$ provided the N10-C11 methyl ether forms 25: $^1H$ NMR (270 MHz, $CD_3OD$) (11S,11aS isomer) δ7.44–7.25 (m, $5H_{arom}$), 7.16 (s, $1H_{arom}$), 6.85 (br s, 1H, $NCH=CCH_2CO_2CH_3$), 6.62 (s, $1H_{arom}$), 5.09 (s, 2H, $PhCH_2O$), 4.52 (d, 1H, J=8.80 Hz, $NCHCHOCH_3$), 4.00–3.85 (m, 1H, $NCHCHOCH_3$), 3.80 (s, 3H, $OCH_3$), 3.69 (s, 3H, $CO_2CH_3$), 3.41 (s, 3H, $NCHCHOCH_3$), 3.24 (br s, 2H, $NCH=CCH_2CO_2CH_3$), 3.20–3.00 (m, 1H, $NCH=CCH_2COCH_3CH_2$), 2.60–2.50 (m, 1H, $NCH=CCH_2CO_2CH_3CH_2$); $^{13}C$ NMR (67.8 MHz, $CD_3OD$) (11S,11aS isomer) δ172.7 ($CO_2CH_3$), 166.8 ($C_{arom}$), 153.3 (NC=O), 146.4 ($C_{arom}$), 139.7 ($C_{arom}$), 138.0 ($C_{arom}$), 132.4 ($C_{arom}$), 129.6, 129.1 and 128.8 (BnC—$H_{arom}$), 127.0 ($NCH=CCH_2CO_2CH_3$), 120.8 ($NCH=CCH_2CO_2CH_3$), 113.7 ($C-H_{arom}$), 109.2 ($C-H_{arom}$), 97.1 ($NCHCHOCH_3$), 71.7 ($PhCH_2O$), 60.2 ($NCHCHOCH_3$), 56.8 ($OCH_3$), 55.2 ($NCHCHOCH_3$), 52.5 ($CO_2CH_3$), 38.7 ($NCH=CCH_2CO_2CH_3$), 34.1 ($NCH=CCH_2CO_2CH_3CH_2$); MS (EI), m/z (relative intensity) 420 ($M^{+\cdot}$, methyl ether, 1), 418 (methyl ether –2, 2), 406 ($M^{+\cdot}$, imine, 23), 404 (41), 375 (2), 345 (6), 333 (7), 313 (22), 299 (10), 285 (6), 253 (6), 242 (4), 225 (2), 214 (2), 198 (2), 183 (4), 168 (2), 155 (6), 136 (3), 105 (3), 91 ($PhCH_2$, 100), 80 (4), 65 (7); IR (NUJOL®) 3318 (br, OH of carbinolamine form), 2923, 2853, 1737, 1692, 1658, 1627, 1601, 1552, 1511, 1501, 1464, 1461, 1452, 1378, 1244, 1072, 1006, 786, 754, 698 $cm^{-1}$; exact mass calculated for $C_{23}H_{22}N_2O_5$ m/e 406.1529, obsd m/e 406.1510.

Figure 3:
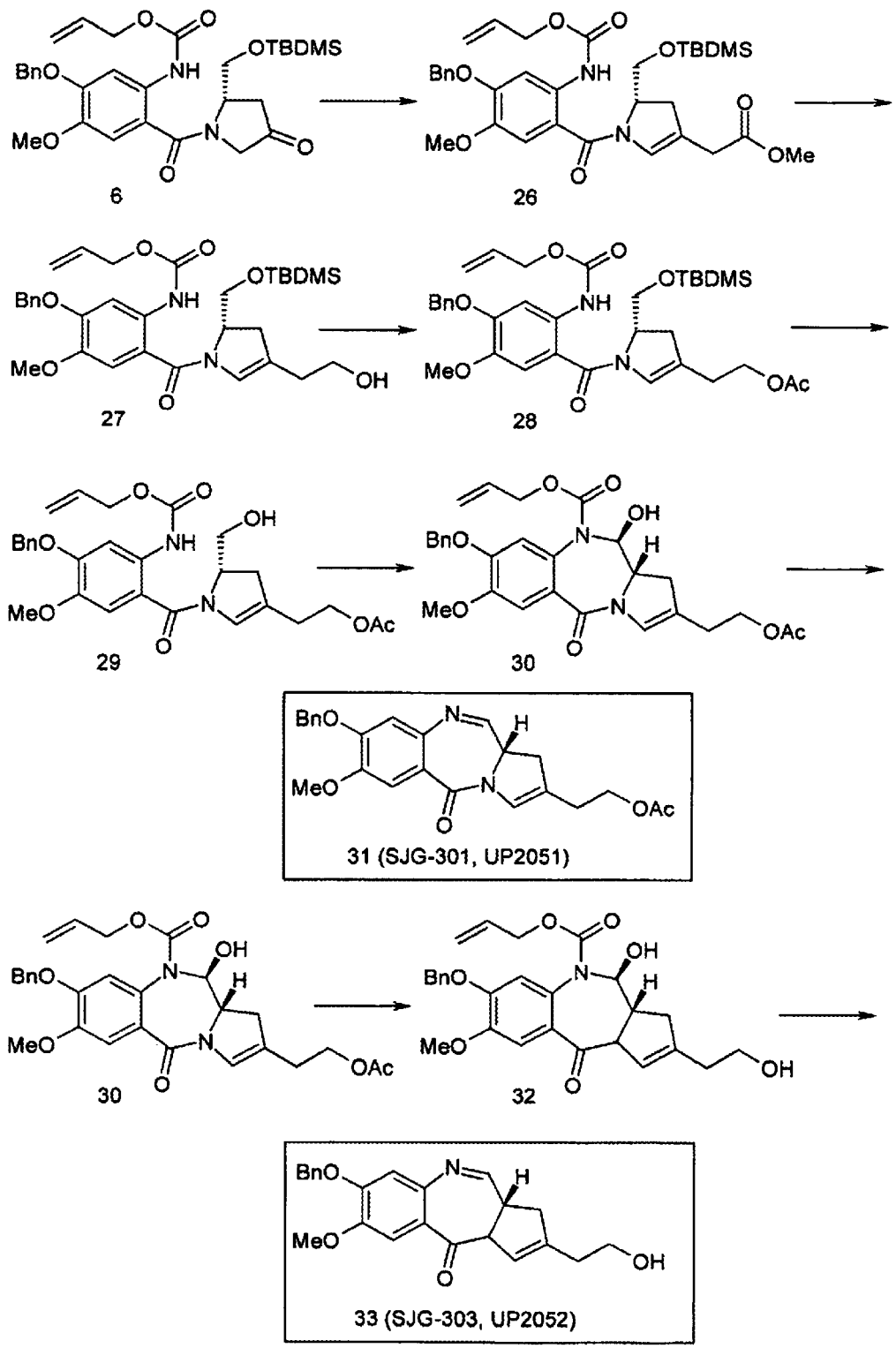

Examples 1(c & d)
Synthesis of SJG-301 (31, UP2051) and SJG-303 (33, UP2052) (See FIG. 3)

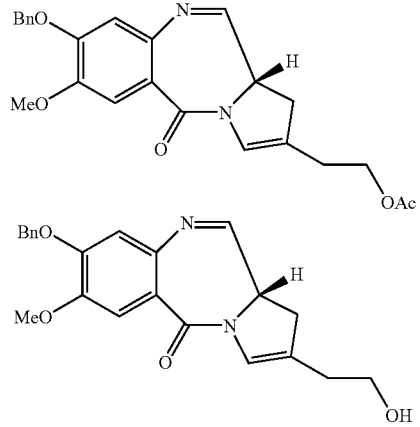

Example 1(c)

Example 1(d)
(2S)-N-[(2-Allyloxycarbonylamino)-4-benzyloxy-5-methoxybenzoyl]-2-(tert-butyldimethylsilyloethythyl)-4-(methoxycarbonylmethyl)-2,3-dihydropyrrole (26)

Petroleum Ether (100 mL) was added to a sample of NaH (1.41 g of a 60% dispersion in oil, 35.25 mmol) and stirred at room temperature under a nitrogen atmosphere. After 0.5 hours the mixture was allowed to settle and the Petroleum Ether was transferred from the flask via a double-tipped needle under nitrogen. THF (80 mL) was added to the remaining residue and the mixture was cooled to 0° C. (ice/acetone). The cool solution was treated dropwise with a solution of methyldiethylphosphonoacetate (6.47 mL, 7.41 g, 35.25 mmol) in THF (80 mL) under nitrogen. After 1.5 hours at room temperature, the mixture was cooled to 0° C. and treated dropwise with a solution of the ketone 6 (8.0 g, 14.1 mmol) in THF (50 mL) under nitrogen. After 16 hours at room temperature, TLC (20% EtOAc/Petroleum Ether) revealed reaction completion. The THF was evaporated in vacuo and the mixture partitioned between saturated $NaHCO_3$ (200 mL) and EtOAc (220 mL). The layers were separated and the aqueous layer extracted with EtOAc (2×200 mL). The combined organic layers were washed with $H_2O$ (200 mL), brine (200 mL), dried ($MgSO_4$), filtered and concentrated in vacuo to give a dark red oil. Purification by flash chromatography (15% EtOAc/Petroleum Ether) furnished the endo-ester 26 (7.02 g, 80%): $[α]^{22}_D$=–93.0° (c=1.04, $CHCl_3$); $^1H$ NMR (270 MHz, $CDCl_3$) δ8.78 (br s, 1H), 7.95 (s, 1H), 7.50–7.29 (m, 5H), 6.82 (s, 1H), 6.46 (br s, 1H), 6.02–5.88 (m, 1H), 5.35 (dd, 1H, J=2.93, 17.22 Hz), 5.24 (d, 1H, J=10.44 Hz), 5.18 (s, 2H), 4.70–4.61 (m, 3H), 3.96–3.82 (m, 5H), 3.68 (s, 3H), 3.08 (s, 2H), 2.91–2.82 (m, 1H), 2.71–2.65 (m, 1H), 0.88 (s, 9H), 0.06 and 0.04 (s×2, 6H); $^{13}C$ NMR (67.8 MHz, $CDCl_3$) δ170.7, 165.8, 153.5, 150.6, 144.0, 136.2, 132.7, 132.5, 128.6, 128.2, 128.1, 127.7, 118.1, 118.0, 114.4, 112.0, 106.0, 70.6, 65.7, 62.3, 59.4, 56.6, 52.0, 34.6, 33.9, 25.8, 18.1, –5.4; MS (EI), m/z (relative intensity) 626 ($M^{+\cdot}$ +1, 3), 625 ($M^{+\cdot}$ +1, 7), 624

(M+·, 14), 568 (5), 567 (11), 509 (3), 476 (3), 341 (5), 340 (17), 339 (4), 299 (3), 286 (18), 285 (87), 282 (11), 256 (4), 242 (3), 229 (3), 228 (14), 226 (11), 168 (10), 166 (3), 152 (6), 141 (5), 140 (50), 139 (9), 108 (3), 92 (10), 91 (100), 89 (6), 80 (11), 75 (11), 73 (10), 65 (5), 57 (6), 41 (12); IR (NEAT) 3332 (br, NH), 3019, 2953, 2930, 2857, 1733, 1622, 1599, 1524, 1491, 1464, 1408, 1362, 1335, 1258, 1205, 1171, 1113, 1051, 1027, 938, 839, 757, 697, 666 cm$^{-1}$; exact mass calcd for $C_{33}H_{44}N_2O_8Si$ m/e 624.2867, obsd m/e 624.2936.

(2S)-N-[(2-Allyloxycarbonylamino)-4-benzyloxy-5-methoxybenzoyl]-2-(tert-butyldimethylsilyloxymethyl)-4-(hydroxy-2-ethyl)-2,3-dihydropyrrole (27)

A solution of the ester 26 (4.0 g, 6.41 mmol) in THF (55 mL) was cooled to 0° C. (ice/acetone) and treated with LiBH$_4$ (0.21 g, 9.62 mmol) in portions. The mixture was allowed to warm to room temperature and stirred under a nitrogen atmosphere for 26 hours at which point TLC (50% EtOAc/Petroleum Ether) revealed the complete consumption of starting material. The mixture was cooled to 0° C. (ice/acetone) and water (14 mL) was carefully added. Following evaporation of the THF in vacuo, the mixture was cooled and then neutralised with 1 N HCl. The solution was then diluted with H$_2$O (100 mL) and extracted with EtOAc (3×100 mL), the combined organic layers washed with brine (100 mL), dried (MgSO$_4$), filtered and evaporated in vacuo. The crude oil was purified by flash chromatography (30→40% EtOAc/Petroleum Ether) to furnish the pure endo-alcohol 27 as a transparent yellow oil (2.11 g, 55%): $[\alpha]^{22}_D$ −86.43° (c=1.38, CHCl$_3$); $^1$H NMR (270 MHz, CDCl$_3$) δ8.76 (br s, 1H), 7.92 (br s, 1H), 7.50–7.28 (m, 5H), 6.82 (s, 1H), 6.36 (br s, 1H), 6.02–5.87 (m, 1H), 5.35 (d, 1H, J=17.22 Hz), 5.24 (d, 1H, J=11.72 Hz), 5.18 (s, 2H), 4.64–4.61 (m, 3H), 4.10–3.99 (m, 1H), 3.80 (s, 3H), 3.79–3.66 (m, 3H), 2.85–2.75 (m, 1H), 2.64–2.60 (m, 1H), 2.30 (t, 2H, J=6.23 Hz), 1.74 (br s, 1H), 0.88 (s, 9H), 0.06 and 0.04 (s×2, 6H); $^{13}$C NMR (67.8 MHz, CDCl$_3$) δ165.3, 153.5, 150.5, 144.2, 136.3, 132.5, 128.6, 128.1, 127.7, 126.7, 122.8, 118.0, 114.3, 112.0, 106.1, 70.7, 65.7, 62.8, 60.4, 59.1, 56.6, 34.4, 31.7, 25.8, 18.2, −5.4; MS (EI), m/z (relative intensity) 598 (M+·2, 3), 597 (M+· +1, 5), 596 (M+·, 13), 581 (2), 541 (2), 540 (4), 539 (9), 448 (2), 341 (2), 340 (12), 282 (7), 259 (5), 258 (20), 257 (100), 256 (3), 227 (3), 226 (12), 200 (5), 168 (6), 124 (3), 113 (3), 112 (50), 111(4), 94 (10), 91 (25), 73 (3); IR (NEAT) 3340 (br), 3066, 3033, 2930, 2857, 1732, 1598, 1520, 1456, 1409, 1328, 1205, 1166, 1113, 1049, 1023, 938, 839, 778, 744, 697, 677, 637 cm$^{-1}$.

(2S)-N-[(2-Allyloxycarbonylamino)-4-benzyloxy-5-methoxybenzoyl]-4-(acyloxy-2-ethyl)-2-(tert-butyldimethylsilyloxymethyl)-2,3-dihydropyrrole (28)

Acetic anhydride (8.17 g, 7.55 mL, 80 mmol) and pyridine (30.2 mL) were added to the alcohol 27 (0.953 g, 1.60 mmol) and the solution stirred for 16 hours under nitrogen at which point TLC revealed reaction completion (50% EtOAc/Petroleum Ether). The reaction mixture was cooled to 0° C. (ice/acetone) and treated dropwise with MeOH (15 mL). After stirring at room temperature for 1 hour the mixture was treated dropwise with H$_2$O (30.2 mL) and allowed to stir for a further 16 h. Following dilution with EtOAc (56 mL), the solution was cooled to 0° C. and treated dropwise with 6 N HCl (56 mL). The layers were separated and the organic phase was washed with 6N HCl (2×28 mL) and the combined aqueous layers were then extracted with EtOAc (70 mL). The combined organic phases were then washed with H$_2$O (60 mL), brine (60 mL), dried (MgSO$_4$), filtered and evaporated in vacuo. The crude oil was a mixture of the desired product 28 and the TBDMS cleaved compound 29 as judged by TLC. Purification by flash chromatography (20→100% EtOAc/Petroleum Ether) provided 29 (0.2 g) and desired acyl-TBDMS compound 28 (0.59 g, 58%) as a colourless oil: $[\alpha]^{22}_D$=−87.04° (c=4.91, CHCl$_3$); $^1$H NMR (270 MHz, CDCl$_3$) (Rotamers) δ8.77 (br s, 1H), 7.94 (br s, 1H), 7.49–7.31 (m, 5H), 6.80 (s, 1H), 6.37 (br s, 1H), 6.02–5.89 (m, 1H), 5.35 (dd, 1H, J=17.22, 1.65 Hz), 5.24 (d, 1H, J=10.30 Hz), 5.19 (s, 2H), 4.64–4.61 (m, 3H), 4.12 (t, 2H, J=6.78 Hz), 4.03–3.95 (m, 1H), 3.83–3.75 (m, 4H), 2.85–2.75 (m, 1H), 2.64–2.60 (m, 1H), 2.40–2.26 (m, 2H,), 2.03 (s, 3H), 0.88 (s, 9H), 0.04, 0.01 and −0.01(s×3, 6H); $^{13}$C NMR (67.8 MHz, CDCl$_3$) δ170.9, 165.5, 153.5, 150.6, 144.1, 136.3, 132.7, 132.5, 128.6, 128.1, 127.7, 126.5, 122.2, 118.0, 114.3, 112.2, 106.1, 70.7, 65.7, 62.4, 60.4, 59.2, 56.7, 34.6, 31.7, 27.9, 25.8, 20.9, 18.2, −5.4; MS (EI), m/z (relative intensity) 640 (M+· +2, 3), 639 (M+· +1, 7), 638 (M+·, 15), 623 (2), 583 (3), 582 (6), 581 (14), 539 (2), 523 (3), 490 (3), 341 (5), 340 (22), 301 (5), 300 (18), 299 (75), 283 (3), 282 (14), 256 (4), 242 (7), 241 (5), 240 (16), 239 (62), 226 (6), 192 (3), 182 (8), 181 (5), 180 (3), 168 (5), 166 (5), 154 (10), 131 (3), 106 (3), 95 (4), 94 (48), 93 (5), 92 (8), 91 (100), 89 (5), 75 (6), 73 (8), 65 (3), 57 (3); IR (NEAT) 3324 (br, NH), 3066, 3018, 2954, 2930, 2857, 1737, 1622, 1598, 1523, 1489, 1464, 1409, 1363, 1327, 1230, 1205, 1168, 1115, 1080, 1030, 994, 937, 839, 756, 697, 667, 638, 606, 472, 459, 443 cm$^{-1}$; exact mass calcd for $C_{34}H_{46}N_2O_8Si$ m/e 638.3024, obsd m/e 638.3223.

(2S)-N-[2-Allyloxycarbonylamino)-4-benzyloxy-5-methoxybenzoyl]-4-(acyloxy-2-ethyl)-2-(hydroxymethyl)-2,3-dihydropyrrole (29)

A solution of the silyl ether 28 (0.83 g, 1.30 mmol) in THF (14 mL) was treated with H$_2$O (14 mL) and glacial acetic acid (42 mL). After 2 hours stirring at room temperature TLC (50% EtOAc/Petroleum Ether) showed the complete consumption of starting material. The mixture was cooled (ice) and treated dropwise with a solution of NaHCO$_3$ (64 g) in H$_2$O (640 mL). The aqueous solution was extracted with EtOAc (3×100 mL) and the combined organic layers were washed with H$_2$O (150 mL), brine (100 mL), dried (MgSO$_4$), filtered and concentrated in vacuo to give the crude product as an orange oil. Purification by flash chromatography (60% EtOAc/Petroleum Ether) furnished the pure alcohol 29 as a white glass (0.537 g, 81%): $[\alpha]^{21}_D$− 83.60° (c=0.25, CHCl$_3$); $^1$H NMR (270 MHz, CDCl$_3$) δ8.56 (br s, 1H), 7.89 (br s, 1H), 7.49–7.29 (m, 5H), 6.81 (s, 1H), 6.28 (br s, 1H), 6.03–5.89 (m, 1H), 5.35 (ddd, 1H, J=17.22, 3.11, 1.46, Hz), 5.25 (d, 1H, J=10.44 Hz), 5.19 (s, 2H), 4.80–4.70 (m, 1H), 4.65–4.62 (m, 2H), 4.41–4.31 (m, 1H), 4.20–4.06 (m, 2H,), 3.84–3.77 (m, 5H), 2.98–2.88 (m, 1H), 2.39 (t, 2H, J=6.51 Hz), 2.33–2.25 (m, 1H,), 2.03 (s, 3H); $^{13}$C NMR (67.8 MHz, CDCl$_3$) δ170.8, 167.1, 153.5, 151.0, 144.3, 136.1, 132.6, 132.4, 128.6, 128.1, 127.7, 126.3, 122.6, 118.1, 112.2, 106.3, 70.7, 66.5, 65.8, 62.0, 61.7, 56.8, 35.4, 31.7, 27.8, 20.9; MS (EI), m/z (relative intensity) 525 (M+· +1, 5), 524 (M+·, 14), 341 (5), 340 (16), 299 (2), 283 (3), 282 (14), 256 (4), 227 (5), 208 (2), 192 (3), 190 (2), 186 (9), 185 (60), 168 (2), 167 (5), 166 (2), 164 (2), 163 (2), 154 (3), 136 (3), 131 (3), 126 (7), 125 (53), 108 (2), 107 (2), 106 (2), 105 (3), 95 (3), 94 (19), 93 (3), 92 (9), 91 (100), 83 (2), 69 (2), 68 (3), 67 (3), 65 (5), 58 (6), 57 (17); IR (CHCl$_3$) 3335 (br), 2933, 1732, 1599, 1524, 1455, 1434, 1408, 1231, 1170, 1112, 1029, 995, 932, 868, 765, 698, 638, 606 cm$^{-1}$; exact mass calcd for $C_{28}H_{32}N_2O$, m/e 524.2159, obsd m/e 524.2074.

(11S,11aS)-2-(Acyloxy-2-ethyl)-10-allyloxycarbonyl-8-benzyloxy-11-hydroxy-7-methoxy-1,10,11,11a-tetrahydro-5H-pyrrolo[2,1-c][1,4]benzodiazepin-5-one (30)

Method A: A solution of DMSO (0.25 mL, 0.27 g, 3.49 mmol) in $CH_2Cl_2$ (10 mL) was added dropwise over 35 minutes to a solution of oxalyl chloride (0.87 mL of a 2.0 M solution in $CH_2Cl_2$, 1.75 mmol) at −45° C. (liq.$N_2$/Chlorobenzene) under a nitrogen atmosphere. After stirring at −45° C. for 40 minutes, a solution of the alcohol 29 (0.51 g, 0.97 mmol) in $CH_2Cl_2$ (7 mL) was added dropwise over 35 minutes at −45° C. After 55 minutes at −45° C., the mixture was treated dropwise with a solution of TEA (0.57 mL, 0.41 g, 4.10 mmol) in $CH_2Cl_2$ (5 mL) over 40 minutes at −45° C. After a further 45 minutes, the reaction mixture was allowed to warm to room temperature and was diluted with $CH_2Cl_2$ (60 mL), washed with 1N HCl (60 mL), $H_2O$ (60 mL), brine (30 mL), dried ($MgSO_4$), filtered and evaporated in vacuo. TLC (80% EtOAc/Petroleum Ether) of the crude material revealed complete reaction. Purification by flash chromatography (50% EtOAc/Petroleum Ether) furnished the protected carbinolamine 30 as a creamy glass (0.25 g, 49%).

Method B: A solution of the alcohol 29 (0.21 g, 0.40 mmol) in $CH_2Cl_2/CH_3CN$ (30 mL, 3:1) was treated with 4 Å powdered molecular sieves (0.15 g) and NMO (69 mg, 0.59 mmol). After 15 minutes stirring at room temperature, TPAP (6.9 mg, 19.8 μmol) was added and stirring continued for a further 1 hour at which point TLC (80% EtOAc/Petroleum Ether) showed product formation along with some unoxidised starting material. The mixture was then treated with a further quantity of NMO (35 mg, 0.30 mmol) and TPAP (3.50 mg, 10 μmol), and allowed to stir for a further 1.5 hours after which time TLC revealed complete reaction. The mixture was evaporated in vacuo onto silica and subjected to flash chromatography (50% EtOAc/Petroleum Ether) to provide the protected carbinolamine 30 as a creamy glass (95 mg, 46%): $[\alpha]^{20}_D$=+113.85° (c=0.95, $CHCl_3$); $^1H$ NMR (270 MHz, $CDCl_3$) δ7.49–7.26 (m, 6H), 6.80 (s, 1H), 6.76 (s, 1H), 5.79–5.59 (m, 1H), 5.75 (d, 1H, J=10.08 Hz), 5.19–5.05 (m, 4H), 4.52–4.29 (m, 2H), 4.28–4.08 (m, 3H), 3.95–3.80 (m, 4H), 2.99 (dd, 1H, J=10.72, 16.94 Hz), 2.66 (d, 1H, J=16.86 Hz), 2.46 (t, 2H, J=6.41 Hz), 2.06 (s, 3H); $^{13}C$ NMR (67.8 MHz, $CDCl_3$) δ171.1, 163.1, 155.9, 150.3, 149.1, 136.1, 131.8, 128.7, 128.6, 128.2, 127.3, 125.3, 124.4, 121.6, 118.0, 114.8, 111.0, 85.9, 71.1, 66.8, 62.0, 70.7, 59.4, 56.2, 37.0, 27.9, 21.0; MS (EI), m/z (relative intensity) 522 ($M^{+\cdot}$, 13), 463 (9), 462 (13), 341 (8), 340 (32), 282 (11), 256 (3), 183 (5), 154 (3), 123 (8), 94 (20), 91 (100), 65 (4), 57 (15); exact mass calcd for $C_{28}H_{30}N_2O_8$ m/e 522.2002, obsd m/e 522.2008.

Example 1(c)

(11aS)-2-(Acyloxy-2-ethyl)-8-benzyloxy-7-methoxy-1,2,3,11a-tetrahydro-5H-pyrrolo[2,1-c][1,4]benzodiazepin-5-one (31,UP2051, SJG-301)

A catalytic amount of tetrakis(triphenylphosphine) palladium (5.26 mg, 4.55 μmol) was added to a stirred solution of the Alloc-protected carbinolamine 30 (95 mg, 0.18 mmol), triphenylphosphine (2.39 mg, 9.10,mol) and pyrrolidine (13.6 mg, 0.19 mmol) in $CH_2Cl_2$ (10 mL). After 1 hour stirring at room temperature under a nitrogen atmosphere, TLC (97% $CHCl_3$/MeOH) revealed the complete consumption of starting material. The solvent was evaporated in vacuo and the crude residue was purified by flash chromatography (99.5% $CHCl_3$/MeOH) to afford the PBD (31, SJG-301, UP2051) as an orange glass which was repeatedly evaporated in vacuo with $CHCl_3$ in order to provide the N10-C11 imine form (66.3 mg, 87%): $[\alpha]^{21}_D$=+741.67° (c=0.66, $CHCl_3$); $^1H$ NMR (270 MHz, $CDCl_3$) (imine) δ7.78 (d, 1H, J=4.03 Hz), 7.70–7.28 (m, 6H), 6.83 (s, 1H), 6.82 (s, 1H), 5.19–5.18 (m, 2H), 4.27–4.16 (m, 2H), 3.94 (s, 3H), 3.44–3.35 (m, 1H), 3.28–3.15 (m, 1H), 3.04–2.97 (m, 1H), 2.52–2.47 (m, 2H), 2.06 (s, 3H); $^{13}C$ NMR (67.8 MHz, $CDCl_3$) (Rotamers) δ170.9, 162.6, 161.1, 150.9, 148.2, 140.1, 136.1, 132.1, 132.0, 128.7, 128.6, 128.1, 127.3, 124.7, 121.4, 111.9, 111.6, 70.8, 61.9, 56.2, 53.6, 37.4, 27.9, 21.0; MS (EI), m/z (relative intensity) 421 ($M^{+\cdot}$ +1, 4), 420 ($M^{+\cdot}$, 14), 419 (12), 418 (36), 361 (6), 360 (20), 328 (3), 313 (8), 270 (4), 269 (7), 268 (9), 267 (22), 256 (4), 129 (3), 105 (3), 94 (4), 93 (3), 92 (12), 91 (100), 83 (3), 80 (3), 73 (5), 71 (3), 69 (3), 65 (5), 60 (4), 57 (5), 55 (4); IR ($CHCl_3$) 3313 (br), 2957, 2934, 1736, 1598, 1509, 1455, 1437, 1384, 1243, 1179, 1120, 1096, 1037, 753, 696, 666, 542 $cm^{-1}$; exact mass calcd for in $C_{24}H_{24}N_2O_5$ m/e 420.1685, obsd m/e 420.1750.

(11s,11aS)-10-Allyloxycarbonyl-8-benzyloxy-11-hydroxy-2-(hydroxy-2-ethyl)-7-methoxy-1,10,11,11a-tetrahydro-5H-pyrrolo[2,1-c][1,4]benzodiazepin-5-one (32)

A solution of $K_2CO_3$ (328 mg, 2.38 mmol) in $H_2O$ (6 mL) was added dropwise to a stirred solution of the acyl compound 30 (0.248 g, 0.475 mmol) in $CH_2CL_2$ (3 mL) and MeOH (8 mL). After stirring for 16 hours at room temperature TLC (EtOAc) revealed complete reaction. The MeOH/$CH_2Cl_2$ was evaporated in vacuo to give a cloudy aqueous solution which was diluted with $H_2O$ (30 mL) and extracted with EtOAc (3×30 mL). The combined organic layers were then washed with brine (30 mL), dried ($MgSO_4$), filtered and evaporated in vacuo to provide a creamy oil. Purification by flash chromatography (97% $CHCl_3$/MeOH) furnished the homoallylic alcohol 32 as a transparent colourless glass (178 mg, 78%): $[\alpha]^{21}_D$+48.43° (c=1.56, $CHCl_3$); $^1H$ NMR (270 MHz, $CDCl_3$) δ7.43–7.24 (m, 6H), 6.84 (s, 1H), 6.73 (s, 1H), 5.74–5.55 (m, 1H), 5.73 (d, 1H, J=8.79 Hz), 5.19–5.06 (m, 4H), 4.46–4.23 (m, 2H), 3.92–3.70 (m, 6H), 3.07–2.97 (m, 1H), 2.67 (d, 1H, J=16.49 Hz), 2.40–2.17 (m, 2H); $^{13}C$ NMR (67.8 MHz, $CDCl_3$) δ163.1, 155.8, 150.3, 149.1, 136.1, 131.8, 128.6, 128.1, 127.7, 127.4, 125.3, 124.1, 124.0, 123.1, 123.0, 117.9, 114.9, 110.9, 86.0, 71.1, 66.7, 60.3, 59.6, 56.2, 37.1, 31.5; MS (EI), m/z (relative intensity) 482 ($M^{+\cdot}$ +2, 4), 481 ($M^{+\cdot}$ +1, 10), 480 ($M^{+\cdot}$, 26), 449 (4), 378 (12), 347 (7), 341 (7), 340 (25), 339 (4), 284 (4), 282 (10), 143 (4), 141 (13), 131 (6), 112 (24), 110 (4), 94 (10), 92 (9), 91 (100), 80 (4), 70 (5), 69 (7), 65 (4), 58 (11), 57 (29); exact mass calcd for $C_{26}H_{28}N_2O_7$ m/e 480.1897, obsd m/e 480.1886.

Example 1(d)

(11aS)-8-Benzyloxy-2-(hydroxy-2-ethyl)-7-methoxy-1,2,3,11a-tetrahydro-5H-pyrrolo[2,1-c][1,4]benzodiazepin-5-one (33, UP2052, SJG-303)

A catalytic amount of tetrakis(triphenylphosphine) palladium (9.39 mg, 8.13 μmol) was added to a stirred solution of the Alloc-protected carbinolamine 30 (156 mg, 0.33 mmol), triphenylphosphine (4.26 mg, 16.3 μmol) and pyrrolidine (24.3 mg, 0.34 mmol) in $CH_2Cl_2$ (15 mL). After 1 hour 50 minutesutes stirring at room temperature under a nitrogen atmosphere, TLC (90% $CHCl_3$/MeOH) revealed the complete consumption of starting material. The solvent was evaporated in vacuo and the crude residue was purified by flash chromatography (98% $CHCl_3$/MeOH) to afford the PBD (33, SJG-303, UP2052) as an orange glass which was repeatedly evaporated in vacuo with $CHCl_3$ in order to provide the N10-C11 imine form (103 mg, 84%): $^1H$ NMR (270 MHz, $CDCl_3$) (Rotamers) δ7.75 (d, 1H, J=4.03 Hz), 7.58–7.22 (m, 6H), 6.82–6.80 (m, 2H), 5.17–4.88 (m, 2H), 4.65–4.20 (m, 2H), 3.91 (s, 3H), 3.35–3.25 (m, 1H), 3.18–3.15 (m, 1H), 3.04–2.97 (m, 1H), 2.52–2.47 (m, 2H); $^{13}$C NMR (67.8 MHz, CDCl$_3$) (Rotamers) δ162.8, 161.1, 152.3, 150.9, 148.1, 142.3, 138.3, 136.4, 128.7, 128.6, 128.2, 127.4, 124.2, 123.1, 111.8, 111.6, 70.8, 60.4, 56.2, 53.6, 37.7, 31.5; MS (EI), m/z (relative intensity) 380 (13), 379 (11), 378 (M$^{+\cdot}$, 42), 377 (36), 376 (77), 375 (6), 347 (8), 345 (5), 334 (5), 333 (19), 288 (14), 287 (14), 286 (36), 285 (50), 272 (6), 271 (22), 269 (6), 268 (6), 267 (5), 259 (5), 257 (13), 255 (24), 243 (15), 155 (6), 136 (5), 124 (7), 106 (6), 93 (6), 92 (38), 91 (100), 65 (16), 63 (5), 51 (5); IR (CHCl$_3$) 3313, 2918, 1623, 1598, 1568, 1509, 1455, 1436, 1386, 1328, 1243, 1218, 1175, 1130 1061, 1007, 870, 831, 792, 752, 697, 662 cm$^{-1}$; exact mass calculated for C$_{22}$H$_{22}$N$_2$O$_4$ m/e 378.1580, obsd m/e 378.1576.

Repeated evaporation in vacuo of UP2052 with CH$_3$OH provided the N10-C11 methyl ether forms: $^1$H NMR (270 MHz, CDCl$_3$) (Rotamers) δ7.66–7.22 (m, 6H), 6.82–6.81 (m, 2H), 5.21–4.76 (m, 2H), 4.61–4.15 (m, 1H), 4.03–3.71 (m, 5H), 3.44 (s, 3H), 3.35–1.92 (m, 7H).

Figure 4:
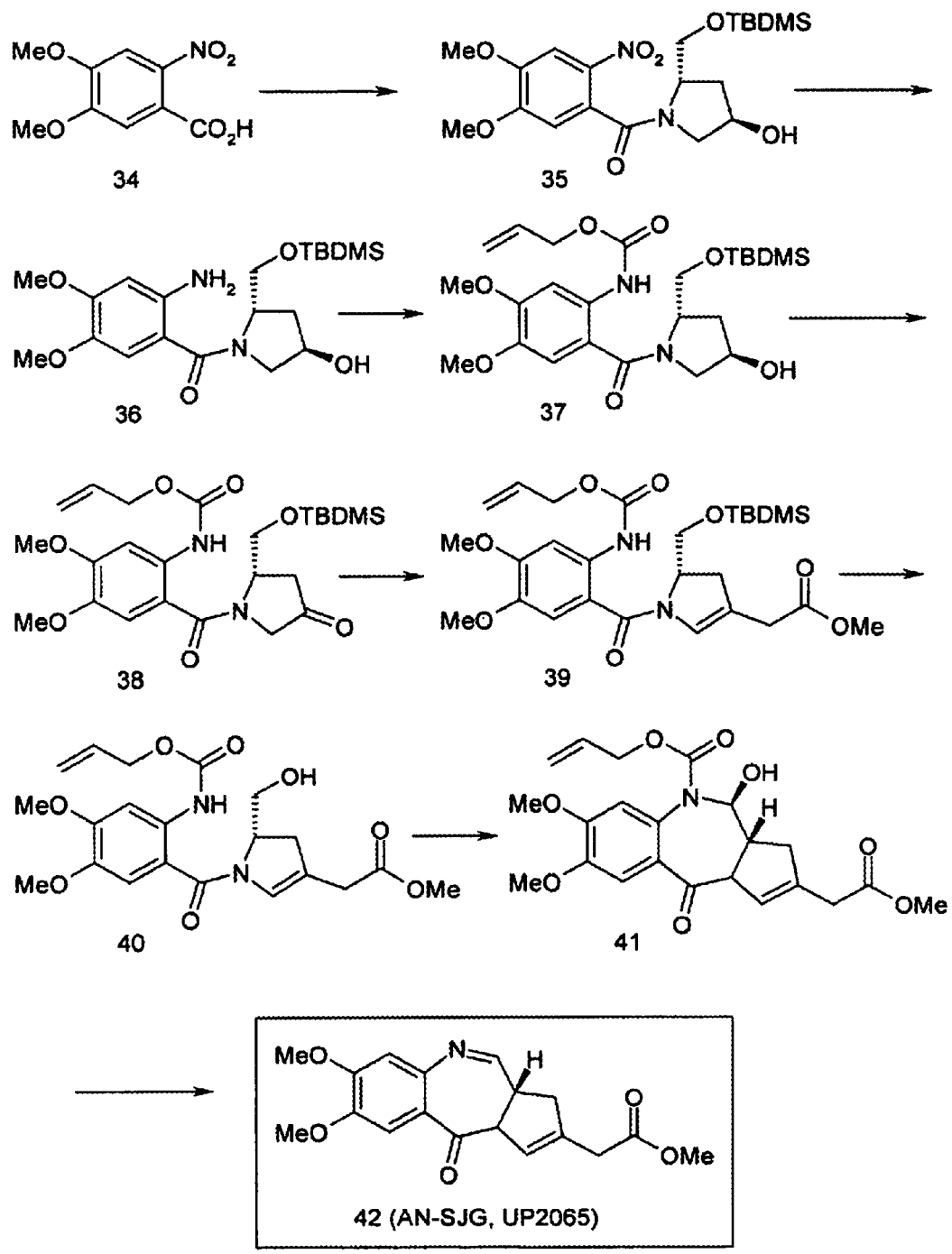

Example 1(e)
Synthesis of the C7,C8-Dimethoxy-C2-Methoxycarbonylmethyl PBD AN-SJG (42, UP2065) (See FIG. 4)

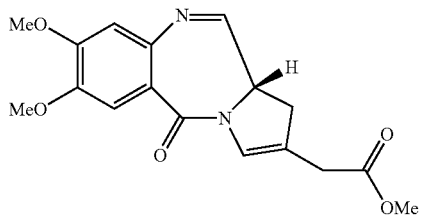

(2S)(4R)-N-(4,5-Dimethoxy-2-nitrobenzoyl)-2-(tert-butyldimethylsilyloxymethyl)-4-hydroxypyrrolidine (35)

A catalytic amount of DMF (2 drops) was added to a stirred solution of the nitro-acid 34 (12.45 g, 54.8 mmol) and oxalyl chloride (5.75 mL, 8.37 g, 65.9 mmol) in CH$_2$Cl$_2$ (300 mL). After 16 hours at room temperature the resulting acid chloride solution was added dropwise over 4.5 hours to a stirred mixture of the amine 2 (12.65 g, 54.8 mmol) and TEA (13.86 g, 19.1 mL, 137 mmol) in CH$_2$Cl$_2$ (300 mL) at 0° C. (ice/acetone) under a nitrogen atmosphere. The reaction mixture was allowed to warm to room temperature and stirred for a further 2.5 h. The mixture was washed with saturated NaHCO$_3$ (300 mL), saturated NH$_4$Cl (300 mL), H$_2$O (250 mL), brine (300 mL), dried (MgSO$_4$), filtered and evaporated in vacuo to give the crude product as a dark orange oil. Purification by flash chromatography (80% EtOAc/Petroleum Ether) isolated the pure amide 35 as a sticky orange oil (18.11 g, 75%): [α]$^{22}_D$=−105.7° (c=1.17, CHCl$_3$); $^1$H NMR (270 MHz, CDCl$_3$) (Rotamers) δ7.71 and 7.68 (s×2, 1H), 6.86 and 6.79 (s×2, 1H), 4.50 and 4.38 (br s×2, 2H), 4.13–4.10 (m, 1H), 3.98 (s, 3H), 3.94 (s, 3H), 3.78–3.74 (m, 1H), 3.35–3.27 (m, 1H), 3.07 (d, 1H, J=11.17 Hz), 3.01–2.79 (br s, 1H), 2.35–2.26 (m, 1H), 2.11–2.04 (m, 1H), 0.91 and 0.81 (s×2, 9H), 0.10, 0.09, −0.07, and −0.10 (s×4, 6H); $^{13}$C NMR (67.8 MHz, CDCl$_3$) (Rotamers) δ166.6, 154.2 and 154.1, 149.3 and 148.9, 137.5, 128.0, 109.2, 107.1, 70.1 and 69.4, 64.7 and 62.5, 59.0 and 54.9, 57.3, 56.6, 56.5, 37.4 and 36.3, 25.9 and 25.7, 18.2, −5.4, −5.5 and −5.7; MS (EI), m/z (relative intensity) 440 (M$^{+\cdot}$, 2), 426 (9), 386 (4), 385 (20), 384 (65), 383 (100), 367 (4), 320 (4), 308 (7), 295 (8), 286 (5), 211 (14), 210 (100), 194 (12), 180 (4), 165 (17), 164 (8), 137 (6), 136 (25), 121 (4), 93 (6), 91 (9), 82 (6), 75 (15), 73 (15), 59 (4), 57 (4); IR (NEAT) 3391 (br, OH), 3012, 2952, 2931, 2857, 1616, 1578, 1522, 1456, 1436, 1388, 1338, 1279, 1225, 1183, 1151, 1074, 1053, 1029, 1004, 939, 870, 836, 816, 785, 757, 668, 650, 620 cm$^{-1}$; exact mass calcd for C$_{20}$H$_{32}$N$_2$O$_7$Si m/e 440.1979, obsd m/e 440.1903.

(2S) (4R)-N-(2-Amino-4,5-dimethoxybenzoyl)-2-(tert-butyldimethylsilyloxymethyl)-4-hydroxypyrrolidine (36)

A solution of hydrazine (6.59 g, 6.40 mL, 205.5 mmol) in MeOH (110 mL) was added dropwise to a solution of the nitro-compound 35 (18.1 g, 41.1 mmol), over anti-bumping granules and Raney Ni (2.6 g) in MeOH (325 mL) and heated at reflux. After 1 hour at reflux TLC (95% CHCl$_3$/MeOH) revealed some amine formation. The reaction mixture was treated with further Raney Ni (2.6 g) and hydrazine (6.40 mL) in MeOH (50 mL) and was heated at reflux for an additional 30 minutes at which point TLC revealed reaction completion. The reaction mixture was then treated with sufficient Raney Ni to decompose any remaining hydrazine and heated at reflux for a further 1.5 h. Following cooling to room temperature the mixture was filtered through a sinter and the resulting filtrate evaporated in vacuo. The resulting residue was then treated with CH$_2$Cl$_2$ (300 mL), dried (MgSO$_4$), filtered and evaporated in vacuo to provide the amine 36 as a green oil (16.03 g, 95%): [α]$^{22}_D$=−116.32° (c=0.31, CHCl$_3$); $^1$H NMR (270 MHz, CDCl$_3$) (Rotamers) δ6.70 (s, 1H), 6.28 (s, 1H), 4.51–4.49 (m, 1H), 4.36–4.34 (m, 1H), 4.06–3.77 (m, 10H), 3.61–3.50 (m, 3H), 2.23–2.21 (m, 1H), 2.01–1.98 (m, 1H), 0.89 (s, 9H), 0.04 (s, 6H); $^{13}$C NMR (67.8 MHz, CDCl$_3$) (Rotamers) δ170.2, 151.5, 141.2, 140.5, 112.2, 112.0, 101.1, 70.4, 62.6, 59.0, 56.9, 56.6, 55.8, 35.7, 25.9 and 25.7, 18.2, −5.4 and −5.5; MS (EI), m/z (relative intensity) 412 (M$^{+\cdot}$ +2, 3), 411 (M$^{+\cdot}$ +1, 10), 410 (M$^{+\cdot}$, 32), 354 (6), 353 (23), 263 (3), 212 (5), 181 (11), 180 (100), 179 (3), 165 (3), 164 (6), 152 (10), 137 (4), 136 (4), 125 (5), 120 (3), 100 (3), 94 (6), 75 (9), 73 (7), 57 (3); IR (CHCl$_3$) 3353 (br), 2953, 2930, 2857, 1623, 1594, 1558, 1517, 1464, 1435, 1404, 1260, 1234, 1215, 1175, 1119, 1060, 1005, 915, 836, 777, 755, 666 cm$^{-1}$; exact mass calcd for C$_{20}$H$_{34}$N$_2$O$_5$Si m/e 410.2237, obsd m/e 410.2281.

(2S)(4R)-N-[(2-Allyloxycarbonylamino)-4,5-dimethoxybenzoyl]-2-(tert-butyldimethylsilyloxymethyl)-4-hydroxypyrrolidine (37)

A solution of the amine 36 (16.03 g, 39 mmol) in CH$_2$Cl$_2$ (450 mL) was cooled to 0° C. (ice/acetone) and treated with pyridine (6.94 mL, 6.78 g, 85.8 mmol). A solution of allyl chloroformate (4.35 mL, 4.94 g, 40.95 mmol) in CH$_2$Cl$_2$ (90 mL) was then added dropwise to the stirred mixture. The reaction mixture was allowed to warm to room temperature and stirred for a further 1.5 h, at which point TLC (EtOAc) revealed complete consumption of amine 36. The reaction mixture was washed with saturated CuSO$_4$ (300 mL), H$_2$O (300 mL), brine (300 mL), dried (MgSO$_4$), filtered and evaporated in vacuo. The crude residue was purified by flash chromatography (35% EtOAc/Petroleum Ether) to afford the pure alloc-amino compound 37 as a clear oil (16.78 g, 87%): [α]$^{23}_D$=−93.35° (c=0.27, CHCl$_3$); $^1$H NMR (270 MHz, CDCl$_3$) (Rotamers) δ8.93 (br s, 1H), 7.72 (S, 1H), 6.77 (S, 1H), 6.01–5.87 (m, 1H), 5.34 (dd, 1H, J=17.22, 3.12 Hz), 5.23 (dd, 1H, J=10.44, 1.29 Hz), 4.63–4.55 (m, 3H), 4.40–4.38 (m, 1H), 4.15–4.08 (m, 1H), 3.91 (S, 3H), 3.81 (s, 3H), 3.62–3.55 (m, 3H), 2.34–2.24 (m, 2H), 2.07–1.99 (m, 1H), 0.89 (s, 9H), 0.05 and 0.04 (s×2, 6H); $^{13}$C NMR (67.8 MHz, CDCl$_3$) (Rotamers) δ169.5, 153.8, 150.9, 143.8, 132.5, 118.0, 115.9, 111.0, 104.6, 70.5, 65.8, 62.2, 59.0, 57.2, 56.2, 56.0, 35.7 and 31.1, 25.8, 18.1, −5.4 and −5.5; MS (EI), m/z (relative intensity) 496 (M$^{+\cdot}$ +2, 6), 495 (M$^{+\cdot}$ +1, 18), 494 (M$^{+\cdot}$, 50), 439 (11), 438 (29), 437 (100), 380

(4), 379 (14), 337 (13), 336(4), 265 (15), 264 (91), 263 (4), 258 (6), 224 (4), 223 (15), 220 (11), 212 (7), 208 (4), 207 (11), 206 (75), 192 (5), 180 (20), 179 (18), 174 (15), 172 (4), 164 (7), 156 (5), 152 (5), 150 (6), 136 (4), 99 (9), 86 (16), 75 (10), 73 (11), 57 (6); IR ($CHCl_3$) 3337 (br), 2952, 2930, 2857, 1733, 1600, 1522, 1458, 1420, 1399, 1327, 1288, 1261, 1229, 1203, 1165, 1121, 1039, 1004, 931, 836, 777, 668 $cm^{-1}$; exact mass calcd for $C_{24}H_{38}N_2O_7Si$ m/e 494.2448, obsd m/e 494.2365.

(2S)-N-[(2-Allyloxycarbonylamino)-4,5-dimethoxybenzoyl]-2-(tert-butyldimethylsilyloxymethyl)-4-oxopyrrolidine (38)

A solution of DMSO (7.24 mL, 7.97 g, 102 mmol) in $CH_2Cl_2$ (150 mL) was added dropwise over 2 hours to a solution of oxalyl chloride (25.5 mL of a 2.0 M solution in $CH_2Cl_2$, 51.0 mmol) at −60° C. (liq.$N_2$/$CHCl_3$) under a nitrogen atmosphere. After stirring at −50° C. for 1 hour, a solution of the alcohol 37 (16.75 g, 33.9 mmol) in $CH_2Cl_2$ (250 mL) was added dropwise over a period of 2 h. After 1 hour at −55° C., the mixture was treated dropwise with a solution of TEA (32.2 mL, 23.4 g, 231 mmol) in $CH_2Cl_2$ (100 mL) and allowed to warm to room temperature. The reaction mixture was treated with brine (250 mL) and washed with cold 1N HCl (2×300 mL). TLC (50% EtOAc/Petroleum Ether) analysis of the $CH_2OC_2$ layer revealed complete reaction. The layers were separated and the organic phase washed with $H_2O$ (300 mL), brine (300 mL), dried ($MgSO_4$), filtered and concentrated in vacuo to give the ketone 38 as an orange glass (16.37 g, 98%): $[\alpha]^{21}_D$=−9.96° (c=1.51, $CHCl_3$); $^1$H NMR (270 MHz, $CDCl_3$) δ8.69 (s, 1H), 7.82 (s, 1H), 6.75 (s, 1H), 6.01–5.89 (m, 1H), 5.36 (dd, 1H, J=17.22, 3.11 Hz), 5.28–5.23 (m, 1H), 5.20–4.95 (m, 1H), 4.65–4.62 (m, 2H), 4.20–3.83 (m, 9H), 3.67–3.56 (m, 1H), 2.74 (dd, 1H, J=17.86, 9.44 Hz), 2.52 (d, 1H, J=17.95 Hz), 0.87 (s, 9H), 0.05 (s, 6H); $^{13}$C NMR (67.8 MHz, $CDCl_3$) (Rotamers) δ208.9, 169.1, 153.5, 151.3, 143.9, 132.4, 118.2, 114.4, 110.1, 104.6, 66.1, 65.8, 56.2, 56.0, 39.7, 25.6, 18.0, −5.7 and −5.8; MS (EI), m/z (relative intensity) 494 ($M^{+·}$ +2, 6), 493 ($M^{+·}$ +1, 16), 492 ($M^{+·}$, 43), 437 (8), 436 (22), 435 (74), 377 (11), 336 (6), 335 (21), 334 (8), 294 (8), 265 (9), 264 (50), 250 (5), 223 (17), 220 (18), 208 (7), 207 (15), 206 (100), 192 (9), 180 (23), 179 (28), 172 (33), 171 (10), 164 (16), 155 (7), 152 (9), 150 (16), 136 (13), 115 (14), 108 (6), 88 (6), 75 (20), 73 (33), 59 (13), 58 (6), 57 (62), 56 (14); IR (NEAT) 3337 (br, NH), 3086, 3019, 2954, 2932, 2858, 1766, 1732, 1623, 1603, 1520, 1464, 1398, 1362, 1332, 1313, 1287, 1262, 1204, 1166, 1110, 1052, 1038, 1004, 938, 870, 838, 810, 756, 666, 621, 600 $cm^{-1}$; exact mass calcd for $C_{24}H_{36}N_2O_7Si$ m/e 492.2292, obsd m/e 492.2349.

2S)-N-[(2-Allyloxycarbonylamino)-4,5-dimethoxybenzoyl]-2-(tert-butyldimethylsilyloxymethyl)-4-(methoxycarbonylmethyl)-2,3-dihydropyrrole (39)

Petroleum ether (70 mL) was added to a sample of NaH (0.41 g of a 60% dispersion in oil, 10.16 mmol) and stirred at room temperature under a nitrogen atmosphere. After 0.5 hours the mixture was allowed to settle and the Petroleum Ether was transferred from the flask via a double-tipped needle under nitrogen. THF (60 mL) was added to the remaining residue and the mixture was cooled to 0° C. (ice/acetone). The cool solution was treated dropwise with a solution of methyldiethylphosphonoacetate (1.86 mL, 2.14 g, 10.16 mmol) in THF (60 mL) under nitrogen. After 1.5 hours at room temperature, the mixture was cooled to 0° C. and treated dropwise with a solution of the ketone 38 (2.0 g, 4.07 mmol) in THF (36 mL) under nitrogen. After 16 hours at room temperature, TLC (20% EtOAc/Petroleum Ether) revealed reaction completion. The THF was evaporated in vacuo and the mixture partitioned between saturated $NaHCO_3$ (100 mL) and EtOAc (100 mL). The layers were separated and the aqueous layer extracted with EtOAc (2×100 mL). The combined organic layers were washed with $H_2O$ (100 mL), brine (100 mL), dried ($MgSO_4$), filtered and concentrated in vacuo to give a dark red oil. Purification by flash chromatography (15% EtOAc/Petroleum Ether) furnished the endo-ester 39 as a golden oil (1.63 g, 73%): $^1$H NMR (270 MHz, $CDCl_3$) (Rotamers) δ8.82 (br s, 1H), 7.86 (s, 1H), 6.79 (s, 1H), 6.46 (br s, 1H), 6.03–5.89 (m, 1H), 5.39–5.32 (m, 1H), 5.24 (dd, 1H, J=10.44, 1.28 Hz), 4.70–4.59 (m, 3H), 3.99–3.61 (m, 11H), 3.08 (s, 2H), 2.91–2.82 (m, 1H), 2.75–2.66 (m, 1H), 0.92–0.79 (m, 9H), 0.12—0.03 (m, 6H); $^{13}$C NMR (67.8 MHz, $CDCl_3$) (Rotamers) δ170.7, 165.8, 153.5, 151.3, 143.7, 132.8, 132.5, 128.2, 118.1, 118.0, 117.9, 111.3, 104.3, 65.7, 62.3, 59.5 and 59.4, 56.4, 56.0, 52.0, 34.7, 33.9, 25.8, 18.1, −5.4; MS (EI), m/z (relative intensity) 549 ($M^{+·}$ +1, 7), 548 ($M^{+·}$, 17), 525 (13), 507 (14), 492 (6), 491 (18), 489 (8), 449 (7), 347 (11), 287 (6), 286 (20), 285 (82), 265 (10), 264 (51), 263 (9), 244 (9), 242 (7), 228 (19), 227 (8), 226 (18), 224 (6), 223 (22), 220 (12), 208 (6), 207 (18), 206 (100), 192 (7), 180 (18), 179 (21), 168 (16), 164 (10),152 (13), 150 (8), 141 (8), 140 (73), 139 (13), 136 (6), 108 (6), 89 (9), 80 (15), 75 (15), 73 (19), 57 (6); exact mass calcd for $C_{27}H_{40}N_2O_8Si$ m/e 548.2554, obsd m/e 548.2560.

(2S)-N-[(2-Allyloxycarbonylamino)-4,5-dimethoxybenzoyl]-2-(hydroxymethyl)-4-(methoxycarbonylmethyl)-2,3-dihydropyrrole (40)

A solution of the silyl ether 39 (1.63 g, 2.97 mmol) in THF (12.6 mL) was treated with $H_2O$ (12.6 mL) and glacial acetic acid (38 mL). After 2 hours stirring at room temperature TLC (60% EtOAc/Petroleum Ether) showed the complete consumption of starting material. The mixture was cooled (ice) and treated dropwise with a solution of $NaHCO_3$ (61.6 g) in $H_2O$ (616 mL). The aqueous solution was extracted with EtOAc (3×150 mL) and the combined organic layers were washed with $H_2O$ (150 mL), brine (100 mL), dried ($MgSO_4$), filtered and concentrated in vacuo to give the crude alcohol 40 as an orange oil (1.27 g, 98%): MS (EI), m/z (relative intensity) 435 ($M^{+·}$ +1, 6), 434 ($M^{+·}$, 23), 347 (5), 317 (4), 281 (6), 265 (8), 264 (44), 263 (8), 224 (5), 223 (24), 222 (5), 220 (9) 207 (15), 206 (94), 192 (5), 180 (18), 179 (18), 172 (12), 171 (100), 164 (12), 152 (7), 150 (7), 141 (6), 140 (53), 136 (9), 112 (11), 108 (6), 80 (12), 69 (7); exact mass calcd for $C_{21}H_{26}N_2O_8$ m/e 434.1689, obsd m/e 434.1606.

(11S,11aS)-10-Allyloxycarbonyl-7,8-dimethoxy-11-hydroxy-2-(methoxycarbonylmethyl)-1,10,11,11a-tetrahydro-5H-pyrrolo[2,1-c][1,4]benzodiazepin-5-one (41)

A solution of DMSO (0.75 mL, 0.82 g, 10.5 mmol) in $CH_2Cl_2$ (22 mL) was added dropwise over 1 hour 20 minutes to a solution of oxalyl chloride (2.63 mL of a 2.0 M solution in $CH_2Cl_2$, 5.26 mmol) at −45° C. (liq.$N_2$/Chlorobenzene) under a nitrogen atmosphere. After stirring at −45° C. for 1 h, a solution of the alcohol 40 (1.27 g, 2.92 mmol) in $CH_2Cl_2$ (22 mL) was added dropwise over 1 hour at −45° C. After 50 minutes at −45° C., the mixture was treated dropwise with a solution of TEA (1.71 mL, 1.24 g, 12.29 mmol) in $CH_2Cl_2$ (11 mL) over 30 minutes at −45° C. After a further 30 minutes, the reaction mixture was allowed to warm to room temperature and was diluted with $CH_2Cl_2$ (20 mL), washed with 1N HCl (100 mL), $H_2O$ (100 mL), brine (100 mL), dried ($MgSO_4$), filtered and evaporated in vacuo. TLC (80% EtOAc/Petroleum Ether) of the crude material revealed reaction completion. Purification by flash chromatography (55% EtOAc/Petroleum Ether) furnished the protected carbinolamine 41 as a white glass (0.68 g, 54%): $[\alpha]^{22}_D$=+219.78° (c=0.12, $CHCl_3$); $^1$H NMR (270

MHz, CDCl₃) δ7.23 (s, 1H), 6.91 (s, 1H), 6.70 (s, 1H), 5.90–5.80 (m, 2H), 5.17–5.13 (m, 2H), 4.70 (dd, 1H, J=13.37, 5.31 Hz), 4.50–4.43 (m, 1H), 3.98–3.75 (m, 8H), 3.71 (s, 3H), 3.20–3.05 (m, 3H), 2.75 (d, 1H, J=17.04 Hz); $^{13}$C NMR (67.8 MHz, CDCl₃) δ170.7, 163.3, 155.9, 151.1, 148.5, 131.7, 128.3, 126.2, 124.7, 118.1, 117.6, 112.6, 110.6, 86.0, 66.8, 59.4, 56.2, 52.1, 37.0, 33.7; MS (EI), m/z (relative intensity) 434 (M$^{+\cdot}$ +2, 6), 433 (M$^{+\cdot}$ +1, 21), 432 (M$^{+\cdot}$, 74), 414 (8), 373 (14), 329 (7), 293 (20), 292 (20), 265 (19), 264 (100), 263 (33), 248 (25), 224 (6), 223 (25), 220 (14), 209 (8), 208 (52), 207 (24), 206 (92), 192 (15), 191 (6), 190 (7), 180 (18), 179 (23), 169 (23), 165 (10), 164 (17), 152 (12), 150 (14), 149 (8), 141 (9), 140 (60), 136 (11), 125 (6), 120 (5), 110 (8), 108 (15), 81 (9), 80 (45), 57 (7); IR (CHCl₃) 3385 (br), 2918, 2849, 1707, 1625, 1605, 1516, 1457, 1436, 1405, 1311, 1282, 1245, 1217, 1172, 1116, 1046, 1001, 968, 933, 874, 855, 666 cm$^{-1}$.

(11aS)-7,8-Dimethoxy-2-(methoxycarbonylmethyl)-1,2,3,11a-tetrahydro-5H-pyrrolo[2,1-c][1,4]benzodiazepin-5-one (42, UP2065, AN-SJG)

A catalytic amount of tetrakis(triphenylphosphine)palladium (44.0 mg, 38.0 μmol) was added to a stirred solution of the Alloc-protected carbinolamine 41 (0.66 g, 1.53 mmol), triphenylphosphine (20.0 mg, 77.0 μmol) and pyrrolidine (114 mg, 1.60 mmol) in CH₂Cl₂ (100 mL). After 2 hours stirring at room temperature under a nitrogen atmosphere, TLC (99% CHCl₃/MeOH) revealed the complete consumption of starting material. The solvent was evaporated in vacuo and the crude residue was purified by flash chromatography (98% CHCl₃/MeOH) to afford the PBD (42, AN-SJG, UP2065) as an orange glass which was repeatedly evaporated in vacuo with CHCl₃ in order to provide the N10-C11 imine form (481 mg, 95%): [α]$^{22}_D$=+ 401.84° (c=1.00, CHCl₃); $^1$H NMR (270 MHz, CDCl₃) δ7.87–7.85 (m, 1H), 7.49 (s, 1H), 6.93 (s, 1H), 6.81 (s, 1H), 4.34–4.27 (m, 1H), 3.95 (s, 3H), 3.93 (s, 3H), 3.74 (s, 3H), 3.34 (d, 1H, J=16.85 Hz), 3.24 (s, 2H), 3.19–3.10 (m, 1H); $^{13}$C NMR (67.8 MHz, CDCl₃) δ170.6, 162.7, 161.4, 151.8, 147.7, 140.4, 126.5, 119.0, 117.4, 111.5, 109.8, 56.2, 56.1, 53.8, 52.1, 37.4, 33.6; MS (EI), m/z (relative intensity) 332 ($^{+\cdot}$ +2, 5), 331 (M$^{+\cdot}$ +1, 9), 330 (M$^{+\cdot}$, 41), 329 (28), 328 (100), 313 (18), 272 (8), 271 (24), 270 (14), 269 (27), 262 (7), 257 (12), 255 (5), 242 (6), 225 (7), 197 (4), 192 (16), 191 (16), 183 (6), 164 (14), 136 (11), 135 (9), 106 (9), 80 (17), 53 (5); IR (CHCl₃) 3329 (br), 3112, 2952, 2842, 1737, 1626, 1602, 1512, 1453, 1436, 1381, 1356, 1246, 1213, 1173, 1096, 1069, 1008, 875, 840, 786, 666, 620, 574, 537 cm$^{-1}$; exact mass calcd for C₁₇H₁₈N₂O, m/e 330.1216, obsd m/e 330.1237.

Figure 5A:
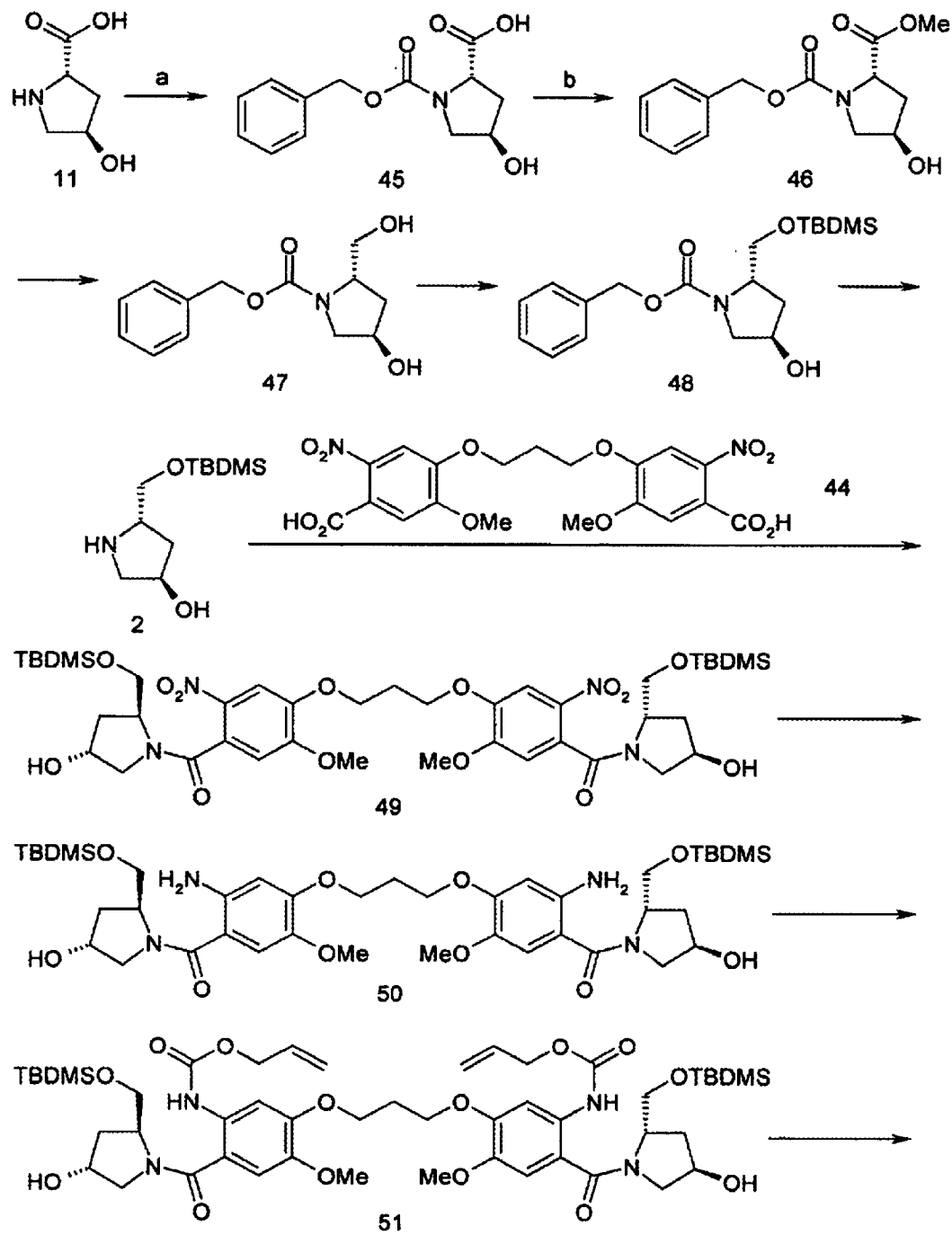
Figure 5B:
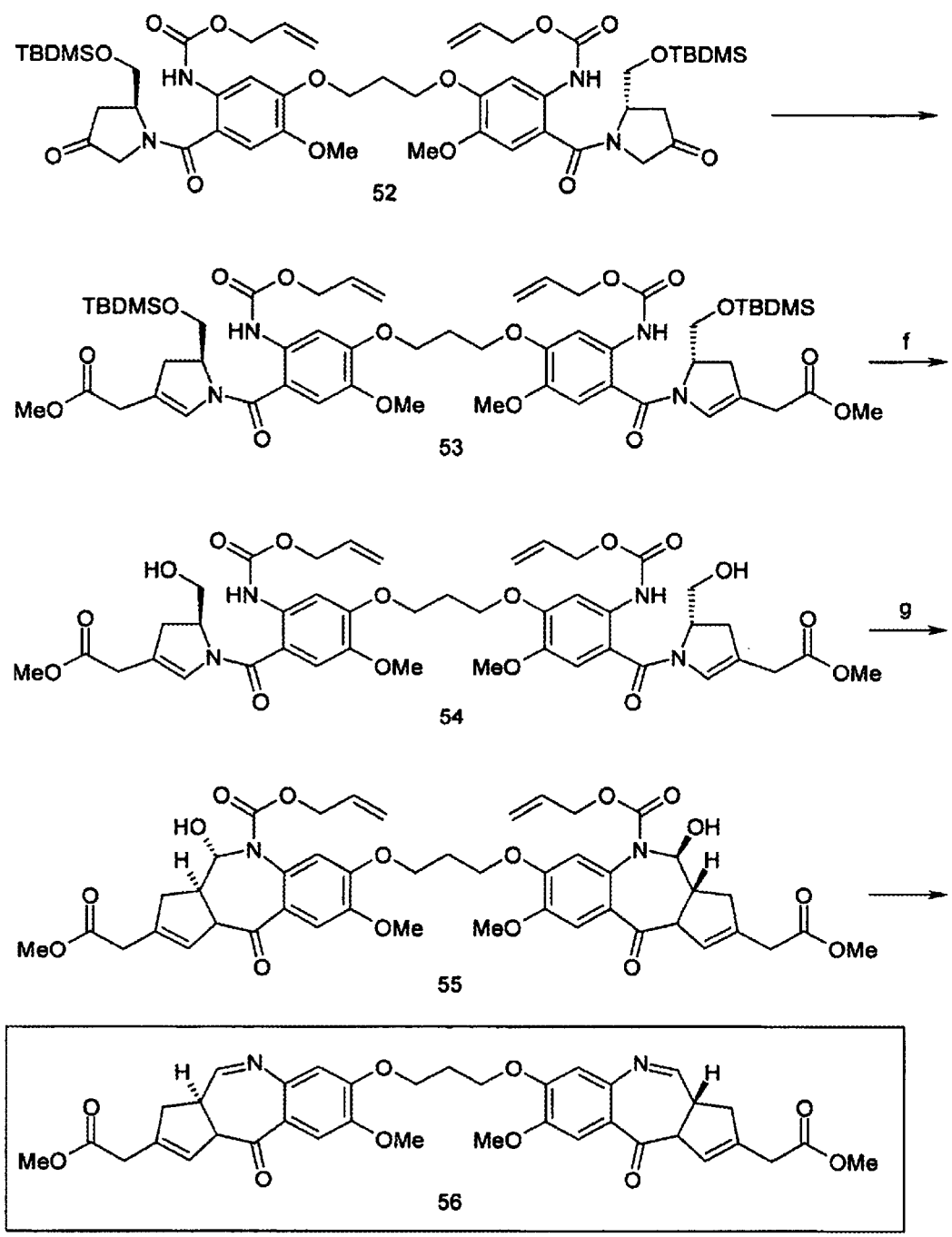

Example 1(f)
Synthesis of KEC-570 (56, UP-2053) (See FIG. 5a/5b)

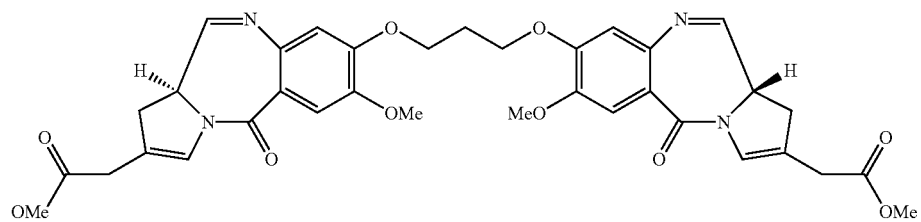

1',3'-Bis(4-carboxy-2-methoxyphenoxy)propane (43)

A solution of diiodopropane (8.79 g, 29.7 mmol) in THF (50 mL), was added dropwise over a period of 4 hours to a vigorously stirred solution of vanillic acid (10 g, 59.5 mmol) in THF (100 mL) and aqueous NaOH (225 mL, 0.5 M) at 65° C. in the absence of light (foil-wrapped flask). After heating at reflux for 48 hours in the dark, the suspension was cooled, washed with hexane (3×100 mL) and the THF removed by evaporation in vacuo. The aqueous residue was acidified to pH 1 with conc. HCl and the resultant precipitate collected by filtration, dried and recrystallised from glacial acetic acid to afford the corresponding bis-carboxylic acid (143) as a white crystalline solid (9.4 g, 84%). mp 238–240° C.; $^1$H-NMR (DMSO-d₆): δ2.23 (t, 2H, J=6.0 Hz, H13), 3.80 (s, 6H, CH₃O), 4.20 (t, 4H, J=6.0 Hz, H12), 7.09 (d, 2H, J=8.4 Hz, H10), 7.45 (d, 2H, J=1.8 Hz, H6) 7.54 (dd, 2H, J=8.4 Hz, 1.8 Hz, H9), 12.76 (bs, 2H, CO₂H); $^{13}$C-NMR (DMSO-d₆) δ28.4 (C13), 55.4 (CH₃O), 64.8 (C12), 111.9 (C9), 112.0 (C6), 122.9 (C10), 123.0 (Q), 148.3 (Q), 151.6 (Q), 167.0 (C=O). IR (KBr): ν=3600–2000, 1680 (C=O), 1600 (C=C), 1515, 1465, 1430, 1345, 1310, 1270, 1225 (C—O—C), 1180, 1140, 1115, 1030, 990, 970, 950, 925, 875, 850, 825, 765, 725, 645 cm$^{-1}$. MS (EI): m/z (relative intensity) 376 (M$^{+\cdot}$, 28), 360 (3), 249 (2), 209 (45), 165 (29), 153 (16), 151 (19), 137 (19), 121 (7), 78 (15), 44 (100); HRMS: Calcd for C₁₉H₂₀O₈=376.1158 found 376.1168.

1',3'-Bis(4-carboxy-2-methoxy-5-nitrophenoxy)propane (44)

The diacid 43 (2.0 g, 5.30 mmol) was added portionwise to conc. HNO₃ (40 mL) at −10° C. and stirred to room temperature over 12 h. The reaction mixture was poured on to ice (400 mL) and the resulting precipitate collected by filtration, washed with ether (3×50 mL) and dried to afford the nitro acid (121) as a yellow solid (1.73 g, 70%). m.p. 243–2460C. $^1$H-NMR (DMSO-d₆): δ2.25 (t, 2H, J=5.9 Hz, H13), 3.90 (s, 6H, CH₃O), 4.27 (t, 4H, J=5.9 Hz, H12), 7.29 (s, 2H, H6), 7.62 (s, 2H, H9), 13.6 (bs, 2H, CO₂H). —C-NMR (DMSO-d₆) δ28.0 (C13), 56.3 (CH₃O), 65.7 (C12), 108.0 (C9), 111.2 (C6), 121.1 (C5), 141.3(Q), 149.1 (C8), 151.7 (O), 165.9 (C=O). IR (KBr): ν=3620–2280, 1700 (C=O), 1595 (C=C), 1570, 1515 (NO₂), 1460, 1415, 1350 (NO₂), 1270, 1210, 1180, 1135, 1045, 930, 880, 810, 750, 730, 645 cm$^{-1}$. MS (EI): m/z (relative intensity) 467 (MH$^{+\cdot}$, 1), 450 (1), 436 (3), 423 (8), 378 (4), 268 (1), 255 (4), 236 (4), 210 (7), 194 (2), 182 (7), 164 (14), 153 (2), 123 (3), 91 (6), 77 (3), 55 (5), 44 (100). HRMS (EI) m/z calcd for C₁₉H₁₈N₂O₁₂=466.0860 found 466.0871.

(2S,4R)-N-(Benzoxycarbonyl)-2-carboxy-4-hydroxypyrrolidine (45)

A solution of benzyl chloroformate (12.5 mL, 87.7 mL) in toluene (40 mL) was added to a solution of trans-4-hydroxy-L-proline 11 (10 g, 76.3 mmol) and NaHCO₃ (16 g, 190 mmol) in H₂O (165 mL) over a period of 15 minutes. After stirring at room temperature for 12 hours the two phases were allowed to separate. The aqueous phase was washed with diethyl ether (4×50 mL), cooled in an ice bath, and then acidified to pH 2 with conc. HCl. The resultant product was extracted with ethyl acetate (5×50 mL) and the combined organic extracts were dried (MgSO$_4$) and the excess solvent evaporated in vacuo to afford a colourless viscous oil (20.30 g, 100%). [α]$^{27}_D$=−565° (c 0.1, MeOH). $^1$H NMR (CDCl$_3$): δ2.07–2.31 (m, 3H, H1), 3.52–3.59 (m, 2H, H3), 4.43–4.53 (m, 2H, H2, H11a), 5.8 and 5.11 (s, 2H, minor and major rotamers of H6, 1:2), 6.0 (bs, 2H, OH), 7.26–7.29 and 7.32–7.34 (m, 5H, minor and major rotamers of H arom, 1:2). IR (thin film): ν=3414 (OH), 2940 (OH), 1682 (C=O), 1495, 1429, 1359 (CO$_2$−), 1314, 1269, 1205, 1180, 1174, 1127, 1082, 1051, 993, 914, 866, 826, 769, 741, 697 cm$^{-1}$. MS (EI): m/e (relative intensity): 266 (M$^+$, 1), 265 (6), 220 (5), 176 (15), 130 (34), 108 (2). 91 (100), 86 (4), 68 (11). HRMS calcd. for C$_{13}$H$_{15}$NO$_5$=265.0950 found 265.0976.

(2S,4R)-N-(Benzoxycarbonyl)-2-methyoxycarbonyl-4-hydroxyproline (46)

A solution of (2S,4R)-N-(Benzoxycarbonyl)-2-carboxy-4-hydroxypyrrolidine (45) (20.30 g, 76.3 mmol) in dry methanol (300 mL) was heated at reflux for 18 hours in the presence of a catalytic amount of conc. H$_2$SO$_4$ (2.20 mL, 7.63 mmol). The reaction mixture was allowed to cool to room temperature and neutralised with Et$_3$N (3.0 mL, 76.3 mmol). The reaction mixture was concentrated in vacuo and the residue redissolved in ethyl acetate (200 mL), washed with brine (1×50 mL), dried (MgSO$_4$) and excess solvent removed under reduced pressure to afford a colourless gum (21.17 g, 99%). [α]$^{20}_D$=−59.4° (c 0.014, CHCl$_3$). $^1$H NMR (CDCl$_3$): δ2.04–2.08 and 2.24–2.35(m, 1H, rotamers of H1, 1:1), 2.64 (bs, 1H, OH), 3.54 and 3.74 (s, 3H, rotamers of OMe, 1:1), 3.66–3.69 (m, 2H, H3), 4.47–4.50 (m, 2H, H2, H11a), 5.07–5.13 (m, 2H, H6), 7.26–7.35 (m, 5H, H arom). $^{13}$C NMR (CDCl$_3$): rotamer ratio 1:1, δ37.8 and 38.5 rotamers of (C1), 51.8 and 52.0 rotamers of (OMe), 54.1 and 54.7 rotamers of (C3), 57.4 and 57.7 rotamers of (C2), 66.9 and 67.0 rotamers of (C6), 68.6 and 69.3 rotamers of (C11a), 127.0, 127.3, 127.4, 127.7, 127.8, 128.0 and 128.1 rotamers of (C arom). IR (thin film): ν=3435 (OH), 3033, 2953 (OH), 1750 (ester), 1680 (C=O), 1586, 1542, 1498, 1422, 1357 (CO$_2$H), 1170, 1124, 1084, 1052 (C—O), 1004, 963, 916, 823, 770, 750, 699, 673 cm$^{-1}$. MS (FAB) m/z (relative intensity): 280 (M$^+$, 24), 236 (20), 234 (4), 216 (8), 214 (4), 213 (2), 206 (2), 204 (7), 203 (4), 202 (10), 201 (2), 181 (5), 144 (16), 102 (23), 91 (100). HRMS calcd. for C$_{14}$H$_{17}$NO$_5$= 279.1107 found 279.1192.

(2S,4R)-N-(Benzoxycarbonyl)-2-hydroxymethyl-4-hydroxyproline (47)

Lithium borohydride (1.57 g, 73 mmol) was added portionwise to a solution of (2S,4R)-N-(benzoxycarbonyl)-2-methyoxycarbonyl-4-hydroxyproline (46) (20.17 g, 73 mmol) in THF (350 mL) at 0° C. The reaction mixture was allowed to warm to room temperature and stir overnight. The resulting suspension was cooled to 0° C. and quenched with water (2–3 mL) until effervescence ceased, at which point 2 M HCl (15 mL) was added to dissolve the precipitate. The product was extracted with ethyl acetate (3×150 mL) and the combined organic phases washed with brine (1×100 mL) and then dried (MgSO$_4$). Concentration in vacuo afforded a white gum (18.25 g, 100%). [α]$^{22.3}_D$=−404° (C=0.043, CHCl$_3$). $^1$H NMR (CDCl$_3$): δ1.24–1.26 (m, 1H, H1), 1.73–2.08 (m, 1H, H1), 3.40–4.30 (m, 6H, H2, H3, H11, H11a), 5.06 (bs, 1H, OH), 5.09 (s, 2H, H6) 7.25–7.31 (m, 5H, H arom). $^{13}$C NMR (CDCl$_3$): δ36.7 (C1), 55.2 (C3), 58.7 (C2), 65.0 (C11), 67.0 (C6), 68.7 (C11a), 127.0, 127.5 (C arom), 127.8 (C arom), 128.2 (C arom). IR (thin film): ν=3390 (OH), 3065, 3033, 2953 (OH), 1681 (C=O carbamate), 1586, 1538, 1498, 1454, 1192, 1122, 978, 914, 862, 770, 698, 673 cm$^{-1}$. MS (FAB) m/z (relative intensity): 252 (M$^+$, 58), 208 (33), 176 (5), 144 (6), 118 (8), 116 (7), 92 (13), 91 (100). HRMS calcd. for C$_{13}$H$_{17}$NO$_4$=251.1158 found 251.1230.

(2S,4R)-N-Benzoxycarbonyl-2-t-butyldimethylsilyloxymethyl-4-hydroxypyrrolidine (48)

t-butyldimethylsilyl chloride (5.78 g, 38.3 mmol) and 1,8-diazabicyclo[5,4,0]undec-7-ene (1.44 mL, 9.6 mmol) were added to a solution of alcohol (47) (12.51 g, 49.8 mmol) and triethylamine (7.0 mL, 49.8 mmol) in dry DCM (200 mL) which had been allowed to stir for 15 minutes at room temperature. The resulting mixture was allowed to stir at room temperature for 18 hours and then diluted with ethyl acetate (300 mL). The organic phase was washed with aqueous saturated ammonium chloride (2×100 mL) and brine (1×100 mL) dried (MgSO$_4$) and the solvent removed under reduced pressure to yield a colourless viscous oil (9.84 g, 70%). [α]$^{22.3}_D$=−263° (c 0.70, CHCl$_3$). $^1$H NMR (CDCl$_3$): δ−0.05 and −0.06(s, 6H, rotamers of H1', H2', 1:1), 0.83 and 0.85 (s, 9H, rotamers of H3', H5', H6', 1:1), 1.95–2.22 (m, 2H, H1,), 2.78 (bs, 1H, OH), 3.44–3.68 (m, 3H, H3, H11), 3.99–4.10 (m, 1H, H2), 4.43–4.46 (m, 1H, H11a), 5.11–5.16 (m, 2H, H6) 7.34–7.35 (m, 5H, H arom) $^{13}$C NMR (CDCl$_3$): rotamer ratio of 1:1, 5–5.50 (C3', C5', C6'), 18.15 (C4'), 25.83 (C1', C2'), 36.55 and 37.27 rotamers of (C1), 55.2 and 55.7 rotamers of (C3), 57.3 and 57.8 rotamers of (C2), 62.8 and 63.9 rotamers of (C11), 66.6 and 67.0 rotamers of (C6), 69.7 and 70.3 rotamers of (C11a), 127.8 (C arom), 127.9 (C arom), 128.0 (C arom), 128.4 (C arom), 128.5 (C arom), 136.5 and 136.8 rotamers of (C7), 154.9 and 155.2 rotamers of (C5). IR (thin film): ν=3415 (OH), 3066, 3034, 2953 (OH), 2930, 2884, 2857, 1703 (C=O carbamate), 1587, 1498, 1424, 1360 (C—CH$_3$), 1288 (CH$_3$Si), 1255 (t-Bu), 1220, 1195 (t-Bu), 1118 (Si—O), 1057, 1003, 917, 836, 774, 751, 698, 670 cm$^{-1}$. MS (EI/CI) m/e (relative intensity): 366 (M$^+$, 100), 308 (14), 258 (2), 91 (2).

(2S,4R)-2-t-butyldimethylsilyloxymethyl-4-hydroxypyrrolidine (2)

A slurry of 10% Pd/C (190 mg) in ethyl acetate (20 mL) was added to a solution of TBDMS ether (48) (1.90 g, 5.19 mmol) in ethanol (100 mL). The reaction mixture was hydrogenated (Parr apparatus) for 16 h. The catalyst was removed by vacuum filtration through Celite and excess solvent was evaporated under reduced pressure to give a yellow oil in quantitative yield (1.20 g, 100%). [α]$^{22}_D$=+35.6° (c 0.042, CHCl$_3$). $^1$H NMR (CDCl$_3$): δ-(0.07–0.08) (m, 6H, H1', H2'), 0.82 (s, 9H, H3', H4', H5'), 1.68–1.73 (m, 2H, H1,), 2.99–3.11 (m, 2H, H11), 3.47–3.50 (m, 3H, H11a, H3), 4.09 (bs, 1H, NH or OH), 4.32 (bs, 1H, NH or OH). $^{13}$C NMR (CDCl$_3$): δ−5.4 (C3', C5', C6'), 18.1 (C4'), 25.8 (C1', C2'), 37.4 (C1), 54.6 (C11), 58.1 (C2), 64.6 (C3), 72.2 (C11a). IR (thin film): ν=3330 (OH), 2928, 2857, 1557, 1421, 1331 (C—CH$_3$), 1249 (CH$_3$—Si), 1204 (t-Bu), 1191 (t-Bu), 1100 (Si—O), 1073, 993, 713 cm$^{-1}$. MS (CI) m/e (relative intensity): 232 (M$^+$, 100), 230 (13), 174 (5), 133 (6), 86 (6).

1,1'-[[(Propane-1,3-diyl)dioxy]bis[2-nitro-5-methoxy-1,4-phenylene)carbonyl]]-bis (2S,4R)-2-t-butyldimethylsilyloxymethyl-4-hydroxypyrrolidine (49)

A catalytic amount of DMF (2 drops) was added to a stirred suspension of bis-nitroacid (44) (2.00 g, 4.28 mmol) and oxalyl chloride (0.94 mL, 10.70 mmol) in dry THF (20 mL), and the reaction mixture was allowed to stir for 4 h. After evaporation of excess THF in vacuo, the resultant yellow residue was dissolved in dry THF (20 mL) and added dropwise over a period of 25 minutes to a vigorously stirred suspension of amine (2) (2.47 g, 10.70 mmol), Et$_3$N (2.50 mL, 17.9 mmol) and ice/water (0.6 mL) cooled in an ice bath. The mixture was then allowed to warm to room temperature for a further 1.5 h. After removal of the THF by evaporation in vacuo, the residue was diluted with water (100 mL) and extracted with ethyl acetate (3×100 mL). The combined organic phase was washed with water (3×25 mL) and brine (3×25 mL), dried (MgSO$_4$), and the solvent removed in vacuo to afford a yellow oil which was purified by flash chromatography (3% MeOH/CHCl$_3$) to afford the bis-amide (49) as a yellow solid (2.05 g, 54%). $[\alpha]^{23.8}{}_D$=−993° (c 0.033, CHCl$_3$). $^1$H NMR (CDCl$_3$): δ−0.05 (s, 12H, H1', H2'), 0.80 (s, 18H, H3', H5', H6'), 1.96–1.99 (m, 2H, H1), 2.14–2.16(m, 2H, H1), 2.19–2.24 (m, 2H, H13), 2.85–2.89 (m, 2H, H2) 3.16–3.19 (m, 4H, H11), 3.63–3.66 (m, 4H, H3), 3.81 (s, 6H, OMe), 3.99–4.10 (m, 2H, H3), 4.23 (t, 4H, J=5.3 Hz, Hi2), 4.38 (bs, 2H, OH); 5.20–5.25 (m, 2H, H11a), 6.65 (s, 2H, H6), 7.55 (s, 2H, H9). $^{13}$C-NMR (CDCl$_3$): 5–5.35 (C1', C2'), 18.2 (C4'), 25.8 (C3', C5', C6'), 28.9 (C13), 36.1 (C1), 54.9 (CH$_3$O), 56.6 (C4), 57.3 (C12), 65.0 (C3), 70.0 (C2), 108.0 (C6), 109.4 (C9), 128.2 (Q), 137.2 (Q), 148.1 (Q), 148.5 (Q), 154.5 (Q), 166.5 (Q). IR (thin film): ν=3392 (OH), 2950, 2856, 1623 (C=O), 1577 (C arom), 1524 (NO$_2$), 1459, 1432, 1381, 1338 (C—CH$_3$), 1278 (CH$_3$—Si), 1219 (t-Bu), 1184 (t-Bu), 1075 1053, 1004, 938, 914, 837, 778, 724, 668, 649, cm$^{-1}$. MS (FAB) m/z (relative intensity): 894 (M$^{+\cdot}$, 8), 893 (19), 878 (6), 835 (2), 779 (9), 761 (6), 517 (3), 459 (5), 258 (7), 100 (3), 86 (4), 75 (29), 73 (100), 59 (17), 58 (6).

1,1'-[[(Propane-1,3-diyl)dioxy]bis[2-amino-5-methoxy-1,4-phenylene)carbonyl]]-bis[(2S,4R)-2-t-butyldimethylsilyloxymethyl-4-hydroxypyrrolidine (50)

A slurry of 10% Pd/C (155 mg) in ethyl acetate (20 mL) was added to a solution of the bis-amide (49) (1.55 g, 1.73 mmol) in ethanol (100 mL). The reaction mixture was hydrogenated (Parr apparatus) for 16 h. The reaction mixture was filtered through Celite and the solvent was removed under reduced pressure to give a yellow oil (50) in quantitative yield (1.44 g, 100%). $^1$H NMR (CDCl$_3$): δ0.00 (s, 12H, H1', H2'), 0.88 (s, 18H, H3', H5', H6'), 2.00–2.25 (m, 6H, H1, H13), 3.50–3.72 (m, 12H, H2, H3, H11, H11a), 3.74 (s, 6H, OMe), 4.16–4.20 (m, 4H, H3), 4.30–4.35 (m, 4H, H12), 4.49 (bs, 2H, OH); 6.23 (S, 2H, H9), 6.64 (s, 2H, H6) $^{13}$C-NMR (CDCl$_3$): 3–5.5 (C1', C2'), 18.1 (C4'), 25.8 (C3', C5', C6'), 29.6 (C13), 35.2 (C1), 56.7 (CH$_3$O), 62.2 (C4), 64.1 (C3), 70.0 (C2), 102.2 (C6), 112.6 (C6), 140.4 (Q), 141.1 (Q), 150.6 (Q), 170.1 (Q); IR (neat): ν=3359 (OH), 2929, 2856, 1621 (C=O), 1591 (C arom), 1469, 1433, 1406, 1358, 1346 (C—CH$_3$), 1261 (CH$_3$—Si), 1232 (t-Bu), 1175 (t-Bu), 1117, 1056, 1006, 866, 835, 776 cm$^{-1}$. MS (FAB) m/z (relative intensity): 834 (M$^{+\cdot}$, 13), 833 (18), 773 (9), 602 (13), 399 (7), 371 (34), 232 (9), 206 (22), 192 (14), 176 (13), 166 (44), 150 (8), 100 (10), 73 (100).

1,1'-[[(Propane-1,3-diyl)dioxy]bis[2-amino-N-allyloxycarbonyl-5-methoxy-1,4-phenyl-ene)-carbonyl]]-bis[(2S,4R)-2-t-butyldimethylsilyloxymethyl-4-hydroxypyrrolidine (51)

A solution of the bis-amide (50) (2.76 g, 3.31 mmol) and pyridine (1.10 mL, 13.60 mmol) in dried DCM (100 mL) was cooled to 0° C. Allyl chloroformate (0.80 mL, 7.53 mmol) in DCM (50 mL) was added dropwise and the resulting mixture allowed to warm to room temperature and stirred for 16 h. The reaction mixture was diluted with DCM (200 mL) and washed with 1 M CuSO$_4$ (3×50 mL), water (1×50 mL) and brine (1×50 mL) before drying (MgSO$_4$). Evaporation of the solvent under reduced pressure followed by flash column chromatography (2.5% MeOH/DCM) afforded (51) as a yellow solid (3.24 g, 97%). $[\alpha]^{21.1}{}_D$=−571° (c 0.007, CHCl$_3$). $^1$H NMR (CDCl$_3$): δ0.00 (s, 12H, H1', H2'), 0.89 (s, 18H, H3', H5', H6'), 2.03–2.36 (m, 6H, H1, H13), 3.51–3.58 (m, 6H, H2, H3), 3.77 (s, 6H, OMe), 4.20–4.26 (m, 8H, H11, H12), 4.28–4.30 (m, 2H, H11a), 4.56–4.60 (m, 6H, H8', OH), 5.25 (dd, J$_{1,2}$=1.5 Hz, J$_{1,3}$=15.0 Hz, 4H, H10'), 5.90–5.95 (m, 2H, H9'), 6.73 (s, 2H, H6), 7.63 (s, 2H, H9), 8.80 (s, 2H, NH). $^{13}$C NMR (CDCl$_3$): 5–5.42 (C1', C2'), 25.8 (C3', C5', C6'), 29.2 (C13), 35.4 (C1), 56.3 (CH$_3$O), 57.1 (C11a), 59.8 (C11), 62.2 (C3), 65.1 (C12), 65.7 (C8'), 70.5 (C2), 106.3 (C9), 111.5 (C6), 116.5 (Q), 118.1 (C10'), 131.7 (Q), 132.5 (C9'), 144.3 (Q), 150.3 (Q), 153.8 (Q), 169.5 (Q). IR (neat): ν=3351 (OH), 2931, 2857, 1762 (Alloc C=O), 1722, 1603 (C=O), 1521 (C arom), 1463, 1404, 1264 (CH$_3$—Si), 1222 (t-Bu), 1106 (t-Bu), 1053, 1015, 936, 872, 837, 775, 629, cm$^{-1}$.

1,1'-[[(Propane-1,3-diyl)dioxy]bis[2-amino-N-allyloxycarbonyl-5-methoxy-1,4-phenylene)-carbonyl]]-bis[(2S)-2-t-butyldimethylsilyloxymethyl-4-oxo-pyrrolidine (52)

A solution of dimethyl sulphoxide (2.10 mL, 28.5 mmol) in dry DCM (20 mL) was added dropwise over a 15 minutes period to a stirred, cooled (−45° C.) solution of oxalyl chloride (1.27 mL, 14.60 mmol) in DCM (30 mL). After 35 minutes, a solution of alcohol (51) (2.54 g, 2.53 mmol) in DCM (20 mL) was added dropwise over a period of 15 minutes to the reaction mixture at −45° C. After 45 minutes a solution of triethylamine (5.75 mL, 40.3 mmol) in DCM (20 mL) was added over a period of 15 minutes and the reaction mixture stirred at −45° C. for 30 minutes before warming to room temperature over 45 minutes. The mixture was then washed with 1 M CuSO$_4$ (3×50 mL), water (2×50 mL) and brine (1×50 mL) before drying (MgSO$_4$) and concentrating in vacuo to give (52) as a yellow solid (2.46 g, 97%). $^1$H NMR (CDCl$_3$): δ0.00 (s, 12H, H1', H2'), 0.86 (s, 18H, H3', H5', H6'), 2.50–2.63 (m, 6H, H1, H13), 3.63–3.70 (m, 4H, H3), 3.80 (s, 6H, OMe), 3.93–3.97 (m, 6H, H$_{11}$, H11a), 4.29–4.32 (m, 4H, H12), 4.62 (d, 4H, J=5.7 Hz, H8'), 5.27–5.32 (m, 4H, H10'), 5.98–6.03 (m, 2H, H9'), 6.74 (s, 2H, H6), 7.74 (s, 2H, H9), 8.80 (s, 2H, NH). $^{13}$C NMR (CDCl$_3$): δ−5.76 (C1', C2'), 18.0 (C4'), 25.7 (C3', C5', C6'), 28.8 (C13), 39.6 (C1), 55.0 (C3), 56.4 (CH$_3$O), 65.3 (C12), 65.8 (C8'), 105.9 (C9), 110.7 (C6), 118.2 (C10'), 132.4 (C9'), 150.7 (Q), 153.5 (Q), 169.1 (Q), 210.0 (C2). IR (neat): ν=3308 (OH), 2931, 2856, 1765 (Alloc C=O), 1730, 1624 (C=O), 1602 (C=O), 1522 (C arom), 1468, 1407, 1332, 1259 (CH$_3$—Si), 1204 (t-Bu), 1105 (t-Bu), 1053, 1010, 937, 870, 837, 808, 778, 674, 657 cm$^{-1}$.

1,1'-[[(Propane-1,3-diyl)dioxy]bis[2-amino-N-allyloxycarbonyl-5-methoxy-1,4-phenylene)-carbonyl]]-bis[(2S)-2-t-butyldimethylsilyloxymethyl-4-methoxycarbonyl methyl-2,3-dihydropyrrole (53)

A solution of diethylmethylphosphonoacetate (0.80 mL, 4.21 mmol) in THF (50 mL) was added to a suspension of NaH (343 mg, 4.21 mmol, 60% dispersion in mineral oil, washed with petroleum ether) in dry THF (50 mL) at 0° C. under a nitrogen atmosphere. After stirring at room temperature for 1 h, a solution of the dimer ketone (52) (2.04 g, 2.00 mmol) in THF (50 mL) was added dropwise at 0° C. The reaction mixture was allowed to warm to room temperature over 18 h. Excess THF was removed under reduced pressure and the residue cooled in an ice bath before adding NaHCO$_3$ (50 mL) followed by EtOAc (50 mL). The layers were separated and the aqueous layer washed with EtOAc (2×50 mL). The combined organic layers were washed with brine (1×50 mL), dried (MgSO$_4$) and the solvent removed in vacuo to give a yellow oil. Flash column chromatography (2.5% MeOH/CH$_2$Cl$_2$) afforded the product (53) as a yellow solid (2.00 g, 88%). $^1$H NMR (CDCl$_3$): δ−0.01 (s, 12H, H1', H2'), 0.83 (s, 18H, H3', H5', H6'), 2.35–2.40 (m, 2H, H13), 2.65–2.86 (m, 4H, H1), 3.03–3.09 (m, 4H, H14), 3.62 (s, 3H, OMe), 3.75 (s, 6H, H16), 3.95–4.10 (m, 4H, $H_{11}$), 4.24–4.35 (m, 4H, H12), 4.58–4.70 (m, 6H, H8', H11a), 5.25–5.33 (m, 4H, H10'), 5.93–5.97 (m, 2H, H9'), 6.33–6.40 (m, 2H, H3), 6.74 (s, 2H, H6), 7.80 (s, 2H, H9), 8.75 (s, 2H, NH). $^{13}$C NMR (CDCl$_3$): δ–5.52 (C1', C2'), 18.0 (C4'), 25.7 (C3', C5', C6'), 28.7 (C13), 33.8 (C14), 34.6 (C1), 51.9 (CH$_3$O), 56.5 (C16), 62.2 (C11), 65.2 (C12), 65.6 (C8'), 105.4 (C9), 111.9 (C6), 117.9 (C10'), 128.2 (C3), 132.5 (C9'), 143.9 (Q), 150.7 (Q), 153.4 (Q), 165.7 (Q), 170.6 (Q). IR (neat): ν=3402 (OH), 2954, 2857, 1735 (ester), 1726 (Alloc C=O), 1642, 1600, 1526 (C arom), 1469, 1435, 1354, 1256 (CH$_3$—Si), 1221, 1201 (t-Bu), 1112 (t-Bu), 1048, 1010, 934, 866, 836, 776 cm$^{-1}$. MS (FAB) m/z (relative intensity): No parent ion, 496 (10), 482 (9), 455 (11), 441 (13), 232 (12), 206 (19), 204 (10), 200 (14), 192 (34), 188 (23), 172 (33), 165 (18), 152 (17), 150 (16), 149 (100), 147 (17), 140 (20), 131 (18), 103 (22), 91 (47), 89 (27), 87 (36), 80 (33), 75 (42), 73 (77), 61 (39), 57 (53).

1,11-[[(Propane-1,3-diyl)dioxy]bis[2-amino-N-allyloxycarbonyl-5-methoxy-1,4-phenylene)-carbonyl]]-bis[(2S)-2-hydroxymethyl-4-methoxycarbonylmethyl-2,3-dihydropyrrole (54)

Hydrofluoric acid.pyridine complex (3.5 mL) was added to a solution of dimer ester (53) (740 mg, 0.67 mmol) in THF (10 mL) under a nitrogen atmosphere at 0° C. The reaction was allowed to stir for 30 minutes at 0° C. and then to warm to room temperature over 1 h. The reaction mixture was neutralised with NaHCO$_3$ until evolution of CO$_2$ ceased. The product was extracted with DCM (3×30 mL), washed with brine (1×20 mL) and then dried (MgSO$_4$). Removal of solvent under reduced pressure gave the product as a yellow gum (530 mg, 90%). $^1$H NMR (CDCl$_3$): δ2.39 (m, 2H, H13), 2.95–2.99 (m, 4H, H1), 3.09–3.12 (m, 4H, H14), 3.68 (s, 3H, OMe), 3.74–3.78 (m, 4H, H11), 3.81 (s, 6H, H16), 4.28–4.34 (m, 4H, H12), 4.62 (d, J=5.5 Hz, 4H, H8'), 4.73–4.75 (m, 2H, H11a), 5.31–5.38 (m, 4H, H10'), 5.96–6.02 (m, 2H, H9'), 6.39–6.50 (m, 2H, H3), 6.80 (s, 2H, H6), 7.72 (s, 2H, H9), 8.57 (s, 2H, NH). $^{13}$C NMR (CDCl$_3$): δ28.8 (C13), 33.5 (C14), 35.5 (C1), 52.1 (CH$_3$O), 56.6 (C16), 65.3 (C12), 66.0 (C8'), 105.6 (C9), 111.8 (C6), 118.1 (CO1'), 128.1 (C3), 132.5 (C9'), 144.4 (Q), 151.0 (Q),153.6 (Q), 167.3 (Q), 170.7 (Q). IR (neat): ν=3416 (OH), 2953, 1731 (ester), 1726 (Alloc C=O), 1606, 1525 (C arom), 1467, 1434, 1358, 1224, 1048, 938, 870, 768 cm$^{-1}$. MS (FAB) m/z (relative intensity): 881 (M$^+$, 0.2), 496 (12), 482 (15), 456 (14), 442 (13), 232 (23), 206 (35), 192 (63), 190 (21), 188 (17), 180 (19), 178 (25), 152 (39), 150 (23), 149 (100), 140 (50), 136 (21), 112 (23), 108 (23), 94 (29), 91 (32), 87 (24), 80 (70), 73 (28), 57 (30).

1,1-[[(Propane-1,3-diyl)dioxy]bis[(11aS)-7-methoxy-10-allyloxycarbonyl-(2S)-2-methoxycarbonylmethyl-2,3-dihydropyrrole-1,3,11a-trihydro-5H-pyrrolo[2,1-c][1,4]benzodiazepin-5-one (55)

A solution of dimethyl sulphoxide (0.27 mL, 3.82 mmol) in dried DCM (10 mL) was added dropwise over a 15 minutes period to a stirred, cooled (–45° C.) solution of oxalyl chloride (0.17 mL, 1.92 mmol) in DCM (10 mL). After 35 minutes, a solution of substrate (54) (600 mg, 0.68 mmol) in DCM (10 mL) was added dropwise over a period of 15 minutes to the reaction mixture at –45° C. After 45 minutes a solution of triethylamine (0.78 mL, 5.42 mmol) in DCM (10 mL) was added over a period of 15 minutes and the reaction mixture stirred at –45° C. for 30 minutes before being allowed to warm to room temperature over 45 minutes. The mixture was then diluted with water (10 mL) and the layers separated. The organic layer was washed with 1 M HCl (3×50 mL), and brine (1×50 mL) before drying (MgSO$_4$) and concentrating in vacuo. Flash column chromatography (1.5% MeOH/CH$_2$Cl$_2$) afforded a yellow glass (457 mg, 78%). [α]$^{20.3}_D$=+69° (c 0.484, CHCl$_3$). $^1$H NMR (CDCl$_3$): δ2.35–2.63 (m, 2H, H13), 2.75–3.10 (m, 4H, H1), 3.14–3.19 (m, 4H, H14), 3.71 (s, 3H, OMe), 3.88 (s, 6H, H16), 4.21–4.40 (m, 4H, H12), 4.45–4.50 (m, 2H, H11a), 4.60–4.62 (m, 4H, H8'), 5.26–5.30 (m, 4H, H10'), 5.77 (d, J=8.61 Hz, 4H, H11) 5.90–5.96 (m, 2H, H9'), 6.75–6.80 (m, 2H, H3), 6.89 (s, 2H, H9), 7.22 (s, 2H, H6). $^{13}$C NMR (CDCl$_3$): δ28.8 (C13), 33.5 (C14), 35.5 (C1), 52.1 (CH$_3$O) 56.6 (C16), 65.3 (C12), 66.0 (C8'), 105.6 (C9), 111.8 (C6), 118.1 (C10'), 128.1 (C3), 132.5 (C9'), 144.4 (Q), 151.0 (Q),153.6 (Q), 167.3 (Q), 170.7 (Q). IR (neat): ν=3583, 3412 (OH), 1730 (ester), 1713 (Alloc C=O), 1644, 1421, 1362, 1273, 1223, 1092, 902, 757, 737, 702, 667 cm$^{-1}$. MS (FAB) m/z (relative intensity): 907 (M$^+$, 1), 456 (6), 245 (7), 232 (16), 218 (13), 206 (23), 205 (10), 204 (14), 192 (42), 190 (17), 178 (22), 177 (10), 176 (16), 166 (17), 165 (10), 164 (16), 152 (23), 151 (12), 150 (18), 149 (100), 140 (16), 93 (18), 91 (22), 89 (13), 87 (26), 80 (58), 75 (19), 73 (28), 57 (25).

1,1'-[[(Propane-1,3-diyl)dioxy]bis[(11aS)-7-methoxy-(2S)-2-methoxycarbonylmethyl-2,3-dihydropyrrole-1,3,11a-trihydro-5H-pyrrolo[2,1-c][1,4]benzodiazepin-5-one (56)

A catalytic amount of tetrakistriphenylphosphinepalladium(0) (16 mg, 0.014 mmol) was added to a solution of carbinolamine (55) (219 mg, 0.25 mmol), triphenylphosphine (7 mg, 0.025 mmol) and pyrrolidine (0.05 mL, 0.80 mmol) in dry DCM (30 mL) at 0° C. The reaction mixture was stirred for 2 hours before being allowed to warm to room temperature over 1 h. The solvent was removed in vacuo and the residue was subjected to flash column chromatography (2% MeOH/CH$_2$Cl$_{21}$ R$_f$=0.25) to yield a yellow glass (109 mg, 66%). [α]$^{19.5}_D$=+ 500° (c 0.043, CHCl$_3$). $^1$H NMR (CDCl$_3$): δ2.17–2.42 (m, 2H, H13), 3.15–3.32 (m, 8H, H1, H14), 3.73 (s, 3H, OMe), 3.91 (s, 6H, H16), 4.26–4.30 (m, 6H, H12, H11a), 6.84 (s, 2H, H9), 6.92–7.06 (m, 2H, H3), 7.47 (s, 2H, H6), 7.83 (d, J=4.0 Hz, 4H, H11). $^{13}$C NMR (CDCl$_3$): δ28.7 (C13), 33.6 (C14), 37.4 (C1), 52.2 (CH$_3$O), 53.8 (C11), 56.2 (C16), 65.4 (C12), 110.9 (C9), 111.8 (C6), 126.5 (C3), 140.2 (Q), 148.0 (Q), 151.0 (Q), 161.4 (Q), 162.6 (C11a), 170.7 (Q). IR (neat): ν=3583, 3394, 2997, 2950, 1736 (ester), 1717 (Alloc C=O), 1628, 1596, 1511, 1483, 1451, 1431, 1382, 1273, 1245, 1197, 1152, 1068, 995, 963, 914, 842, 753 cm$^{-1}$. FABMS m/z (relative intensity): 673 (M$^+$, 2), 279 (6), 277 (4), 201 (7), 185 (55), 181 (7), 110 (5), 93 (100), 91 (24), 75 (28), 73 (20), 61 (12), 57 (33).

Example 1(v)

Figure 6A:
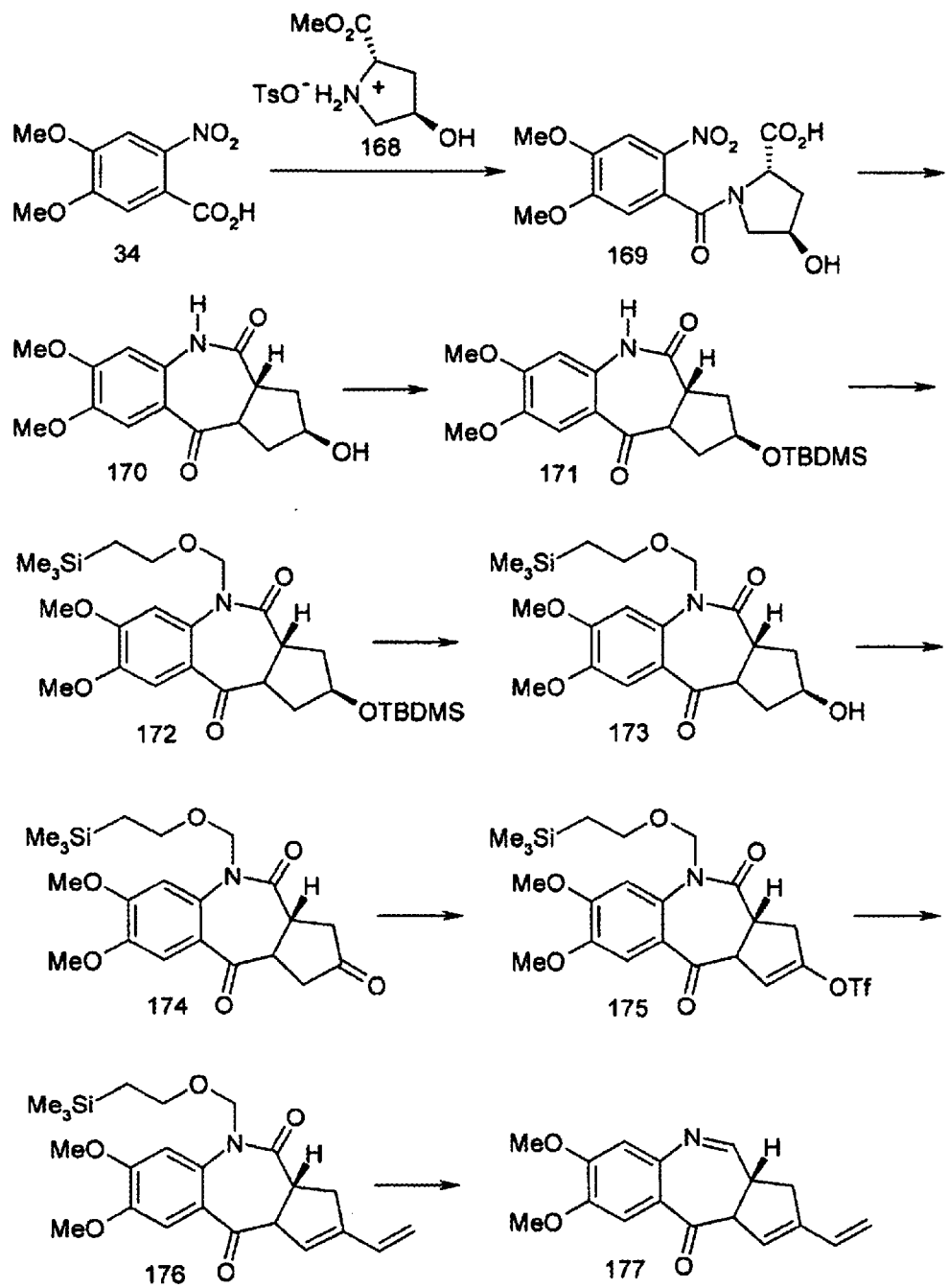
Figure 6B:
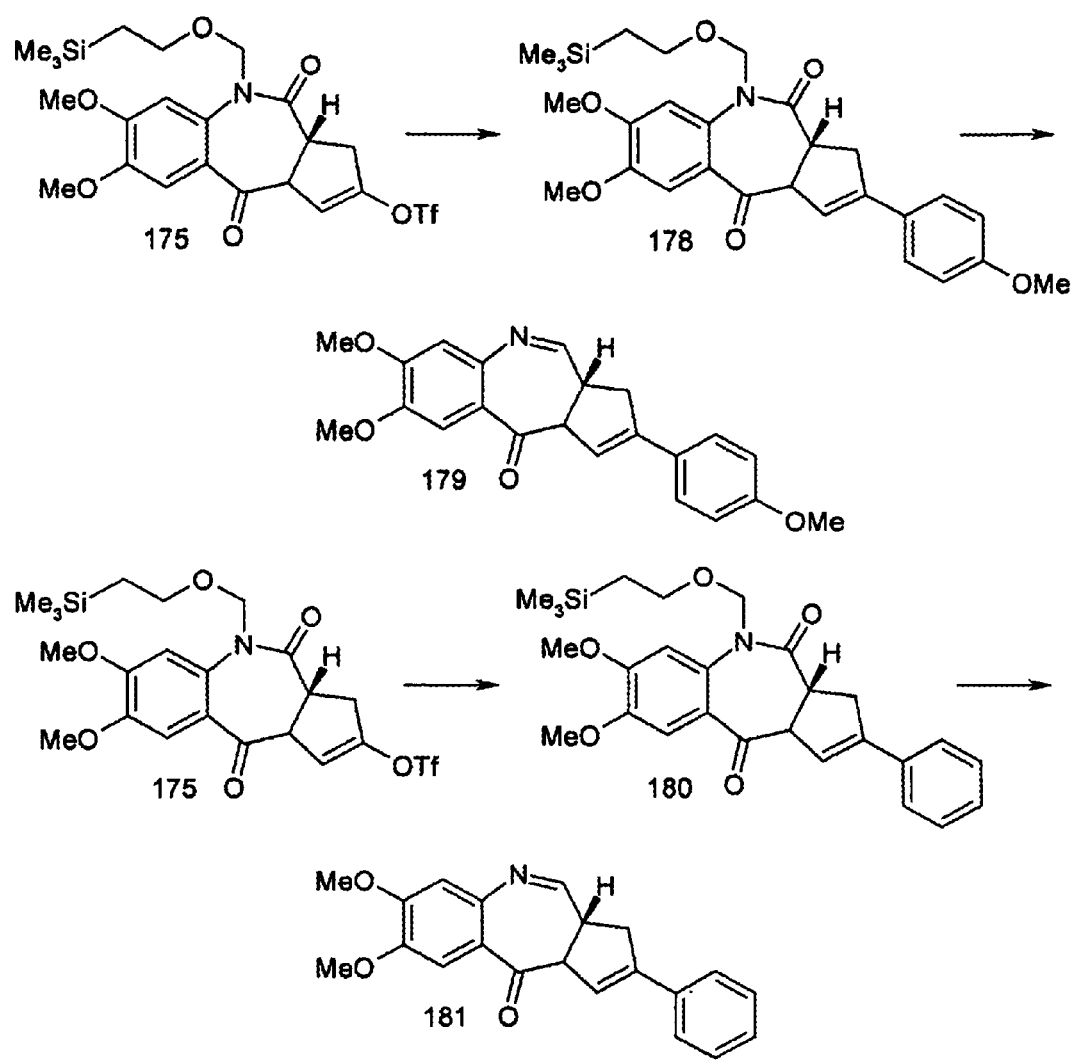

Synthesis of (11aS)-1,11a-dihydro-7,8-dimethoxy-2-ethenyl-5H-pyrrolo[2,1-c][1,4]benzodiazepin-5-one (See FIGS. 6a/b)

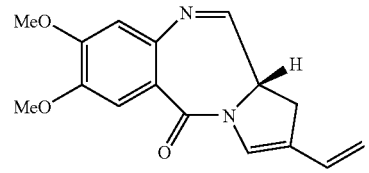

DRH360 N-(4,5-dimethoxy-2-nitrobenzoyl)hydroxyproline Methyl Ester (169)

Oxalyl chloride (15.38 g, 121.11 mmol) was added in one portion to a stirred suspension of 2-nitro-4,5- dimethoxybenzoic acid (34) (25.01 g, 110.10 mmol) in anhydrous DCM (100 mL) at room temperature. A catalytic amount of DMF (2 drops) was added (CARE!—increased gas evolution) and the reaction mixture was allowed to stir for 16 hours under an inert atmosphere. The acid chloride solution was added dropwise to a vigorously stirred solution of the pyrrolo C-ring (168) (34.90 g, 110.10 mmol, JOC 5, 13, 1994, 3621) and TEA (45.95 mL, 33.36 g, 330.29 mmol) in anhydrous DCM (100 mL) at −20° C. The reaction mixture was allowed to stir for 16 hours at room temperature. The reaction mixture was washed with saturated NaHCO$_3$ (2×200 mL), saturated NH$_4$Cl (2×200 mL), water (2×200 mL), brine (2×200 mL) and dried over anhydrous MgSO$_4$. Filtration and evaporation of the solvent in vacuo afforded the crude product (169), which was purified by flash column chromatography using EtOAc as eluent. Pure fractions were combined and evaporation of excess eluent in vacuo afforded the product as a foam (33.26 g, 93.9 mmol, 85%). $^1$H NMR (270 MHz, CDCl$_3$) d 7.69 (s, 1H), 6.87 (s, 1H), 5.31 (s, 2H), 4.97–4.82 (m, 1H), 4.44 (br s, 1H), 3.99 (s, 3H), 3.98 (s, 3H), 3.81 (s, 3H), 3.54–3.48 (m, 1H), 3.18 (d, 1H, J=2.02 Hz), 2.87 (br s, 1H), 2.45–2.16 (m, 2H); $^{13}$C NMR (67.8 MHz, CDCl$_3$) d 172.6, 172.5, 167.5, 166.8, 154.4, 154.0, 149.3, 137.5, 137.4, 127.0, 126.2, 109.5, 107.2, 107.1, 69.9, 69.1, 59.2, 57.4, 56.9, 56.8, 56.6, 56.4, 54.6, 53.5, 52.5, 52.4, 39.4, 38.0.

(11aS)-6,7-dimethoxy-2(R)-hydroxy-2,3,5,10,11,11a-hexahydro-5,11-dioxo-1H-pyrrolo[2,1-c][1,4-]benzodiazepine (170)

10% Pd/C catalyst (3.3 g) was added to a solution of 169 (33.0 g, 93.1 mmol) in absolute EtOH (250 mL). The reaction mixture was hydrogenated under pressure using a Parr hydrogenator at 55 psi H$_2$ for 18 h. The reaction mixture was filtered through celite, and the celite washed with hot MeOH, taking care not to allow the filter cake to dry out. Removal of excess solvent afforded the crude product (20.14 g). The crude product was allowed to stir in 1 N HCl (200 mL) and CHCl$_3$ (200 mL) for 30 minutes. The organic layer was washed with 1 N HCl (100 mL) and the aqueous layers were combined and neutralised with saturated aqueous NaHCO$_3$. On leaving the aqueous extract overnight, a fine white precipitate formed (170) which was collected by filtration and dried (7.81 g, 26.72 mmol, 29%). $^1$H NMR (270 MHz, CDCl$_3$) d 10.06 (s, 1H, NH), 7.61 (s, 1H, ArH), 7.36 (s, 1H, ArH), 4.49–4.41 (m, 1H, 2), 4.22–4.17 (m, 1H, 11a), 3.88 (s, 6H), 3.82–3.55 (m, 2H, 3), 3.20 (br s, 1H, OH), 2.87–2.77 (m, 1H, 1), 2.10–2.05 (m, 1H, 1); $^{13}$C NMR (CDCl$_3$) d 170.2, 165.9, 152.0, 145.7, 130.7, 118.2, 111.9, 104.2, 68.1, 56.0, 55.6, 54.2, 34.6, 18.8.

(11aS)-6,7-dimethoxy-2(R)-[(tert-butyldimethylsilyl)oxy]-2,3,5,10,11,11a-hexahydro-5,11-dioxo-1H-pyrrolo[2,1-c][1,4-]benzodiazepine (171)

Solid TBDMS Chloride (8.22 g, 54.44 mmol) was added in one portion to a solution of 170 (7.23 g, 24.74 mmol) and imidazole (8.42 g, 123.72 mmol) in anhydrous DMF (75 mL) and allowed to stir at room temperature for 16 h. The reaction mixture was poured into water (500 mL) and filtered to afford the crude product (171), which was purified by recrystallisation from EtOH (800 mL) as fine white needles (6.995 g, 17.21 mmol, 70%). $^1$H NMR (270 MHz, CDCl$_3$) δ10.06 (s, 1H, NH), 7.37 (s, 1H, ArH), 6.68 (s, 1H, ArH), 4.19–4.14 (m, 1H, 2), 4.06–4.01 (m, 1H, 11a), 3.90 (s, 3H, OMe), 3.88 (s, 3H, OMe), 3.69–3.63 (m, 2H, 3), 2.85–2.80 (m, 1H, 1), 2.05–2.01 (m, 1H, 1); $^{13}$C NMR (67.8 MHz, CDCl$_3$) δ170.4, 170.2, 165.9, 152.1, 145.8, 145.6, 131.1, 130.7, 118.1, 111.9, 104.3, 104.1, 69.2, 69.1, 56.0, 55.9, 55.7, 54.3, 54.0, 35.0, 25.8, 25.7, 25.6, 17.9, −3.0, −3.5, −4.9, −5.0.

(11aS)-6,7-dimethoxy-2(R)-[(tert-butyldimethylsilyl)oxy]-2,3,5,10,11,11a-hexahydro-10-[2-(trimethylsilyl)ethoxymethyl]-5,11-dioxo-1H-pyrrolo[2,1-c][1,4-]benzodiazepine (172)

A solution of 171 (6.50 g, 15.99 mmol) in anhydrous DMF (27.5 mL) was added dropwise to a stirred suspension of NaH (0.422 g, 0.704 g of a 60% dispersion in mineral oil, 18.34 mmol) at 0° C. and the reaction mixture was allowed to stir for 30 minutes. A solution of SEM chloride (3.11 mL, 2.93 g, 17.59 mmol) in anhydrous DMF (5 mL) was added dropwise to the stirred reaction mixture at 0° C. and allowed to stir at room temperature for 16 h. The reaction mixture was poured into water (200 mL) to afford a white precipitate, which was extracted with diethyl ether (4×300 mL). The organic layer was washed with water (2×50 mL), brine (2×50 mL) and dried over anhydrous MgSO$_4$. Filtration and evaporation of the solvent in vacuo afforded the crude product, which was purified by flash column chromatography using an 80:20 mixture of petroleum ether:EtOAc as eluent. Pure fractions were combined and evaporated in vacuo to afford the product (172) as a yellow oil (7.01 g, 13.1 mmol, 82%). $^1$H NMR (270 MHz, CDCl$_3$) δ7.35 (s, 1H, ArH), 7.24 (s, 1H, ArH), 5.52 (d, 2H, J=9.89 Hz, SEM amino acetal CH$_2$), 4.65 (d, 2H, J=9.90 Hz, SEM amino acetal CH$_2$), 4.61–4.56 (m, 1H, 2), 4.23 (dd, 1H, J=4.40 Hz, 8.24 Hz, 11a), 3.94 (s, 3H, OMe), 3.92 (s, 3H, OMe), 3.68 (m, 4H, SEM 1' CH$_2$+3), 2.86 (m, 1H, 1), 2.02 (m, 1H, 1), 0.98 (t, 2H, J=8.25 Hz, SEM 2' CH$_2$), 0.88 (s, 9H, TBDMS t-Bu CH$_3$), 0.10 (s, 6H, 2×TBDMS SiCH$_3$), 0.03 (s, 9H, 3× SEM SiCH$_3$); $^{13}$C NMR (67.8 MHz, CDCl$_3$) δ170.0, 165.6, 151.8, 147.1, 133.9, 121.5, 111.2, 105.5, 78.1, 69.6, 67.0, 56.5, 56.2, 56.1, 53.6, 35.5, 25.7, 18.4, −1.3, −4.8.

(11aS)-6,7-dimethoxy-2(R)-hydroxy-2,3,5,10,11,11a-hexahydro-10-[2-(trimethylsilyl)ethoxymethyl]-5,11-dioxo-1H-pyrrolo[2,1-c][1,4-]benzodiazepine (173)

A solution of 1 N TBAF in THF (19.58 mL, 19.58 mmol) was added to a stirred solution of 172 (7.0 g, 13.05 mmol) in THF (50 mL). The reaction mixture was allowed to stir at room temperature for 2 hours and diluted with DCM (200 mL), washed with water (2×200 mL), brine (2×200 mL) and dried over anhydrous MgSO$_4$. Filtration and removal of excess solvent afforded the crude product, which was purified by flash column chromatography using 50:50 petroleum ether:EtOAc as eluent. Evaporation in vacuo of the pure fractions afforded the product (173) (5.9 g). $^1$H NMR (270 MHz, CDCl$_3$) δ7.30 (s, 1H, ArH), 7.24 (s, 1H, ArH), 5.52 (d, 1H, J=9.9 Hz, SEM amino acetal CH$_2$), 4.68–4.64 (m, 2H, SEM amino acetal CH$_2$+2), 4.30 (dd, 1H, J=5.86, 8.24 Hz), 3.91 (s, 3H, OMe), 3.90 (s, 3H, OMe), 3.87–3.51 (m, 4H, SEM 1' CH$_2$+3), 2.95 (dt, 1H, J=5.31, 13.56 Hz, 1), 2.17–2.08 (m, 1H, 1), 1.02–0.93 (m, 2H, SEM 2' CH$_2$), 0.03 (s, 9H, 3× SiCH$_3$); $^{13}$C NMR (67.8 MHz, CDCl$_3$) δ169.7, 165.9, 151.9, 147.1, 134.0, 121.1, 111.2, 105.5, 78.2, 69.1, 67.1, 56.5, 56.1, 53.9, 34.9, 18.4, −1.3.

(11aS)-6,7-dimethoxy-2,3,5,10,11,11a-hexahydro-10-[2-(trimethylsilyl)ethoxymethyl]-2,5,11-trioxo-1H-pyrrolo[2,1-c][1,4-]benzodiazepine (174)

Anhydrous DMSO (3.28 g, 41.94 mmol) in dry DCM (20 mL) was added dropwise over 5 minutes to a stirred solution of oxalyl chloride (10.48 mL of a 2 N solution in DCM, 20.97 mmol) under a nitrogen atmosphere at −50° C. After stirring for 5 minutess, a solution 173 (5.90 g, 13.98 mmol), in dry DCM (45 mL) was added dropwise over 45 minutesutes to the reaction mixture, which was then stirred for a further 45 minutesutes at −50° C. TEA (9.89 g; 97.87 mmol) was added dropwise to the mixture over 15 minutes followed by stirring for a further 15 minutes. The reaction mixture was left to warm to room temperature, diluted with H₂O (150 mL) and DCM (100 mL). The organic phase was washed with 1 N HCl (2×100 mL), water (2×100 mL), brine (2×100 mL) and dried over MgSO₄. Filtration and evaporation afforded the crude product (174), which was purified by flash column chromatography using 50:50 petroleum ether (40–60°):EtOAc as eluent. Evaporation of the pure fractions in vacuo afforded the product (4.33 g, 10.3 mmol, 74%). ¹H NMR (270 MHz, CDCl₃) δ7.30 (s, 1H, ArH), 7.24 (s, 1H, ArH), 5.60 (d, 1H, J=9.89 Hz, SEM amino acetal CH₂), 4.69 (d, 1H, J=9.89 Hz, SEM amino acetal CH₂), 4.62 (dd, 1H, J=9.89, 3.12 Hz, 11a), 4.26–4.19 (m, 1H, 3), 3.95 (s, 3H, Ome), 3.94 (s, 3H, OMe), 3.81–3.49 (m, 4H, SEM 1' CH₂+1+3), 2.82–2.71 (m, 1H, 1), 0.95 (t, 2H, J=2.01 Hz, SEM 2' CH₂), −0.04 (s, 9H, SEM CH₃); ¹³C NNR (67.8 MHz, CDCl₃) δ206.8, 168.8, 165.9, 152.4, 147.5, 134.0, 120.4, 111.1, 105.6, 78.2, 67.2, 56.2, 54.8, 52.3, 37.3, 18.3, −1.3.

(11aS)-5,10,11,11a-tetrahydro-7,8-dimethoxy-10-[2-trimethylsilyl)ethoxymethyl]-2-[[(trifluoromethyl) sulphonyl]oxy]-5,11-dioxo-1H-pyrrolo[2,1-c][1,4] benzodiazepine (175)

Anhydrous pyridine (0.46 mL, 0.452 g, 5.73 mmol) was added in one portion to a vigorously stirred solution of 174 (2.0 g, 4.77 mmol) in anhydrous DCM (100 mL) and the mixture left to stir for 10 minutes at room temperature. Anhydrous triflic anhydride (1.25 mL, 1.48 g, 5.25 mmol) was added quickly, in one portion, and the reaction mixture was allowed to stir at room temperature for 4.5 h. The darkened, homogenous reaction mixture was poured into cold saturated NaHCO₃ (200 mL) and the mixture was extracted with DCM (3×50 mL). The organic layers were combined, washed with water (2×200 mL), brine (2×200 mL) and dried over anhydrous MgSO₄. Filtration and evaporation afforded the crude product, which was purified by flash column chromatography using 80:20 petroleum ether:EtOAc as eluent. Evaporation of the pure fractions in vacuo afforded the product (175) as a yellow oil (1.79 g, 3.25 mmol, 68%). ¹H NMR (270 MHz, CDCl₃) δ7.29 (s, 1H, ArH), 7.23 (s, 1H, ArH), 7.15 (t, 1H, J=2.01 Hz, H3), 5.53 (d, 1H, J=10.07 Hz, SEM amino acetal CH₂), 4.68 (d, 1H, J=9.89 Hz, SEM amino acetal CH₂).

(11aS)-7,8-Dimethoxy-2-ethenyl-5,10,11,11a-tetrahydro-10-(2-(trimethylsilyl)ethoxymethyl)-5,11-dioxo-1H-pyrrolo[2,1-c][1,4]benzodiazepine (176)

A catalytic amount of tetrakistriphenylphosphine palladium [0] (4 mol %, 0.142 g, 0.123 mmol) was added to a stirred mixture of 175 (1.69 g, 3.06 mmol), LiCl (0.39 g, 9.19 mmol), and tributylvinyltin (1.16 mL, 1.26 g, 3.98 mmol) in anhydrous THF (100 mL) and heated at reflux for 2.5 h. The cooled reaction mixture was diluted with DCM (100 mL) and the mixture washed with 10% aqueous ammonium hydroxide (200 mL). The organic layer was washed with brine (2×200 mL) and dried over anhydrous MgSO₄. Filtration and evaporation of the solvent in vacuo afforded the crude product, which was further purified by flash column chromatography using a 80:20 mixture of petroleum ether:EtOAc as eluent. Pure fractions were combined and evaporation of the solvent in vacuo afforded the product (176) as a colourless oil (0.992 g, 2.312 mmol, 75.5%). %). ¹H NMR (270 MHz, CDCl₃) δ7.32 (s, 1H, ArH), 7.22 (s, 1H, ArH), 6.94 (s, 1H, H3), 6.51 (dd, 1H, J=10.62, 17.22 Hz, alkene CH), 5.51 (d, 1H, J=10.07 Hz, SEM amino acetal CH₂), 5.20 (d, 1H, J=8.24 Hz, alkene CH₂), 5.15 (s, 1H, alkene CH₂), 4.66 (d, 1H, J=9.89 Hz, SEM amino acetal CH₂), 4.54 (dd, 1H, J=3.30, 10.62 Hz, H11a), 3.90 (s, 3H, OMe), 3.89 (s, 3H, OMe), 3.82–3.60 (m, 3H, SEM 1' CH₂+H1), 2.91–2.82 (m, 1H, H1), 0.96 (t, 2H, J=8.42 Hz, SEM 2' CH₂), −0.04 (s, 9H, SEM CH₃); ¹³C NMR (67.8 MHz, CDCl₃) δ169.3, 161.8, 152.1, 147.3, 133.8, 129.8, 126.0, 125.1, 121.2, 115.1, 111.4, 105.9, 78.5, 67.1, 57.6, 56.2, 56.2, 29.6, 18.4, −1.34.

(11aS)-1,11a-Dihydro-7,8-dimethoxy-2-ethenyl-5H-pyrrolo[2,1-c][1,4]benzodiazepin-5-one (177)

Solid sodium tetraborohydride (NaBH₄, 81 mg, 2.175 mmol) was added in one portion to a rapidly stirred solution of 176 (101 mg, 0.233 mmol) in a mixture of anhydrous EtOH (2 mL) and anhydrous THF (4 mL) at room temperature and allowed to stir for 4 h. The reaction mixture was diluted with water (5 mL) and extracted with CHCl₃ (3×5 mL). The organic layers were washed with brine (10 mL) and dried over anhydrous MgSO₄. Filtration and evaporation afforded the crude product, which was stirred for 30 minutes with silica gel (0.25 g) in MeOH (5 mL). Excess methanol was removed by rotary evaporation, causing the crude product to be absorbed onto the silica gel. The plug of silica gel was added to the top of a silica gel column and the product was purified by flash column chromatography eluting with a 60:40 mixture of petroleum ether:EtOAc. Pure fractions were combined and evaporation of the solvent in vacuo afforded the product (177) as a yellow solid (33 mg, 0.116 mmol, 50%). ¹H NMR (270 MHz, CDCl₃) δ7.86 (d, 1H, J=3.84 Hz, imine CH), 7.50 (s, 1H, ArH), 7.05 (br s, 1H, H3), 6.82 (s, 1H, ArH), 6.58 (dd, 1H, J=10.62, 17.22 Hz, alkene CH), 5.20–5.05 (m, 2H, alkene CH₂), 4.39–4.31 (m, 1H, H11a), 3.96 (s, 3H, OMe), 3.94 (s, 3H, OMe), 3.39–3.12 (m, 2H, H1); ¹³C NMR (67.8 MHz, CDCl₃) δ162.7, 161.5, 151.9, 147.8, 140.4, 129.9, 126.9, 123.9, 118.9, 114.4, 111.6, 109.8, 77.3, 56.2, 53.9, 33.7.

Example 1(h)

Synthesis of (11aS)-1,11a-Dihydro-7,8-dimethoxy-2-(4-methoxyphenyl)-5H-pyrrolo[2,1-c][1,4]benzodiazepin-5-one (See FIGS. 6a/b)

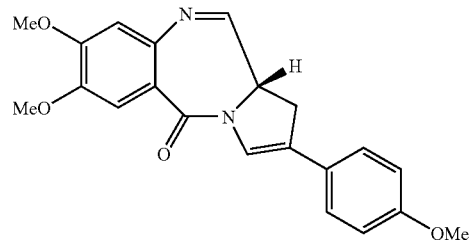

(11aS)-7,8-Dimethoxy-2-(4-methoxyphenyl)-5,10,11,11a-tetrahydro-10-(2-(trimethylsilyl)ethoxymethyl)-5,11-dioxo-1H-pyrrolo[2,1-c][1,4]benzodiazepine (178)

A solution of para-methoxyphenylboronic acid (301 mg, 1.98 mmol) in DME (10 mL) was added to a stirred solution of vinyl triflate (175—see example 1(g)) (715 mg, 1.29 mmol) in DME (10 mL) under a nitrogen atmosphere. An aqueous solution of Na₂CO₃ (2 N, 9.9 mL) was added followed by LiCl (178 mg, 4.185 mmol) and tetrakis (triphenylphosphine)palladium(0) (5 mol %, 81 mg) and the mixture was stirred for 1 hour at room temperature followed by heating at reflux for 1 h. After concentration in vacuo, the residue was resuspended in a mixture of DCM (50 mL), aqueous 2 N Na₂CO₃ (50 mL) and conc. NH₄OH solution (3 mL). The aqueous layer was extracted with DCM (3×20 mL) and the combined organic extracts were dried over anhydrous MgSO₄. Filtration and evaporation afforded a residue which was purified by flash column chromatography on silica gel eluting with 60:40 petroleum ether:EtOAc. Pure fractions were combined and evaporation of the solvent in vacuo afforded the product (178) as a yellow solid (559 mg, 1.095 mmol, 85%). ¹H NMR (270 MHz, CDCl₃) δ7.40–7.35 (m, 3H, ArH+Suzuki ArH), 7.33 (t, 1H, J=2.01 Hz, H3), 7.27 (s, 1H, ArH), 6.88 (d, 2H, J=6.93 Hz, Suzuki ArH), 5.56 (d, 1H, J=9.89 Hz, SEM amino acetal CH₂), 4.71 (d, 1H, J=9.89 Hz, SEM amino acetal CH₂), 4.63 (dd, 1H, J=3.30, 10.62 Hz, H11a), 3.95 (s, 3H, Ode), 3.94 (s, 3H, OMe), 3.87–3.65 (m, 6H, SEM 1' CH₂+H1+Suzuki ArOMe), 3.14 (ddd, 1H, J=2.38, 10.62, 16.12 Hz, H1), 0.96 (t, 2H, J=8.42 Hz, SEM 2' CH₂), −0.04 (s, 9H, SEM CH₃); ¹³C NMR (67.8 MHz, CDCl₃) d 168.4, 161.6, 160.2, 153.0, 147.3, 133.7, 126.5, 126.1, 125.4, 121.3, 120.2, 114.1, 111.3, 105.8, 78.4, 67.1, 57.5, 56.2, 56.2, 55.3, 31.5, 18.4, −1.34.

(11aS)-1,11a-dihydro-7,8-Dimethoxy-2-(4-methoxyphenyl)-5H-pyrrolo[2,1-c][1,4]benzodiazepin-5-one (179)

Solid sodium tetraborohydride (NaBH₄, 70 mg, 1.88 mmol) was added in one portion to a rapidly stirring solution of 178 (100 mg, 0.2 mmol) in a mixture of anhydrous EtOH (2 mL) and anhydrous THF (4 mL) and left to stir at room temperature for 9 h. The reaction mixture was diluted with water (10 mL) and stirred for 30 minutes with silica gel (2.0 g). The mixture was extracted with EtOAc (3×10 mL). The organic layers were washed with brine (10 mL) and dried over anhydrous MgSO₄. Filtration and evaporation afforded the crude product (179), which was purified by flash column chromatography eluting with a 50:50 mixture of petroleum ether:EtOAc. Pure fractions were combined and evaporation of the solvent in vacuo afforded the product as a yellow glass (28 mg, 0.08 mmol, 38%). ¹H NMR (270 MHz, CDCl₃) δ7.89 (d, 1H, J=4.03 Hz, Imine CH), 7.53 (s, 1H, ArH), 7.39 (t, 1H, J=1.83 Hz, H3), 7.33 (d, 2H, J=8.97 Hz, methoxyphenyl ArH), 6.91 (d, 2H, J=8.98 Hz, methoxyphenyl ArH), 6.83 (s, 1H, ArH), 4.44–4.36 (m, 1H, H11a), 3.97 (s, 3H, OMe), 3.94 (s, 3H, OMe), 3.91–3.79 (m, 4H, H1+Suzuki ArOMe), 3.64–3.34 (m, 1H, H1); ¹³C NMR (67.8 MHz, CDCl₃) δ162.7, 161.3, 159.2, 151.8, 147.8, 140.4, 126.3, 126.2, 126.0, 125.9, 123.2, 121.9 114.3, 114.1, 111.6, 109.8, 56.2, 56.1, 55.6, 35.6.

Example 1(i)
Synthesis of (11aS)-1,11a-Dihydro-7,8-dimethoxy-2-phenyl-5H-pyrrolo[2,1-c][1,4]benzodiazepin-5-one (See FIGS. 6a/b)

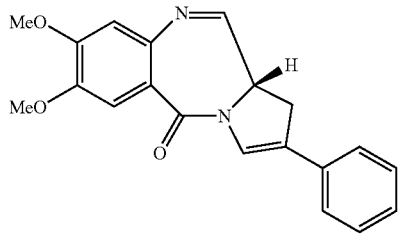

(11aS)-7,8-Dimethoxy-2-phenyl-5,10,11,11a-tetrahydro-10-(2-(trimethylsilyl)ethoxymethyl)-5,11-dioxo-1H-pyrrolo[2,1-c][1,4]benzodiazepine (180)

Phenylboronic acid (334 mg, 2.74 mmol, 2.54 equiv.), Na₂CO₃ (343.4 mg, 3.24, 3 equiv) and tetrakis (triphenylphosphine) palladium(0) (49.9 mg, 2% mmol) was added to a solution of the triflate (175—see example 1(g)) (600 mg. 1.08 mmol) in ethanol (21.6 mL) water (21.6 mL) and the reaction mixture was allowed to stir at room temperature for 2 hrs. The reaction mixture was diluted with ethyl acetate (200 mL, washed with water (2×200 mL), brine (200 mL). and dried over magnesium sulphate. Filtration and evaporation of excess solvent afforded the crude product, which was subjected to flash column chromatography on silica gel (70% 40–60° petroleum ether; 30% ethyl acetate) to afford, after removal of excess eluent, the compound 180 (405 mg, 0.84 mmol, 78% yield). ¹H NMR (270 MHz, CDCl₃) δ7.5–7.1 (m, 8H), 5.53 (d, 1H, J=10.08 Hz), 4.67 (d, 1H, J=10.08 Hz) 4.65–4.59 (m, 1H) 4.0–3.60 (m 9H), 3.12 (dd, 1H, J=10.63, 16.12 Hz), 0.99–0.93 (m, 2H) 0.00 (s, 9H); ¹³C NMR (67.8 MHz, CDCl₃) δ168.3, 161.9, 152.1, 147.3, 133.9, 132.7, 128.7, 127.6, 125.7, 121.8, 121.1, 111.3, 105.8, 78.4, 67.2, 57.6, 56.2, 31.3, 18.4, −1.3

(11aS)-1,11a-Dihydro-7,8-dimethoxy-2-phenyl-5H-pyrrolo[2,1-c][1,4]benzodiazepin-5-one (181)

Solid sodium tetraborohydride (287 mg, 7.6 mmol, 10 equiv.) was added in one portion to a rapidly stirred solution of 180 (365 mg, 0.76 mmol) in a mixture of anhydrous EtOH (8 mL) and anhydrous THF (8 mL) at 0° C. The reaction mixture was allowed to stir at room temperature for 1 hour at room temperature at which time TLC (5% methanol; 95% chloroform) revealed the complete consumption of starting material. The reaction mixture was diluted with ethyl acetate (100 mL), washed with water (2×100 mL), brine (100 mL) and dried over magnesium sulphate. Filtration and evaporation of excess solvent afforded the crude product as a brown viscous oil. Flash chromatography (silica gel, 70% 40–60° petroleum ether, 30% ethyl acetate yield the final product (181) (271 mg, 0.77 mmol, 74%). ¹H NMR (270 MHz, CDCl₃) δ7.89 (d, 1H, J=4.03 Hz), 7.53 (s, 1H), 7.51 (s, 1H), 7.40–7.20 (m, 5H), 6.83 (s, 1H), 4.50–4.35 (m, 1H), 3.96 (s, 3H), 3.94 (s, 3H), 3.66–3.36 (m, 2H). ¹³C NMR (67.8 MHz, CDCl₃) δ162.6, 161.5, 151.9, 147.8, 140.4, 133.3, 128.8, 127.6, 127.1, 124.9, 123.6, 119.0, 111.6, 109.8, 56.2, 53.9, 35.4. HRMS (FAB) calcd for C₂₀H₁₉N₂O₃ (M⁺.+1) 335.1398, found 335.1396.

Figure 7:
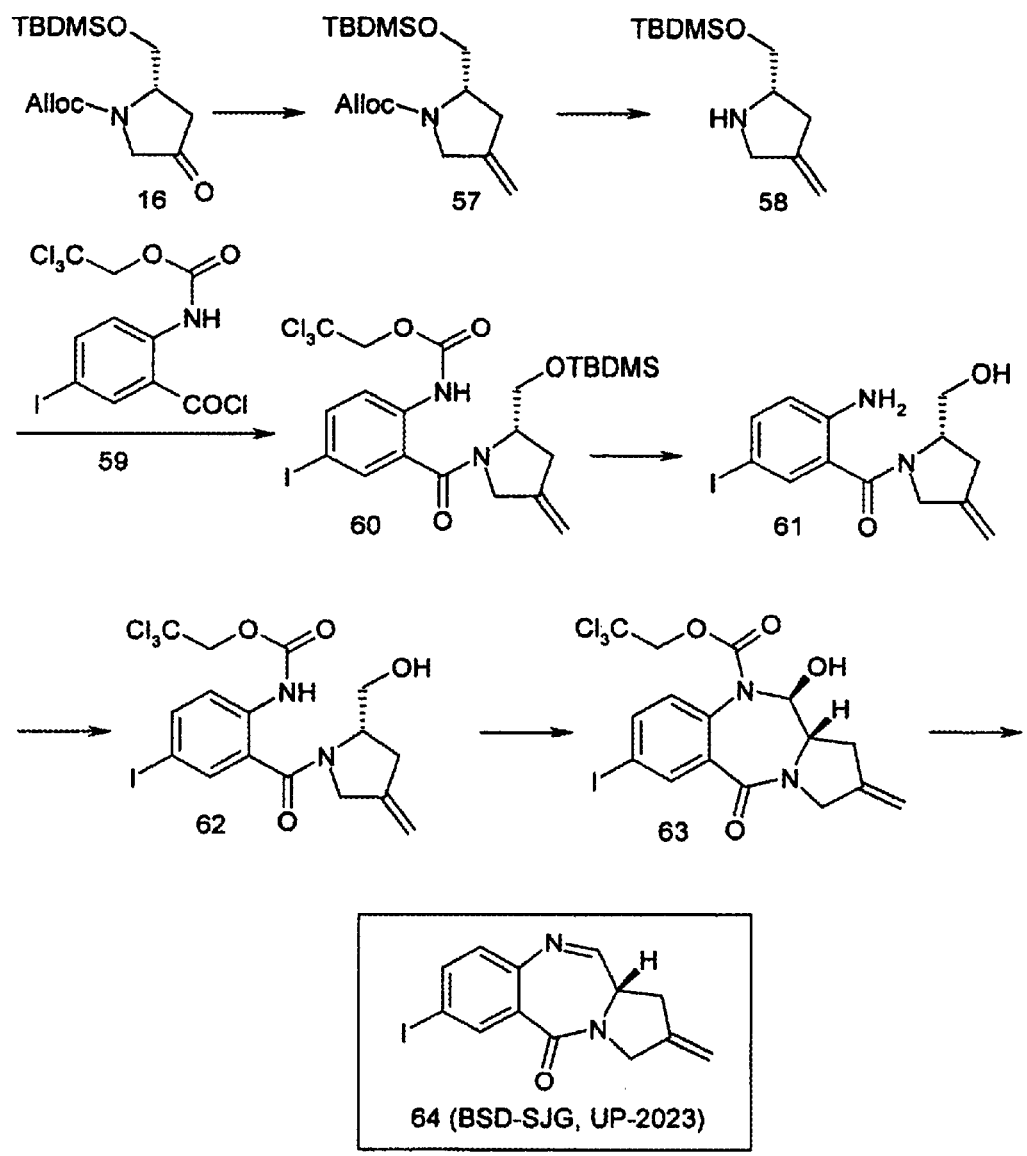
FIGS. 7 to 14 are synthesis routes for compounds of formula II of the present invention.

Example 2(a)
Synthesis of the C7-Iodo-C2-methlene PBD Monomer BSD-SJG (64, UP-2023) (See FIG. 7)

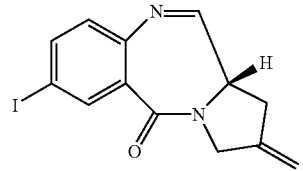

(S)-N-(Allyloxycarbonyl)-2-(tert-butyldimethylsilyloxymethyl)-4-methylidenepyrrolidine (57)

Potassium tert-butoxide (41.0 mL of a 0.5 M solution in THF, 20.5 mmol) was added dropwise to a suspension of methyltriphenylphosphonium bromide (7.29 g, 20.4 mmol) in THF (20 mL) at 0° C. (ice/acetone) under nitrogen. After stirring for 2 hours at 0° C., a solution of the ketone 16 (example 1(b)) (3.20 g, 10.2 mmol) in THF (10 mL) was added dropwise and the mixture allowed to warm to room temperature. After stirring for a further 30 minutes the reaction mixture was diluted with EtOAc (150 mL) and water (150 mL) and the organic layer separated, washed with brine, dried (MgSO₄), filtered and evaporated in vacuo to give a yellow oil in which crystals (TPO) formed upon standing in the freezer. Purification by flash chromatography (5% EtOAc/Petroleum Ether) isolated the pure olefin 57 as a colourless oil (2.76 g, 87%): [α]²¹_D=−22.2° (c=0.25, CHCl₃); ¹H NMR (270 MHz, CDCl₃) (Rotamers)

δ 6.02–5.87 (m, 1H, NCO$_2$CH$_2$CH=CH$_2$), 5.31 (ddd, 1H, J=1.65, 3.11, 17.20 Hz, NCO$_2$CH$_2$CH=CH$_2$), 5.21 (dd, 1H, J=1.46, 10.40 Hz, NCO$_2$CH$_2$CH=CH$_2$), 4.99–4.61 (m, 2H, NCH$_2$C=CH$_2$), 4.60 (d, 2H, J=4.94 Hz, NCO$_2$CH$_2$CH=CH$_2$), 4.19–3.98 (m, 2H, NCHCH$_2$OTBDMS), 3.93–3.87 (m, 1H, NCHCH$_2$OTBDMS), 3.66–3.42 (m, 2H, NCH$_2$C=CH$_2$), 2.80–2.56 (m, 2H, NCH$_2$C=CH$_2$CH$_2$), 0.87 (s, 9H, SiC(CH$_3$)$_3$), 0.03–0.02 (m, 6H, Si(CH$_3$)$_2$); $^{13}$C NMR (67.8 MHz, CDCl$_3$) (Rotamers) δ154.4 (NC=O), 145.1 and 144.1 (NCH$_2$C=CH$_2$), 133.1 (NCO$_2$CH$_2$CH=CH$_2$), 117.5 and 117.2 (NCO$_2$CH$_2$CH=CH$_2$), 107.5 and 106.9 (NCH$_2$C=CH$_2$), 65.8 and 65.6 (NCO$_2$CH$_2$CH=CH$_2$), 63.7 and 63.1 (NCHCH$_2$OTBDMS), 58.7 and 58.3 (NCHCH$_2$OTBDMS), 51.1 (NCH$_2$C=CH$_2$), 34.9 and 34.2 (NCH$_2$C=CH$_2$CH$_2$), 25.8 (SiC(CH$_3$)$_3$), 18.2 (SiC(CH$_3$)$_3$), –5.5 (Si(CH$_3$)$_2$); MS (CI), m/z (relative intensity) 312 (M$^+$·+1, 82), 296 (9), 279 (5), 255 (20), 254 (M—OC$_3$H$_5$ or M—$^t$Bu, 100), 168 (8), 122 (14); IR (Neat) 3083 (C=CH$_2$), 2954, 2847, 1709 (NC=O), 1533, 1467, 1404 (SiCH$_3$), 1360, 1310, 1252 (SiCH$_3$), 1207, 1174, 1103, 1076, 1006, 836, 776, 680 cm$^{-1}$.

(2S)-2-(tert-butyldimethylsilyloxymethyl)-4-methylidenepyrrolidine (58)

A catalytic amount of PdCl$_2$(PPh$_3$)$_2$ (92 mg, 0.131 mmol) was added to a solution of the allyl carbamate 57 (1.0 g, 3.22 mmol) and H$_2$O (0.34 mL, 18.9 mmol) in CH$_2$Cl$_2$ (30 mL). After 5 minutes stirring at room temperature, Bu$_3$SnH (0.96 mL, 1.04 g, 3.57 mmol) was added rapidly in one portion. A slightly exothermic reaction with vigorous gas evolution immediately ensued. The mixture was stirred for 16 hours at room temperature under nitrogen at which point TLC (50% EtOAc/Petroleum Ether) revealed the formation of amine. After diluting with CH$_2$Cl$_2$ (30 mL), the organic solution was dried (MgSO$_4$), filtered and evaporated in vacuo to give an orange oil which was purified by flash chromatography (50–100% EtOAc/Petroleum Ether) to afford the amine 58 as a slightly orange oil (0.56 g, 77%): [α]$^{21}_D$=–3.9° (c=5.0, CHCl$_3$); $^1$H NMR (270 MHz, CDCl$_3$) δ4.93 (t, 1H, J=2.02 Hz, NCH$_2$C=CH$_2$), 4.90 (t, 1H, J=2.02 Hz, NCH$_2$C=CH$_2$), 3.68–3.46 (m, 4H, NCHCH$_2$OTBDMS and NCH$_2$C=CH$_2$), 3.30–3.21 (m, 1H, NCHCH$_2$OTBDMS), 2.53–2.41 (m, 2H, NCH$_2$C=CH$_2$CH$_2$ and NH), 2.26–2.17 (m, 1H, NCH$_2$C=CH$_2$CH$_2$), 0.90 (s, 9H, SiC(CH$_3$)$_3$), 0.06 (s, 6H, Si(CH$_3$)$_2$); $^{13}$C NMR (67.8 MHz, CDCl$_3$) δ150.0 (NCH$_2$C=CH$_2$), 104.7 (NCH$_2$C=CH$_2$), 64.7 (NCHCH$_2$OTBDMS), 60.5 (NCHCH$_2$OTBDMS), 51.3 (NCH$_2$C=CH$_2$), 34.9 (NCH$_2$C=CH$_2$CH$_2$), 25.9 (SiC(CH$_3$)$_3$), 18.3 (SiC(CH$_3$)$_3$), –5.4 (Si(CH3)$_2$); MS (EI), m/z (relative intensity) 227 (M$^+$·, 8), 212 (6), 170 (M—$^t$Bu, 36), 96 (8), 82 (M—CH$_2$OTBDMS, 100), 75 (11); IR (Neat) 3550–3100 (br, NH), 3074 (C=CH$_{12}$), 2929, 2857, 1664 (C=C), 1472, 1424, 1391, 1380, 1361, 1255, 1190, 1101, 1006, 939, 880, 838, 777, 723, 668 cm$^{-1}$.

(2S)-N-[5-Iodo-2-(2,2,2-trichloroethyloxycarbonylamino)benzoyl]-2-(tert-butyldimethylsilyloxymethyl)-4-methylidinepyrrolidine (60)

A catalytic amount of DMF (3 drops) was added to a stirred solution of the Troc protected anthranilic acid 59 (0.46 g, 1.04 mmol) and oxalyl chloride (0.10 mL, 0.15 g, 1.15 mmol) in CH$_2$Cl$_2$ (30 mL). After 16 hours at room temperature the resulting acid chloride solution was added dropwise over 30 minutes to a stirred mixture of the amine 58 (0.26 g, 1.15 mmol) and TEA (0.26 g, 0.36 mL, 2.58 mmol) in CH$_2$Cl$_2$ (15 mL) at –20° C. (CCl$_4$/liq.N$_2$) under a nitrogen atmosphere. The reaction mixture was allowed to warm to room temperature and stirred for a further 45 minutes. At this point TLC analysis (50% EtOAc/Petroleum Ether) revealed complete reaction. The mixture was washed with saturated NaHCO$_3$ (30 mL), saturated NH$_4$Cl (30 mL), H$_2$O (25 mL), brine (30 mL), dried (MgSO$_4$), filtered and evaporated in vacuo to give the amide 60 as a dark oil (0.65 g, 96%): $^1$H NMR (270 MHz, CDCl$_3$) (Rotamers) δ8.92 (br s, 1H), 8.05–7.88 (m, 1H), 7.74–7.64 (m, 1H), 7.56–7.46 (m, 1H), 5.08–4.95 (m, 2H), 4.84 (d, 1H, J=11.91 Hz), 4.75 (d, 1H, J=11.91 Hz), 4.74–4.65 (m, 1H), 4.21–3.68 (m, 4H), 2.96–2.65 (m, 2H), 0.95–0.87 (m, 9H), 0.1–0.03 (m, 6H).

(2S)-N-(2-Amino-5-iodobenzoyl)-2-(hydroxymethyl)-4-methylidenepyrrolidine (61)

A solution of TBAF (1.24 mL of a 1M solution in THF, 1.24 mmol) was added to the silyl-ether 60 (0.64 g, 0.99 mmol) in THF (15 mL) at 0° C. (ice/acetone). The reaction mixture was allowed to warm to room temperature and after 45 minutes TLC (50% EtOAc/Pet-Ether 40°–60°) revealed the complete disappearance of starting material. Saturated NH$_4$Cl (75 mL) was added and the reaction mixture extracted with EtOAc (3×30 mL), washed with brine (30 mL), dried (MgSO$_4$), filtered and evaporated in vacuo to give an orange oil. Purification by flash chromatography (50% EtOAc/Pet-Ether 40°–60°) provided the pure amino-alcohol 61 as a viscous oil (0.18 g, 51%): $^1$H NMR (270 MHz, CDCl$_3$) δ7.72–7.61 (m, 1H), 7.55–7.40 (m, 1H), 6.51–6.49 (m, 1H), 5.02–4.94 (m, 2H), 4.80–3.80 (m, 8H), 2.81–2.79 (m, 1H), 2.43–2.40 (m, 1H); MS (EI), m/z (relative intensity) 359 (M$^+$·1, 5), 358 (M$^+$·, 33), 328 (3), 327 (10), 254 (3), 247 (11), 246 (100), 218 (18), 164 (2), 127 (4), 120 (4), 119 (10), 113 (9), 112 (91), 94 (2), 91 (20), 90 (5), 82 (10), 67 (2), 64 (3), 63 (3), 52 (3). ps (2S)-N-[5-Iodo-2-(2,2,2-trichloroethyloxycarbonylamino)benzoyl]-2-(hydroxymethyl)-4-methylidinepyrrolidine (62)

A solution of the amine 61 (179 mg, 0.50 mmol) in CH$_2$Cl$_2$ (15 mL) was cooled to 0° C. (ice/acetone) and treated with pyridine (81 μL, 79 mg, 1.0 mmol). A solution of 2,2,2-trichloroethylchloroformate (76 μL, 117 mg, 0.55 mmol) in CH$_2$Cl$_2$ (5 mL) was then added dropwise to the stirred mixture. The reaction mixture was allowed to warm to room temperature and stirred for a further 2 h, at which point TLC (EtOAc) revealed complete consumption of amine 61. The reaction mixture was washed with saturated CuSO$_4$ (25 mL), H$_2$O (25 mL), brine (25 mL), dried (MgSO$_4$), filtered and evaporated in vacuo. The crude residue was purified by flash chromatography (50% EtOAc/Petroleum Ether) to afford the pure troc-amino compound 62 as an oil (189 mg, 71%): $^1$H NMR (270 MHz, CDCl$_3$) δ8.90 (br s, 1H), 7.75–7.66 (m, 3H), 5.02–4.92 (m, 3H), 4.87 (d, 1H, J=12.09 Hz), 4.72 (d, 1H, J=12.09 Hz), 4.15–4.08 (m, 2H), 3.90–3.85 (m, 2H), 3.65–3.63 (m, 1H), 2.80–2.71 (m, 1H), 2.50 (d, 1H, J=14.83 Hz); $^{13}$C NMR (67.8 MHz, CDCl$_3$) δ167.7, 151.9, 142.7, 139.6, 135.6, 134.8, 127.7, 123.4, 108.4, 95.1, 86.6, 74.3, 63.9, 59.0, 53.5, 33.7; MS (EI), m/z (relative intensity) 536 (5), 535 (3), 534 (15), 533 (M$^+$·, 3), 532 (15), 503 (2), 501 (2), 422 (4), 420 (5), 385 (8), 384 (8), 366 (3), 353 (11), 290 (9), 273 (8), 272 (76), 246 (6), 245 (18), 218 (4), 217 (5), 216 (8), 146 (4), 145 (10), 133 (4), 131 (4), 119 (6), 117 (7), 115 (11), 113 (17), 112 (39), 97 (4), 96 (3), 95 (12), 90 (5), 84 (5), 83 (7), 82 (100), 79 (7), 77 (21), 67 (2), 63 (4), 61 (3), 51 (6); exact mass calcd for C$_{16}$H$_{11}$N$_2$O$_4$Cl$_3$I m/e 531.9221, obsd m/e 531.9155.

(11S,11aS)-11-Hydroxy-7-iodo-2-methylidene-10-(2,2,2-trichloroethyloxycarbonylamino)-1,2,3,10,11,11a-hexahydro-5H-pyrrolo[2,1-c][1,4]benzodiazepin-5-one (63)

A solution of the alcohol 62 (189 mg, 0.35 mmol) in CH$_2$Cl$_2$/CH$_3$CN (12 mL, 3:1) was treated with 4 A powdered molecular sieves (100 mg) and NMO (62 mg, 0.53 mmol). After 15 minutes stirring at room temperature, TPAP (6.2 mg, 17.7 Amos) was added and stirring continued for a further 1 hour at which point TLC (50% EtOAc/Petroleum Ether) showed product formation along with some unoxidised starting material. The mixture was then treated with a further quantity of NMO (62 mg, 0.53 mmol) and TPAP (6.2 mg, 17.7 µmol) and allowed to stir for a further 30 minutes after which time TLC revealed complete reaction. The mixture was evaporated in vacuo onto silica and subjected to flash chromatography (40% EtOAc/Petroleum Ether) to provide the protected carbinolamine 63 as a white glass (93 mg, 49%): $^1$H NMR (270 MHz, CDCl$_3$) δ8.09 (d, 1H, J=2.01 Hz), 7.80 (dd, 1H, J=8.43, 2.20 Hz), 7.10 (d, 1H, J=8.43 Hz), 5.60 (d, 1H, J=9.71 Hz), 5.20–5.04 (m, 3H), 4.79–4.50 (m, 1H), 4.32–4.08 (m, 3H), 3.63 (t, 1H, J=8.79 Hz), 2.99–2.89 (m, 1H), 2.72 (d, 1H, J=15.94 Hz); $^{13}$C NMR (67.8 MHz, CDCl$_3$) δ165.0, 154.1, 141.0, 140.2, 137.7, 134.5, 133.6, 132.0, 110.4, 94.7, 93.4, 85.7, 75.0, 59.4, 50.7, 35.0; MS (EI), m/z (relative intensity) 533 (6), 532 (22), 531 (M$^+$, 8), 530 (17), 529 (10), 449 (5), 383 (6), 354 (7), 353 (5), 338 (6), 325 (5), 290 (5), 274 (15), 273 (8), 272 (43), 254 (5), 245 (8), 218 (5), 216 (12), 147 (5), 146 (6), 145 (9), 133 (10), 131 (9), 128 (5), 127 (15), 119 (11), 117 (5), 97 (6), 95 (9), 92 (6), 91 (6), 90 (5), 83 (11), 82 (100), 81 (7), 80 (8), 75 (5), 63 (7), 53 (5); exact mass calcd for C$_{16}$H$_{14}$N$_2$O$_4$ICl$_3$ m/e 531.9037, obsd m/e 531.8988.

(11aS)-7-Iodo-2-methylidene-1,2,3,11a-tetrahydro-5H-pyrrolo[2,1-c][1,4]benzodiazepin-5-one (64, UP2023, BSD-SJG)

10% cadmium-lead couple (109 mg, 0.875 mmol) was added to a stirred solution of the Troc-protected carbinolamine 63 (93 mg, 0.175 mmol) in THF (1 mL) and aqueous 1N ammonium acetate (1 mL). After 45 minutes at room temperature TLC revealed complete reaction (70% EtOAc/Petroleum Ether). The mixture was diluted with EtOAc (30 mL), dried (MgSO$_4$), filtered and evaporated in vacuo. The crude residue was purified by flash chromatography (70% EtOAc/Petroleum Ether) to provide the novel PBD (64, BSD-SJG, UP2023) as a white solid (27 mg, 46%): mp ° C.; $^1$H NMR (270 MHz, CDCl$_3$+CD$_3$OD) (11S,11aS isomer) δ8.10 (d, 1H, J=1.46 Hz), 7.65 (d, 1H, J=8.79 Hz), 6.86 (d, 1H, J=8.06 Hz), 5.14–5.10 (m, 2H), 4.66 (d, 1H, J=5.13 Hz), 4.34 (d, 1H, J=16.12 Hz), 4.23 (d, 1H, J=16.12 Hz), 3.80–3.71 (m, 1H), 3.34 (s, 3H), 3.03–2.86 (m, 1H), 2.65 (d, 1H, J=16.02 Hz); MS (ET), m/z (relative intensity) (N10-C11 imine form) 339 (M$^+$, +1, 20), 338 (M$^+$, 100), 337 (17), 323 (5), 311 (4), 310 (5), 257 (5), 230 (4), 229 (13), 211 (4), 203 (4), 202 (8), 184 (8), 183 (4), 103 (5), 82 (17), 81 (4), 80 (5), 76 (6), 75 (16), 74 (5), 55 (4), 53 (4); IR (NUJOL®) 3295 (br), 2923, 2853, 1716, 1615, 1506, 1457, 1377, 1317, 1278, 1238, 1169, 1118, 1063, 999, 895, 818, 751, 718 cm$^{-1}$; exact mass calcd for C$_{13}$H$_{11}$N$_2$OI m/e 337.9916, obsd m/e 337.9870.

Figure 8:
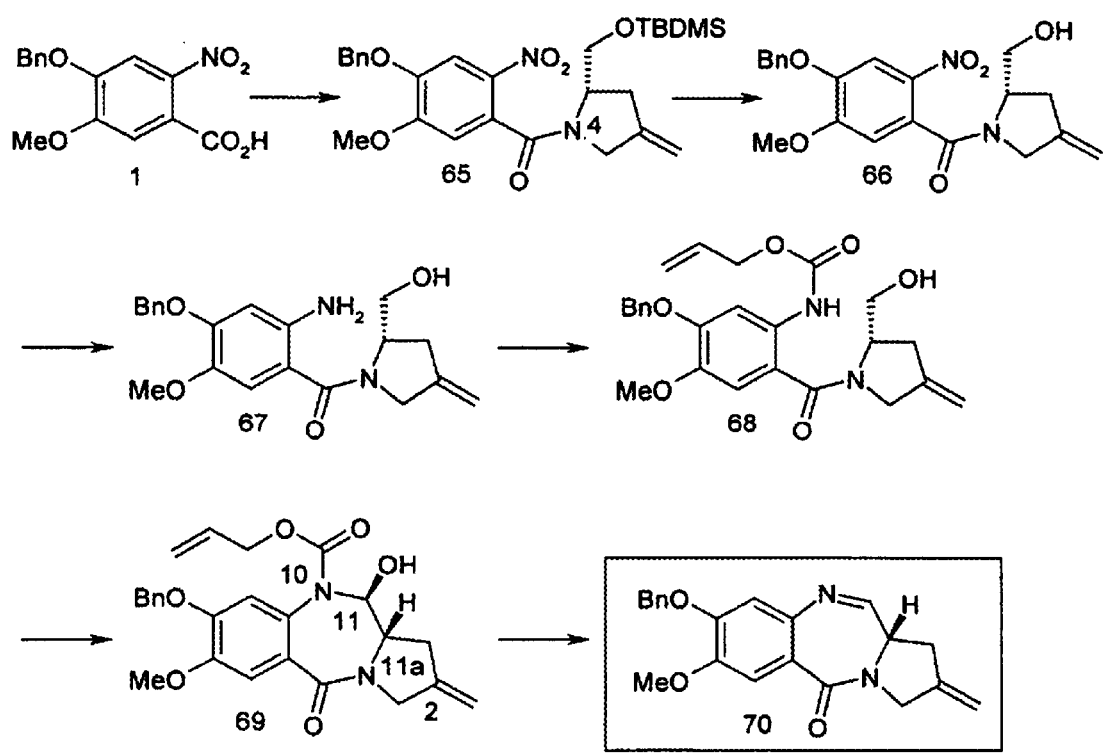

Example 2(b)
Synthesis of the C8-Benzyl-C7-Methoxy-C2-methlene PBD Monomer SJG-244 (70) (See FIG. 8)

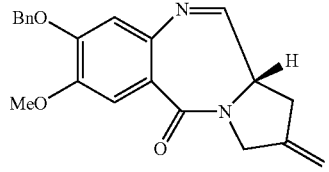

(2S)-N-(4-Benzyloxy-5-methoxy-2-nitrobenzoyl)-2-(tert-butyldimethylsilyloxymethyl)-4-methylidenepyrrolidine (65)

A catalytic amount of DMF (2 drops) was added to a stirred solution of the nitro-acid 1 (0.645 g, 2.13 mmol) and oxalyl chloride (0.23 mL, 0.33 g, 2.60 mmol) in CH$_2$Cl$_2$ (40 mL). After 16 hours at room temperature the resulting acid chloride solution was added dropwise to a stirred mixture of the amine 58 (0.522 g, 2.30 mmol) and TEA (0.58 g, 0.80 mL, 5.73 mmol) in CH$_2$Cl$_2$ (5 mL) at 0° C. (ice/acetone) under a nitrogen atmosphere. The reaction mixture was allowed to warm to room temperature and stirred for a further 2.5 h. The mixture was diluted with CH$_2$Cl$_2$ (50 mL), washed with saturated NaHCO$_3$ (50 mL), saturated NH$_4$Cl (50 mL), H$_2$O (50 mL), brine (50 mL), dried (MgSO$_4$), filtered and evaporated in vacuo to give the crude product as a dark orange oil. Purification by flash chromatography (20% EtOAc/Petroleum Ether) isolated the pure amide 65 as a sticky orange oil (0.86 g, 79%): [α]$^{22}_D$=−47.2° (c=2.79, CHCl$_3$); $^1$H NMR (270 MHz, CDCl$_3$) (Rotamers) δ7.78 and 7.77 (s×2, 1H$_{arom}$), 7.48–7.35 (m, 5H$_{arom}$), 6.82 and 6.78 (s×2, 1H$_{arom}$), 5.23 and 5.21 (s×2, 2H, PhCH$_2$O), 5.09–4.83 (m, 2H, NCH$_2$C=CH$_2$), 4.59–4.49 (m, 1H, NCHCH$_2$OTBDMS), 4.03–3.08 (m, 7H, NCHCH$_2$OTBDMS, NCH$_2$C=CH$_2$ and OCH$_3$), 2.80–2.56 (m, 2H, NCH$_2$C=CH$_2$CH$_2$), 0.89 and 0.79 (s×2, 9H, SiC(CH$_3$)$_3$), 0.122, −0.11 and −0.14 (s×3, 6H, Si(CH$_3$)$_2$); $^{13}$C NMR (67.8 MHz, CDCl$_3$) (Rotamers) δ166.2 (NC=O), 154.8 and 154.6 (C$_{quat}$), 148.2 and 148.0 (C$_{quat}$), 144.1 and 143.2 (C$_{quat}$), 137.1 (C$_{quat}$), 135.3 (C$_{quat}$), 128.8 and 128.5 (BnC—H$_{arom}$), 128.2 (C$_{quat}$), 127.6 (BnC–H$_{arom}$), 110.1 and 109.2 (C—H$_{arom}$), 109.0 and 108.5 (C—H$_{arom}$), 107.5 (NCH$_2$C=CH$_2$), 71.3 (PhCH$_2$O), 63.7 (NCHCH$_2$OTBDMS), 60.2 (NCHCH$_2$OTBDMS), 58.1 and 56.6 (OCH3), 52.8 and 50.5 (NCH$_2$C$_2$=CH$_2$), 34.9 and 33.9 (NCH$_2$C=CH$_2$CH$_2$), 25.8 and 25.7 (SiC(CH$_3$)$_3$), 18.2 (SiC(CH$_3$)$_3$), −5.4 and −5.6 (Si(CH$_3$)$_2$); MS (EI), m/z (relative intensity) 512 (M$^+$, 3), 497 (M—CH$_3$, 4), 455 (M—$^t$Bu, 100), 380 (2), 364 (5), 286 (M—NCH$_2$=CH$_2$CH$_2$CHCH$_2$OTBDMS, 40), 279 (9), 226 (NCH$_2$C=CH$_2$CH$_2$CHCH$_2$OTBDMS, 5), 168 (10), 149 (27), 91 (PhCH$_2$, 62), 73 (8), 57 (9); IR (NEAT) 3066, 3034, 2953, 2856, 2245, 1644 (NC=O), 1578, 1520, 1454, 1426, 1379, 1335, 1276, 1220, 1186, 1106, 1059, 1016, 910, 836, 815, 779, 734, 697, 655, 614 cm$^1$.

(2S)-N-(4-Benzyloxy-5-methoxy-2-nitrobenzoyl)-2-(hydroxymethyl)-4-methylidenepyrrolidine (66)

A solution of TBAF (2.10 mL of a 1M solution in THF, 2.10 mmol) was added to the silyl-ether 65 (0.86 g, 1.68 mmol) in THF (20 mL) at 0° C. (ice/acetone). The reaction mixture was allowed to warm to room temperature following a colour change (yellow-dark red). After a further 40 minutes TLC (50% EtOAc/Pet-Ether 40°–60°) revealed the complete disappearance of starting material. Saturated NH$_4$Cl (100 mL) was added and the reaction mixture extracted with EtOAc (3×40 mL), washed with brine (30 mL), dried (MgSO$_4$), filtered and evaporated in vacuo to give a dark orange oil which was purified by flash chromatography (60% EtOAc/Petroleum Ether) to provide the pure alcohol 66 as a white solid (0.64 g, 96%): [α]$^{19}_D$=−22.9° (c=0.20, MeOH); $^1$H NMR (270 MHz, CDCl$_3$) (Rotamers) δ7.78 and 7.76 (s×2, 1H$_{arom}$), 7.49–7.33 (m, 5H$_{arom}$), 6.91 and 6.82 (s×2, 1H$_{arom}$), 5.22 (s, 2H, PhCH$_2$O), 5.10 (m, 1H, OH), 5.03–5.01 (m, 1H, NCH$_2$C=CH$_2$), 4.90–4.85 (m, 1H, NCH$_2$C=CH$_2$), 4.65–4.55 (m, 1H, NCHCH$_2$OH), 3.99 and 3.95 (s×2, 3H, OCH$_3$), 3.90–3.72 (m, 4H, NCHCH$_2$OH and NCH$_2$C=CH$_2$), 2.90–2.87 (m, 1H, NCH$_2$C=CH$_2$CH$_2$), 2.53–2.47 (m, 1H, NCH$_2$C=CH$_2$CH$_2$); $^{13}$C NMR (67.8 MHz, CDCl$_3$) (Rotamers) δ177.4 (NC=O), 155.1 (C$_{quat}$), 148.3 (C$_{quat}$), 142.6 (C$_{quat}$), 137.0 (C$_{quat}$), 135.2 (C$_{quat}$), 128.9, 128.6 and 127.6 (BnC—H$_{arom}$), 109.1 (C—H$_{arom}$), 108.5 (C—H$_{arom}$), 108.3 (NCH$_2$C=CH$_2$), 71.4 (PhCH$_2$O), 65.2 and 63.7 (NCHCH$_2$OH), 60.4 (NCHCH$_2$OH), 56.8 and 56.7 (OCH3), 53.0 and 50.1 (NCH$_2$C=CH$_2$), 35.1 and 34.4 (NCH$_2$C=CH$_2$CH$_2$); MS (EI), m/z (relative intensity) 398 (M$^{+\cdot}$, 2), 380 (3), 368 (4), 354 (1), 286 (M—NCH$_2$C=CH$_2$CH$_2$CHCH$_2$OH, 54), 270 (2), 256 (1), 164 (2), 136 (4), 135 (3), 121 (4), 112 (NCH$_2$C=CH$_2$CH$_2$CHCH$_2$OH, 3), 91 (PhCH$_2$, 100), 82 (3), 69 (4), 65 (6); IR (NUJOL®) 3600–3200 (br, OH), 2923, 2853, 1718, 1663, 1611 (NC=O), 1577, 1517, 1460, 1376, 1332, 1275, 1224, 1176, 1052, 990, 925, 886, 862, 796, 759, 723, 702 615 cm$^{-1}$; exact mass calcd for C$_{21}$H$_{22}$N$_2$O$_6$ m/e 398.1478, obsd m/e 398.1490.

(2S)-N-(2-Amino-4-benzyloxy-5-methoxybenzoyl)-2-(hydroxymethyl)-4-methylidenepyrrolidine (67)

The nitro-alcohol 66 (0.637 g, 1.60 mmol), SnCl$_2$ 2H$_2$O (1.81 g, 8.0 mmol) and methanol (36 mL) were heated at reflux and monitored by TLC (90% CHCl$_3$/MeOH). After 1 hour the MeOH was evaporated in vacuo and the resulting residue cooled (ice), and treated carefully with saturated NaHCO$_3$ (120 mL). The mixture was diluted with EtOAc (120 mL), and after 16 hours stirring at room temperature the inorganic precipitate was removed by filtration through celite. The organic layer was separated, washed with brine (100 mL), dried (MgSO$_4$), filtered and evaporated in vacuo to give an orange glass. Flash chromatography (EtOAc) afforded the pure amine 67 as a pale yellow glass (0.37 g, 63%): $[\alpha]^{23}_D$=-42.7° (c=3.7, CHCl$_3$); $^1$H NMR (270 MHz, CDCl$_3$) δ7.44–7.29 (m, 5H$_{arom}$), 6.77 (s, 1H$_{arom}$) 6.27 (s, 1H$_{arom}$), 5.12 (s, 2H, PhCH$_2$O), 5.06–5.00 (m, 1H, NCH$_2$C=CH$_2$), 4.99–4.92 (m, 1H, NCH$_2$C=CH$_2$), 4.63–4.53 (m, 1H, NCHCH$_2$OH), 4.25–3.60 (m, 10H, NCHCH$_2$OH, NCH$_2$C=CH$_2$, OCH$_3$, OH and NH$_2$), 2.77 (dd, 1H, J=8.52, 15.85 Hz, NCH$_2$C=CH$_2$CH$_2$), 2.43–2.39 (m, 1H, NCH$_2$C=CH$_2$CH$_2$); $^{13}$C NMR (67.8 MHz, CDCl$_3$) δ171.4 (NC=O), 151.0 (C$_{quat}$), 143.3 (C$_{quat}$), 141.5 (C$_{quat}$), 140.6 (C$_{quat}$), 136.5 (C$_{quat}$), 128.6 and 128.0 (BnC—H$_{arom}$), 127.8 (C$_{quat}$), 127.1 (BnC—H$_{arom}$), 112.5 (C—H$_{arom}$), 107.8 (NCH$_2$C=CH$_2$), 103.0 (C—H$_{arom}$), 70.6 (PhCH$_2$O), 65.9 (NCHCH$_2$OH), 60.0 (NCHCH$_2$OH), 57.1 (OCH$_3$), 53.3 (NCH$_2$C=CH$_2$), 34.4 (NCH$_2$C=CH$_2$CH$_2$); MS (EI), m/z (relative intensity) 368 (M$^{+\cdot}$, 100), 353 (M—CH$_3$, 2), 340 (1), 286 (2), 273 (4), 256 (M—NCH$_2$C=CH$_2$CH$_2$CHCH$_2$OH, 59), 249 (8), 226 (4), 200 (2), 196 (2), 166 (5), 138 (17), 112 (NCH$_2$C=CH$_2$CH$_2$CHCH$_2$OH, 39), 91 (PhCH$_2$, 70), 82 (5), 65 (5); IR (NEAT) 3600–3000 (br, NH$_2$ and OH), 3065, 3052, 2932, 2869, 2246, 1668, 1620, 1592, 1513, 1454, 1408, 1264, 1229, 1197, 1176, 1113, 1079, 1002, 909, 733, 698, 645 cm$^{-1}$; exact mass calcd for C$_{21}$H$_{24}$N$_2$O$_4$ m/e 368.1736, obsd m/e 368.1662.

(2S)-N-[(2-Allyloxycarbonylamino)-4-benzyloxy-5-methoxybenzoyl]-2-(hydroxymethyl)-4-methylidenepyrrolidine (68)

A solution of the amino-alcohol 67 (0.33 g, 0.90 mmol) in CH$_2$Cl$_2$ (20 mL) was cooled to 0° C. (ice/acetone) and treated with pyridine (0.14 mL, 0.14 g, 1.77 mmol). A solution of allyl chloroformate (87 μL, 99 mg, 0.82 mmol) in CH$_2$Cl$_2$ (7 mL) was then added dropwise to the stirred mixture. The reaction mixture was allowed to warm to room temperature and stirred for a further 2.5 h, at which point TLC (EtOAc) revealed complete consumption of amine 67. The reaction mixture was diluted with CH$_2$Cl$_2$ (30 mL) and washed with saturated CuSO$_4$ (40 mL), H$_2$O (40 mL), brine (40 mL), dried (MgSO$_4$), filtered and evaporated in vacuo. The crude residue was purified by flash chromatography (80% EtOAc/Petroleum Ether) to afford the pure alloc-amino compound 68 as a white solid (0.34 g, 84%): $[\alpha]^{22}_D$= 22.4° (c=3.4, CHCl$_3$); $^1$H NMR (270 MHz, CDCl$_3$) δ8.52 (br s, 1H, NH), 7.82 (br s, 1H$_{arom}$), 7.49–7.29 (m, 5H$_{arom}$), 6.84 (s, 1H$_{arom}$), 6.02–5.88 (m, 1H, NCO$_2$CH$_2$CH=CH$_2$), 5.39–5.22 (m, 2H, NCO$_2$CH$_2$CH=CH$_2$), 5.17 (s, 2H, PhCH$_2$O), 5.01 (br s, 1H, NCH$_2$C=CH$_2$), 4.94 (br s, 1H, NCH$_2$C=CH$_2$), 4.64–4.59 (m, 3H, NCHCH$_2$OH and NCO$_2$CH$_2$CH=CH$_2$), 4.21–3.60 (m, 8H, NCHCH$_2$OH, NCH$_2$C=CH$_2$, OCH$_3$ and OH), 2.77 (dd, 1H, J=8.61, 15.94 Hz, NCH$_2$C=CH$_2$CH$_2$), 2.46 (d, 1H, J=15.94 Hz, NCH$_2$C=CH$_2$CH$_2$); $^{13}$C NMR (67.8 MHz, CDCl$_3$) δ171.4 (NC=O$_{amide}$), 153.7 (NC=O$_{carbamate}$), 150.3 (C$_{quat}$), 144.5 (C$_{quat}$), 143.0 (C$_{quat}$), 136.2 (C$_{quat}$), 132.4 (NCO$_2$CH$_2$CH=CH$_2$), 131.3 (C$_{quat}$), 128.6, 128.1, and 127.7 (BnC—H$_{arom}$), 118.1 (NCO$_2$CH$_2$CH=CH$_2$), 111.1 (C—H$_{arom}$), 108.1 (NCH$_2$C=CH$_2$), 106.5 (C—H$_{arom}$), 70.7 (PhCH$_2$O), 65.8 (NCO$_2$CH$_2$CH=CH$_2$), 65.5 (NCHCH$_2$OH), 59.9 (NCHCH$_2$OH), 56.7 (OCH$_3$), 54.0 (NCH$_2$C=CH$_2$), 34.1 (NCH$_2$C=CH$_2$CH$_2$); MS (EI), m/z (relative intensity) 452 (M$^{+\cdot}$, 38), 395 (M—OC$_3$H$_5$, 4), 394 (10), 340 (M—NCH$_2$C=CH$_2$CH$_2$CHCH$_2$OH, 20), 298 (7), 282 (22), 255 (8), 206 (2), 192 (2), 163 (3), 136 (3), 114 (6), 112 (NCH$_2$C=CH$_2$CH$_2$CHCH$_2$OH, 12), 91 (PhCH$_2$, 100), 82 (10), 65 (4), 57 (OC$_3$H$_5$, 7); IR (NUJOL®) 3600–2000 (br, OH), 3335, 3242, 2922, 2854, 1724, 1614, 1537, 1463, 1407, 1378, 1349, 1280, 1214, 1178, 1117, 1054, 1028, 995, 947, 908, 892, 853, 821, 768, 735, 697, 629, 601, 514 cm$^{-1}$; exact mass calcd for C$_{25}$H$_{28}$N$_2$O$_6$ m/e 452.1947, obsd m/e 452.1923.

(11S,11aS)-10-Allyloxycarbonyl-8-benzyloxy-11-hydroxy-7-methoxy-2-methylidene-1,2,3,10,11,11a-hexahydro-5H-pyrrolo[2,1-c][1,4]benzodiazepin-5-one (69)

A solution of DMSO (0.18 mL, 0.20 g, 2.56 mmol) in CH$_2$Cl$_2$ (4 mL) was added dropwise over 30 minutes to a solution of oxalyl chloride (0.63 mL of a 2.0 M solution in CH$_2$Cl$_2$, 1.26 mmol) at -45° C. (dry ice/CH$_3$CN) under a nitrogen atmosphere. After stirring at -45° C. for 30 minutes, a solution of the alcohol 68 (0.42 g, 0.93 mmol) dissolved in CH$_2$Cl$_2$ (8 mL) was added dropwise over 35 minutes at -45° C. After 45 minutes at -45° C., the mixture was treated dropwise with TEA (0.50 mL, 0.36 g, 3.56 mmol) in CH$_2$Cl$_2$ (4 mL) over 30 minutes at -45° C. After 35 minutes, the reaction mixture was allowed to warm to room temperature and was diluted with CH$_2$Cl$_2$ (30 mL), washed with 1N HCl (20 mL), H$_2$O (20 mL), brine (30 mL), dried (MgSO$_4$), filtered and evaporated in vacuo. TLC (80% EtOAc/Petroleum Ether) of the crude material revealed sufficient product formation and a trace of unoxidised starting material. Purification by flash chromatography (50% EtOAc/Petroleum Ether) furnished the protected carbinolamine 69 as white glass (0.172 g, 41%): $^1$H NMR (270 MHz, CDCl$_3$) δ7.48–7.27 (m, 5H$_{arom}$) 7.25 (s, 1H$_{arom}$), 6.74 (br s, 1H$_{arom}$), 5.65–5.53 (m, 1H, NCO$_2$CH$_2$CH=CH$_2$), 5.56 (d, 1H, J=9.89 Hz, NCHCHOH), 5.22–5.04 (m, 6H, NCH$_2$C=CH$_2$, NCO$_2$CH$_2$CH=CH$_2$ and PhCH$_2$O), 4.64–4.42 (m, 3H, NCO$_2$CH$_2$CH=CH$_2$ and OH), 4.28 (d, 1H, J=15.94 Hz, NCH$_2$C=CH$_2$), 4.09 (d, 1H, J=15.94 Hz, NCH$_2$C=CH$_2$), 3.92 (s, 3H, OCH$_{13}$), 3.62 (t, 1H, J=8.79 Hz, NCHCHOH), 2.90 (dd, 1H, J=8.97, 16.03 Hz, NCH$_2$C=CH$_2$CH$_2$), 2.67 (d, 1H, J=16.03 Hz, NCH$_2$C=CH$_2$CH$_2$); $^{13}$C NMR (67.8 MHz, CDCl$_3$) δ166.8 (NC=O$_{amide}$), 156.0 (NC=O$_{carbamate}$), 150.1 (C$_{quat}$), 149.0 (C$_{quat}$), 141.8 (C$_{quat}$), 136.1 (C$_{quat}$), 131.8 (NCO$_2$CH$_2$CH=CH$_2$,), 128.6, 128.1 and 127.3 (BnC—H$_{arom}$), 125.6 (C$_{quat}$), 118.0 (NCO$_2$CH$_2$CH=CH$_2$), 14.6 (C—H$_{arom}$), 110.6 (C—H$_{arom}$), 109.8 (NCH$_2$C=CH$_2$), 85.8 (NCHCHOH), 71.0 (PhCH$_2$O), 66.7 (NCO$_2$CH$_2$CH=CH$_2$), 59.8 (NCHCHOH), 56.2 (OCH3), 50.7 (NCH$_2$C=CH$_2$), 35.0 (NCH$_2$C=CH$_2$CH$_2$); MS (EI), m/z (relative intensity) 450 (M$^{+\cdot}$, 24), 422 (1), 392 (1), 364 (1), 348 (3), 340 (12), 298 (6), 282 (8), 257 (2), 229 (2), 192 (3), 178 (2), 164 (4), 136 (3), 110 (3), 91 (PhCH$_2$, 100), 82 (17), 65 (7); IR (NUJOL™) 3600–2500 (br, OH), 2923, 2854, 1711, 1619, 1601, 1513, 1463, 1405, 1377, 1300, 1278, 1202, 1119, 1045, 993, 956, 909, 790, 768, 724, 697, 637 cm$^{-1}$; exact mass calcd for C$_{25}$H$_{26}$N$_2$O$_6$ m/e 450.1791, obsd m/e 450.1790.

Alternative Synthesis (11S,11aS)-10-Allyloxycarbonyl-8-benzyloxy-11-hydroxy-7-methoxy-2-methylidene-1,2,3,10,11,11a-hexahydro-5H-pyrrolo[2,1-c][1,4]benzodiazepin-5-one (69)

A solution of the alcohol 68 (0.32 g, 0.71 mmol) in CH$_2$Cl$_2$/CH$_3$CN (30 mL, 3:1) was treated with 4 Å powdered molecular sieves (0.2 g) and NMO (126 mg, 1.08 mmol). After 15 minutes stirring at room temperature, TPAP (12.6 mg, 35.9 μmol) was added and stirring continued for a further 1 hour 20 minutes at which point TLC (80% EtOAc/Petroleum Ether) revealed product formation along with some unoxidised starting material. The mixture was then treated with a further quantity of NMO (126 mg, 1.08 mmol) and TPAP (12.6 mg, 35.9 μmol), and allowed to stir for a further 0.5 hours after which time TLC revealed reaction completion. The mixture was evaporated in vacuo onto silica and subjected to flash chromatography (50% EtOAc/Petroleum Ether) to provide the protected carbinolamine 69 as a white glass (153 mg, 48%): [α]$^{23}_D$=+129.8° (c=1.5, CHCl$_3$); $^1$H NMR (270 MHz, CDCl$_3$) δ7.48–7.27 (m, 5H$_{arom}$), 7.25 (s, 1H$_{arom}$), 6.74 (br s, 1H$_{arom}$), 5.65–5.53 (m, 1H, NCO$_2$CH$_2$CH=CH$_2$), 5.56 (d, 1H, J=9.89 Hz, NCHCHOH), 5.22–5.04 (m, 6H, NCH$_2$C=CH$_2$, NCO$_2$CH$_2$CH=CH$_2$ and PhCH$_2$O), 4.64–4.42 (m, 3H, NCO$_2$CH2CH=CH$_2$ and OH), 4.28 (d, 1H, J=15.94 Hz, NCH$_2$C=CH$_2$), 4.09 (d, 1H, J=15.94 Hz, NCH$_2$C=CH$_2$), 3.92 (s, 3H, OCH$_3$), 3.62 (t, 1H, J=8.79 Hz, NCHCHOH), 2.90 (dd, 1H, J=8.97, 16.03 Hz, NCH$_2$C=CH$_2$CH$_2$), 2.67 (d, 1H, J=16.03 Hz, NCH$_2$C=CH$_2$CH$_2$); $^{13}$C NMR (67.8 MHz, CDCl$_3$) δ166.8 (NC=O$_{amide}$), 156.0 (NC=O$_{carbamate}$), 150.1 (C$_{quat}$), 149.0 (C$_{quat}$), 141.8 (C$_{quat}$), 136.1 (C$_{quat}$), 131.8 (NCO$_2$CH$_2$CH=CH$_2$), 128.6, 128.1 and 127.3 (BnC—H$_{arom}$), 125.6 (C$_{quat}$), 118.0 (NCO$_2$CH$_2$CH=CH$_2$), 114.6 (C—H$_{arom}$), 110.6 (C—H$_{arom}$), 109.8 (NCH$_2$C=CH$_2$), 85.8 (NCHCHOH), 71.0 (PhCH$_2$O), 66.7 (NCO$_2$CH$_2$CH=CH$_2$), 59.8 (NCHCHOH), 56.2 (OCH$_3$), 50.7 (NCH$_2$C=CH$_2$), 35.0 (NCH$_2$C=CH$_2$CH$_2$); MS (EI), m/z (relative intensity) 450 (M$^{+\cdot}$, 24), 422 (1), 392 (1), 364 (1), 348 (3), 340 (12), 298 (6), 282 (8), 257 (2), 229 (2), 192 (3), 178 (2), 164 (4), 136 (3), 110 (3), 91 (PhCH$_2$, 100), 82 (17), 65 (7); IR (NUJOL®) 3600–2500 (br, OH), 2923, 2854, 1711, 1619, 1601, 1513, 1463, 1405, 1377, 1300, 1278, 1202, 1119, 1045, 993, 956, 909, 790, 768, 724, 697, 637 cm$^{-1}$; exact mass calcd for C$_{25}$H$_{26}$N$_2$O$_6$ m/e 450.1791, obsd ml/e 450.1790.

(11aS)-8-Benzyloxy-7-methoxy-2-methylidene-1,2,3,11a-tetrahydro-5H-pyrrolo[2,1-c][1,4]benzodiazepin-5-one (70, SJG-244)

A catalytic amount of tetrakis(triphenylphosphine)palladium (12.0 mg, 10.4 μmol) was added to a stirred solution of the Alloc-protected carbinolamine 69 (0.18 g, 0.40 mmol), triphenylphosphine (5.25 mg, 20 μmol) and pyrrolidine (29 mg, 0.41 mmol) in CH$_2$Cl$_2$ (15 mL). After 2 hours stirring at room temperature under a nitrogen atmosphere, TLC (98% CHCl$_3$/MeOH) revealed the complete consumption of starting material. The solvent was evaporated in vacuo and the crude residue was purified by flash chromatography (60% EtOAc/Petroleum Ether) to afford 70 (SJG-244) as a white glass (116 mg, 83%) which was repeatedly evaporated in vacuo with CHCl$_3$ in an attempt to provide the N10-C11 imine form: [α]$^{22}_D$=+754.2° (c=0.54, CHCl$_3$); $^1$H NMR (270 MHz, CDCl$_3$) (mainly imine, plus trace of carbinolamine form) δ7.70–7.30 (m, 7H, HC=N and 6H$_{arom}$), 6.84 (s, 1H$_{arom}$), 5.25–5.13 (m, 4H, NCH$_2$C=CH$_2$ and PhCH$_2$O), 4.42 (br s, 2H, NCH$_2$C=CH$_2$), 3.95 (s, 3H, OCH$_3$), 3.88–3.66 (m, 1H, NCHHC=N), 3.09 (dd, 1H, J 8.98, 16.12 Hz, NCH$_2$C=CH$_2$CH$_2$), 2.94–2.87 (m, 1H, NCH$_2$C=CH$_2$CH$_2$); $^{13}$C NMR (67.8 MHz, CDCl$_3$) δ164.7 (NC=O), 162.6 (HC=N), 150.6 (C$_{quat}$), 148.1 (C$_{quat}$), 141.6 (C$_{quat}$), 140.5 (C$_{quat}$), 136.1 (C$_{quat}$), 132.0, 128.7, 128.6, 128.1 and 127.3 (BnC—H$_{arom}$), 120.1 (C$_{quat}$), 111.5 (C—H$_{arom}$), 111.2 (C—H$_{arom}$), 109.4 (NCH$_2$C=CH$_2$), 70.8 (PhCH$_2$O), 56.2 (OCH$_3$), 53.7 (NCHHC=N), 51.3 (NCH$_2$C=CH$_2$), 35.4 (NCH$_2$C=CH$_2$CH$_2$); MS (EI), m/z (relative intensity) (imine form) 348 (M$^{+\cdot}$, 100), 333 (M—CH$_3$, 42), 319 (3), 269 (5), 257 (M—PhCH$_2$, 25), 241 (11), 229 (56), 227 (11), 213 (5), 186 (4), 156 (6), 136 (22), 122 (4), 91 (PhCH$_2$, 85), 82 (5), 65 (22); IR (NUJOL™) 3318 (br, OH of carbinolamine form), 2923, 2853, 1722, 1668, 1600, 1557, 1504, 1462, 1377, 1261, 1216, 1120, 1003, 892, 789, 722, 695, 623, 542 cm$^{-1}$; exact mass calcd for C$_{21}$H$_{20}$N$_2$O$_3$ m/e 348.1474, obsd m/e 348.1469.

Example 2(c)

Figure 9:
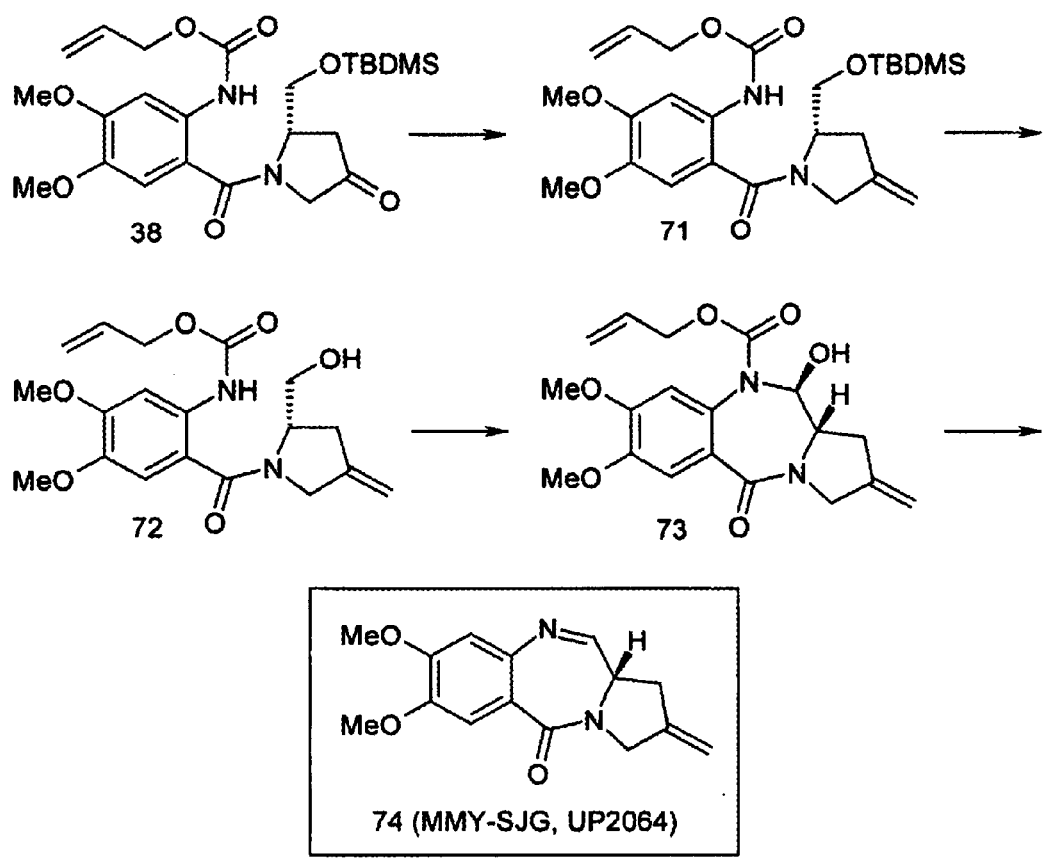

Synthesis of MMY-SJG (74, UP2064) (See FIG. 9)

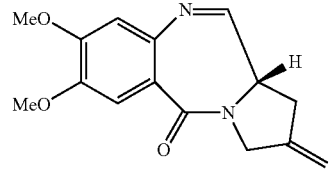

(2s)-N-[(2-Allyloxycarbonylamino)-4,5-dimethoxybenzoyl]-2-(tert-butyldimethylsilyloxymethyl)-4-methylidinepyrrolidine (71)

Potassium tert-butoxide (21.2 mL of a 0.5 M solution in THF, 10.6 mmol) was added dropwise to a suspension of methyltriphenylphosphonium bromide (3.78 g, 10.6 mmol) in THF (11 mL) at 0° C. (ice/acetone) under nitrogen. After stirring for 2 hours at 0° C., a solution of the ketone 38 (Example 1(e)) (2.0 g, 4.07 mmol) in THF (7 mL) was added dropwise and the mixture allowed to warm to room temperature. After stirring for a further 45 minutes the reaction mixture was diluted with EtOAc (60 mL) and water (60 mL). The organic layer was separated, washed with brine, dried (MgSO$_4$), filtered and evaporated in vacuo to give a dark oil. Purification by flash chromatography (20% EtOAc/Petroleum Ether) isolated the pure olefin 71 as a transparent oil (1.71 g, 86%): [α]$^{22}_D$=-44.55° (c=0.20, CHCl$_3$); $^1$H NMR (270 MHz, CDCl$_3$) (Rotamers) δ8.85 (br s, 1H), 7.86 (s, 1H), 6.82 (s, 1H), 6.03–5.89 (m, 1H), 5.35 (ddd, 1H, J=17.22, 3.11, 1.47 Hz), 5.24 (ddd, 1H, J=10.44, 2.75, 1.28 Hz), 4.99–4.92 (m, 2H), 4.70–4.57 (m, 3H), 4.23–3.57 (m, 10H), 2.72–2.68 (m, 2H), 0.96–0.85 (m, 9H), 0.09–0.03 (m, 6H); $^{13}$C NMR (67.8 MHz, CDCl$_3$) (Rotamers) δ168.7, 153.6, 150.9, 143.6, 132.5, 132.2, 118.1, 115.3, 110.6, 107.1, 104.3, 65.7, 63.6, 56.3, 56.0, 33.1, 25.8, 18.1, -5.5 and -5.6; MS (EI), m/z (relative intensity) 492 (M$^{+\cdot}$ +2, 7), 491 (M$^{+\cdot}$ +1, 20), 490 (M$^{+\cdot}$, 50), 475 (4), 435 (10), 447 (3), 434 (29), 433 (94), 376 (4), 375 (13), 348 (5), 333 (11), 332 (6), 294 (3), 265 (16), 264 (100), 227 (8), 226 (24), 224 (5), 223 (18), 220 (15), 210 (4), 208 (5), 207 (13), 206 (96), 192 (7), 180 (18), 179 (25), 170 (21), 169 (8), 168 (28), 164 (13), 152 (7), 150 (13), 136 (10), 108 (5), 96 (5), 95 (12), 94 (7), 89 (8), 82 (25), 75 (20), 73 (30), 59 (7), 58 (5), 57 (41), 56 (7), 55 (4); IR (NEAT) 3324 (br, NH), 3082, 2953, 2930, 2857, 1732, 1600, 1523, 1490, 1464, 1419, 1397, 1360, 1333, 1287, 1259, 1228, 1203, 1172, 1115, 1039, 1004, 939, 837, 814, 777 666 cm$^{-1}$.

(2S)-N-[(2-Allyloxycarbonylamino)-4,5-dimethoxybenzoyl]-2-(hydroxymethyl)-4-methylidinepyrrolidine (72)

A solution of TBAF (4.29 mL of a 1M solution in THF, 4.29 mmol) was added to the silyl-ether 71 (1.68 g, 3.43 mmol) in THF (45 mL) at 0° C. (ice/acetone). The reaction mixture was allowed to warm to room temperature and after 1 hour TLC (50% EtOAc/Pet-Ether 40°–60°) revealed the complete disappearance of starting material. Saturated NH$_4$Cl (110 mL) was added and the reaction mixture extracted with EtOAc (3×50 mL), washed with brine (100 mL), dried (MgSO$_4$), filtered and evaporated in vacuo to give a dark orange oil. Purification by flash chromatography (99% CHCl$_3$/MeOH) provided the pure alcohol 72 as a white solid (1.15 g, 89%): [α]$^{21}_D$=−13.17° (c=0.15, CHCl$_3$); $^1$H NMR (270 MHz, CDCl$_3$) δ8.59 (br s, 1H), 7.69 (s, 1H), 6.82 (s, 1H), 6.03–5.89 (m, 1H), 5.35 (ddd, 1H, J=17.22, 3.11, 1.65 Hz), 5.24 (ddd, 1H, J=10.44, 2.75, 1.28 Hz), 5.02–4.94 (m, 2H), 4.66–4.62 (m, 3H), 4.23–3.57 (m, 11H), 2.77 (dd, 1H, J=15.94, 8.42 Hz), 2.48 (d, 1H, J=15.94 Hz); $^{13}$C NMR (67.8 MHz, CDCl) δ170.3, 153.8, 151.0, 144.2, 143.1, 132.5, 131.2, 118.1, 115.9, 110.4, 108.1, 104.9, 65.8, 65.1, 59.8, 56.4, 56.0, 54.2, 34.1; MS (EI), m/z (relative intensity) 378 (M$^{+\cdot}$ +2, 3), 377 (M$^{+\cdot}$ +1, 14), 376 (M$^{+\cdot}$, 51), 319 (3), 265 (10), 264 (62), 263 (4), 259 (8), 224 (4), 223 (18), 220 (17), 208 (5), 207 (14), 206 (100), 192 (8), 190 (5), 180 (27), 179 (29), 178 (4), 164 (23), 163 (4), 152 (12), 151 (6), 150 (19), 137 (5), 136 (22), 135 (6), 125 (6), 120 (6), 113 (6), 112 (31), 109 (6), 108 (11), 95 (4), 94 (9), 82 (28), 80 (8), 67 (5), 57 (5), 54 (7), 53 (7); IR (NUJOL®) 3341 and 3245 (br, OH and NH), 3115, 2918, 2850, 1727, 1616, 1540, 1464, 1399, 1378, 1351, 1283, 1264, 1205, 1179, 1117, 1055, 1040, 996, 946, 909, 894, 855, 823, 768, 754, 722, 696, 623, 602 cm$^{-1}$; exact mass calcd for C$_{11}$H$_{24}$N$_2$O$_6$ m/e 376.1634, obsd m/e 376.1614.

(11S,11aS)-10-Allyloxycarbonyl-7,8-dimethoxy-11-hydroxy-2-methylidene-1,2,3,10,11,11a-hexahydro-5H-pyrrolo[2,1-c][1,4]benzodiazepin-5-one (73)

A solution of DMSO (0.75 mL, 0.82 g, 10.5 mmol) in CH$_2$Cl$_2$ (27 mL) was added dropwise over 38 minutes to a solution of oxalyl chloride (2.64 mL of a 2.0 M solution in CH$_2$Cl$_2$, 5.27 mmol) at −45° C. (liq.N$_2$/Chlorobenzene) under a nitrogen atmosphere. After stirring at −45° C. for 1 h, a solution of the alcohol 72 (1.10 g, 2.93 mmol) in CH$_2$Cl$_2$ (27 mL) was added dropwise over 1 hour at −45° C. After 1 hour at −45° C., the mixture was treated dropwise with a solution of TEA (1.71 mL, 1.24 g, 12.29 mmol) in CH$_2$Cl$_2$ (15 mL) over 40 minutes at −45° C. After a further 30 minutes, the reaction mixture was allowed to warm to room temperature and was diluted with CH$_2$Cl$_2$ (50 mL), washed with 1N HCl (50 mL), H$_2$O (50 mL), brine (50 mL), dried (MgSO$_4$), filtered and evaporated in vacuo. TLC (80% EtOAc/Petroleum Ether) of the crude material revealed reaction completion. Purification by flash chromatography (60% EtOAc/Petroleum Ether) furnished the protected carbinolamine 73 as a white glass (0.45 g, 41%): [α]$^{22}_D$=+ 236.51° (c=0.14, CHCl$_3$); $^1$H NMR (270 MHz, CDCl$_3$) δ7.23 (s, 1H), 6.69 (s, 1H), 5.83–5.81 (m, 1H), 5.60–5.58 (m, 1H), 5.34–5.23 (m, 4H), 4.74–4.66 (m, 1H), 4.50–4.40 (m, 1H), 4.30 (d, 1H, J=15.94 Hz), 4.15 (d, 1H, J=15.93 Hz), 3.96–3.86 (m, 7H), 3.65 (t, 1H, J=8.61 Hz), 2.92 (dd, 1H, 16.21, 9.07 Hz), 2.70 (d, 1H, J=15.94 Hz); $^{13}$C NMR (67.8 MHz, CDCl$_3$) δ166.7, 156.0, 150.8, 148.4, 141.8, 131.7, 128.5, 125.2, 118.1, 112.4, 110.3, 109.8, 85.9, 66.8, 59.6, 56.3, 56.1, 50.7, 35.0; MS (EI), m/z (relative intensity) 376 (M$^{+\cdot}$ +2, 6), 375 (Me$^+$1, 22), 374 (M$^{+\cdot}$, 100), 346 (5), 293 (8), 288 (10), 271 (5), 265 (11), 264 (67), 248 (5), 237 (5), 223 (10), 220 (9), 209 (6), 208 (42), 207 (14), 206 (70), 192 (7), 190 (5), 180 (17), 179 (16), 165 (8), 164 (15), 153 (5), 152 (10), 150 (12), 149 (7), 137 (6), 136 (10), 135 (5), 125 (8), 110 (8), 108 (5), 94 (5), 83 (5), 82 (59), 80 (7), ; IR (CHCl$_3$) 3275 (br, OH), 3075, 2936, 2851, 1706, 1624, 1604, 1516, 1457, 1436, 1403, 1368, 1312, 1301, 1278, 1262, 1218, 1119, 1074, 1045, 940, 916, 893, 867, 851, 666, 637 cm$^{-1}$; exact mass calcd for C$_{19}$H$_{22}$N$_2$O$_6$ m/e 374.1478, obsd m/e 374.1687.

(11aS)-7,8-Dimethoxy-2-methylidene-1,2,3,11a-tetrahydro-5H-pyrrolo[2,1-c][1,4]benzodiazepin-5-one (74, UP2064, MMY-SJG)

A catalytic amount of tetrakis(triphenylphosphine) palladium (32.4 mg, 28.1 μmol) was added to a stirred solution of the Alloc-protected carbinolamine 73 (0.42 g, 1.12 mmol), triphenylphosphine (14.7 mg, 56.2 μmol) and pyrrolidine (83.9 mg, 1.18 mmol) in CH$_2$Cl$_2$ (55 mL). After 2.5 hours stirring at room temperature under a nitrogen atmosphere, TLC (95% CHCl$_3$/MeOH) revealed the complete consumption of starting material. The solvent was evaporated in vacuo and the crude residue was purified by flash chromatography (CHCl$_3$) to afford the novel PBD (74, MMY-SJG, UP2064) as a yellow oil which was repeatedly evaporated in vacuo with CHCl$_3$ in order to provide the N10-C11 imine form (259 mg, 85%): [α]$^{22}_D$=+583.14° (c=1.42, CHCl$_3$); $^1$H NMR (270 MHz, CDCl$_3$) δ7.69 (d, 1H, J=4.39 Hz), 7.51 (s, 1H), 6.82 (s, 1H), 5.21–5.17 (m, 2H), 4.44–4.23 (m, 2H), 3.96–3.81 (m, 7H), 3.17–3.08 (m, 1H), 2.95 (d, 1H, J=14.29 Hz); $^{13}$C NMR (67.8 MHz, CDCl$_3$) δ164.7, 162.6, 151.5, 147.6, 141.6, 140.8, 119.8, 111.2, 109.4, 109.4, 56.2, 56.1, 53.8, 51.4, 35.5; MS (EI), m/z (relative intensity) 273 (M$^{+\cdot}$ +1, 16), 272 (M$^{+\cdot}$, 100), 271 (35), 270 (9), 255 (5), 243 (7), 241 (7), 230 (6), 228 (6), 226 (5), 212 (3), 192 (4), 191 (16), 165 (4), 164 (19), 163 (4), 136 (22), 93 (6), 82 (7), 80 (3), 53 (3); IR (NEAT) 3312 (br), 3083, 2936, 2843, 1624, 1603, 1505, 1434, 1380, 1264, 1217, 1180, 1130, 1096, 1069, 1007, 935, 895, 837, 786, 696, 666, 594, 542 cm$^{-1}$; exact mass calcd for C$_{11}$H$_{16}$N$_2$O$_3$ m/e 272.1161, obsd m/e 272.1154.

Example 2(d)

Figure 10:
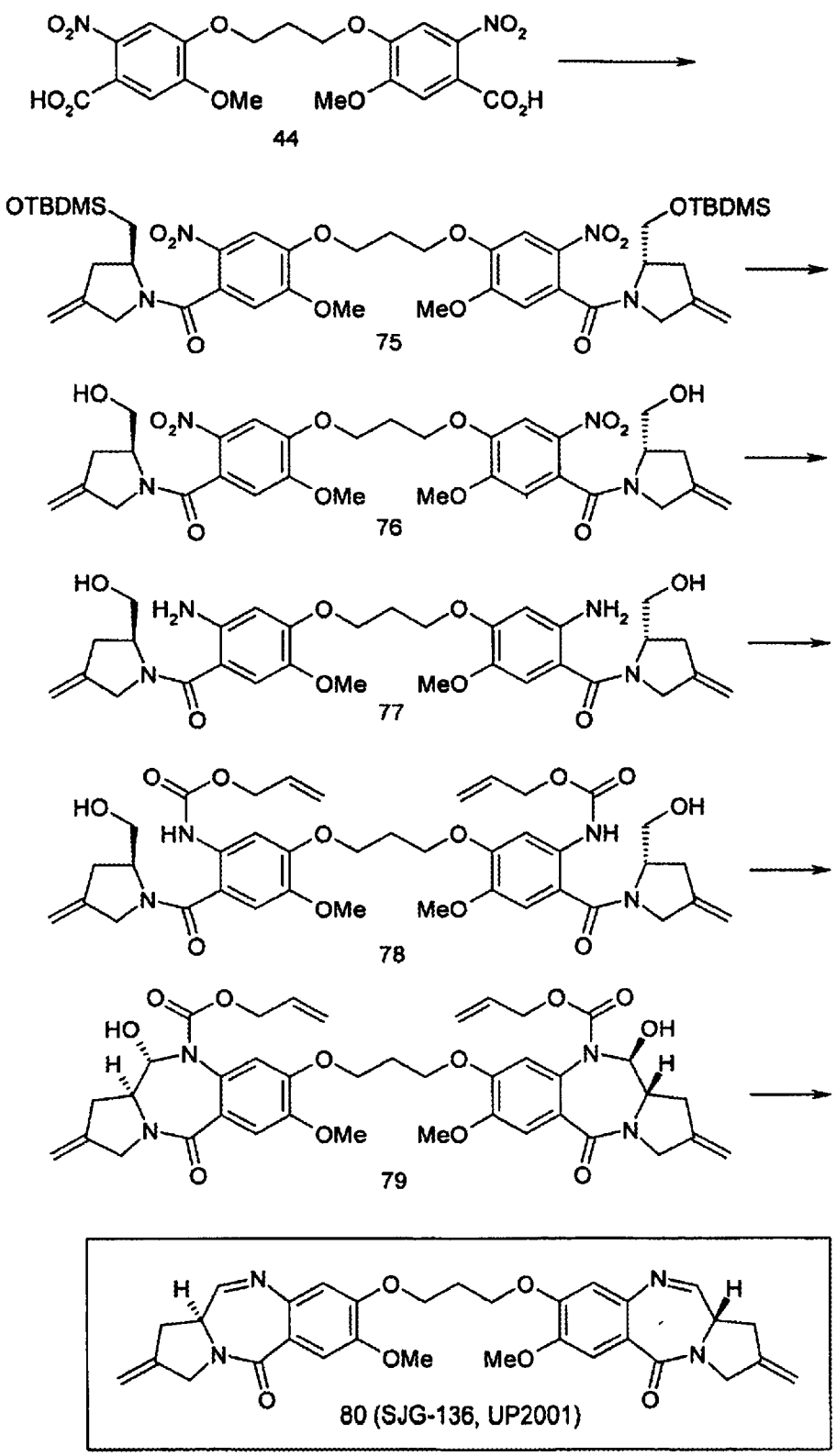

Synthesis of the PBD Dimer SJG-136 (UP2001) (See FIG. 10)

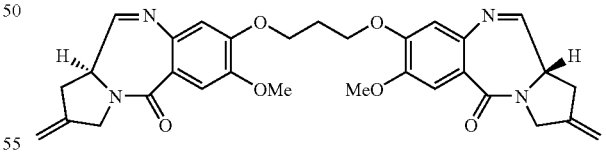

(2S)-1,1'-[[(Propane-1,3-diyl)dioxy]bis[(2-nitro-5-methoxy-1,4-phenylene)carbonyl]]bis[2-(tert-butyldimethylsilyloxymethyl)-4-methylidenepyrrolidine] (75)

A catalytic amount of DMF (2 drops) was added to a solution of the dimer acid 44 (0.66 g, 1.42 mmol) and oxalyl chloride (0.31 mL, 0.45 g, 3.55 mmol) in THF (12 mL). The reaction mixture was stirred for 16 hours under nitrogen, concentrated in vacuo, and redissolved in THF (10 mL). The resulting solution of bis-acid chloride was added dropwise to the amine 58 (0.65 g, 2.86 mmol), H$_2$O (0.84 mL) and TEA (0.83 mL, 0.60 g, 5.93 mmol) in THF (2 mL) at 0° C. (ice/acetone) under nitrogen. The reaction mixture was allowed to warm to room temperature and stirred for a further 2 hours at which time TLC (EtOAc) revealed reaction completion. After removal of the THF by evaporation in vacuo, the residue was partitioned between $H_2O$ (100 mL) and EtOAc (100 mL). The aqueous layer was washed with EtOAc (3×50 mL), and the combined organic layers washed with saturated $NH_4CL$ (100 mL), brine (100 mL), dried ($MgSO_4$), filtered and concentrated in vacuo to give the crude product as a dark orange oil. Purification by flash chromatography (50% EtOAc/Petroleum Ether) afforded the pure amide 75 as a pale yellow glass (0.93 g, 74%): $[\alpha]^{21}_D$=−51.1° (c=0.08, $CHCl_3$); $^1$H NMR (270 MHz, $CDCl_3$) (Rotamers) δ7.77 and 7.74 (s×2, $2H_{arom}$), 6.81 and 6.76 (s×2, $2H_{arom}$), 5.09–4.83 (m, 4H, $NCH_2C=CH_2$), 4.60 (m, 2H, $NCHCH_2OTBDMS$), 4.35–4.31 (m, 4H, $OCH_2CH_2CH_2O$), 4.08–3.74 (m, 14H, $NCHCH_2OTBDMS$, $NCH_2C=CH_2$ and $OCH_3$), 2.72–2.45 (m, 6H, $NCH_2C=CH_2CH_2$ and $OCH_2CH_2CH_2O$), 0.91 and 0.79 (s×2, 18H, $SiC(CH_3)_3$), 0.09, −0.09, and −0.12 (s×3, 12H, $Si(CH_3)_2$); $^{13}$C NMR (67.8 MHz, $CDCl_3$) (Rotamers) δ166.2 (NC=O), 154.7 and 154.5 ($C_{quat}$), 148.4 and 148.2 ($C_{quat}$), 144.1 and 143.2 ($C_{quat}$), 137.2 ($C_{quat}$), 128.2 and 127.4 ($C_{quat}$), 110.1 and 108.6 (C—$H_{arom}$), 109.1 and 108.3 (C—$H_{arom}$), 107.5 ($NCH_2C=CH_2$), 65.7 and 65.5 ($OCH_2CH_2CH_2O$), 63.9 and 62.6 ($NCHCH_{12}TBDMS$), 60.2 ($NCHCH_2OTBDMS$), 58.1 and 56.6 ($OCH_3$), 52.8 and 50.5 ($NCH2C=CH_2$), 35.0 and 33.9 ($NCH_2C=CH_2CH_2$), 30.8 and 28.6 ($OCH_2CH_2CH_2O$), 25.8 and 25.7 (SiC ($CH_3)_3$), 18.2 ($SiC(CH_3)_3$), −5.5 and −5.6 ($Si(CH_3)_2$); MS (EI), m/z (relative intensity) 885 ($M^{+\cdot}$, 7), 828 (M—$^tBu$, 100), 740 (M—$CH_2OTBDMS$, 20), 603 (3), 479 (26), 391 (27), 385 (25), 301 (7), 365 (10), 310 (14), 226 (8), 222 (13), 170 (21), 168 (61), 82 (39), 75 (92); IR (NUJOL™) 2923, 2853, 2360, 1647, 1587, 1523 ($NO_2$), 1461, 1429, 1371, 1336 ($NO_2$), 1277, 1217, 1114, 1061, 1021, 891, 836 772, 739 cm$^{-1}$.

(2S)-1,1'-[[(Propane-1,3-diyl)dioxy]bis[(2-nitro-5-methoxy-1,4-phenylene)carbonyl]]bis [2-(hydroxymethyl)-4-methylidenepyrrolidine] (76)

A solution of TBAF (3.98 mL of a 1M solution in THF, 3.98 mmol) was added to the bis-silyl ether 75 (1.41 g, 1.59 mmol) in THF (35 mL) at 0° C. (ice/acetone). The reaction mixture was allowed to warm to room temperature and after a further 30 minutes saturated $NH_4Cl$ (120 mL) was added. The aqueous solution was extracted with EtOAc (3×80 mL), washed with brine (80 mL), dried ($MgSO_4$), filtered and evaporated in vacuo to give a dark orange oil which was purified by flash chromatography (97% $CHCl_3$/MeOH) to provide the pure diol 76 as a light orange solid (0.98 g, 94%): $[\alpha]^{19}_D$=−31.9° (c=0.09, $CHCl_3$); $^1$H NMR (270 MHz, $CDCl_3$) (Rotamers) δ7.75 and 7.71 (s×2, $2H_{arom}$), 6.96 and 6.84 (s×2, $2H_{arom}$), 5.08, 5.02 and 4.88 (br s×3, 4H, $NCH_2C=CH_2$), 4.61–4.50 (m, 2H, $NCHCH_2OH$), 4.35–4.33 (m, 4H, $OCH_2CH_2CH_2O$), 4.02–3.65 (m, 14H, $NCHCH_2OH$, $NCH_2C=CH_2$ and OCH,), 2.88–2.43 (m, 6H, $NCH_2C=CH_2CH_2$ and $OCH_2CH_2CH_2O$); $^{13}$C NMR (67.8 MHz, $CDCl_3$) (Rotamers) δ167.9 and 166.9 (NC=O), 154.9 and 154.3 ($C_{quat}$), 148.4 and 148.2 ($C_{quat}$), 143.3 and 142.6 ($C_{quat}$), 137.2 and 137.0 ($C_{quat}$), 127.6 and 127.3 ($C_{quat}$), 109.1 (C—$H_{arom}$), 108.4 ($NCH_2C=CH_2$), 108.2 (C—$H_{arom}$), 65.6 and 65.4 ($OCH_2CH_2CH_2O$), 64.5 and 63.3 ($NCHCH_2OH$), 60.5 and 60.0 ($NCHCH_2OH$), 56.8 and 56.7 ($OCH_3$), 52.9 ($NCH_2C=CH_2$), 35.0 and 34.3 ($NCH_2C=CH_2CH_2$), 29.6 and 28.6 ($OCH_2CH_2CH_2O$); MS (FAB) (Relative Intensity) 657 ($M^{+\cdot}$ +1, 10), 639 (M—OH, 2), 612 (1), 544 (M—$NCH_2CCH_2CH_2CHCH_2OH$, 4), 539 (1), 449 (16), 433(9), 404 (8), 236 (32), 166 (65), 151 (81), 112 (82), 82 (100); IR (NUJOL®) 3600–3200 (br, OH), 2923, 2853, 2360, 1618, 1582, 1522 ($NO_2$), 1459, 1408, 1375, 1335 ($NO_2$), 1278, 1218, 1061, 908, 810, 757 cm$^{-1}$.

(2S)-1,1'-[[(Propane-1,3-diyl)dioxy]bis[(2-amino-5-methoxy-1,4-phenylene)carbonyl]]bis[2-(hydroxymethyl)-4-methylidenepyrrolidine] (77)

A mixture of the diol 76 (0.98 g, 1.49 mmol) and $SnCl_2 \cdot 2H_2O$ (3.36 g, 14.9 mmol) in MeOH (35 mL) was heated at reflux and the progress of the reaction monitored by TLC (90% $CHCl_3$/MeOH). After 45 minutes, the MeOH was evaporated in vacuo and the resulting residue was cooled (ice), and treated carefully with saturated $NaHCO_3$ (120 mL). The mixture was diluted with EtOAc (120 mL), and after 16 hours stirring at room temperature the inorganic precipitate was removed by filtration through celite. The organic layer was separated, washed with brine (100 mL), dried ($MgSO_4$), filtered and evaporated in vacuo to give a brown solid. Flash chromatography (95% $CHCl_3$/MeOH) afforded the pure bis-amine 77 as an orange solid (0.54 g, 61%): $[\alpha]^{19}_D$=−31.8° (c=0.30, $CHCl_3$); $^1$H NMR (270 MHz, $CDCl_3$) δ6.74 (s, $2H_{arom}$), 6.32 (s, $2H_{arom}$), 5.00 (br s, 2H, $NCH_2C=CH_2$), 4.93 (br s, 2H, $NCH_2C=CH_2$), 4.54 (br s, 2H, $NCHCH_2OH$), 4.24–4.14 (m, 4H, $OCH_2CH_2CH_2O$), 3.98–3.50 (m, 14H, $NCHCH_2OH$, $NCH_2C=CH_2$ and $OCH_3$), 2.76 (dd, 2H, J=8.61, 15.91 Hz, $NCH_2C=CH_2CH_2$), 2.46–2.41 (m, 2H, $NCH_2C=CH_2CH_2$), 2.33–2.28 (m, 2H, $OCH_2CH_2CH_2O$); $^{13}$C NMR (67.8 MHz, $CDCl_3$) δ171.0 (NC=O), 151.0 ($C_{quat}$), 143.5 ($C_{quat}$), 141.3 ($C_{quat}$), 140.6 ($C_{quat}$), 112.4 (C—$H_{arom}$), 111.9 ($C_{quat}$), 107.8 ($NCH_2C=CH_2$), 102.4 (C—$H_{arom}$), 65.2 ($OCH_2CH_2CH_2O$), 65.0 ($NCHCH_2OH$), 59.8 ($NCHCH_2OH$), 57.1 ($OCH_3$), 53.3 ($NCH_2C=CH_2$), 34.4 ($NCH_2C=CH_2CH_2$), 29.0 ($OCH_2CH_2CH_2O$); MS (FAB) (Relative Intensity) 596 ($M^{+\cdot}$, 13), 484 (M—$NCH_2CCH_2CH_2CHCH_2OH$, 14), 389 (10), 371 (29), 345 (5), 224 (8), 206 (44), 166 (100), 149 (24), 112 (39), 96 (34), 81 (28); IR (NUJOL™) 3600–3000 (br, OH), 3349 ($NH_2$), 2922, 2852, 2363, 1615, 1591 ($NH_2$), 1514, 1464, 1401, 1359, 1263, 1216, 1187, 1169, 1114, 1043, 891, 832, 761 cm$^{-1}$. (2S,4R)&(2S,4S)-1,1'-[[(Propane-1,3-diyl)dioxy] bis[(2-amino-5-methoxy-1,4-phenylene)carbonyl]]bis[2-(hydroxymethyl)-4-methylpyrrolidine] (77).

A solution of hydrazine (23 mg, 23 μL, 0.72 mmol) in MeOH (5 mL) was added dropwise to a solution of the diol 76 (95 mg, 0.145 mmol) and Raney Ni (20 mg) in MeOH (15 mL) heated at reflux. After 1 hour at reflux TLC (90% $CHCl_3$/MeOH) revealed some amine formation. The reaction mixture was treated with further Raney Ni (20 mg) and hydrazine (23 mg, 23,L, 0.72 mmol) in MeOH (5 mL) and was heated at reflux for an additional 30 minutes at which point TLC revealed complete reaction. The reaction mixture was then treated with enough Raney Ni to decompose any remaining hydrazine and heated at reflux for a further 1.5 hours. Following cooling to room temperature the mixture was filtered through a sinter and the resulting filtrate evaporated in vacuo. The resulting residue was then treated with $CH_2Cl_2$ (30 mL), dried ($MgSO_4$), filtered and evaporated in vacuo to provide the bis-amine (77) as a yellow oil (54 mg, 63%): $^1$H NMR (270 MHz, $CDCl_3$) (diastereoisomers) δ6.73 (s, $2H_{arom}$), 6.32 (s, $2H_{arom}$), 4.60–4.30 (m, 2H, $NCHCH_2OH$), 4.19 (t, 4H, J=5.87 Hz, $OCH_2CH_2CH_2O$), 3.78–3.50 (m, 14H, $NCHCH_2OH$, $NCH_2CHCH_3$ and $OCH_3$), 2.40–1.55 (m, 8H, $NCH_2CHCH_3$, $OCH_2CH_2CH_2O$ and $NCH_2CHCH_3CH_2$), 1.00–0.95 (m, 6H, $NCH_2CHCH_3$); MS (EI), m/z (relative intensity) 600 ($M^{+\cdot}$, 16), 459 (46), 345

(16), 206 (13), 186 (17), 180 (31), 166 (37), 149 (6), 142 (76), 100 (6), 98 (13), 97 (29), 84 (81), 69 (7), 55 (100).

(2S)-1,1'-[[(Propane-1,3-diyl)dioxy]bis[(2-allyloxycarbonylamino-5-methoxy-1,4-phenylene)carbonyl]]bis[2-(hydroxymethyl)-4-methylidenepyrrolidine] (78)

Pyridine (0.47 mL, 0.46 g, 5.82 mmol) was added to a stirred solution of the bis-amine 77 (0.857 g, 1.44 mmol) in $CH_2Cl_2$ (30 mL) at 0° C. (ice/acetone). The cool mixture was then treated dropwise with a solution of allyl chloroformate (0.33 mL, 0.38 g, 3.15 mmol) in $CH_2Cl_2$ (10 mL). After 2.5 hours stirring at room temperature, the mixture was diluted with $CH_2Cl_2$ (60 mL), washed with 1N HCl (2×50 mL), $H_2O$ (80 mL), brine (80 mL), dried ($MgSO_4$), filtered and evaporated in vacuo. The crude residue was purified by flash chromatography (70–100% EtOAc/Petroleum Ether) to afford the allyl cartamate compound 78 as a slightly orange glass (0.548 g, 50%): $^1H$ NMR (270 MHz, $CDCl_3$) δ8.58 (br s, 2H, NH), 7.56 (s, $2H_{arom}$), 6.78 (s, $2H_{arom}$), 6.03–5.88 (m, 2H, $NCO_2CH_2CH=CH_2$), 5.39–5.21 (m, 4H, $NCO_2CH_2CH=CH_1$), 5.00 (br s, 2H, $NCH_2C=CH_2$), 4.93 (br s, 2H, $NCH_2C=CH_2$), 4.70–4.57 (m, 4H, $NCO_2CH_2CH=CH_2$), 4.30–4.25 (m, 4H, $OCH_2CH_2CH_2O$), 4.17–3.90 (m, 8H, $NCHCH_2OH$ and $NCH_2C=CH_2$), 3.81–3.54 (m, 8H, $NCHCH_2OH$ and $OCH_3$), 2.76 (dd, 2H, J=8.52, 15.85 Hz, $NCH_2C=CH_2CH_2$), 2.49–2.44 (m, 2H, $NCH_2C=CH_2CH_2$), 2.36–2.28 (m, 2H, $OCH_2CH_2CH_2O$); $^{13}C$ NMR (67.8 MHz, $CDCl_3$) δ170.3 ($NC=O_{amide}$), 153.8 ($NC=O_{carbamate}$), 150.5 ($C_{quat}$), 144.8 ($C_{quat}$), 143.1 ($C_{quat}$), 132.5 ($NCO_2CH_2CH=CH_2$), 130.7 ($C_{quat}$), 118.1 ($NCO_2CH_2CH=CH_2$), 116.8 ($C_{quat}$), 110.9 ($C-H_{arom}$), 108.1 ($NCH_2C=CH_2$), 106.9 ($C-H_{arom}$), 65.7 ($NCO_2CH_2CH=CH_2$), 65.4 ($OCH_2CH_2CH_2O$), 65.1 ($NCHCH_2OH$), 59.8 ($NCHCH_2OH$), 56.5 ($OCH_3$), 53.9 ($NCH_2C=CH_2$), 34.2 ($NCH_2C=CH_2CH_2$), 29.7 and 29.2 ($OCH_2CH_2CH_2O$); MS (FAB) (Relative Intensity) 765 ($M^{+·}$ +1, 10), 652 ($M-NCH_2CCH_2CH_2CHCH_2OH$, 32), 594 (4), 539 (2), 481 (51), 441 (31), 290 (3), 249 (13), 232 (38), 192 (83), 166 (49), 149 (32), 114 (100).

1,1'-[[(Propane-1,3-diyl)dioxy]bis[(11S,1aS)-10-(allyloxycarbonyl)-11-hydroxy-7-methoxy-2-methylidene-1,2,3,10,11,11a-hexahydro-5H-pyrrolo[2,1-c][1,4]benzodiazepin-5-one] (79)

A solution of the bis-alloc compound 78 (150 mg, 0.196 mmol) in $CH_2Cl_2/CH_3CN$ (12 mL, 3:1) was treated with 4 Å powdered molecular sieves (0.2 g) and NMO (70 mg, 0.598 mmol). After 15 minutes stirring at room temperature, TPAP (7 mg, 19.9 µmol) was added and stirring continued for a further 2 hours at which time TLC (95% $CHCl_3$/MeOH) indicated formation, of the fully cyclised product along with the presumed semi-cyclised product 79, and unreacted starting material 78 present in the reaction mixture. The mixture was then treated with a further quantity of NMO (35 mg, 0.299 mmol) and TPAP (3.5 mg, 9.96 µmol), and allowed to stir for a further 0.5 hours when TLC revealed reaction completion. The solvent was evaporated in vacuo and the black residue was subjected to flash chromatography (98% $CHCl_3$/MeOH) to provide the pure protected carbinolamine 79 as a white solid (47 mg, 32%): $^1H$ NMR (270 MHz, $CDCl_3$) δ7.23 (s, $2H_{arom}$), 6.74 (s, 2Ha,), 5.90–5.65 (m, 2H, $NCO_2CH_2CH=CH_2$), 5.57 (d, 2H, J=8.24 Hz, NCHCHOH), 5.26–5.07 (m, 8H, $NCH_2C=CH_2$ and $NCO_2CH_2CH=CH_2$), 4.67–4.10 (m, 14H, $NCO_2CH_2CH_2=CH_2$, $NCH_2C=CH_2$, $OCH_2CH_2CH_2O$ and OH), 3.89 (S, 6H, $OCH_3$), 3.63 (m, 2H, NCHCHOH), 2.91 (dd, 2H, J=8.79, 15.76 Hz, $NCH_2C=CH_2CH_2$), 2.68 (d, 2H, J=16.10 Hz, $NCH_2C=CH_2CH_2$), 2.42–2.24 (m, 2H, $OCH_2CH_2CH_2O$); $^{13}C$ NMR (67.8 MHz, $CDCl_3$) δ166.7 ($NC=O_{amide}$), 150.1 ($C_{quat}$), 149.0 ($C_{quat}$), 141.7 ($C_{quat}$), 131.7 ($NCO_2CH_2CH=CH_2$), 130.6 ($C_{quat}$), 128.9 ($C_{quat}$), 128.8 ($C_{quat}$), 118.3 ($NCO_2CH_2CH=CH_2$), 114.7 ($C-H_{arom}$), 110.7 ($C-H_{arom}$), 109.8 ($NCH_2C=CH_2$), 85.9 (NCHCHOH), 66.9 ($NCO_2CH_2CH=CH_2$), 66.0 ($OCH_2CH_2CH_2O$), 59.7 (NCHCHOH), 56.1 ($OCH_3$), 50.7 ($NCH_2C=CH_2$), 35.0 ($NCH_2C=CH_2CH_2$), 29.7 and 29.1 ($OCH_2CH_2CH_2O$); MS (FAB) (Relative Intensity) 743 ($M^{+·}$ -17, 16), 725 (17), 632 (13), 574 (8), 548 (13), 490 (10), 481 (9), 441 (7), 425 (6), 257 (12), 232 (20), 192 (46), 166 (52), 149 (100), 91 (59); IR (NUJOL®) 3234 (br, OH), 2923, 2853, 2361, 1707, 1604, 1515, 1464, 1410, 1377, 1302, 1267, 1205, 1163, 1120, 1045, 999, 955, 768, 722 $cm^{-1}$.

1,1'-[[(Propane-1,3-diyl)dioxy]bis[(11aS)-7-methoxy-2-methylidene-1,2,3,11a-tetrahydro-5H-pyrrolo[2,1-c][1,4]benzodiazepin-5-one] (80, SJG-136)

A catalytic amount of tetrakis(triphenylphosphine) palladium (11 mg, 9.52 µmol) was added to a stirred solution of the bis-alloc-carbinolamine 79 (139 mg, 0.183 mmol), triphenylphosphine (4.8 mg, 18.3 µmol) and pyrrolidine (27 mg, 0.380 mmol) in $CH_2Cl_2/CH_3CN$ (13 mL, 10:3) at 0° C. (ice/acetone) under a nitrogen atmosphere. The reaction mixture was allowed to warm to room temperature and the progress monitored by TLC (95% $CHCl_3$/MeOH). After 2 hours 15 minutes TLC revealed the reaction was complete, proceeding via the presumed half-imine product 261, to give a TLC spot which fluoresced brightly under UV. The solvent was evaporated in vacuo and the resulting residue subjected to flash chromatography (98% $CHCl_3$/MeOH) to give the bis-imine target molecule 80 (SJG-136) as a pale orange glass (78 mg, 77%) which was repeatedly evaporated in vacuo with $CHCl_3$ to provide the imine form: $[α]^{21}_D$=+357.7° (c=0.07, $CHCl_3$); Reverse Phase HPLC (C, stationary phase, 65% $MeOH/H_2O$ mobile phase, 254 nm), Retention time 6.27 minutes, % Peak area =97.5%; $^1H$ NMR (270 MHz, $CDCl_3$) (imine form) δ7.68 (d, 2H, J=4.4 Hz, HC=N), 7.49 (S, $2H_{arom}$), 6.85 (s, $2H_{arom}$), 5.20 (s, 2H, $NCH_2C=CH_2$), 5.17 (s, 2H, $NCH_2C—CH_2$), 4.46–4.19 (m, 4H, $OCH_2CH_2CH_2O$), 3.92 (S, 6H, $OCH_3$), 3.89–3.68 (m, 6H, $NCH_2C=CH_2$ and NCHHC=N), 3.12 (dd, 2H, J=8.61, 16.21 Hz, $NCH_2C=CH_2CH_2$), 2.68 (d, 2H, J=16.30 Hz, $NCH_2C=CH_2CH_2$), 2.45–2.38 (m, 2H, $OCH_2CH_2CH_2O$); $^{13}C$ NMR (67.8 MHz, $CDCl_3$) (imine form) δ164.7 (NC=O), 162.6 (HC=N), 150.7 ($C_{quat}$), 147.9 ($C_{quat}$), 141.5 ($C_{quat}$), 140.6 ($C_{quat}$), 119.8 ($C_{quat}$), 111.5 ($C-H_{arom}$), 110.7 ($C-H_{arom}$), 109.4 ($NCH_2C=CH_2$), 65.4 ($OCH_2CH_2CH_2O$), 56.1 ($OCH_3$), 53.8 (NCHHC=N), 51.4 ($NCH_2C=CH_2$), 35.4 ($NCH_2C=CH_2CH_2$), 28.8 ($OCH_2CH_2CH_2O$); MS (FAB) (Relative Intensity) (imine form) 773 ($M^{+·}$ +1+(Thioglycerol adduct X 2), 3), 665 ($M^{+·}$ +1+Thioglycerol adduct, 7), 557 ($M^{+·}$ +1, 9), 464 (3), 279 (12), 257 (5), 201 (5), 185 (43), 166 (6), 149 (12), 93 (100); IR (NUJOL®) 3600–3100 (br, OH of carbinolamine form), 2923, 2849, 1599, 1511, 1458, 1435, 1391, 1277, 1228, 1054, 1011, 870, 804, 761, 739 $cm^{-1}$.

Figure 11:
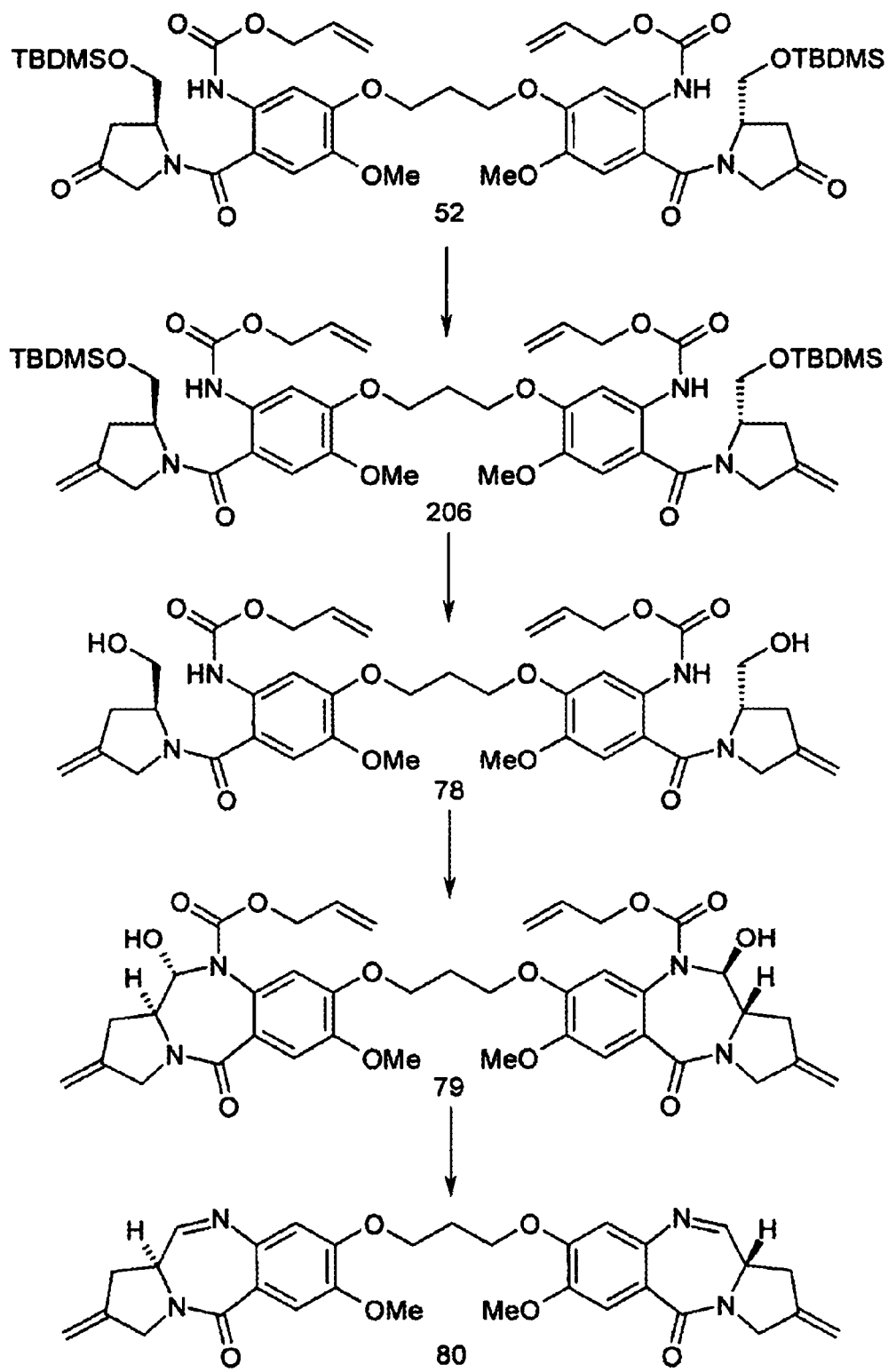

Alternative Synthesis of UP2001, SJG-136 (80) (See FIG. 11)

UP2001 was also prepared by an alternative synthesis based the bis -ketone 52 (See Example 11(f)).

1,1'-[[(Propane-1,3-diyl)dioxy]bis[2-amino-N-allyloxycarbonyl-5-methoxy-1,4-phenylene)carbonyl]]-bis[(2S)-2-t-butyldimethylsilyloxymethyl-4-methylidene-2,3-dihydropyrrole] (206)

A solution of potassium-t-butoxide in dry THF (0.5 M, 4.00 mL, 2.00 mmol) was added to as suspension of methyltriphenylphosphonium bromide (0.716 g, 2.00 mmol) in dry THF (2.00 mL). The resulting yellow ylide suspension was allowed to stir at 0° C. for 2 hours before the addition of a solution of the bis-ketone 52 (0.50 g, 0.50 mmol) in THF (10 mL) at 10° C. The reaction mixture was allowed to warm to room temperature and stirring was continued for a further hour. The reaction mixture was partitioned between ethyl acetate (15 mL) and water (15 mL) and the organic layer was washed the sat. sodium chloride (20 mL) and dried over magnesium sulphate. Removal of excess solvent gave a brown oil that was subjected to flash column chromatography (50% ethyl acetate, 50% 40–60° petroleum ether) to afford the product as a yellow glass 206 (250 mg, 51%). $[\alpha]^{23.4}_D = -32°$ (c 0.265, CHCl$_3$). $^1$H NMR (CDCl$_3$): δ0.00 (s, 12H), 0.88 (s, 18H), 2.37–2.40 (m, 2H), 2.69–2.75 (m, 4H), 3.80–4.62 (m, 20H), 4.61–4.63 (m, 4H), 4.98 (bs, 4H), 5.30–5.38 (m, 4H), 5.94–6.00 (m, 2H), 6.81 (S, 2H), 7.84 (s, 2H), 8.80 (bs, 2H).

1,1'-[[(Propane-1,3-diyl)dioxy]bis[2-amino-N-allyloxycarbonyl-5-methoxy-1,4-phenylene)carbonyl]]-bis[(2S)-2-hydroxymethyl-4-methylidene-2,3-dihydropyrrole] (78)

An aliquot of hydrogen fluoride/pyridine complex (0.8 mL, 70% HF, 30% pyridine) was added to a solution of the bis-silyl ether 206 (285 mg, 0.287 mmol) in THF (10 mL) at 0° C. under a nitrogen atmosphere. Stirring was continued at 0° C. for 30 minutes and the reaction mixture was then allowed to rise to room temperature over a 1 hour period. The reaction mixture was neutralised with sodium bicarbonate and extracted with dichloromethane (3×30 mL). The combined organic phase was washed with brine and dried over magnesium sulphate. Removal of excess solvent under reduced pressure afforded the product 78 as a yellow gum (218 mg).

1,1'[[(Propane-1,3-diyl)dioxy]bis(11S,11aS)-10-(allyloxycarbonyl)-11-hydroxy-7-methoxy-2-methylidene-1,2,3,10,11,11a-hexahydro-5H-pyrrolo[2,1-c][1,4-benzodiazepin-5-one] (79)

A solution of dimethyl sulphoxide (0.55 mL, 7.75 mmol) in dry dichloromethane (10 mL) was added dropwise, over a 15 minute period, to a stirred solution of oxalyl chloride (0.32 mL, 3.67 mmol) in dichloromethane (10 mL) at −45° C. under a nitrogen atmosphere. The reaction mixture was allowed to stir for 35 minutes at −45° C. followed by addition of the diol 78 (1.01 g, 1.32 mmol) in dichloromethane (10 mL), at the same temperature, over 15 minutes. After a further 45 minutes a solution of triethylamine (1.50 mL, 10.76 mmol) in dichloromethane (10 mL) was added over a period of 15 minutes. The reaction mixture was allowed to stir at −45° C. for 30 minutes before being allowed to warm to room temperature over 45 minutes. The reaction mixture was diluted with water and the phases were allowed to separate. The organic phase was washed with 1M HCl (3×50 mL), sat. sodium chloride (50 mL) and dried over magnesium sulphate. Removal of excess solvent yielded the crude product, which was purified by flash column chromatography (1.5% methanol, 98.5% chloroform) to afford the product 79 (0.785 g, 77%).

1,1'[[(propane-1,3-diyl)dioxy]bis[(11aS)-7-methoxy-2-methylidene-1,2,3,11a-tetrahydro-5H-pyrrolo[2,1-c][1,4] benzodiazein-5-one] (80, SJG-136)

A catalytic amount of tetrakis(triphenylphosphine) palladium (21 mg, 0.018 mmol) was added to a stirred solution of the bis-alloc-carbinolamine 79 (250 mg, 0.33 mmol), triphenylphosphine (10 mg, 0.033 mmol) and pyrrolidine (0.05 mL, 0.66 mmol) in dry CH$_2$Cl$_2$ (30 mL) at 0° C. (ice/acetone) under a nitrogen. atmosphere. The reaction mixture was allowed to stir for 2 hours before warming to room temperature over 1 hour. The solvent was evaporated under reduced pressure and the resulting residue subjected to flash chromatography (98% CHCl$_3$/MeOH) to give the bis-imine target molecule 80 (SJG-136).

Example 2(e)

Figure 12A:
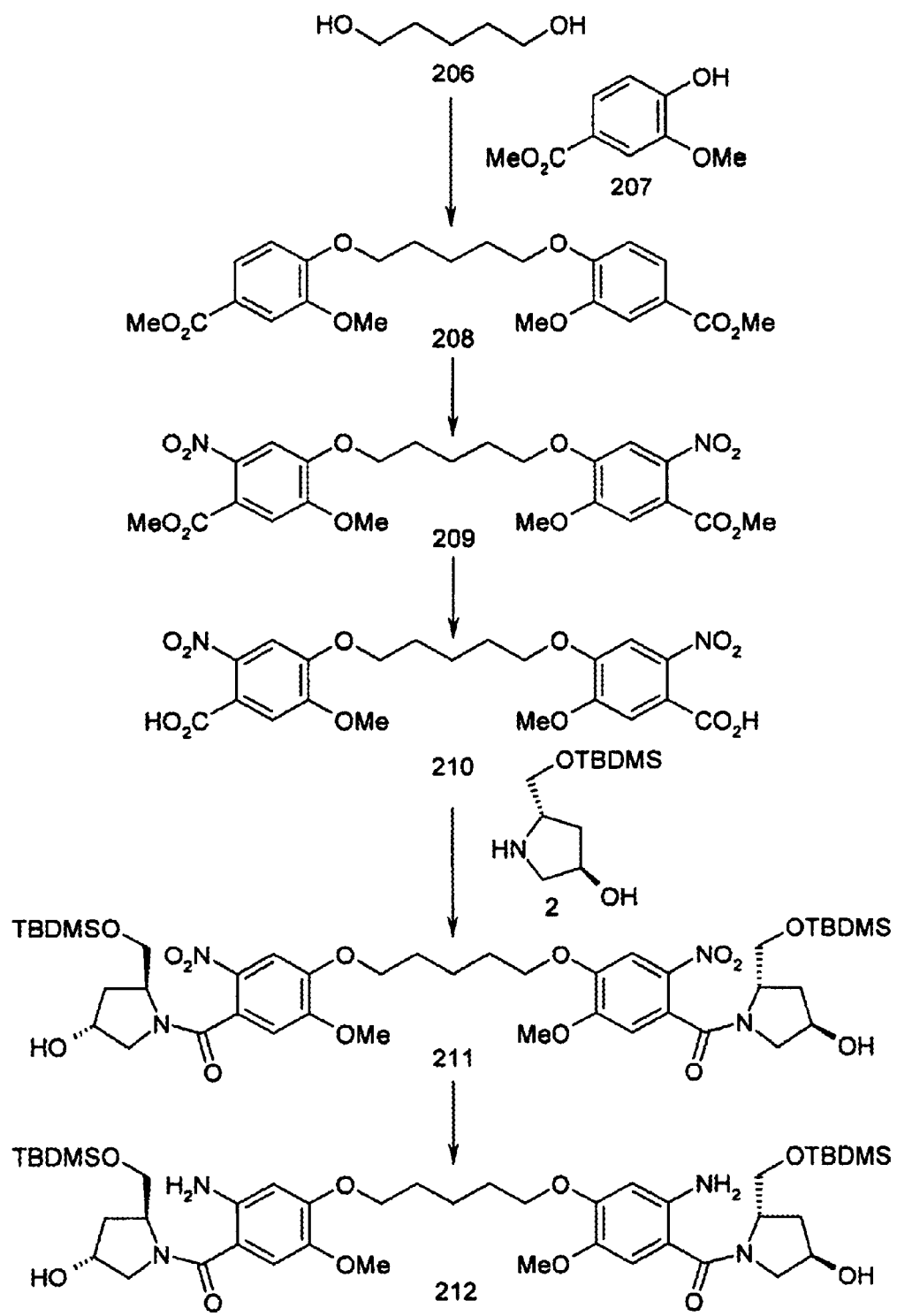
Figure 12B:
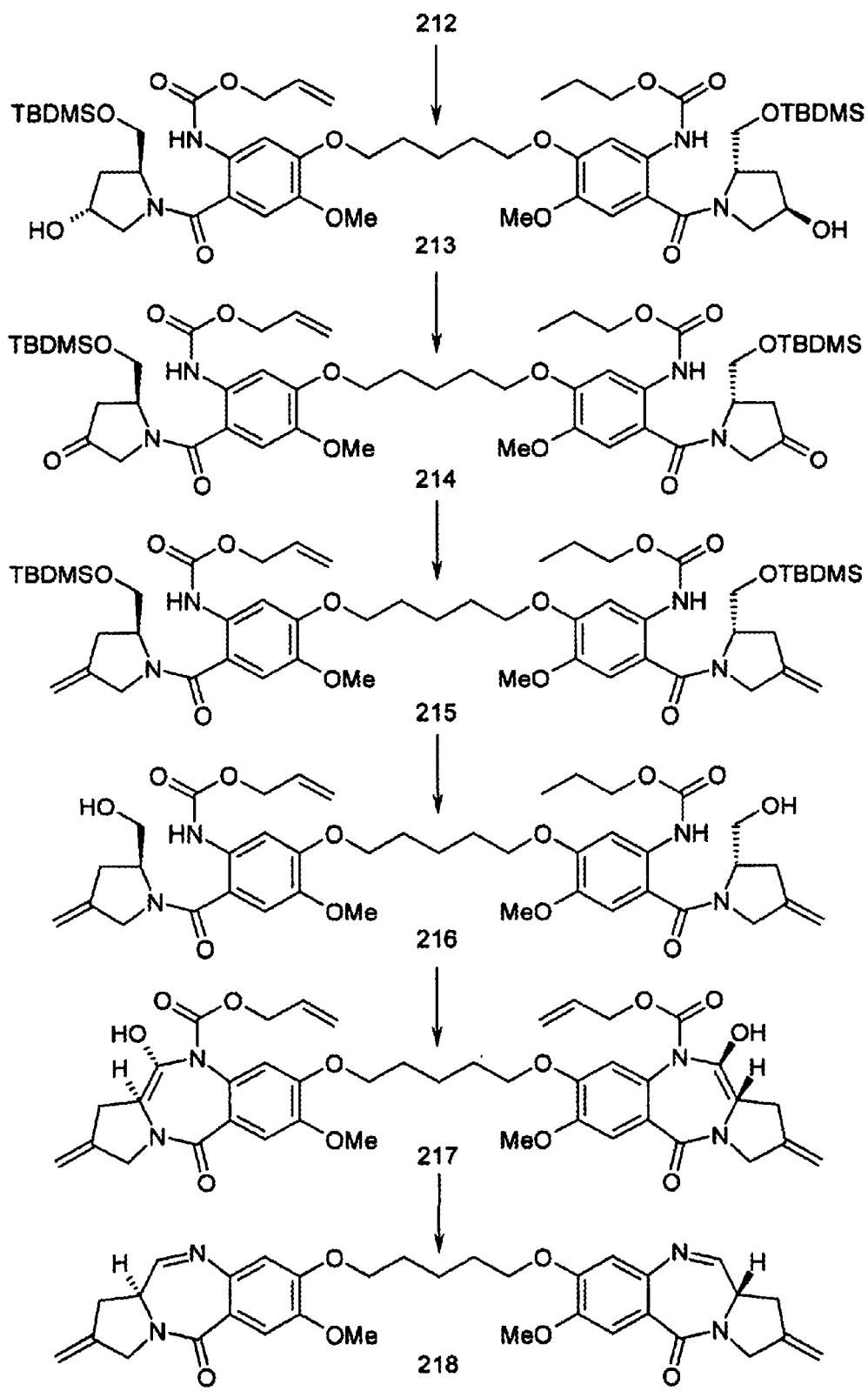

Synthesis of 1,1'[[(pentane-1,5-diyl)dioxy]bis[(11aS)-7-methoxy-2-methylidene-1,2,3,11a-tetrahydro-5H-pyrrolo[2,1-c][1,4]benzodiazepin-5-one] (218) (See FIGS. 12a/b)

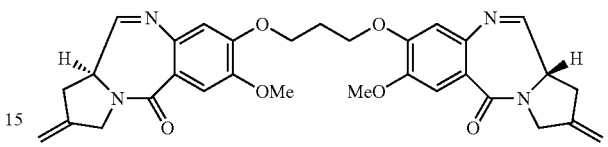

Preparation of Nitro Dimer Core
1',5'-Bis[2-methoxy-4-(methoxycarbonyl)phenoxy]pentane (208)

Neat diethyl azidodicarboxylate (19.02 mL, 21.04 g, 120.8 mmol) was added dropwise over 30 minutes to a stirred solution of methyl vanillate (206) (20 g, 109.8 mmol) and triphenylphosphine (43.2 g, 164.7 mmol) in anhydrous THF (400 mL) and the reaction mixture was allowed to stir at 0° C. for 1 h. The cold reaction mixture was treated dropwise over 20 minutes with a solution of 1,5-pentanediol (207) (3.83 mL, 4.03 g, 53.0 mmol) in THF (4 mL). The reaction mixture was allowed to stir overnight at room temperature and the precipitated product (208) was collected by vacuum filtration. Dilution of the filtrate with methanol precipitated further product (208). The combined precipitate (12.3 g, 52% based on pentanediol) was used in the next step without further purification: $^1$H NMR (270 MHz, CDCl$_3$) δ7.65 (dd, 2H, J=2.01, 8.42 Hz), 7.54 (d, 2H, J=2.01 Hz), 6.87 (d, 2H, J=8.42 Hz), 4.10 (t, 4H, J=6.59 Hz), 3.90 (s, 6H), 3.89 (s, 6H), 2.10–1.90 (m, 4H), 1.85–1.26 (m, 2H).

1',5'-Bis[2-methoxy-4-(methoxycarbonyl)-5-nitrophenoxy] pentane (209)

Solid copper (II) nitrate trihydrate (16.79 g, 69.5 mmol) was added slowly to a stirred solution of the bis-ester (208) (12 g, 27.8 mmol) in acetic anhydride (73 mL) at 0° C. The reaction mixture was allowed to stir for 1 hour at 0° C., the ice bath was removed and the reaction mixture was allowed to warm to room temperature a mild exotherm, c. 40° C., accompanied by the evolution of NO$_2$ occurred at this stage. After the exotherm had subsided stirring at room temperature was continued for 2 hours. The reaction mixture was poured into ice water and the aqueous suspension allowed to stir for 1 h. The resulting yellow precipitate was collected by vacuum filtration and dried in air to afford the desired bis nitro compound (209) (14.23 g, 98%): $^1$H NMR (400 MHz, CDCl$_3$+DMSO) δ7.45 (s, 2H), 7.09 (s, 2H), 4.14 (t, 4H, J=6.31 Hz), 3.97 (s, 6H), 3.90 (s, 6H), 2.20–1.94 (m, 4H), 1.75–1.70 (m, 2H).

1',5'-Bis(4-carboxy-2-methoxy-5-nitrophenoxy)pentane (210)

A suspension of the ester 209 (9.0 g, 17.2 mmol) in aqueous sodium hydroxide (1 M, 180 mL) and THF (180 mL) was allowed to stir until a homogenous solution was obtained (2 days). THF was evaporated under reduced pressure and the resulting aqueous suspension was filtered to remove any unreacted starting material. The filtrate was adjusted to pH 1, the precipitated product was collected by filtration and air dried to afford the desired bis-acid (210) (8.88 g). A higher than theoretical yield was obtained due to the inclusion of the sodium salt of acid. The salt may be removed by dissolving the bulk of the material in THF and removing the insoluble material by filtration: $^1$H NMR (400 MHz, CDCl$_3$) δ7.39 (s, 2H), 7.16 (s, 2H), 4.12 (t, 4H, J=6.59 Hz), 3.95 (s, 6H), 2.00–1.85 (m, 4H), 1.75–1.67 (m, 2H).

Assembling the Bis Ketone Intermediate 1,1'-[[(Pentane-1,5-diyl)dioxy]bis[2-nitro-5-methoxy-1,4-phenylene)carbonyl]]-bis[(2S,4R)-2-t-butyldimethylsilyloxymethyl-4-hydroxypyrrolidine] (211)

A catalytic amount of DMF (5 drops) was added to as stirred suspension of the acid 210 (5.39 g, 10.9 mmol) and oxalyl chloride (3.47 g, 2.38 mL, 27.3 mmol) in anhydrous THF (50 mL). Initial effervescence was observed followed by the formation of a homogenous solution, however after stirring overnight a suspension of the newly formed acid chloride was formed. Excess THF and oxalyl chloride was removed by rotary evaporation under reduced pressure and the acid chloride was resuspended in fresh THF (49 mL). The acid chloride solution was added dropwise to a solution of the (2S, 4R)-2-t-butyldimethylsilyloxymethyl-4-hydroxypyrrolidine (2) (6.3 g, 27.3 mmol), triethylamine (4.42 g, 6.09 mL, 43.7 mmol) and water (1.47 mL) in THF (33 mL) at 0° C. under a nitrogen atmosphere. The reaction mixture was allowed to warm to room temperature and stirring was continued for 3 h. Excess THF was removed by rotary evaporation under reduced pressure and the resulting residue was partitioned between water (300 mL) and ethyl acetate (300 mL). The layers were allowed to separate and the aqueous layer was extracted with ethyl acetate (3×150 mL). The combined organic layers were then washed with ammonium chloride (150 mL), sat. sodium bicarbonate (150 mL), brine (150 mL) and dried over magnesium sulphate. Filtration followed by rotary evaporation under reduced pressure afforded the crude product as a dark oil. The crude product was subjected to flash column chromatography (3% methanol, 97% chloroform) and removal of excess eluent isolated (211) (3.70 g, 37% yield): $^1$H NMR (270 MHz, CDCl$_3$) δ7.65 (s, 2H), 6.77 (s, 2H), 4.52 (bs, 2H), 4.40 (bs, 2H), 4.17–4.10 (m, 6H), 3.92 (s, 6H), 3.77 (d, 2H, J=10.26 Hz), 3.32 (td, 2H, J=4.40, 11.35 Hz), 3.08 (d, 2H, J=11.35 Hz), 2.37–2.27 (m, 2H), 2.10–2.00 (m, 6H), 1.75–1.60 (m, 2H), 0.91 (s, 18H), 0.10 (s, 12H).

1,1'-[[(Pentane-1,5-diyl)dioxy]bis[2-amino-5-methoxy-1,4-phenylene)carbonyl]]-bis[(2S,4R)-2-t-butyldimethylsilyloxymethyl-4-hydroxypyrrolidine] (212)

A methanolic solution of hydrazine hydrate (1.25 mL, 1.29 g, 40.2 mmol of hydrazine, 20 mL of methanol) was added dropwise to a solution of the bis-nitro compound 211 (3.6 g, 3.91 mmol) in methanol (68 mL) gently refluxing over Raney nickel (510 mg of a thick slurry). After 5 minutes at reflux TLC (10% MeOH, 90% chloroform) revealed the incomplete consumption of starting material. The reaction mixture was treated with additional Raney nickel (c 510 mg) and hydrazine (1.25 mL) in methanol (20 mL) resulting in complete consumption of starting material. Excess Raney nickel was added to the reaction mixture to decompose unreacted hydrazine hydrate and the reaction mixture was then allowed to cool. The reaction mixture was filtered through celite to remove excess Raney nickel and the filter pad washed with additional methanol (Caution! Raney nickel is pyrophoric, do not allow filter pad to dry, use conc. HCl to destroy nickel). The combined filtrate was evaporated by rotary evaporation under reduced pressure and the residue re-dissolved in dichloromethane. The dichloromethane solution was dried over magnesium sulphate (to remove water associated with the hydrazine), filtered and evaporated to afford the product (212) as a foam (3.37 g, 91%): $^1$H NMR (270 MHz, CDCl$_3$) δ6.69 (s, 2H), 6.24 (s, 2H), 4.40–3.40 (m, 28H), 2.40–1.60 (m, 10H), 0.88 (s, 18H), 0.03 (s, 12H).

1,1'-[[(Pentane-1,5-diyl)dioxy]bis[2-amino-N-allyloxycarbonyl-5-methoxy-1,4-phenylene)carbonyl]]-bis[(2S,4R)-2-t-butyldimethylsilyloxymethyl-4-hydroxypyrrolidine] (213)

A solution of allyl chloroformate (0.806 mL, 0.916 g, 7.6 mmol) in dry dichloromethane (63 mL) was added, dropwise, to a solution of the bis-amine 212 (3.27 g, 3.8 mmol) and pyridine (1.26 g, 1.29 mL, 15.9 mmol) in dichloromethane (128 mL) at 0° C. under a nitrogen atmosphere. The reaction mixture was allowed to warm to room temperature and to stir for 16 h. At which time TLC (10% MeOH, 90% Chloroform) revealed reaction to be complete. The reaction mixture was diluted with dichloromethane (40 mL) and washed with sat. copper II sulphate (2×140 mL), water (120 mL) and sat. sodium chloride (120 mL). The organic phase was dried over magnesium sulphate, filtered and evaporated under reduced pressure to afford 213 as a foam (3.60 g, 92%): $^1$H NMR (270 MHz, CDCl$_3$) δ8.87 (bs, 2H), 7.66 (s, 2H), 6.77 (s, 2H), 6.05–5.80 (m, 2H), 5.40–5.15 (m, 4H), 4.70–4.50 (m, 6H), 4.38 (bs, 2H), 4.20–4.00 (m, 4H), 3.78 (s, 6H), 3.70–3.40 (m, 8H), 2.40–2.20 (m, 2H), 2.10–1.80 (m, 6H), 1.75–1.55 (m, 2H), 0.89 (s, 18H), 0.04 (s, 12H).

1,1'-[[(Pentane-1,5-diyl)dioxy]bis[2-amino-N-allyloxycarbonyl-5-methoxy-1,4-phenylene)carbonyl]]-bis[(2s)-2-t-butyldimethylsilyloxymethyl-4-oxo-pyrrolidine] (214)

A solution of dimethyl sulphoxide (1.47 mL, 1.62 g, 20.7 mmol) in dry dichloromethane (32 mL) was added dropwise over 45 minutes to a stirred solution of oxalyl chloride (5.18 mL of a 2 M solution in dichloromethane, 10.35 mmol) at −60° C. under a nitrogen atmosphere. After stirring at −50° C. for 30 minutes, a solution of the bis-alcohol 213 (3.55 g, 3.45 mmol) in dichloromethane (53 mL) was added dropwise over a period of 50 minutes. The reaction mixture was allowed to stir at −60° C. for 30 minutes prior to the dropwise addition of a solution of triethylamine (4.75 g, 6.54 mL, 46.9 mmol) in dichloromethane (27 mL). Stirring was continued at −60° C. for 45 minutes and then allowed to warm to 0° C. The reaction mixture was diluted with dichloromethane (20 mL), washed with cold 1 M HCl (2×100 mL), sat. sodium chloride (100 mL) and dried over magnesium sulphate. Removal of excess solvent afforded the crude bis-ketone which was purified by flash column chromatography (50% ethyl acetate, 50% 40–60° petroleum ether) to yield the pure bis-ketone (214) as a pale yellow foam (2.54 g, 72%): $^1$H NMR (270 MHz, CDCl$_3$) δ8.69 (bs, 2H), 7.78 (s, 2H), 6.75 (s, 2H), 6.05–5.80 (m, 2H), 5.40–5.20 (m, 4H), 4.65–4.60 (m, 4H), 4.20–3.60 (m, 20H), 2.74 (dd, 2H, J=9.25, 18.1 Hz), 2.51 (d, 2H, J=17.4 Hz), 2.00–1.90 (m, 4H), 1.75–1.65 (m, 2H), 0.87 (s, 18H), 0.05 (s, 12H).

Elaboration of Bis Ketone and Preparation of the Target Molecule 1,1'-[[(Pentane-1,5-diyl)dioxy]bis[2-amino-N-allyloxycarbonyl-5-methoxy-1,4-phenylene)carbonyl]]-bis[(2aS)-2-t-butyldimethylsilyloxymethyl-4-methylidene-2,3-dihydropyrrole] (215)

A solution of potassium-t-butoxide in dry THF (0.5 M, 25.2 mL, 12.6 mmol) was added dropwise to a suspension of methyltriphenylphosphonium bromide (4.50 g, 12.6 mmol) in dry THF (15 mL). The resulting yellow ylide suspension was allowed to stir at 0° C. for 2 hours before the addition of a solution of the bis-ketone 214 (2.48 g, 2.42 mmol) in THF (10 mL) at 10° C. The reaction mixture was allowed to warm to room temperature and stirring was continued for a further hour. The reaction mixture was partitioned between ethyl acetate (100 mL) and water (100 mL) and the organic layer was washed with sat. sodium chloride (200 mL) and dried over magnesium sulphate. Removal of excess solvent gave a brown oil that was subjected to flash column chromatography (50% ethyl acetate, 50% 40–60° petroleum ether) to afford the product (215) as a yellow glass (865 mg, 35%): $^1$H NMR (400 MHz, CDCl$_3$) δ8.90 (bs, 2H), 7.83 (s, 2H), 6.82 (s, 2H), 6.05–5.90 (m, 2H), 5.40–5.20 (m, 4H), 4.99 (bs, 2H), 4.91 (bs, 2H), 4.65–4.60 (m, 4H), 4.20–3.60 (m, 20H), 2.70 (bs, 4H), 2.00–1.90 (m, 4H), 1.75–1.63 (m, 2H), 0.88 (s, 18H), 0.03 (s, 12H).

1,1'-[[(Pentane-1,5-diyl)dioxy]bis[2-amino-N-allyloxycarbonyl-5-methoxy-1,4-phenylene)carbonyl]]-bis[(2S)-2-hydroxymethyl-4-methylidene-2,3-dihydropyrrole] (216)

A solution of TBAF (3.02 mL of a 1 M solution in THF, 3.02 mmol) was added to the bis-silyl ether (215) (1.23 g, 1.21 mmol) in THF (30 mL) at 0° C. (ice/acetone). The reaction mixture was allowed to warm to room temperature and to stir overnight, the following day, TLC (50:50 EtOAc/ Pet-Ether 40 °–60°) revealed the complete disappearance of starting material. Saturated NH$_4$Cl (150 mL) was added and the reaction mixture extracted with EtOAc (3×60 mL), washed with sat. sodium chloride (150 mL), dried (MgSO$_4$), filtered and evaporated in vacuo to give a yellow oil. Purification by flash chromatography (97% CHCl$_3$/3% MeOH) provided the pure alcohol (216) (916 mg, 96%): $^1$H NMR (400 MHz, CDCl$_3$) δ8.61 (bs, 2H), 7.58 (s, 2H), 6.79 (s, 2H), 6.05–5.90 (m, 2H), 5.40–5.20 (m, 4H), 5.01 (bs, 2H), 4.93 (bs, 2H), 4.65–4.60 (m, 4H), 4.20–3.60 (m, 20H), 2.76 (dd, 2H, , J=8.42, 15.74 Hz), 2.47 (d, 2H, J=15.93 Hz), 2.00–1.90 (m, 4H), 1.80–1.63 (m, 2H).

1,1'[[(Pentane-1,5-diyl)dioxy]bis(11S,11aS)-10-(allyloxycarbonyl)-11-hydroxy-7-methoxy-2-methylidene-1,2,3,10,11,11a-hexahydro-5H-pyrrolo[2,1-c][1,4-benzodiazepin-5-one] (217)

A solution of dimethyl sulphoxide (0.57 mL, 0.63 g, 8.07 mmol) in dry dichloromethane (17 mL) was added dropwise, over a 40 minute period, to a stirred solution of oxalyl chloride (2.02 mL, of a 2 M solution, 4.04 mmol) at −45° C. under a nitrogen atmosphere. The reaction mixture was allowed to stir for 40 minutes at −45° C. followed by addition of the diol 216 (0.89 g, 1.12 mmol) in dichloromethane (17 mL), at the same temperature, over 15 minutes. After a further 60 minutes a solution of triethylamine (1.31 mL, 9.42 mmol) in dichloromethane (9 mL) was added over a period of 40 minutes. The reaction mixture was allowed to stir at −45° C. for 40 minutes before being allowed to warm to room temperature over 45 minutes. The reaction mixture was diluted with water and the phases were allowed to separate. The organic phase was washed with 1 M HCl (2×40 mL), water (40 mL), sat. sodium chloride (40 mL) and dried over magnesium sulphate. Removal of excess solvent yielded the crude product, which was purified by flash column chromatography (1% methanol, 99% chloroform) to afford the product 217 (0.175 g, 20%): $^1$H NMR (400 MHz, CDCl$_3$) δ7.22 (s, 2H), 6.65 (s, 2H), 5.82–5.70 (m, 2H), 5.58 (d, 2H, J=9.70 Hz), 5.25–5.00 (m, 8H), 5.75–4.35 (m, 4H), 4.30 (d, 2H, J=16.10 Hz), 4.15 (d, 2H, J=17.03 Hz), 4.01 (t, 4H, J=6.32 Hz), 3.90 (s, 6H), 3.64 (t, 2H, J=8.70 Hz), 3.00–2.85 (m, 2H), 2.71 (d, 2H, J=16.29 Hz), 2.00–1.85 (m, 4H), 1.70–1.60 (m, 2H).

1,1'[[(pentane-1,5-diyl)dioxy]bis[(11aS)-7-methoxy-2-methylidene-1,2,3,11a-tetrahydro-5H-pyrrolo[2,1-c][1,4] benzodiazepin-5-one] (218)

A catalytic amount of tetrakis(triphenylphosphine) palladium (13 mg, 11.2 mmol) was added to a stirred solution of the bis-alloc-carbinolamine (217) (170 mg, 0.22 mmol), triphenylphosphine (5.7 mg, 21.6 mmol) and pyrrolidine (31 mg, 37.3 mL 0.45 mmol) in DCM (13 mL) at 0° C. (ice/acetone) under a nitrogen. atmosphere. The reaction mixture was allowed to warm to room temperature and the progress of reaction monitored by TLC (95% CHCl$_3$/ MeOH). After 2 hours TLC revealed the reaction was complete to give a spot, which fluoresced brightly under UV light. The solvent was evaporated under reduced pressure and the resulting residue subjected to flash chromatography (99% to 98 CHCl$_3$/MeOH) to give the bis-imine target molecule 218 as a pale yellow glass (84.5 mg, 75%) which was repeatedly evaporated in vacuo with CHCl$_3$ to provide the imine form: $^1$H NMR (400 MHz, CDCl$_3$) δ7.68 (d, 2H, J=4.39 Hz), 7.49 (s, 2H), 6.80 (s, 2H), 5.19 (bs, 2H), 5.16 (bs, 2H), 4.28 (bs, 4H), 4.15–4.00 (m, 4H), 3.92 (s, 6H), 3.90–3.80 (m, 2H), 3.12 (dd, 2H, , J=8.97, 15.93 Hz), 2.95 (d, 2H, J=15.93 Hz), 2.00–1.85 (m, 4H), 1.72–1.67 (m, 2H).

Example 2(f)

Figure 13:
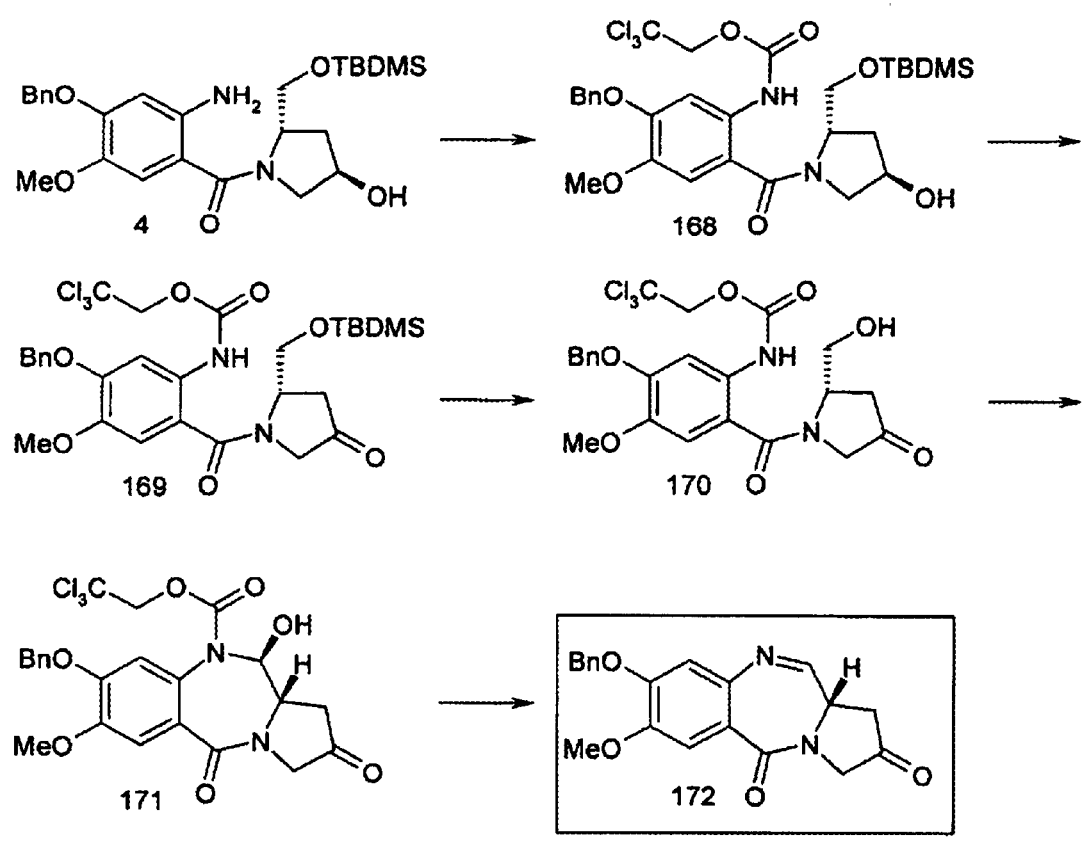

Synthesis of PBD with Ketone on C-Ring (172, UP-2067) (See FIG. 13)

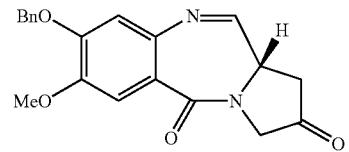

(2S)(4R)-N-[4-benzyloxy-5-methoxy-2-(2',2',2'-trichloroethoxy)carbonyl]-2-(tert-butyldimethylsilyloxymethyl)-4-hydroxypyrrolidine (168)

A solution of 2,2,2-trichloroethylchloroformate (8.74 g, 5.68 mL, 41.2 mmol) in dichloromethane (50 mL) was added to a solution of 4 (18.2 g, 37.5 mmol) and pyridine (5.92 g, 6.1 mL, 75.0 mmol) in dry dichloromethane (200 mL) at 0° C. under a nitrogen atmosphere. The reaction mixture was allowed to stir overnight at room temperature and was then washed with saturated copper sulphate solution (100 mL), water (100 mL) and brine (100 mL). The organic phase was dried over magnesium sulphate, filtered and excess solvent removed by rotary evaporation to afford the product 168 (22.01 g, 33.2 mmol, 89%) which was used in the subsequent reaction without further purification. $^1$H NMR (270 MHz, CDCl$_3$) δ9.31 (bs, 1H); 7.48 (s, 1H); 7.45–7.28 (m, 5H); 6.82 (s, 1H); 5.17 (bs, 2H); 4.89 (d, J=11.9 Hz, 1H); 4.70 (d, J=11.9 Hz, 1H); 4.56 (bs, 1H); 4.40 (bs, 1H); 4.20–4.00 (m, 1H); 3.95–3.40 (m, 7H); 2.40–2.00 (m, 2H); 0.09 (s, 9H); 0.04 (s, 6H). $^{13}$C NMR (67.8 MHz, CDCl$_3$) δ169.2, 152.1, 150.2, 136.1, 128.6, 128.1, 127.7, 111.6, 106.2, 95.2, 74.4, 70.7, 70.5, 62.1, 57.2, 56.4, 35.4, 25.8, 18.1, −5.46.

(2S)-N-[4-benzyloxy-5-methoxy-2-(2',2',2'-trichloroethoxy) carbonyl amino]-2-(tert-butyldimethylsilyloxymethyl)-4-oxopyrrolidine (169)

A solution of DMSO (7.80 g, 99.8 mmol) in dry dichloromethane (18 mL) was added dropwise, over 30 minutes, to a solution of oxalyl chloride (6.34 g, 49.9 mmol) in dry dichloromethane (25 mL) at −45° C. under a nitrogen atmosphere and the reaction mixture allowed to stir for a further 15 minutes. A solution of the substrate 168 (22.01 g, 33.3 mmol) in dichloromethane (50 mL) was added dropwise over 40 minutes to the reaction mixture, which was then allowed to stir for 45 minutes at −45° C. Finally, neat triethylamine (23.52 g, 232.9 mmol) was added dropwise over 30 minutes and the reaction mixture allowed to stir at −45° C. for 15 minutes. The reaction mixture was allowed to warm to room temperature, diluted with water (150 mL) and the organic phase washed with dilute HCl (1N, 100 mL), water (100 mL) and brine (100 mL). The organic phase was dried over magnesium sulphate, filtered and concentrated in vacuo to afford the crude product which was subjected to column chromatography (ethyl acetate/40–60 petroleum ether, 50:50). Removal of excess eluent afforded the product (20.15 g, 92% yield). $^1$H NMR (270 MHz, CDCl$_3$) δ7.88 (bs, 1H); 7.49–7.28 (m, 5H); 6.80 (s, 1H); 5.22 (d, J=12.1 Hz, 1H); 5.17 (d, J=12.1 Hz, 1H); 4.80 (bs, 2H); 4.10–3.60 (m, 8H); 2.75 (dd, J 18.0, 9.5 Hz, 1H); 2.52 (d, J=18.0 Hz, 1H); 0.87 (s, 9H); 0.06 (s, 3H); 0.05 (s, 3H). $^{13}$C NMR (67.8 MHz) δ208.7, 168.8, 151.8, 150.6, 144.7, 136.0, 128.5, 128.1, 127.7, 110.9, 106.4, 95.2, 74.4, 70.7, 66.0, 56.8, 56.4, 39.4, 25.8, 18.0, −5.7.

(2S)-N-[4-benzyloxy-5-methoxy-2-(2',2',2'-trichloroethoxy) carbonyl amino]-2-(hydroxymethyl)-4-oxopyrrolidine (170)

Glacial acetic acid (60 mL) and water (20 mL) were added to a solution of ketone 169 (9.44 g, 14.3 mmol) in THF (20 mL) and the reaction mixture allowed to stir for 3 hr. (reaction complete by TLC). The reaction mixture was diluted with dichloromethane (200 mL) and neutralized dropwise with sat. sodium bicarbonate (1.5 L) in a 5 L flask (effervescence!). The phases were allowed to separate and the aqueous layer extracted with dichloromethane (2×100 mL). The combined organic layers were washed with brine and dried over magnesium sulphate. Removal of excess solvent afforded the crude product which was subjected to column chromatography on silica (ethyl acetate/40–60 petroleum ether, 50:50) to give the pure product (6.44 g, 83%). $^1$H NMR (270 MHz, CDCl$_3$) δ8.77 (bs, 1H); 7.57 (s, 1H); 7.46–7.28 (m, 5H); 6.83 (s, 1H), 5.13 (s, 2H); 4.85–4.70 (m, 3H); 4.07–3.60 (m, 7H); 2.77 (dd, J=18.5, 9.5 Hz, 1H); 2.54 (d, J=18.5 Hz, 1H). $^{13}$C NMR (67.8 MHz, CDCl$_3$) δ209.0, 169.4, 152.3, 150.6, 145.5, 136.0, 130.0, 128.6, 128.3, 127.6, 110.9, 107.4, 95.2, 74.5, 70.8, 64.4, 60.4, 56.6, 55.9, 39.5.

(11s,11aS)-4-benzyloxy-11-hydroxy-5-methoxy-4-oxo-10-(2',2',2'-trichloroethoxy)carbonyl-amino 1,10,11,11a-tetrahydro-5H-pyrrolo-[2,1-c][1,4]benzodiazepin-5-one (171)

A solution of DMSO (4.45 g, 4.04 mL, 56.9 mmol) in dry dichloromethane (25 mL) was added dropwise, over 5 minutes, to a solution of oxalyl chloride (3.58 g, 49.9 mmol) in dry dichloromethane (14 mL) at −60° C. under a nitrogen atmosphere and the reaction mixture allowed to stir for a further 15 minutes. A solution of the substrate 170 (10.93 g, 20.0 mmol) in dichloromethane (25 mL) was added dropwise over 30 minutes to the reaction mixture, which was then allowed to stir for 30 minutes at −60° C. Finally, neat triethylamine (11.15 g, 232.9 mmol) was added dropwise over 30 minutes and the reaction mixture allowed to stir at −60° C. for 15 minutes. The reaction mixture was allowed to warm to room temperature, diluted with water (150 mL) and the organic phase washed with dilute HCl (1N, 100 mL), water (100 mL) and brine (100 mL). The organic phase was dried over magnesium sulphate, filtered and concentrated in vacuo to afford the crude product which was subjected to column chromatography (ethyl acetate/40–60 petroleum ether, 50:50). Removal of excess eluent afforded the product 171 (9.66 g, 89% yield). $^1$H NMR (270 MHz, CDCl$_3$) δ7.45–7.33 (m, 5H); 7.27 (s, 1H); 6.95 (s, 1H); 5.76 (d, J=9.9 Hz, 1H); 5.52–5.00 (m, 3H), 4.33 (d, J=6.8 Hz, 1H); 4.30 (d, J=19.2 Hz, 1H); 4.00–3.70 (m, 5H); 2.98 (dd, J=20.0, 10.4 Hz, 1H); 2.94 (d, J=20.0 Hz, 1H). $^{13}$C NMR (67.8 MHz) δ207.7, 167.5, 154.5, 152.6, 150.8, 149.6, 135.8, 128.9–127.3, 124.0, 114.5, 110.8, 95.0, 86.6, 75.0, 71.1, 56.8, 56.2, 52.6, 40.2.

(11aS)-4-benzyloxy-5-methoxy-4-oxo-1,10,11,11a-tetrahydro-5H-pyrrolo[2,1-c][1,4]benzodiazepin-5-one (172)

Cadmium/lead couple (1.15 g) was added to a solution of cyclized ketone (1 g, 1.84 mmol) in THF (5 mL) and aqueous ammonium acetate (1N, 15 mL). The reaction mixture was allowed to stir for 90 minutes and then filtered through celite. The celite pad was washed with ethyl acetate (2×25 mL) and the organic layer separated. The organic layer was washed with brine (50 mL) and dried over magnesium sulphate. Removal of excess solvent followed by column chromatography afforded the pyrrolobenzodiazepine 172 (0.324 g, 0.93 mmol). $^1$H NMR (270 MHz, CDCl$_3$) δ7.75 (d, J=4.4 Hz, 1H); 7.51 (s, 1H); 7.46–7.27 (m, 5H); 5.23 (d, J=12.3 Hz, 1H); 5.17 (d, J=12.3 Hz, 1H), 4.24–4.40 (m, 3H); 3.96 (s, 3H); 3.12 (dd, J=19.6, 8.8 Hz, 1H); 2.99 (dd, J=5.0 Hz, 1H). $^{13}$C NMR (67.8 MHz) δ206.7, 165.5, 161.4, 151.1, 148.5, 140.5, 136.0, 128.7–127.1, 118.9, 111.7, 111.3, 70.9, 56.4, 53.4, 51.0, 40.0.

Example 2(g)

Figure 14:
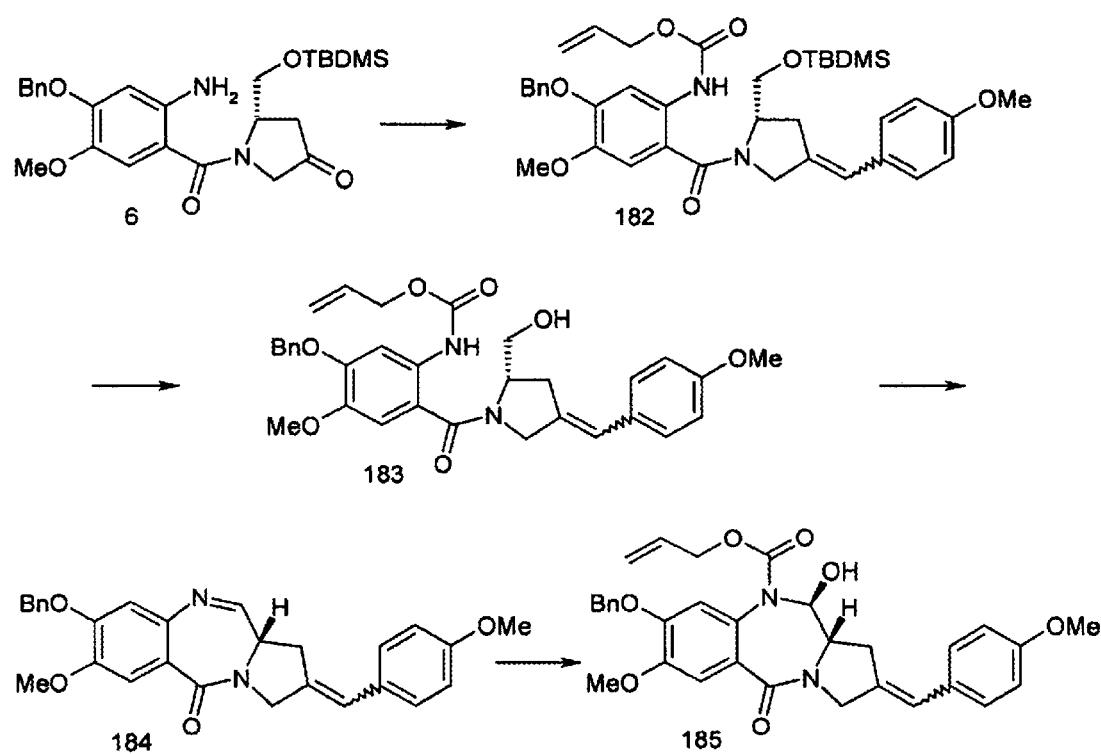

Synthesis of (11aS)-8-Benzyloxy-7-methoxy-2-(4-methoxybenzylidene-1,2,3,11a,-tetrahydro-5H-pyrrolo[2,1-c][1,4]benzodiazepine-5-one (185) (See FIG. 14)

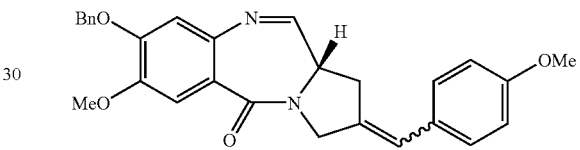

(2S)-N-[(2-allyloxycarbanylamino)-4-benzyloxy-5-methoxy]-2-(tert butyldimethylsilyloxymethyl)-4-methylidenepyrrolidine (182)

The Wittig reagent, 4-methoxybenzylphosphonium bromide (3.686 g, 0.88 mmol) was added portionwise to a suspension of sodium hydride (352 mg of a 60% dispersion, 8.80 mmol) in anhydrous toluene (25 mL) under a nitrogen atmosphere at 0° C. The mixture was allowed to warm to room temperature and then heated at reflux for 30 minutes. The colour of the reaction mixture darkened progressively from yellow through to orange. At this stage a solution of the ketone (6—see Example 1a) (0.5 g, 0.88 mmol) in dry toluene (25 mL) was added dropwise to the reaction mixture at reflux. After 10 minutes TLC (50% ethyl acetate, 50% 40–600 petroleum ether) revealed the complete consumption of ketone. Excess toluene was removed by rotary evaporation under reduced pressure to yield a brown residue, which was partitioned between ethyl acetate (100 mL) and saturated sodium hydrogen carbonate (100 mL). The organic layer was washed with brine (100 mL) and dried over magnesium sulphate) removal of excess solvent by rotary evaporation under reduced pressure gave a dark oil, which was subjected to flash chromatography on silica gel (20% ethyl acetate, 70% 40–60° petroleum ether). Removal of excess eluent afforded the product (182) as an oil which solidified on standing (420 mg, 0.62 mmol, 71%). [α]$^{21}_D$− 7.48° (c=1.002 CHCl$_3$). $^1$H NMR (270 MHz, CDCl$_3$) cis/trans mixture, rotamers δ8.90 (bs, 1H), 7.95 (s, 1H), 7.76–7.65 (m, 2H), 7.55 (m, 7H), 6.9 (s, 1H), 6.4) and 6.30 (2×bs, 1H), 6.02–5.88 (m, 1H), 5.40–5.17 (s, 4H), 4.64–4.59 (m, 2H), 3.91–3.70 (m, 9H), 3.00–2.95 (m, 2H). HRMS (FAB) 673 (M+1). Anal. Calcd for C$_{38}$H$_{48}$N$_2$O$_7$Si: C, 67.83; H, 7.19; N, 4.16. Found C, 67.64; H, 7.33; N, 4.03.

(2S)-N-(2-allyloxycarnoylamino)-4-benzyloxy-5-methoxy]-2-(hydroxymethyl)-4-(4-methoxybenzylidene)pyrrolidine (183)

A solution of TBAF in THF (1.21 mL, 1 M solution, 1.21 mmol) was added to a solution of 182 (0.65 g, 0.97 mmol) in THF (15 mL) at 0° C. The reaction mixture was allowed to warm to room temperature and stir overnight. Excess THF was removed by rotary evaporation under reduced pressure and the residue was partitioned between ethyl acetate (100 mL) and saturated ammonium chloride (1 mL). The organic phase was washed with brine (100 mL) and dried over magnesium sulphate. Excess solvent as evaporated under reduced pressure and the resulting residue was subjected to flash column chromatography (silica gel, 50% ethyl acetate and 50% 40–60° petroleum ether). Removal of excess eluent by rotary evaporation under reduced pressure afforded the compound 183 (0.9 g, 1.61 mmol, 65%). $^1$H NMR (270 MHz, CDCl$_3$) cis/trans mixture δ8.55 (bs, 1H), 7.50–7.10 (m, 8H), 6.80–6.90 (m, 3H), 6.40 and 6.29 (2×bs, 1H), 6.02–5.88 (m, 1H), 5.40–5.10 (m, 4H), 4.55–4.70 (m, 2H), 4.50–4.30 (m, 1), 3.95–3.80 (m, 8H), 3.10–3.90 (m, 1H), 3.50–3.70 (m, 1H). HRMS (FAB) Calcd for C$_{32}$H$_{35}$N$_2$O$_7$ (M+H) 559.2444; Found 559.2462.

(11S,11aS)-10-allyloxycarbonyl-8-benzyloxy-11-hydroxy-7-methoxy-2-(4-methoxybenzylidene)-1,2,3,10,11,11a-hexahydro-5H-pyrrolo[2,1-c][1,4]benzodiazepine-5-one (184)

A solution of DMSO (0.41 mL, 5.80 mmol) in dry DCM (50 mL) was added dropwise to a stirred solution of oxalyl chloride (1.45 ml of a 2M solution, 2.90 mmol)at −40° C. under a nitrogen atmosphere. After 45 minutes stirring at −45° C., a solution of 183 (0.9 g, 1.61 mmol) in DCM (50 mL) was added dropwise to the mixture over 45 minutes. After stirring at −45° C. for 45 minutes the reaction mixture was treated dropwise with a solution of TEA (0.94 mL, 6.76 mmol) in DCM (20 mL) over 30 minutes. After a stirring at −45° C. for a further 40 minutes the reaction mixture was allowed to warm to room temperature and then diluted with DCM (30 mL). The diluted reaction mixture was washed with dilute hydrochloric acid (1 N, 300 mL), water (150 mL), brine (150 mL) and dried over magnesium sulphate. Removal of excess solvent afforded the crude product, which was subjected to column chromatography (silica gel, 50% ethyl acetate and 50% 40–60° petroleum ether). Removal of excess eluent afforded the product 184 as an oil (0.62 g, 1.11 mmol, 69%). $^1$H NMR (270 MHz, CDCl$_3$) cis/trans mix δ7.50–7.10 (m, 8H), 6.90–6.85 (m, 2H), 6.74 (s, 1H), 6.50 and 6.45 (2×bs, 1H), 6.70–5.00 (m, 6H), 4.70–4.20 (m, 4H), 3.98 (s, 3H), 3.90–3.70 (m, 4H), 3.10–2.80 (m, 2H). HRMS (FAB) Calcd for C$_{32}$H$_{33}$N$_2$O$_7$ (M+H) 557.2288; Found 559.2277.

(11aS)-8-Benzyloxy-7-methoxy-2-(4-methoxybenzylidene-1,2,3,11a,-tetrahydro-5H-pyrrolo[2,1-c][1,4]benzodiazepine-5-one (185)

Triphenylphosphine, pyrrolidine and palladium tetrakistriphenylphosphine were addaed sequentially to a stirred solution of substrate in dry DCM. The reaction mixture was allowed to stir at room temperature under a nitrogen atmosphere for 2 h, at which time TLC (50% ethyl acetate and 50% 40–60° petroleum ether) revealed the complete consumption of starting material. The reaction mixture was evaporated to dryness and the resulting residue subjected to gravity column chromatography (silica gel, gradient elution: 30% ethyl acetate, 70% 40–600 petroleum ether to 70% ethyl acetate, 30% 40–60° petroleum ether). Removal of excess eluent afforded the PBD (185) as a yellow glass that was reprecipitated from ethyl acetate with 40–60° petroleum ether.

$^1$H NMR (270 MHz, CDCl$_3$) cis/trans mix δ7.69 (d, 1H, J=4.39 Hz), 7.52 (s, 1H), 7.46–7.30 (m, 5H), 7.20–7.16 (m, 2H), 6.92–6.88 (m, 2H), 6.84 (s, 1H), 6.53 (bs, 1H), 5.20–5.17 (m, 2H), 4.52 (m, 2H), 3.96 (s, 3H), 3.90–3.75 (m, 4H), 3.34–3.26 (m, 1H), 3.12–3.00 (m, 1H).

Example 3
Synthesis of Compounds of formula III
Overview of Synthesis

The Biaryl PBDs 136, 138 and 140 were obtained by removal of the Troc protecting group from the protected carbinolamines 135, 137 and 139. For compounds 136 and 138 the deprotection method of Dong et al, was employed (Cd/Pb, ammonium acetate buffer), however, this approach could not be applied to the preparation of 140 as this molecule contained a nitro group sensitive to the Cd/Pb couple. In this case a novel deprotection procedure involving the use of tetrabutyl ammonium fluoride was used. The protected biaryl carbinolamines were prepared by the Suzuki reaction, the common 7-iodo substituted protected carbinolamine 134 was exposed to the appropriate boronic acid in the presence of a palladium catalyst. This reaction is of wide scope as over 70 boronic acids are commercially available. The iodo substituted protected carbinolamine 134 was furnished by Swern oxidation of the primary alcohol 133. The Swern procedure was particularly effective in this case but other oxidizing agents such as the Dess-Martin reagent, TPAP or pyridine sulphur trioxide complex and DMSO could also be employed. The primary alcohol 133 was afforded by coupling commercially available pyrrolidinemethanol to the Troc protected anthranilic acid chloride obtained by 132 by treatment with oxalyl chloride. The Troc protected acid was in turn prepared by exposing the anthranilic acid 131 to 2,2,2-trichloroethyl chloroformate. Other protecting groups can be used in place of Troc such as Nvoc, Teoc and Fmoc but care must be taken in choosing a protecting group as some groups such as Boc spontaneously form the isatoic anhydride when exposed to oxalyl chloride prior to the coupling step.

The 9-methoxy PBD (101) was prepared in an analogous fashion demonstrating the versatility of the approach.

The 8-amino PBD (151) was prepared by the removal of a Troc protecting group from the amino substituted protected carbinolamine 150. The free amine was obtained by removal of an Fmoc protecting group under standard conditions (piperidine/DMF) from the protected carbinolamine 149. Swern oxidation of the primary alcohol 148 furnished 149 in good yield, the substrate for oxidation reaction was prepared by Fmoc protection of the aniline 147. Reduction of the nitro compound 146, with tin chloride furnished the aniline, hydrogenation could not be employed to reduce the nitro group as the Troc system does not withstand these conditions. The nitro compound 146 was prepared by the coupling of the acid chloride derived from 145 with pyrrolidinemethanol in the presence of base. Finally, the protected anthranilic acid 145 was furnished by exposing the commercially available 4 nitro anthranilic acid 144 to Troc Chloroformate.

The 8-benzyloxy-7,9-dimethoxy PBD (143, UP2022) was prepared by a slightly different approach which does not involve the use of anthranilic acid starting materials but proceeds through 2-nitrobenzoic acid intermediates. The PBD was obtained from the protected carbinolamine 142 by removal of the Troc protecting group under the usual conditions. The protected carbinolamine was furnished by Swern oxidation of primary alcohol 141 which in turn was prepared by selective protection of the amino alcohol 126 as the Troc carbamate by exposure to Troc Chloroformate in the presence of pyridine. The amino alcohol was obtained by reduction of the nitro compound 125 with Raney Nickel and hydrazine (again hydrogenation could not be employed due to the presence of a benzyl group). The nitro alcohol 125 was prepared by coupling pyrrolidine methanol to the requisite 2-nitrobenzoic acid 124. This nitro benzoic acid was not commercially available and was prepared in four steps from the available syringic acid 87. Nitration of the ester 122 was proceeded smoothly using Copper nitrate in acetic anhydride. The ester 122 was obtained by standard methods.

The PBDs 96, 113, 120 and 194 were obtained in an identical fashion from the 2-nitrobenzoic acids 19, 108, 115 and 186.

The dimer 90 was prepared in an analogous fashion from the core nitro compound 85; the core was assembled by joining together two units of the phenol 84 via mitsonobu etherification. The phenol 84 was derived from syringic acid 83 in a three step synthesis, the crucial step being the nitration of 82 which was performed with 70% nitric acid.

The phenolic PBD 130 was prepared by an analogous route to that used for the synthesis of the PBD 143, however the requirement to incorporate a phenolic group prompted the use of a different protecting group, Teoc. The free PBD was obtained by treating the Teoc protected carbinolamine 129 with TBAF in warm acetonitrile. The phenol 129 was unmasked by the hydrogenolysis of the benzyloxy moiety of 128 in the presence of the Teoc protecting group (Troc would not survive under these conditions). The benzyloxy compound 128 was obtained by Swern oxidation of the primary alcohol 127 which was prepared by treating the amino alcohol 126 with Teoc chloroformate in the presence of base.

Figure 15:
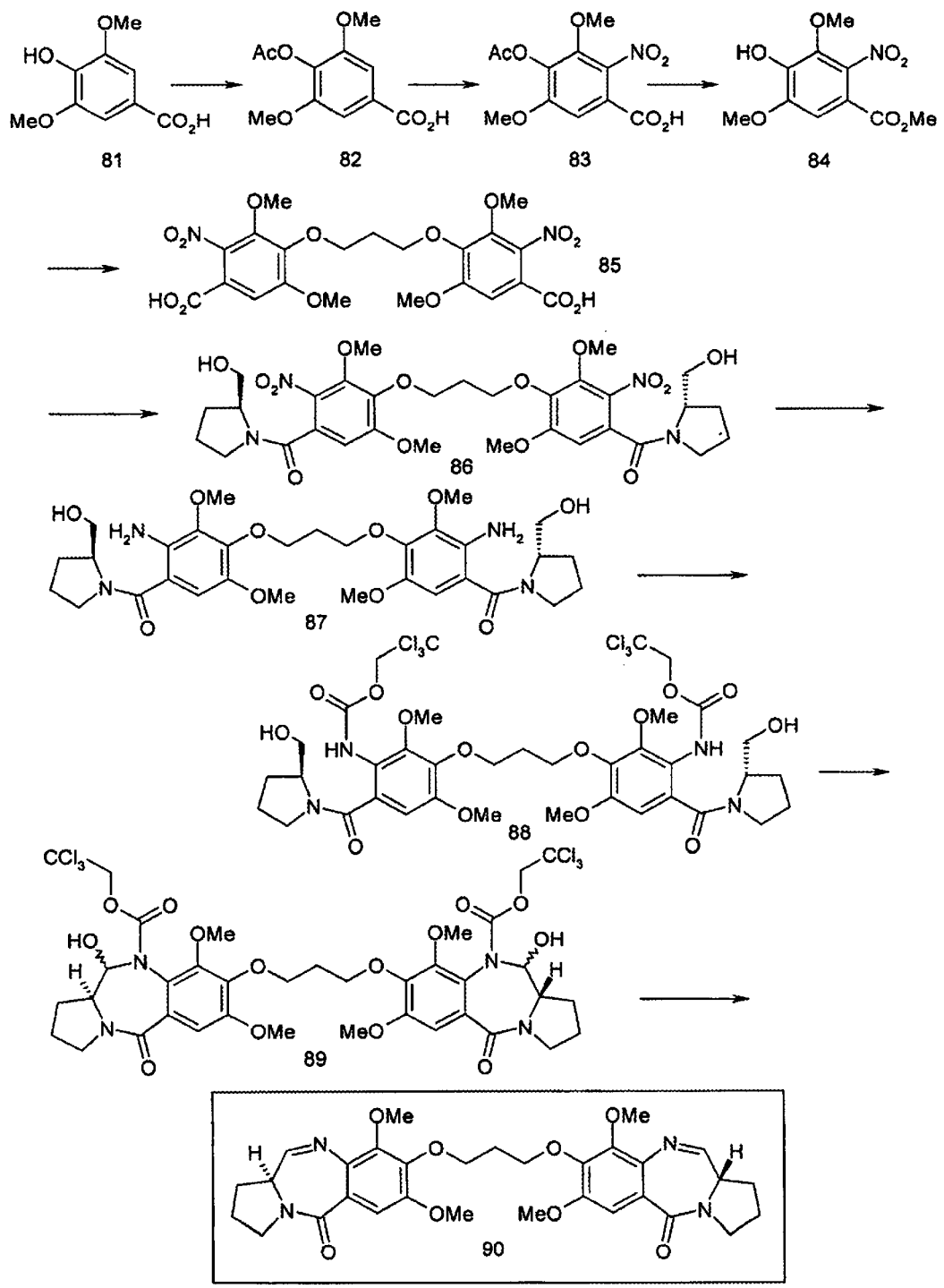
FIGS. 15 to 24 are synthesis routes for compounds of formula III of the present invention.

Example 3(a)
Synthesis of the C9/C9'-Dimethoxy PBD Dimer (90, DRH-165) (See FIG. 15)

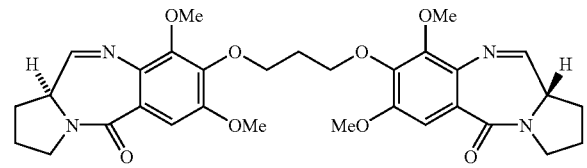

O-Acetylsyringic Acid (82)

A suspension of syringic acid 81 (10.0 g, 50.5 mmol) in acetic anhydride (30.0 g, 27.7 mL, 294.1 mmol) was warmed gently until a clear solution was obtained. Fused sodium acetate (0.5 g, 6.10 mmol) was added to the solution which was allowed to stir for 16 hours at room temperature. The solution was poured into water (100 mL) and stirred thoroughly to ensure hydrolysis of any excess anhydride. Crude O-Acetyl-syringic acid was recrystallized from water to afford the product as an off-white powder (11.2 g, 46.7 mmol). $H^1$ NMR (270 MHz, CDCl$_3$) δ7.36 (s, 2H), 5.94 (br s, 1H), 3.87 (s, 6H), 2.35 (s, 3H). HRMS calcd for 240.0634, found 240.0637

4-Acetoxy-3,5-dimethoxy-2-nitrobenzoic Acid (83)

Fuming nitric acid (5.2 mL) was added, carefully, to a solution of o-acetylsyringic acid 82 (11.1 g, 46.2 mmol) in acetic anhydride (33 g, mmol) at 5° C. and the reaction mixture was then allowed to stir for 3 hours at room temperature. The reaction mixture was poured over ice (300 mL) and the yellow precipitate was collected by filtration, washed with water (3×100 mL) and dried in vacuo to afford the product as a pale yellow solid (12.4 g). $H^1$ NMR (270 MHz, CDCl$_3$) δ7.37 (s, 1H), 3.92 (s, 3H), 3.90 (s, 3H), 2.39 (s, 3H).

Methyl 3,5-dimethoxy-4-hydroxy-2-nitrobenzoate (84)

A catalytic amount of DMF (5 drops) was added to a solution of oxalyl chloride (6.3 g, 49.8 mmol) and o-nitrobenzoic acid 83 (12.4 g, 45.2 mmol) in anhydrous THF (100 mL) and the reaction mixture allowed to stir at room temperature for 16 h. The resulting acid chloride was quenched dropwise with anhydrous methanol (100 mL) at 0° C. The reaction mixture was treated with potassium carbonate and allowed to stir at room temperature for 3 h. Excess solvent was removed by rotary evaporation at reduced pressure and the residue dissolved in water. The aqueous solution was acidified to pH 8 and the resulting white precipitate was collected by filtration, washed with water (2×100 mL) and dried to afford the product as an off-white solid (10.6 g, 83%). $H^1$ NMR (270 MHz, CDCl$_3$) δ10.07 (br s, 1H), 7.26 (s, 1H), 3.97 (s, 3H), 3.91 (s, 3H), 3.85 (s, 3H).

1',3'-Bis(4-carboxy-2,6-dimethoxy-5-nitrophenoxy)propane (85)

Diethylazidodicarboxylate (7.19 g, 41.3 mmol) was added dropwise over 0.5 hours to a cooled, stirred solution of the phenol 84 (10.61 g, 41.3 mmol) and TPP (16.24 g, 61.9 mmol) in anhydrous THF (100 mL), and allowed to stir for 1 h. A solution of 1,3-propanediol (1.57 g, 20.6 mmol) in THF (30 mL) was added dropwise and the reaction mixture allowed to stir for 16 h. The reaction mixture was then treated with 1N aqueous NaOH (200 mL) and heated at reflux for 3 h. Excess solvent was removed by rotary evaporation under reduced pressure to afford an aqueous suspension which was extracted with EtOAc (3×300 mL). The aqueous extract was acidified with concentrated HCl and the precipitate collected by vacuum filtration. The precipitate was suspended in water (500 mL) and after stirring for 10 minutes, the suspension was filtered to afford the product as an orange solid (6.11 g, 60%). $H^1$ NMR (270 MHz, CDCl$_3$) δ7.32 (s, 2H), 4.36 (t, 4H,), 3.92 (s, 6H) 3.90 (s, 6H), 2.20 (t, 2H).

(2S)-1,1'-[[(propane-1,3-diyl)dioxy]bis[2-nitro-3,5-dimethoxy-1,4-phenylene)carbonyl]]bis[2-(hydroxymethylpyrrolidine] (86)

A catalytic amount of DMF (3 drops) was added to a solution of the acid 85 (6.1 g, 12.4 mmol) and oxalyl chloride (2.37 mL, 3.45 g, 27.2 mmol) in anhydrous DCM (60 mL) and the reaction mixture allowed to stir at room temperature for 16 h. The resulting acid chloride was added dropwise over 0.5 hours to a stirred solution of TEA (6.26 g, 61.8 mmol) and pyrrolidinemethanol (2.75 g, 27.2 mmol) in anhydrous DCM (60 mL) at −10° C. The reaction mixture was then allowed to stir at room temperature for 6 h. The reaction mixture was washed with 1N HCl (3×100 mL), water (3×100 mL), saturated NaHCO$_3$ (3×100 mL), brine (3×100 mL) and dried over MgSO$_4$. Removal of excess solvent by rotary evaporation under reduced pressure afforded the product as a yellow glass (8.25 g, 11.9 mmol). $H^1$ NMR (270 MHz, CDCl$_3$) δ6.66 (s, 2H), 4.32–4.26 (m, 6H), 3.98 (s, 6H), 3.90 (s, 6H), 3.86–3.67 (m, 4H), 3.41–3.27 (m, 4H), 2.23–2.12 (m, 2H), 2.11–1.72 (m, 8H).

(2S)-1,1'-[[(propane-1,3-diyl)dioxy]bis[2-amino-3,5-dimethoxy-1,4-phenylene)carbonyl]]bis[2-(hydroxymethylpyrrolidine] (87)

Hydrazine (3.45 g, 107.9 mmol) was added dropwise to a solution of 86 (1 g, 1.45 mmol) in anhydrous methanol (40 mL) heated at reflux over Raney nickel (5 g, slurry). Heating was continued for a further 3 hours after which time the reaction mixture was allowed to cool and filtered through celite to remove excess Raney nickel. The filtrate was evaporated to dryness and dissolved in DCM (200 mL) and the organic solution washed with water (2×100 mL), brine (2×100 mL) and dried over MgSO$_4$. Filtration and evaporation of excess solvent in vacuo afforded the product as a pink glass (5.59 g, 8.9 mmol, 98%). H$^1$ NMR (270 MHz, CDCl$_3$) δ6.54 (s, 2H), 4.35 (br s, 2H), 4.29 (t, 4H), 3.85 (s, 3H), 3.83–3.46 (m, 14H), 2.20–2.13 (m, 2H), 1.97–1.66 (m, 8H).

(2S)-1,1'-[[(propane-1,3-diyl)dioxy]bis[2-(2',2',2'-trichloroethoxycarbonyl)amino-3,5-methoxy-1,4-phenylene)carbonyl]]bis[2-(hydroxymethylpyrrolidine] (88)

A solution of 2,2,2-trichloroethylchloroformate (1.45 g, 6.86 mmol, 1.9 eq) in dry DCM (10 mL) was added dropwise over the space of 0.5 hours to a solution of 87 (2.28 g, 3.6 mmol) and pyridine (1.14 g, 14.4 mmol, 4 eq) in dry DCM (50 mL) and allowed to stir for 16 hours at room temperature. The reaction mixture was diluted with DCM (200 mL) and washed with 1N HCl (3×200 mL), H$_2$O (3×200 mL), brine (2×300 mL) and dried over anhydrous MgSO$_4$. Purification by flash chromatography (silica gel, EtOAc) afforded the product as a pale yellow glass (1.43 g). H$^1$ NMR (270 MHz, CDCl$_3$) Rotamers δ9.21 and 8.40 (2×br s, 2H), 6.49 and 6.54 (2×s, 2H), 5.08–3.59 (m, 26H), 3.33–3.30 (m, 4H), 2.04–1.69 (m, 10H).

1,1'-[[Propane-1,3-diyl)dioxy]bis[(11S,11aS)-10-(2',2',2'-trichloroethoxycarbonyl)-11-hydroxy-7,9-dimethoxy-1,2,3,10,11,11a-hexahydro-5H-pyrrolo[2,1-c][1,4]benzodiazepin-5-one. (89)

A solution of dry DMSO (14.9 mmol, 1.17 g, 1.06 mL) in dry DCM (5 mL) was added dropwise over 20 minutes to a stirred solution of oxalyl chloride in DCM (7.38 mmol, 3.69 mL of a 2N solution in DCM) under a nitrogen atmosphere at −45° C. After stirring for an additional 15 minutes, a solution of 88 (2.58 g, 2.63 mmol) in dry DCM (5 mL) was added dropwise over 45 minutes at −45° C. and stirred for 45 minutes at −45° C. TEA (2.12 g, 21.0 mmol) was added dropwise over 30 minutes and stirred for a further 15 minutes. The reaction mixture was allowed to warm to room temperature, and diluted with water (100 mL). The organic layer was washed with 1N HCl (3×100 mL), water (3×100 mL), brine (3×100 mL) and dried over anhydrous MgSO$_4$. Filtration and evaporation of the solvent in vacuo afforded the product as a yellow glass (0.73 g). H$^1$ NMR (270 MHz, CDCl$_3$) δ7.06 (s, 2H), 5.61 (dd, 2H, J=3.39, 9.9 Hz), 4.74 (d, 2H, J=11.72 Hz), 4.62 (d, 2H, J=11.91 Hz), 4.29–4.21 (m, 6H), 3.97–3.46 (m, 16H), 2.28–2.01 (m, 10H).

Preparation of 10% Cd/Pb Couple

Yellow lead oxide (litharge, 1.8 g, 4.9 mmol) was dissolved in warm 50% aq. AcOH (50 mL) and the solution was slowly added to a vigorously stirred suspension of Cd dust (Aldrich, 100 mesh, 5.46 g, 49 mmol) in deionised water (100 mL). The Cd darkened as Pb deposited on its surface, and formed clumps that were gently broken up with a glass rod. The dark non-pyrophoric Cd/Pb couple was filtered, washed with water, acetone, crushed and dried prior to storage and use.

1,1'-[[Propane-1,3-diyl)dioxy]bis[(11aS)-7,9-dimethoxy-1,2,3,11a-tetrahydro-5H-pyrrolo[2,1-c][1,4]benzodiazepin-5-one. (90)

Cadmium/lead couple (3.8 mmol Cd, 0.47 g of C\Pb couple) was added to a vigorously stirred solution of 89 (0.76 g, 0.8 mmol) in THF (10 mL) and 1N NH$_4$OAc (10 mL) and stirring continued for 2.5 h. The reaction mixture was diluted with DCM (150 mL) and dried over MgSO$_4$. Filtration and evaporation of the solvent in vacuo afforded the product as a yellow glass (0.32 g, 0.55 mmol, 71%). H$^1$ NMR (270 MHz, CDCl$_3$) mixture of C11/C11'R/S carbinolamines δ7.08 (s, 2H), 5.53 (br s, 2H), 5.38 (br s, 2H), 4.90 (d, 2H, J=9 Hz), 4.79 (d, 2H, J=9 Hz), 4.38–3.54 (m, 22H), 2.27–1.79 (m, 10H). MS (FAB) m/e (relative intensity) 594 (M+2, 27%), 593 (M+1, 69%)

Example 3(b)

Figure 16:
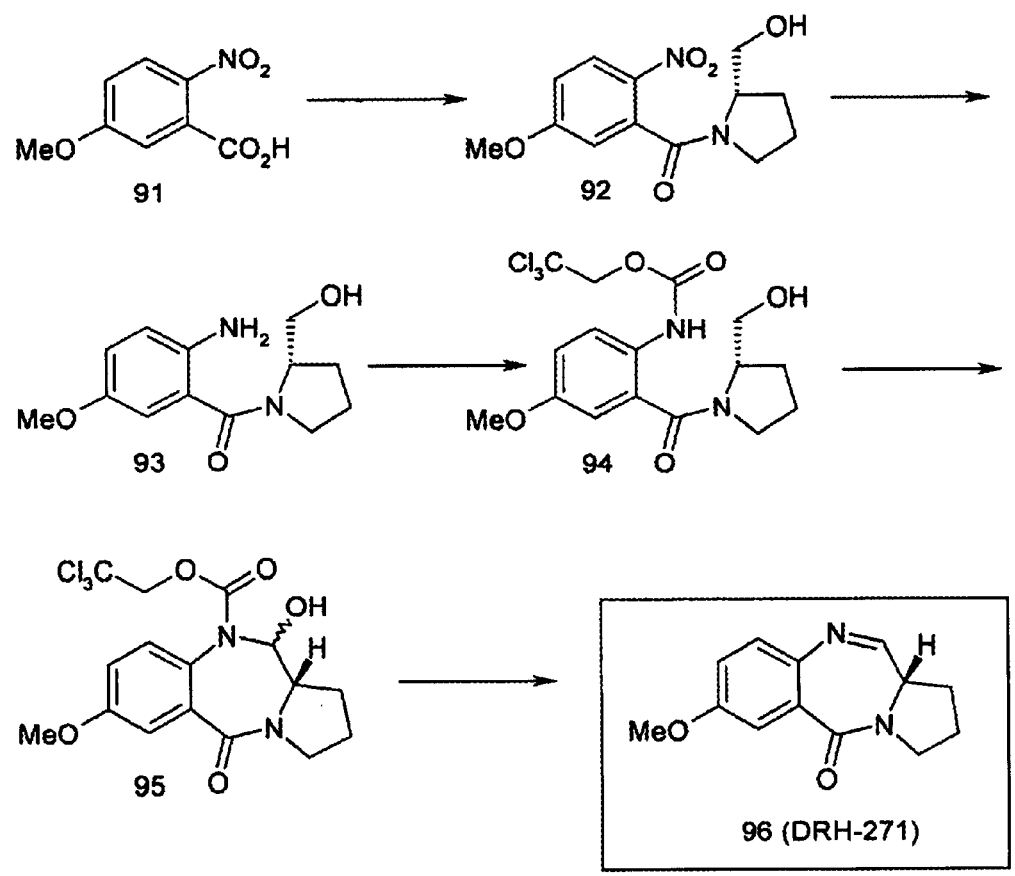

Synthesis of the C7-Methoxy PBD (96, DRH-271) (See FIG. 16)

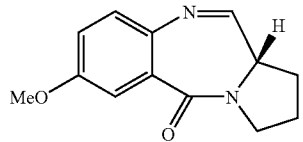

N-(3-Methoxy-2-nitrobenzoyl)pyrrolidin-2-methanol (92)

A catalytic amount of DMF (2 drops) was added to a stirred solution of 3-methoxy-2-nitro-benzoic acid 91 (5.01 g, 25.4 mmol) and oxalyl chloride (3.54 g, 27.9 mmol) in dry CHCl$_2$(50 mL) under a nitrogen atmosphere. The reaction mixture was allowed to stir overnight, before being used directly in the preparation of 92. A solution of the acid chloride in anhydrous CHCl$_2$(50 mL) was added dropwise over 1 hour to a vigorously stirred solution of pyrrolidinemethanol (2.57 g, 25.4 mmol) and TEA (6.42 g, 63.6 mmol) in anhydrous CHCl$_2$(50 mL) under a nitrogen atmosphere at 0° C. and allowed to stir overnight at room temperature. The reaction mixture was washed with 1N HCl (1×100 mL), H$_2$O (3×100 mL) and brine (3×100 mL). The organic layer was dried over anhydrous MgSO$_4$, and evaporation of the solvent afforded a brown oil (6.37 g, 22.7 mmol, 89%).

N-(2-Amino-3-Methoxybenzoyl)pyrrolidin-2-methanol (93)

Hydrazine hydrate (4.37 g, 136.4 mmol) was added dropwise to a solution of 92 (6.37 g, 22.7 mmol) in gently refluxing methanol (100 mL) over Raney nickel (2.4 g, slurry). The resulting vigorous evolution of hydrogen gas subsided after approximately 10 minutes and the reaction was deemed to be complete by TLC after 2 h. The reaction mixture was filtered through celite and the solvent evaporated. Distilled water (100 mL) was added to the residue, and the aqueous mixture was extracted with EtOAc (3×100 mL) and washed with H$_2$O (3×100 mL) and brine (3×100 mL) and dried over anhydrous MgSO$_4$. Evaporation of the solvent afforded a brown glass (5.49 g, 21.8 mmol) as a single spot by TLC.

N-(3-Methoxy-2-((2',2',2'-trichloroethoxy)carbonylaminobenzoyl)pyrrolidin-2-methanol (94)

A solution of 2,2,2-trichloroethyl chloroformate (4.61 g, 21.8 mmol) in distilled dichloromethane (50 mL) was added dropwise over 0.5 hours to a stirred solution of the substrate, 93 (5.46 g, 21.8 mmol) and anhydrous pyridine (3.44 g, 43.5 mmol) in distilled dichloromethane (100 mL) at 0° C. The reaction mixture was allowed to stir for 2.5 hours at which time TLC showed reaction to be complete. The reaction mixture was diluted with anhydrous DCM (100 mL) and washed with 1N HCl (2×200 mL), H$_2$O (200 mL), brine (200 mL) and dried over anhydrous MgSO$_4$. Evaporation of the solvent afforded a brown oil which was purified by flash column chromatography eluting with EtOAc to afford the product as a yellow solid (6.14 g, 14.4 mmol); $^1$H NMR (270 MHz, CDCl$_3$) δ1.75–2.25 (m, 4H), 3.4–3.75 (m, 2H), 3.8 (s, 3H), 3.85–4.2 (m, 2H), 4.40 (m, 1H), 4.73–4.86 (m, 2H), 6.86–6.97 (m, 2H), 7.85 (br d, 1H, J=9 Hz); $^{13}$C NMR (67.8 MHz, CDCl$_3$) δ169.9, 155.6, 152.4, 128.2, 127.8, 123.6, 116.0, 113.0, 95.4, 74.4, 65.9, 60.9, 55.7, 51.0, 28.3, 24.9.

(11S,11aS)-10-(2',2',2'-trichloroethoxy)carbonyl-7-methoxy-11-hydroxy-1,2,3,10,11,-11a-hexahydro-5H-pyrrolo[2,1-c][1,4]benzodiazepin-5-one(95)

Anhydrous DMSO (3.14 g, 40.2 mmol) in dry DCM (25 mL) was added dropwise over 5 minutes to a stirred solution of oxalyl chloride (2.53 g, 9.96 mL of a 2 N solution in DCM) under a nitrogen atmosphere at −50° C. After stirring for 5 minutes, the substrate 94 (6.03 g, 14.2 mmol) in dry DCM (25 mL) was added dropwise over 45 minutes to the reaction mixture, which was then allowed to stir for a further 45 minutes at −50° C. after the addition of the substrate. Dry TEA (5.72 g, 56.64 mmol) was added dropwise to the mixture over 0.5 hours and the reaction mixture allowed to stir for a further 15 minutes. The reaction mixture was left to warm to room temperature and diluted with $H_2O$ (100 mL). The organic phase was washed with 1N HCl (2×200 mL), $H_2O$ (2×200 mL), brine (2×200 mL) and dried over anhydrous $MgSO_4$. The solvent was evaporated to afford a yellow oil (6.68 g). The oil was subjected to flash chromatography with EtOAc as eluent to afford the product as a yellow solid (5.87 g, 13.9 mmol); $^1$H NMR (270 MHz, $CDCl_3$) δ1.99–2.14 (m, 4H), 3.45–3.77 (m, 2H), 3.85 (s, 3H), 4.19 (br s, 1H), 4.28 (d, 1H, J=11.91 Hz), 5.14 (d, 1H, J=11.91 Hz), 5.66 (d, 1H, J=9.71 Hz), 6.97–7.02 (m, 1H), 7.23–7.27 (m, 2H); $^{13}$C NMR (67.8 MHz, $CDCl_3$) d 166.8, 159.1, 154.7, 134.3, 131.5, 129.9, 126.6, 118.106, 112.5, 112.3, 95.0, 86.0, 75.2, 75.1, 59.8, 55.7, 46.7, 46.4, 28.7, 23.0, 21.0, 14.2.

7-methoxy-1,2,3,11a-tetrahydro-5H-pyrrolo[2,1-c][1,4]benzodiazepin-5-one (96)

10% Cd/Pb couple (2.50 g, 20 mmol Cd) was added to a rapidly stirring solution of 95 (1.71 g, 4.03 mmol) in a mixture of THF (30 mL) and 1N $NH_{40}Ac$ (30 mL). Upon addition, the solution turned cloudy and after 2 hours TLC showed the reaction to be complete. The reaction mixture was diluted with EtOAc (150 mL) and dried over anhydrous $MgSO_4$. The solids were filtered and rinsed with EtOAc (50 mL). Removal of excess solvent by rotary evaporation under reduced pressure afforded the product as a yellow solid (0.84 g, 3.6 mmol, 90%)

Figure 17:
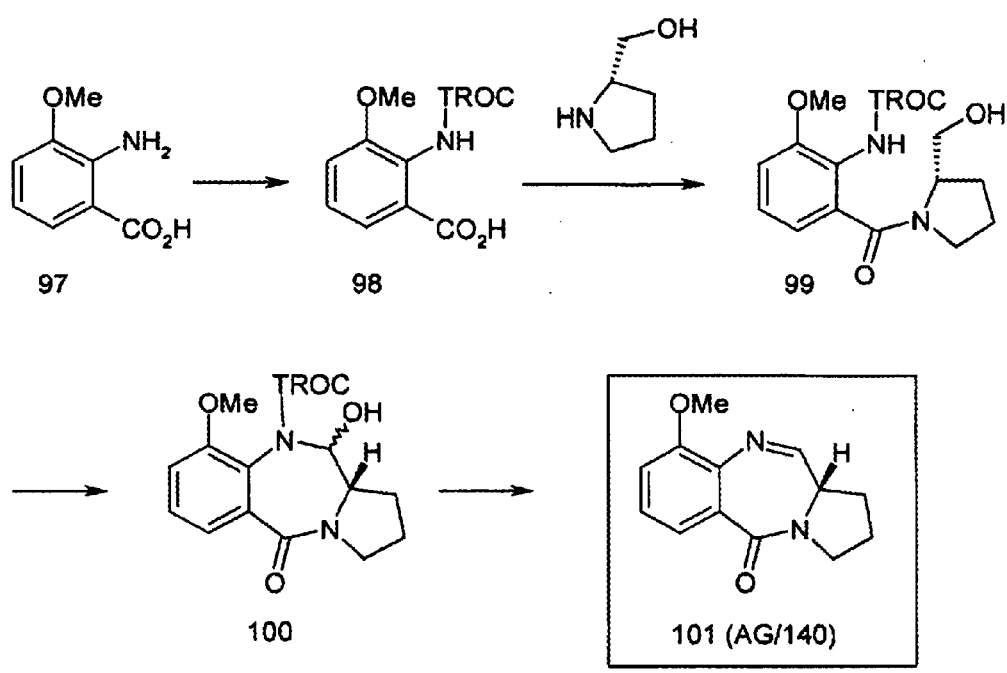

Example 3(c)
Synthesis of the C7-Methoxy PBD (101, AG/140)(See FIG. 17)

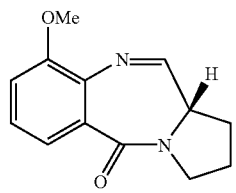

3-methoxy-2-(2',2',2'-trichloroethoxycarbonylamino)benzoic acid (98)

2-amino-3-methoxybenzoic acid 97 (1 g, 6.0 mmol) and pyridine (0.97 mL, 12.0 mmol) were dissolved in dry dichloromethane (30 mL). The resulting mixture was cooled and Troc-Cl (0.9 mL, 6.6 mmol) was added drop wise. The reaction mixture was allowed to stir overnight at room temperature, then washed with HCl (1N, 50 mL), water (50 mL) and brine (50 mL). The organic phase was dried over $MgSO_4$ and evaporated to yield 1.42 g of crude product, which was used in the next step without further purification.

N-(3-methoxy-2-(2',2',2'-trichloroethoxycarbonylamino)benzoyl)-pyrrolidine-2-methanol (99)

Oxalyl chloride (0.57 mL, 6.58 mmol) together with 2 drops of dry DMF was added to a solution of the crude product obtained from the previous reaction in dry dichloromethane (20 mL). After initial strong effervescence, the mixture was allowed to stir at room temperature overnight. The resulting acid chloride was added drop wise, over 30 minutes to a solution of 2S-(+)-pyrrolidinemethanol (0.66 g, 6.58 mmol) and TEA (2.1 mL, 14.95 mmol) in dry dichloromethane (20 mL) at −16° C. Once coupling was complete the reaction mixture was diluted with ethyl acetate (20 mL), and washed with 1N HCl (2×25 mL), satd. aqueous $NaHCO_3$ (2×25 mL), water (25 mL) and brine (25 mL). The organic layer was then dried over $MgSO_4$ and evaporated to give a yellow oil. The crude product was purified by flash chromatography (petroleum ether/ethyl acetate, 50/50) to afford 0.54 g, of a pale yellow oil: $^1$H NMR (270 MHz, $CDCl_3$) d 1.6–1.8 (m, 1H); 1.81–2.0 (m, 2H); 2.02–2.21 (m, 1H); 3.4 (m, 1H); 3.6 (m, 2H); 3.86 (m, 4H); 4.22 (dd, J=5.1, J=12.3 Hz, 1H); 4.72 (d, J=12 Hz, 1H); 4.79 (d, J=12 Hz, 1H); 4.86 (m, 1H); 6.91 (s, 1H); 6.94 (s, 1H); 7.2 (dd, J=7.5, J=8.4 Hz, 1H); 7.36 (bs, 1H). $^{13}$C NMR (67.8 MHz, $CDCl_3$) δ24.6; 28.8; 50.7; 55.9; 61.3; 66.5; 74.8; 75.3; 111.7; 111.9; 119.1; 122.3; 126.3; 132.9; 152.7; 170.3 IR (Nujol): $cm^{-1}$ 3410, 2969, 1738, 1613, 1583, 1514, 1429, 1268, 1218, 1109, 1079, 1049, 809, 759. MS: m/e (relative intensity) 425 (M+, 10), 394 (20), 323 (30), 276 (35), 245 (100), 176 (100), 149 (45), 120 (40), 106 (20), 77 (30), 70 (100). HRMS Calculated for $C_{16}H_19Cl_3N_2O_5$:424.0357. Found: 424.0359. $[α]^{25}_D$=−45.1° (c=0.63, $CHCl_3$).

(11S,11aS)-11-hydroxy-9-methoxy-10-N-(2',2',2'-trichloroethoxycarbonyl)-1,2,-3,10,11,11a-hexahydro-5H-pyrrolo [2,1-c][1,4] benzodiazepin-5-one (100)

A solution of DMSO (0.46 ml, 6.63 mmol) in of dry dichloromethane (10 mL) was added drop wise over 30 minutes to a solution oxalyl chloride (3.30 mmol,) in dry dichloromethane (11.65 mL) at −40° C. The mixture was allowed to stir for a further 30 minutes, a solution of 99 (1 g, 2.37 mmol) in dichloromethane (15 mL) was then added drop wise over 1 hour. Following the end of addition the mixture was allowed to stir at −45° C. for 60 minutes, then a solution of TEA (1.31 mL) in dichloromethane (6 mL) was added drop wise and the mixture was allowed to warm to room temperature. The reaction mixture was washed with water (50 mL), 1N HCl (2×25 mL), satd. aqueous $NaHCO_3$ (2×25 mL), and brine (50 mL). The organic solution was dried over $MgSO_4$ and evaporated. The crude product was purified by flash chromatography (silica gel EtOAc/petroleum ether 1/1) to give a colourless oil (0.64 g, 63%): $^1$H NMR (270 MHz, $CDCl_3$) δ2.01–2.15 (m, 4H); 3.43–3.58 (m, 2H); 3.73 (m, 2H); 3.83 (s, 3H); 4.35 (d, J=12, 1H); 4.98 (d, J=12, 1H); 5.66 (dd, J=3.8, J=9.6 Hz, 1H); 7.02 (dd, J=2.2, J=7.5 Hz, 1H); 7.35 (m, 2H). $^{13}$C NMR (67.8 MHz, $CDCl_3$) δ23.0; 28.6; 46.2; 56.1; 59.9; 75.3; 86.2; 94.8; 113.4; 120.2; 123.1; 129.4; 134.9; 154.7; 155.4; 166.7. IR (Nujol): $cm^{-1}$ 3291, 2924, 1724, 1616, 1580, 1463, 1318, 1278, 1075, 945, 812, 739. MS: m/e (relative intensity) 422 (M−1, 40), 387 (3), 275 (10), 245 (15), 217 (10), 176 (100), 150 (8), 120 (6), 70 (95). HRMS Calculated for $C_{16}H_{17}Cl_3N_2O_5$: 422.0202. Found: 422.0203. $[α]^{25}_D$=+136.5° (c=0.19, $CHCl_3$).

(11aS)-9-methoxy-1,2,3,11a-tetrahydro-5H-pyrrolo[2,1-c][1,4]benzodiazepin-5-one (101)

Finely ground Cd/Pb couple (1.02 g). was added in small portions to a stirred solution of 100 (0.64 g, 1.51 mmol) in THF (10 mL) and 1M $NH_4OAc$ (10 mL). The reaction was followed by TLC (EtOAc), when no more starting material was observed, the mixture was poured into ethyl acetate (200 mL). The organic phase was dried over $MgSO_4$ and evaporated to yield the product as a pale yellow oil (0.28 g, 80%): $^1$H NMR (270 MHz, CDCl$_3$) δ2.15 (m, 4H); 3.52 (m, 2H); 3.87 (s, 3H); 5.15 (m, 1H); 6.8–7.2 (m, 3H); 7.8 (d, J=4.7 Hz, 1H, imine H11). IR (Nujol): cm$^{-1}$ 3373, 2975, 1621, 1576, 1440, 1419, 1250, 1075, 750. MS: m/e (relative intensity) 230 (M$^+$, 100), 215 (45), 201 (20), 187 (5), 160 (5), 146 (4), 133 (20), 105 (10), 76 (25), 70 (45), 63 (3), 51 (3). HRMS Calculated for C$_{13}$H$_{14}$N$_2$O$_2$: 230.1055. Found: 230.1055. [α]$^{25}_D$=+455.3° (c=0.6, CHCl$_3$).

Example 3(d)

Figure 18:
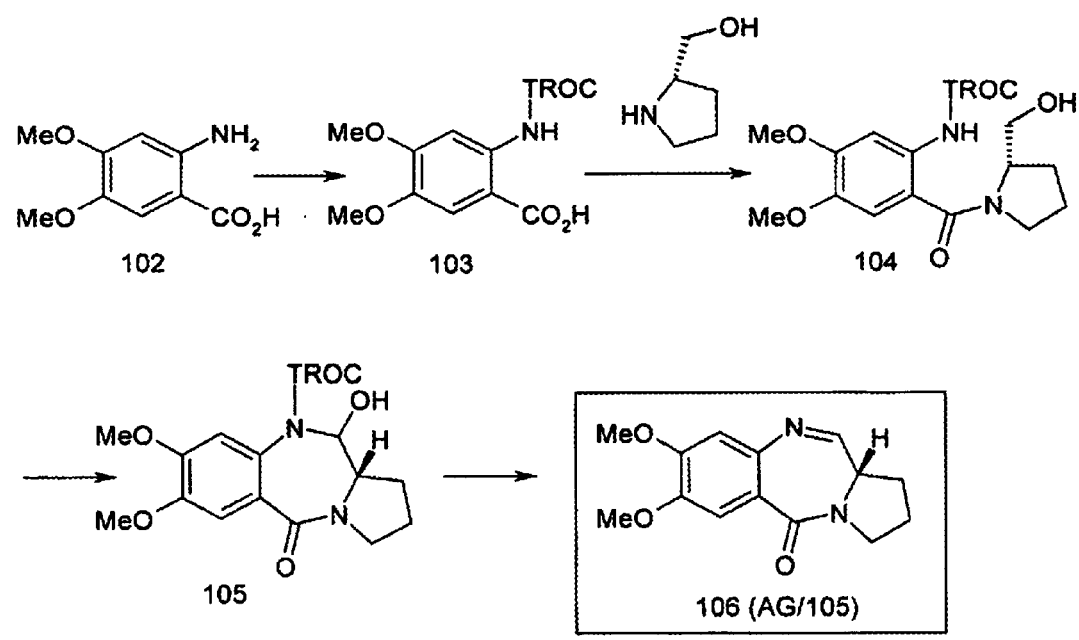

Synthesis of the 7,8-Dimethoxy PBD (106, AG/105) (See FIG. 18)

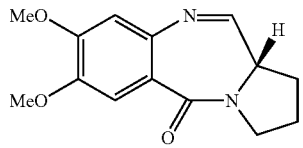

4,5-dimethoxy-2-(2',2',2'-trichloroethoxycarbonylamino) benzoic acid (103)

A solution of Troc-Cl (0.76 ml, 5.56 mmol) in dry dichloromethane (10 mL) was added dropwise to 2-amino-4,5-dimethoxybenzoic acid 102 (1 g, 5.1 mmol) and pyridine (0.82 ml, 10.1 mmol) in dry dichloromethane (20 ml) at 0° C. The reaction mixture was allowed to stir overnight at room temperature and then washed with dilute HCl (1N, 2×25 ml), water (2×25 ml) and brine (20 ml). The organic phase was dried over MgSO$_4$ and evaporated to yield of crude product (1.6 g), which was used in the next step without further purification.

N-(4,5-dimethoxy-2'-(2",2",2"-trichloroethoxycarbonylamino)benzoyl)-pyrrolidine-2-methanol (104)

Oxalyl chloride (0.38 mL, 4.33 mmol) was added to the crude Troc-protected anthranilic acid, prepared in the previous reaction, together with 2 drops of dry DMF in dry dichloromethane (30 mL). After initial strong effervescence, the mixture was allowed to stir at room temperature overnight. The resulting acid chloride was added dropwise, over 30 minutes, to a solution of 2S-(+)-pyrrolidinemethanol (0.44 g, 4.33 mmol) and TEA (1.37 ml, 9.85 mmol) of dry dichloromethane (15 mL) at −16° C. The reaction mixture was diluted with ethyl acetate (20 mL), and washed with dilute HCl (1N, 2×30 mL), satd. aqueous NaHCO$_3$ (2×30 mL), water (30 mL) and brine (30 mL). The organic layer was then dried over MgSO$_4$ and evaporated to give a yellow oil. The crude product was purified by flash chromatography (petroleum ether/ethyl acetate=50/50) to yield the product (1.2 g, 70%) as a pale yellow oil: $^1$H NMR (270 MHz, CDCl$_3$) δ1.75 (m, 2H); 1.92 (m, 1H); 2.17 (m, 1H); 3.53 (m, 2H); 3.72 (m, 1H); 3.86 (s, 3H); 3.93 (s, 3H); 4.19 (m, 1H); 4.43 (m, 1H); 4.77 (d, J=12 Hz, 1H); 4.85 (d, J=12 Hz, 1H); 6.85 (s, 1H); 7.69 (s, 1H); 9.08 (bs, 1H). $^{13}$C NMR (67.8 MHz, CDCl$_3$) δ25.1; 28.2; 51.4; 56.0; 56.4; 60.8; 65.9; 74.4; 95.3; 104.7; 110.7; 116.3; 130.8; 144.4; 151.0; 152.1; 170.4. MS: m/e (relative intensity) 454 (M−1, 5), 356 (3), 306 (10), 275 (5), 206 (100), 179 (15), 150 (10), 136 (3), 70 (45). HRMS Calculated for C$_{17}$H$_{21}$C$_{13}$N$_2$O$_6$: 454.0465. Found: 454.0464. [α]$^{25}_D$=−72.2° (c=0.18, CHCl$_3$).

(11s,11aS)-7,8-dimethoxy-11-hydroxy-10-N-(2',2',2'-trichloroethoxycarbonyl)-1,2,3,10,11,11a-hexahydro-5H-pyrrolo[2,1-c][1,4]benzodiazepin-5-one (105)

A solution of DMSO (0.9 ml, 12.9 mmol) in dry dichloromethane (15 mL) was added dropwise over 30 minutes to a solution of oxalyl chloride (6.4 mmol) of dry dichloromethane (15 mL) keeping the temperature below −40° C. The reaction mixture was allowed to stir for further a 30 minutes at which point a solution of 104 (2.1 g, 4.61 mmol) in dichloromethane (35 mL) was added drop wise over 1 hour. After addition of the substrate the reaction mixture was allowed to stir at −45° C. for 60 minutes, and then treated with a solution of TEA (2.56 mL) in of dichloromethane (10 mL) were added drop wise and the mixture was allowed to warm to room temperature. The reaction mixture was washed with water (75 mL), dilute HCl (1N, 75 mL), water (75 mL), brine (75 mL) dried over MgSO$_4$ and evaporated. The crude product was purified by flash chromatography (EtOAc/petroleum ether 40/60) to give a colourless oil (1.19 g, 57%): $^1$H NMR (270 MHz, CDCl$_3$) δ2.04 (m, 2H); 2.11 (m, 2H); 3.47–3.59 (m, 2H); 3.68–3.75 (m, 1H); 3.91 (s, 3H); 3.94 (s, 3H); 4.21 (d, J=12.1 Hz, 1H); 4.43 (d, J=4.76 Hz, 1H); 5.27 (d, J=12.1 Hz, 1H); 5.65–5.7 (dd, J=4.58, J=9.71 Hz, 1H); 6.82 (s, 1H); 7.26 (s, 1H). $^{13}$C NMR (67.8 MHz, CDCl$_3$) δ23.1; 28.6; 46.4; 56.0; 56.1; 60.0; 74.9; 86.4; 95.1; 110.3; 112.7; 125.6; 148.6; 150.8; 154.5; 167.0. MS: m/e (relative intensity) 452 (M−1, 30), 424 (7), 354 (10), 276 (25), 206 (100), 180 (10), 150 (10), 70 (100). HRMS Calculated for C$_{17}$H$_{19}$C$_{13}$N$_2$O$_6$: 452.0308. Found: 452.0309. [α]$^{25}_D$=+104.7° (c=0.27, CHCl$_3$).

(11aS)-7,8-dimethoxy-1,2,3,11a-tetrahydro-5H-pyrrolo[2,1-c][1,4]benzodiazepin-5-one (106, AG/105)

Finely ground Cd/Pb couple (3.12 g) was added portion wise to a solution of 105 (1 g, 2.2 mmol) THF (10 mL) and NH$_4$OAc (1M, 10 mL). The reaction was followed by TLC (EtOAc), when no starting material was present, the mixture was poured into ethyl acetate (400 mL). The organic phase was dried over MgSO$_4$ and evaporated to yield the crude product, which was purified by flash chromatography (EtOAc) to give of the pure compound as a pale yellow oil (0.45 g, 78%): $^1$H NMR (270 MHz, CDCl$_3$) δ2.08 (m, 2H); 2.29 (m, 2H); 3.53–3.63 (m, 1H); 3.72 (m, 1H); 3.79–3.85 (m, 1H); 3.93 (s, 3H); 3.96 (s, 3H); 6.82 (s, 1H); 7.52 (s, 1H); 7.68 (d, J=4.4, 1H). $^{13}$C NMR (67.8 MHz, CDCl$_3$) δ24.2; 29.6; 46.7; 53.7; 56.0; 56.1; 109.4; 111.2; 140.7; 147.5; 151.3; 162.5; 164.6. IR (Nujol): cm$^{-1}$ 3000–2800, 1601, 1450, 1434, 1500, 1453, 1263, 1217, 1010, 908, 735. MS: m/e (relative intensity) 260 (M+, 100), 245 (50), 231 (25), 217 (10), 191 (20), 164 (25), 136 (20), 121 (5), 93 (8), 70 (10). HRMS Calculated for C$_{14}$H$_{16}$N$_2$O$_3$: 260.1160. Found: 260.1161. [α]$^{25}_D$=+1004.7° (c=0.17, CHCl$_3$).

Example 3(e)

Figure 19:
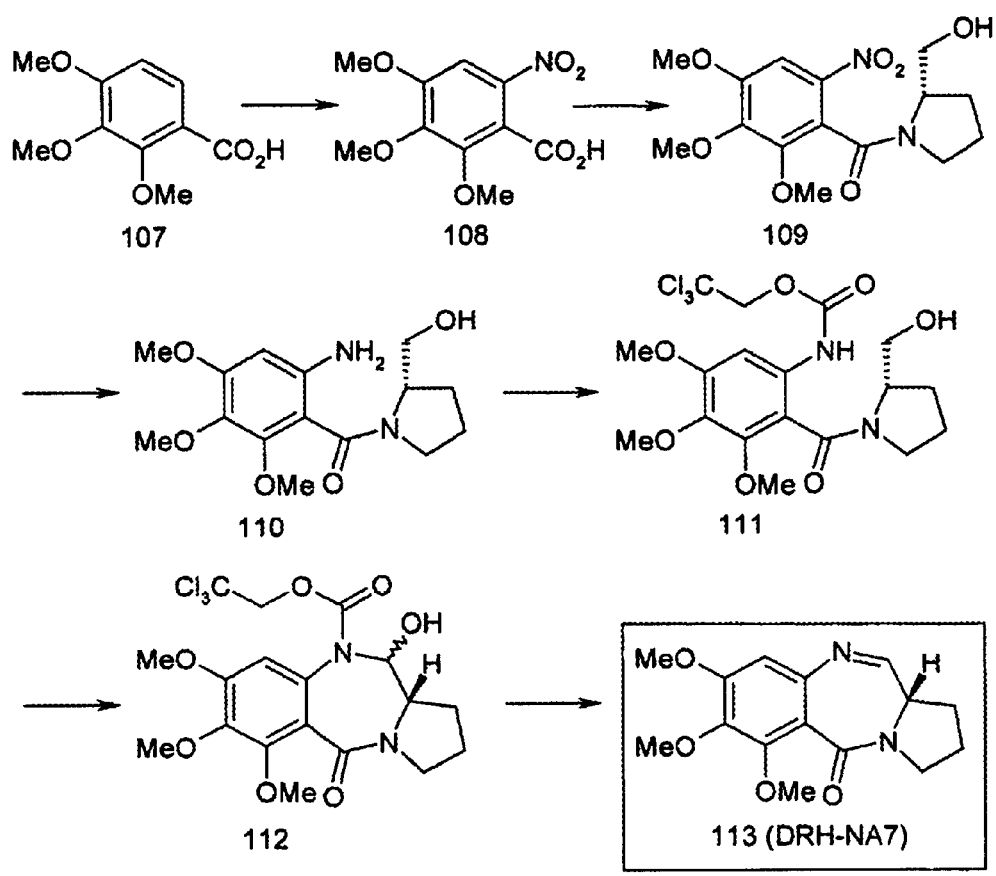

Synthesis of the 6,7,8-Trimethoxy PBD (113, DRH-NA7) (See FIG. 19)

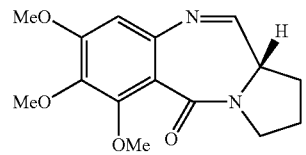

2,3,4-Trimethoxy-6-nitrobenzoic acid (108)

2,3,4-trimethoxybenzoic acid 107 (25 g, 117.8 mmol) was added portionwise to a stirred solution of 70% nitric acid at 0° C. for 30 minutes. The reaction mixture was poured into cold water (1250 mL) and stirring was continued for 30 minutes. The reaction mixture was extracted with EtOAc (2×200 mL) and the combined organic layers were washed with brine (2×200 mL) and dried over anhydrous MgSO4. Evaporation of excess solvent in vacuo afforded the product as a pure white crystalline solid (18.67 g, 60%): R$_f$=0.5 (silica, EtOAc); IR (nujol) 2922, 1713, 1618, 1570, 1504, 1464, 1401, 1308, 1246, 1168, 1111, 1028, 920, 852, 789, 773, 728, 689 cm$^{-1}$; $^1$H NMR (270 MHz, CDCl$_3$) δ7.76 (1H, s), 4.0 (3H, s), 3.95 (3H, s), 3.90 (3H, s); $^{13}$C NMR (67.8 MHz, CDCl$_3$) δ166.0, 153.2, 150.1, 147.79, 139.6, 120.8, 103.6, 62.2, 61.1, 56.5; MS (EI) m/z 258 (M+1), 240, 214.

N-(2-Nitro-4,5,6-trimethoxybenzoyl)pyrrolidine-2-methanol (109)

A catalytic quantity of DMF (2 drops) was added to a stirred solution of 108 (10 g, 38.9 mmol) and oxalyl chloride (5.87 g, 46.2 mmol) in dry CHCl$_2$ (100 mL) under a nitrogen atmosphere. The reaction mixture was allowed to stir overnight, and the product was used directly in the next stage of the reaction. The newly formed acid chloride was added dropwise to a stirred solution of pyrrolidinemethanol (3.92 g, 38.8 mmol) and anhydrous triethylamine (12.4 mL, 9.8 g, 97.0 mmoles) in anhydrous DCM (50 mL) at 0° C. under nitrogen. Once the addition was complete, the reaction mixture was left to warm to room temperature and left to stir overnight. The reaction mixture was washed with 1N HCl (100 mL), water (100 mL), and brine (2×100 mL). The combined organic layers were dried (MgSO$_4$) and the solvent was removed in vacuo to afford 109 (12.1 g, 91%) as a pale yellow oil: R$_f$=0.39 (silica, EtOAc); [α]$^{21.9}_D$+135° (c=0.1, DCM); IR (neat) 3400, 3105, 2947, 2878, 1652, 1568, 1538, 1455, 1348, 1250, 1195, 1115, 975, 922, 849, 822, 792, 758, 733, 646 cm$^{-1}$; $^1$H NMR (270 MHz, CDCl$_3$) δ7.59 (1H, s), 4.46 (2H, d, J=2.93 Hz), 4.07 (3H, s), 4.03 (3H, s), 4.01 (3H, s), 3.89 (3H, t), 3.45–3.29 (2H, m), 2.24–2.17 (2H, m), 2.00–1.84 (2H, m); $^{13}$C NMR (67.8 MHz, CDCl$_3$, rotamers) δ165.7, 165.1, 153.3, 149.2, 148.1, 138.8, 122.5, 104.1, 66.4, 65.5, 62.4, 62.3, 61.3, 56.6, 49.2, 49.0, 28.7 24.3; MS (EI) m/z 341 (M+1), 324, 309, 293, 277, 264, 254.

N-(2-Amino-4,5,6-trimethoxybenzoyl)pyrrolidine methanol (110)

Hydrazine hydrate (5.67 g, 177.2 mmol) was added dropwise to a solution of 109 (12.1 g, 35.47 mmol) in gently refluxing methanol (142 mL) over Raney nickel (3.45 g, slurry). The resulting vigorous evolution of hydrogen gas subsided after approximately 10 minutes and the reaction was deemed to be complete by TLC after 3 h. The reaction mixture was filtered through celite and the solvent evaporated. Distilled water (200 mL) was added to the residue, and the aqueous mixture was extracted with DCM (2×100 mL) and the combined organic phase washed with H$_2$O (3×100 mL) and brine (3×100 mL) and dried over anhydrous MgSO$_4$. Evaporation of the solvent afforded 110 (11.24 g) as a yellow oil. R$_f$=0.14 (silica, EtOAc); [α]$^{21.8}_D$=+100° (c=0.1, DCM); IR (neat) cm$^{-1}$ 3355, 2940, 2879, 2843, 1614, 1498, 1463, 1428, 1410, 1365, 1339, 1240, 1199, 1123, 1078, 1039, 997, 915, 817, 731, 646; $^1$H NMR (270 MHz, CDCl$_3$) δ6.10 (1H, s), 4.37 (2H, d, J=3.67 Hz), 3.93 (3H, s), 3.88 (3H, s), 3.86 (3H, s), 3.67 (2H, t), 2.17–2.02 (2H, m), 1.87–1.82 (2H, m) $^{13}$C NMR (67.8 MHz, CDCl$_3$) δ168.8, 154.7, 150.9, 149.6, 140.6, 133.8, 95.8, 66.5, 61.8, 61.4, 61.3, 61.1, 49.2, 28.6, 24.4; MS (EI) m/z 310 (M$^+$), 294, 279, 229, 210, 194, 180, 149, 124, 102, 83, 70, 57.

N-(2-[2',2',2'-Trichloroethoxycarbonylamino]-4,5,6-trimethoxybenzoyl)pyrrolidine-2-methanol (111)

A stirred solution of 110 (11.24 g, 36.3 mmol) in DCM (150 mL) and pyridine (5.86 mL, 5.73 g, 72.5 mmol) was treated dropwise with 2,2,2-trichloroethyl chloroformate (5 mL, 7.61 g, 35.9 mmol) in DCM (50 mL) under a nitrogen atmosphere at 0° C. One hour after the addition of 2,2,2-trichloroethyl chloroformate, the reaction mixture was diluted with DCM (100 mL) and washed with 1N HCl (100 mL), water (2×150 mL), brine (2×100 mL) and dried (MgSO$_4$). The solvent was removed in vacuo to afford 111 (15.44 g, 88%) as a clear brown oil: R$_f$=0.44 (silica, EtOAc); IR (neat) cm$^{-1}$ 3437, 2948, 1738, 1628, 1497, 1458, 1422, 1397, 1238, 1115, 1027, 1008, 823, 760, 624; $^1$H NMR (270 MHz, DMSO) δ6.82 (1H, s), 5.06 (2H, s), 4.04 (2H, d, J=6.83 Hz), 3.85 (3H, s), 3.84 (3H, s), 3.79 (3H, s), 3.67 (2H, t), 2.00–1.97 (2H, m), 1.96–1.88 (2H, m) $^{13}$C NMR (67.8 MHz, DMSO) δ164.2, 153.5, 149.6, 139.6, 129.4, 121.3, 96.2, 73.9, 61.4, 60.9, 58.7, 56.2, 47.9, 27.5, 23.7; HRMS (FAB) calcd for C$_{18}$H$_{23}$N$_2$O$_7$Cl$_3$ (M$^+$) 484.0571, found 484.0944.

6,7,8-Trimethoxy-10-(2',2',2'-trichloroethoxycarbonyl)-1,2,3,10,11,11a-hexahydro-5H-pyrrolo[2,1-c][1,4]benzodiazepin-5-one (112)

A solution of oxalyl chloride in DCM (22.3 mL of a 2N solution, 44.7 mmol) diluted with anhydrous DCM (42 mL) at −45° C. was treated dropwise with a solution of anhydrous DMSO (6.39 mL, 90.2 mmol) in anhydrous DCM (16.24 mL) over a period of 15 minutes. The reaction mixture was stirred at −45° C. for 15 minutes and treated with a solution of 111 (15.44 g, 31.7 mmol) in dry DCM (34.3 mL) and stirred at −45° C. for 45 minutes. Triethylamine (17.7 mL, 127.1 mmol) was added dropwise to the reaction mixture over 0.5 h, and then allowed to stir for a further 15 minutes. The reaction mixture was allowed to warm to room temperature and diluted with water (100 mL). The organic layer was washed with 1N HCl (200 mL), water (200 mL), brine (200 mL) and dried (MgSO$_4$). The reaction mixture was evaporated and purified by flash column chromatography (EtOAc) to afford the product 112 (8.27 g, 54%) as a clear yellow glass: R$_f$=0.48 (silica, EtOAc); [α]$^{22.2}_D$+190° (c 0.15, DCM); IR (neat) cm$^{-1}$ 3262, 2979, 2943, 2885, 1732, 1613, 1493, 1456, 1399, 1372, 1334, 1299, 1264, 1244, 1201, 1118, 1059, 1014, 969, 926, 888, 838, 784, 756, 720, 693, 624; $^1$H NMR (270 MHz, CDCl$_3$) δ6.64 (1H, s), 5.58 (1H, s), 5.31 (1H, s), 4.34 (1H, d, J=19.78 Hz), 4.15–4.00 (1H, m), 3.95 (3H, s), 3.91 (3H, s), 3.90 (3H, s), 3.77 (2H, t), 3.55 (1H, t), 2.17–2.14 (2H, m), 2.14–2.10 (2H, m). $^{13}$C NMR (67.8 MHz, CDCl$_3$) δ163.49, 154.32, 152.30, 142.69, 129.51, 121.16, 109.35, 95.20, 85.63, 62.30, 61.36, 60.48, 56.09, 45.56, 28.44, 22.85; MS (EI) m/z 485 (M+1), 467, 398, 384, 350, 291, 254, 236, 222, 194, 131, 102, 82, 70, 57.

6,7,8-Trimethoxy-1,2,3,10,11,11a-hexahydro-5H-pyrrolo[2,1-c][1,4]benzodiazepin-5-one (113)

10% Cd/Pb couple (2.57 g, 20.6 mmol Cd) was added to a stirred solution of 112 (2.00 g, 4.1 mmol) in THF (20 mL) and 1N NH$_4$OAc buffer (20 mL) and left at room temperature for 4 h. The reaction mixture was diluted with EtOAc (200 mL) and washed with water (2×100 mL). The organic layer was washed with brine (2×100 mL) and dried (MgSO$_4$). The solvent was removed in vacuo to give 113 (0.76 g, 64%) as a yellow glass: R$_f$=0.1 (silica, EtOAc); [α]$^{20.7}_D$=+505° (c=0.1, DCM); IR (neat) cm$^{-1}$ 3339, 2976, 2939, 1614, 1455, 1428, 1392, 1359, 1275, 1245, 1203, 1113, 1052, 1035, 1000, 926, 804, 751, 665; $^1$H NMR (270 MHz, CDCl$_3$) δ (1H, d, J=4.39 Hz), 6.61 (1H, s), 6.14 (1H, d, J=8.24 Hz), 4.36 (1H, d, J=8.79 Hz), 4.01 (3H, s), 3.98 (3H, s), 3.84 (3H, s), 3.48–3.46 (2H, m) 2.26–2.23 (2H, m), 2.16–1.93 (2H, m); HRMS (FAB) calcd for C$_{15}$H$_{18}$N$_2$O$_4$ (M+1) 290.1266, found 290.1208.

Figure 20:
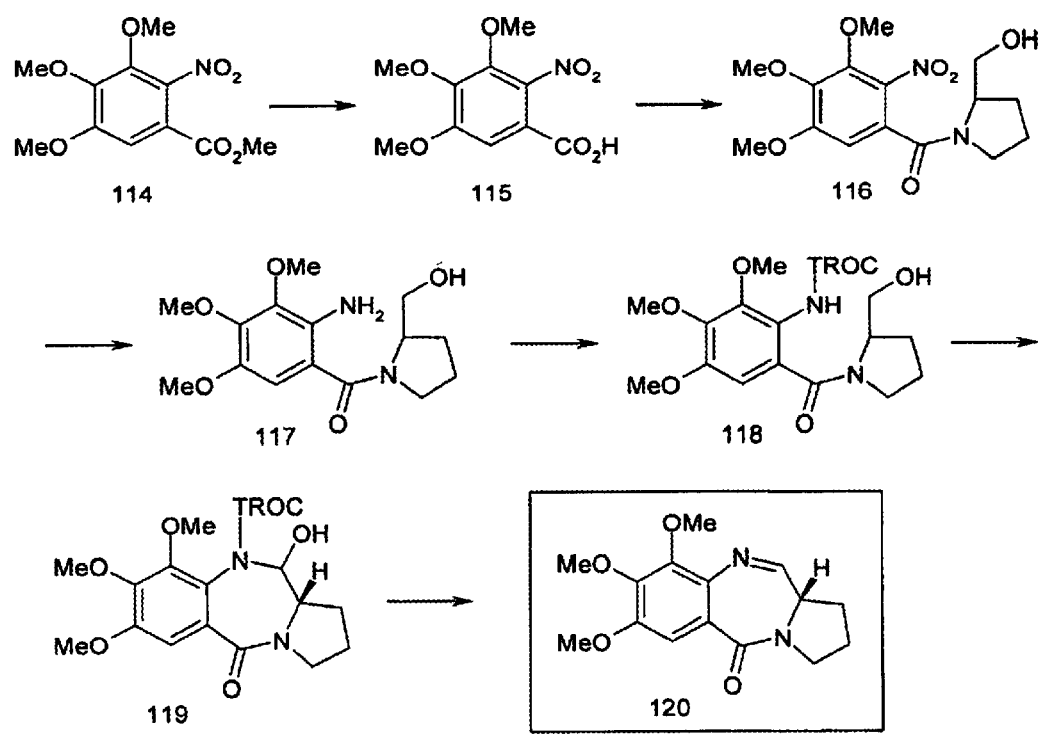

Example 3(f)
Synthesis of the 7,8,9-Trimethoxy PBD (120, DRH-69) (See FIG. 20)

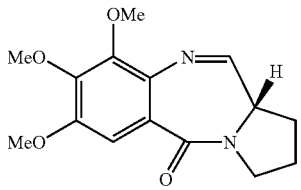

3,4,5-Trimethoxy-2-nitrobenzoic acid (115)

Methyl 3,4,5-trimethoxy-2-nitrobenzoic 114 (24.37 g, 89.9 mmol) was added to a 5% solution of KOH (18 g) in MeOH (357 mL). The mixture was heated at reflux for 50 minutes. Evaporation of the solvent afforded a grey residue, which was dissolved in $H_2O$ (200 mL) The resulting alkaline solution was acidified to pH1 with concentrated HCl, and extracted with $CHCl_3$ (3×100 mL). The organic layer was washed with $H_2O$ (3×100 mL), brine (3×100 mL) and dried over anhydrous $MgSO_4$. Filtration and evaporation of the solvent afforded a pure white crystalline solid (20.67 g, 80.4 mmol): $^1$H NMR (270 MHz, $CDCl_3$) δ3.9 (s, 3H), 4.0 (s, 3H), 4.1 (s, 3H), 7.4 (s, 1H), 12.4 (br s, 1H).

N-(2-Nitro-3,4,5-trimethoxybenzoyl)pyrrolidine-2-methanol (116)

A catalytic amount of DMF (2 drops) was added to a stirred solution of 115 (2.57 g, 10 mmol) and oxalyl chloride (1.40 g, 11 mmol) in dry $CH_2Cl_2$ (40 mL) under an inert atmosphere. The reaction mixture was allowed to stir overnight, the resulting solution of the acid chloride, (2.76 g, 10 mmol) in anhydrous $CH_2Cl_2$ (40 mL) was added dropwise over 1 hour to a vigorously stirred solution of pyrrolidinemethanol (1.11 g, 11 mmol) and TEA (2.52 g, 25 mmol) in anhydrous $CH_2Cl_2$ (40 mL) under a nitrogen atmosphere at 0° C. and allowed to stir overnight at room temperature. The reaction mixture was washed with 1N HCl (1×50 mL), 1N NaOH (1×50 mL), $H_2O$ (3×50 mL) and brine (3×50 mL) and dried over anhydrous $MgSO_4$. Filtration and evaporation of the solvent afforded a yellow oil (2.81 g, 8.3 mmol): Rf=0.47 (5% MeOH/$CHCl_3$); $^1$H NMR (270 MHz, $CDCl_3$) δ1.7–2.0 (m, 3H), 2.1–2.2 (m, 1H), 3.3–3.5 (m, 2H), 3.7–3.9 (m, 2H), 3.9–4.0 (2×s, 6H), 4.0–4.1 (s, 3H), 4.2–4.3 (m, 1H), 6.7 (s, 1H); $^{13}$C NMR (67.8 MHz, $CDCl_3$) δ167.3, 156.5, 147.9, 143.5, 128.8, 104.8, 65.8, 62.6, 61.4, 61.2, 56.6, 50.2, 28.4, 28.1, 24.5, 14.2.

N-(2-Amino-3,4,5-trimethoxybenzoyl)pyrrolidine-2-methanol (117)

Hydrazine hydrate (1.33 mL, 41.5 mmol) was added dropwise to a solution of 116 (2.83 g, 8.3 mmol) in methanol (142 mL) gently refluxing over Raney nickel (500 mg, slurry). The resulting vigorous evolution of hydrogen gas subsided after approximately 10 minutes and the reaction was deemed to be complete by TLC after 2 h. The reaction mixture was filtered through celite and the solvent evaporated. Distilled water (100 mL) was added to the residue, and the aqueous mixture was extracted with EtOAc (3×100 mL) and the combined organic phase washed with $H_2O$ (3×100 mL) and brine (3×100 mL) and dried over anhydrous $MgSO_4$. Evaporation of the solvent afforded the product (2.18 g, 6.5 mmol) as a brown oil: $^1$H NMR (270 MHz, $CDCl_3$) δ1.6–2.0 (m, 3H), 2.1–2.2 (m, 1H), 3.4–3.7 (m, 4H), 3.8 (s, 3H), 3.8–3.9 (2×s, 6H), 4.4 (br s, 1H), 4.7–4.3 (br s, 1H), 6.6 (s, 1H); $^{13}$C NMR (67.8 MHz, $CDCl_3$) δ144.7, 144.5, 141.6, 134.6, 107.1, 66.9, 61.0, 60.9, 60.5, 56.8, 50.9, 28.6, 24.9, 21.1, 14.2.

N-2-(Trichloroethoxycarbonylamino)-3,4,5-trimethoxybenzoyl)pyrrolidine-2-methanol (118)

A solution of 2,2,2-trichloroethylchloroformate (1.37 g, 6.5 mmol) in distilled dichloromethane (40 mL) was added dropwise over 0.5 hours to a solution of anhydrous pyridine (0.93 g, 11.8 mmol) and the substrate, 117 (1.82 g, 5.9 mmol) in distilled dichloromethane (60 mL) at 0° C. After 1.5 h. the reaction mixture was diluted with anhydrous DCM (100 mL) and washed with 1N HCl (2×100 mL), $H_2O$ (100 mL), brine (100 mL) and dried over anhydrous $MgSO_4$. Evaporation of the solvent yielded a brown oil which was purified by flash column chromatography eluting with 1% MeOH/99% $CHCl_3$ to afford the product as a yellow oil (1.83 g, 3.8 mmol): $^1$H NMR (270 MHz, $CDCl_3$) δ1.6–1.9 (m, 3H), 2.1–2.2 (m, 1H), 3.3–3.6 (m, 2H), 3.6–3.85 (m, 2H), 3.8–3.9 (m, 9H), 4.2–4.3 (m, 1H), 4.7–4.8 (br s, 1H), 4.8 (s, 2H), 6.6 (s, 1H); $^{13}$C NMR (67.8 MHz, $CDCl_3$) δ169.9, 153.2, 151.9, 143.1, 128.5, 120.1, 105.2, 95.3, 74.6, 66.3, 61.2, 61.2, 61.0, 56.3, 50.6, 28.7, 24.6.

(11S,11aS)7,8,9-trimethoxy-11-hydroxy-10-N-(2',2',21-trichloroethoxycarbonyl)-1,2,3,10,11,11a-hexahydro-5H-pyrrolo[2,1-c][1,4]benzodiazepin-5-one (119)

Anhydrous DMSO (3.15 mL, 44.3 mmol) in dry DCM (8.2 mL) was added dropwise over 20 minutes to a stirred solution of oxalyl chloride (2.79 g, 11.0 mL of a 2N solution in DCN; 22.0 mmol) in dry DCM (20.6 mL) under an inert atmosphere at –45° C. (varied between –38° and –48° C.). After stirring for 15 minutes, the substrate (7.59 g ; 15.6 mmol) in dry DCM (17 mL) was added dropwise over 45 minutes to the reaction mixture, which was then stirred for a further 45 minutes at –45° C. after the final addition of the substrate. Dry TEA (4.84 g, 48.0 mmol, 4 eq) was added dropwise to the mixture over 0.5 hours and stirred for a further 15 minutes. The reaction mixture was allowed to warm to room temperature and the reaction mixture diluted with $H_2O$ (80 mL). The organic phase was separated, washed with brine (2×100 mL) and dried over anhydrous $MgSO_4$. The solvent was evaporated to afford the product as an off-white solid (4.39 g, 9.1 mmol): $^1$H NMR (270 MHz, $CDCl_3$) δ1.95–2.2 (m, 4H), 3.4–3.8 (m, 2H), 3.8–3.9 (m, 9H), 4.05 (d, 1H), 4.5–4.8 (dd, 2H), 5.6–5.7 (q, 1H), 7.1 (s, 1H); $^{13}$C NMR ($CDCl_3$) rotamers δ166.7, 166.5, 155.2, 153.5, 153.3, 150.0, 144.5, 129.5, 129.0, 121.7, 106.4, 106.2, 94.6, 86.1, 85.9, 75.7 75.2, 61.5, 61.3, 60.9, 60.1 59.8, 56.2, 56.1, 46.5, 46.3, 28.7, 28.6, 23.0.

7,8,9-Trimethoxy-1,2,3,11a-tetrahydro-5H-pyrrolo[2,1-c][1,4]benzodiazepin-5-one (120, DRH-69)

10% Cd/Pb couple (1.25 g, 10 mmol Cd) was added to a rapidly stirring solution of the Troc-carbamate, 119 (1.00 g, 2.1 mmol) in a mixture of THF (13 mL) and 1N $NH_4OAc$ (8 mL). Upon addition, the reaction mixture went cloudy. After 40 minutes, TLC showed the reaction to be complete and the reaction mixture was diluted with EtOAc (200 mL). The solution was dried over anhydrous $MgSO_4$ and the solids were filtered and rinsed with EtOAc (50 mL). Evaporation of the solvent yielded the product as a yellow glass (0.581 g, 2.0 mmol). $^1$H NMR (270 MHz, $CDCl_3$) δ7.73 (d, 1H, J=4.57 Hz), 7.08 (s, 1H), 4.0–3.4 (m, 12H), 2.4–1.8 (m, 4H)

Example 3(g)

8-Hydroxy-7,9-dimethoxy-1,2,3,11a-tetrahydropyrrolo[2,1-c][1,4]benzodiazepin-5-one (130, DRH-168)

Methyl 4-hydroxy-3,5-dimethoxybenzoate (121)

Concentrated sulphuric acid (3 mL), was added dropwise to a solution of 81 (20.24 g, 102.1 mmol) in refluxing methanol (70 mL). The reaction mixture was heated at reflux for a further 5 hours and then cooled to room temperature and concentrated to a third of its original volume. The concentrate was poured onto crushed ice (c. 150 ml) and allowed to stand for 30 minutes. The aqueous mixture was extracted with ethyl acetate (3×100 mL) and the combined organic phase washed with distilled water (3×100 mL), brine (3×100 mL) and dried over anhydrous $MgSO_4$. Removal of ecxess solvent under reduced pressure afforded the product as a yellow solid, 121 (18.39 g, 86.7 mmol; $^1$H NMR (270 MHz, $CDCl_3$) δ3.9 (s, 3H), 3.95 (s, 3H), 3.975 (s, 3H), 6.1 (s, 1H), 7.3 (s, 2H); $^{13}$C NMR (67.8 MHz, $CDCl_3$) 3 166.9, 146.6, 139.2, 121.0, 106.6, 56.4, 52.1.

Methyl 4-Benzyloxy-3,5-dimethoxybenzoate (122)

Benzyl chloride (11.04 g, 86.9 mmol) was added to a stirred solution of 121 (19.22 g, 90.8 mmol) over $K_2CO_3$ (6.59 g, 47.7 mmol) in anhydrous MeOH (175 mL) and the mixture was heated at reflux for 12 h. Excess solvent was removed under reduced pressure and the residue was extracted with benzene (3×100 mL). The organic layer was washed with $H_2O$ (3×100 mL), brine (3×100 mL) and dried over anhydrous $MgSO_4$. Evaporation of the solvent afforded an orange oil which crystallised on standing. The solid was redissolved in EtOAc, and briefly washed with 1N NaOH (100 mL), $H_2O$ (100 mL), brine (100 mL) and dried over $MgSO_4$. Evaporation of excess solvent yielded the product as a yellow solid 122 (19.20 g, 63.6 mmol); $^1$H NMR (270 MHz, $CDCl_3$) δ3.8 (s, 3H), 3.85 (s, 3H), 3.9 (s, 3H), 5.1 (s, 2H), 7.3–7.5 (m, 7H); $^{13}$C NMR (67.8 MHz, $CDCl_3$) δ166.7, 153.2, 140.8, 137.3, 128.7, 128.6, 128.4, 128.4, 128.2, 128.0, 127.7, 125.3, 106.7, 74.9, 56.1, 52.2.

Methyl 2-nitro-4-benzyloxy-3,5-dimethoxybenzoate (123)

Finely ground copper nitrate ($Cu(NO_3)_2$, 14.79 g, 78.7 mmol) was added portionwise to a vigorously stirred solution of the substrate (19.00 g, 62.9 mmol) in acetic anhydride (120 mL) whilst keeping the reaction temperature below 40° C. The reaction mixture was stirred for 1 hour and then poured over ice (800 mL). The aqueous mixture was left to stir for 1 hour and the product collected by filtration to afford a yellow solid (18.7 g); $^1$H NMR (270 MHz, $CDCl_3$) δ3.85 (s, 3H), 3.95 (s, 3H), 3.96 (s, 3H), 5.19 (s, 2H), 7.3–7.5 (m, 6H); $^{13}$C NMR (67.8 MHz, $CDCl_3$) δ163.2, 154.3, 146.0, 145.2, 136.2, 128.7, 128.5, 128.4, 128.3, 117.8, 108.52, 75.5, 62.7, 56.5, 53.0.

2-Nitro-4-benzyloxy-3,5-dimethoxybenzoic acid (124)

Potassium hydroxide (10.84 g, 193.6 mmol) was added to a stirred solution of the substrate (18.7 g, 53.9 mmol) in anhydrous methanol (220 mL) and the reaction mixture heated at reflux for 2 h. The reaction mixture was allowed to cool and acidified to pH2 with 1N HCl and extracted with chloroform (3×100 mL). The combined organic layers were washed with water (3×200 mL), brine (3×200 mL) and dried over $MgSO_4$. Evaporation of excess solvent by rotary evaporation under reduced pressure afforded the product as a yellow solid (17.01 g, 51.1 mmol, 95%); $^1$H NMR (270 MHz, $CDCl_3$) δ3.9 (br s, 3H), 3.9 (br s, 3H), 5.1 (br s, 2H), 7.2–7.5 (m, 6H).

N-(4-Benzyloxy-3,5-dimethoxy-2-nitrobenzoyl) pyrrolidine-2-methanol (125)

A catalytic amount of DMF (5 drops) was added to a stirred solution of 124 (10 g, 30.0 mmol) and oxalyl chloride (4.65 g, 36.0 mmol) in dry $CH_3CN$ (115 mL) under a nitrogen atmosphere. The reaction mixture was allowed to stir overnight and the resulting acid chloride used directly in the next part of the procedure. 4-benzyloxy-3,5-dimethoxy-2-nitro-benzoyl chloride in anhydrous $CH_3CN$ (115 mL) was added dropwise over 0.5 hours to a stirring solution of pyrrolidine methanol (3.34 g, 33.03 mmol, 1.1 eq) and TEA (7.58 g, 75.1 mmol, 2.5 eq) in anhydrous DCM (100 mL) at 0° C. under a nitrogen atmosphere and the reaction mixture was allowed to stir overnight at room temperature. The reaction mixture was washed with 1N HCl (2×100 mL), and the organic layer was washed with distilled $H_2O$ (2×100 mL), brine (2×100 mL) and dried over anhydrous $MgSO_4$. Evaporation of the solvent yielded a brown glass (8.71 g, 20.9 mmol, 70%); $^1$H NMR (270 MHz, $CDCl_3$) δ1.7–2.2 (m, 4H), 3.3–3.5 (m, 2H), 3.7–3.9 (m, 2H), 3.9 (s, 3H), 4.0 (s, 3H), 4.2–4.3 (m, 1H), 5.1 (s, 2H), 6.85 (s, 1H), 7.3–7.5 (m, 5H); $^{13}$C NMR (67.8 MHz, $CDCl_3$) δ167.3, 156.8, 148.2, 142.3, 136.4, 136.0, 129.0, 128.5, 128.4, 104.8, 75.6, 65.7, 62.8, 61.4, 56.6, 50.2, 28.3, 24.5.

N-(2-Amino-4-Benzyloxy-3,5-dimethoxybenzoyl) pyrrolidine-2-methanol (126)

Hydrazine hydrate (2.31 g, 72.2 mmol) was added dropwise to a solution of 125 (6.01 g, 14.4 mmol) in methanol (60 mL) gently refluxing over Raney nickel (1.1 g, slurry). The resulting vigorous evolution of hydrogen gas subsided after approximately 10 minutes and the reaction was deemed to be complete by TLC after 2 h. The reaction mixture was filtered through celite and the solvent evaporated. Distilled water (100 mL) was added to the residue, and the aqueous mixture was extracted with EtOAc (3×100 mL) and the combined organic phase washed with $H_2O$ (3×100 mL) and brine (3×100 mL) and dried over anhydrous $MgSO_4$. Evaporation of the solvent afforded the produce as a brown oil (3.97 g, 10.3 mmol, 73%); $^1$H NMR (270 MHz, $CDCl_3$) δ1.6–2.2 (m, 4H), 3.5–3.8 (m, 4H), 3.8 (s, 3H), 3.9 (s, 3H), 4.4 (br s, 1H), 5.1 (s, 2H), 6.6 (s, 1H), 7.3–7.6 (m, 5H); $^{13}$C NMR (67.8 MHz, $CDCl_3$) δ171.5, 144.9, 143.5, 141.9, 137.5, 134.6, 128.6, 128.5, 128.3, 128.2, 128.0, 115.1, 107.3, 75.1, 66.9, 61.0, 60.6, 60.4, 56.9, 50.9, 28.5, 24.9, 21.1, 14.2.

N-(4-Benzyloxy-3,5-dimethoxy-2-[(2'-trimethylsilylethoxy)carbonylamino[benzoyl)pyrrolidine-2-methanol (127)

A solution of anhydrous pyridine (0.21 g, 2.6 mmol) in anhydrous DCM (10 mL) was added dropwise over 15 minutes to a stirred solution of 2-(trimethylsilyl)ethanol (0.92 g, 7.8 mmol) and triphosgene (0.77 g, 2.6 mmol) in anhydrous DCM (30 mL). The reaction mixture was allowed to stir overnight and the resulting solution of 2-(trimethylsilyl)ethyl chloroformate added dropwise over 0.5 hours to the amine 126 (1.98 g, 5.1 mmol) and anhydrous pyridine (1.22 g, 15.4 mmol) in distilled dichloromethane (70 mL) at 0° C. The reaction mixture was allowed to stir overnight at room temperature, diluted with anhydrous DCM (100 mL), washed with 1N HCl (3×100 mL), $H_2O$ (3×100 mL), brine (3×100 mL) and dried over anhydrous $MgSO_4$. Filtration and evaporation of the solvent yielded the product as a colourless glass (1.43 g, 2.7 mmol, 53%); $^1$H NMR (270 MHz, $CDCl_3$) δ−0.05 (s, 9H), 0.94–0.99 (m, 2H), 1.66–2.12 (m, 4H), 3.32–3.54 (m, 2H), 3.74–3.88 (m, 8H), 4.05–4.22 (m, 3H), 4.69 (br s, 1H), 4.97 (s, 2H), 6.57 (s, 1H), 6.64 (br s, 1H), 7.23–7.43 (m, 5H); $^{13}$C NMR (67.8 MHz, $CDCl_3$) δ170.1, 155.1, 151.4, 148.1, 142.0, 137.1, 128.4, 128.3, 128.1, 121.2, 105.6, 75.3, 66.1, 64.0, 61.3, 61.0, 56.3, 50.6, 28.7, 24.7, 17.6, −1.5.

(11S,11aS)-8-benzyloxy-7,9-dimethoxy-11-hydroxy-10-N-(2'-trimethylsilylethoxycarbonyl)-1,2,3,10,11,11a-hexahydro-5H-pyrrolo[2,1-c][1,4] benzodiazepin-5-one. (128)

Anhydrous DMSO (0.57 g, 7.2 mmol) in dry DCM (5 mL) was added dropwise over 30 minutes to a stirred solution of oxalyl chloride (0.46 g, 3.6 mmol) in dry DCM (5 mL) under a nitrogen atmosphere at −45° C. After stirring for 15 minutes, the substrate (1.35 g, 2.6 mmol) in dry DCM (15 mL) was added dropwise over 45 minutes to the reaction mixture, which was then stirred for a further 45 minutes at −45° C. TEA (1.0 g, 10.2 mmol) was added dropwise to the mixture over 0.5 hours and stirred for a further 15 minutes. The reaction mixture was left to warm to room temperature and diluted with $H_2O$ (100 mL) and the phases separated. The organic phase was washed with 1N HCl (3×50 mL), water (3×50 mL), brine (3×50 mL) and dried over $MgSO_4$. Filtration and evaporation of excess solvent afforded the product as an off-white glass (1.24 g, 2.3 mmol, 92%); $^1$H NMR (270 MHz, $CDCl_3$) δ−0.05 (s, 9H), 0.88–0.95 (m, 2H), 2.06–2.23 (m, 4H), 3.46–3.64 (m, 2H), 3.75–4.02 (m, 7H), 4.11–4.27 (m, 2H), 5.13 (s, 2H), 5.65 (d, 1H, J=9.71 Hz), 7.11 (s, 1H), 7.34–7.54 (m, 5H); $^{13}$C NMR (67.8 MHz, $CDCl_3$) δ166.8, 157.2, 153.1, 150.5, 143.4, 137.1, 129.2, 128.4, 128.3, 128.3, 128.1, 123.0, 106.2, 85.7, 75.0, 64.7, 61.7, 59.8, 56.1, 46.4, 28.6, 23.0, 17.5, −1.5, −1.6.

(11S,11aS)-8,11-dihydroxy-7,9-dimethoxy-10-N-(2'-trimethylsilylethoxycarbonyl)-1,2,3,10,11,11a-hexahydro-5H-pyrrolo[2,1-c][1,4]benzodiazepin-5-one (129)

10% Pd/C catalyst (0.22 g) was added to a solution of the substrate 128 (0.95 g, 2.1 mmol) in absolute EtOH (200 mL). The reaction mixture was hydrogenated under pressure using a Parr hydrogenator at 55 psi $H_2$ for 18 h. The reaction mixture was filtered through celite, and the celite washed with hot EtOH, taking care not to allow the filtration pad to dry out. Removal of excess solvent afforded the product as a colourless glass (0.84 g, 1.9 mmol, 92%); $^1$H NMR (270 MHz, $CDCl_3$) δ0.07 (s, 9H), 0.91–0.97 (m, 2H), 2.07–2.20 (m, 4H), 3.52–3.75 (m, 2H), 3.98–4.26 (m, 9H), 5.65 (d, 1H, J=9.71 Hz), 6.26 (br s, 1H), 7.14 (s, 1H); $^{13}$C NMR ($CDCl_3$) δ167.0, 157.3, 146.8, 143.4, 141.3, 124.9, 123.5, 105.5, 105.2, 85.8, 64.8, 64.6, 64.5, 61.2, 60.0, 56.4, 46.4, 28.9, 28.7, 23.1, 23.0, 17.3, −1.3, −1.5, −1.7.

7,9-dimethoxy-8-Hydroxy-1,2,3,11a-tetrahydropyrrolo[2,1-c][1,4]benzodiazepin-2-one (130)

A solution of TBAF in THF (4.3 mL of a 1N solution, 4.3 mmol) was added to a rapidly stirred solution of 129 (0.37 g, 0.9 mmol) in THF (10 mL) and the reaction mixture heated to 35° C. for 2 h. The reaction mixture was diluted with EtOAc (50 mL), dried over anhydrous $MgSO_4$, filtered and removal of excess solvent by rotary evaporation under reduced pressure afforded the product as a brown oil (0.18 g, 0.7 mmol, 78%). $H^1$ NMR ($CDCl_3$) mixture of C11/C11'R/S carbinolamine methyl ethers δ7.08 (s, 1H), 4.43 (d, 1H, J=8.79 Hz), 4.05–3.23 (m, 12H), 2.3–1.48 (m, 4H).

Examples 3(h) to (i)

Figure 21:
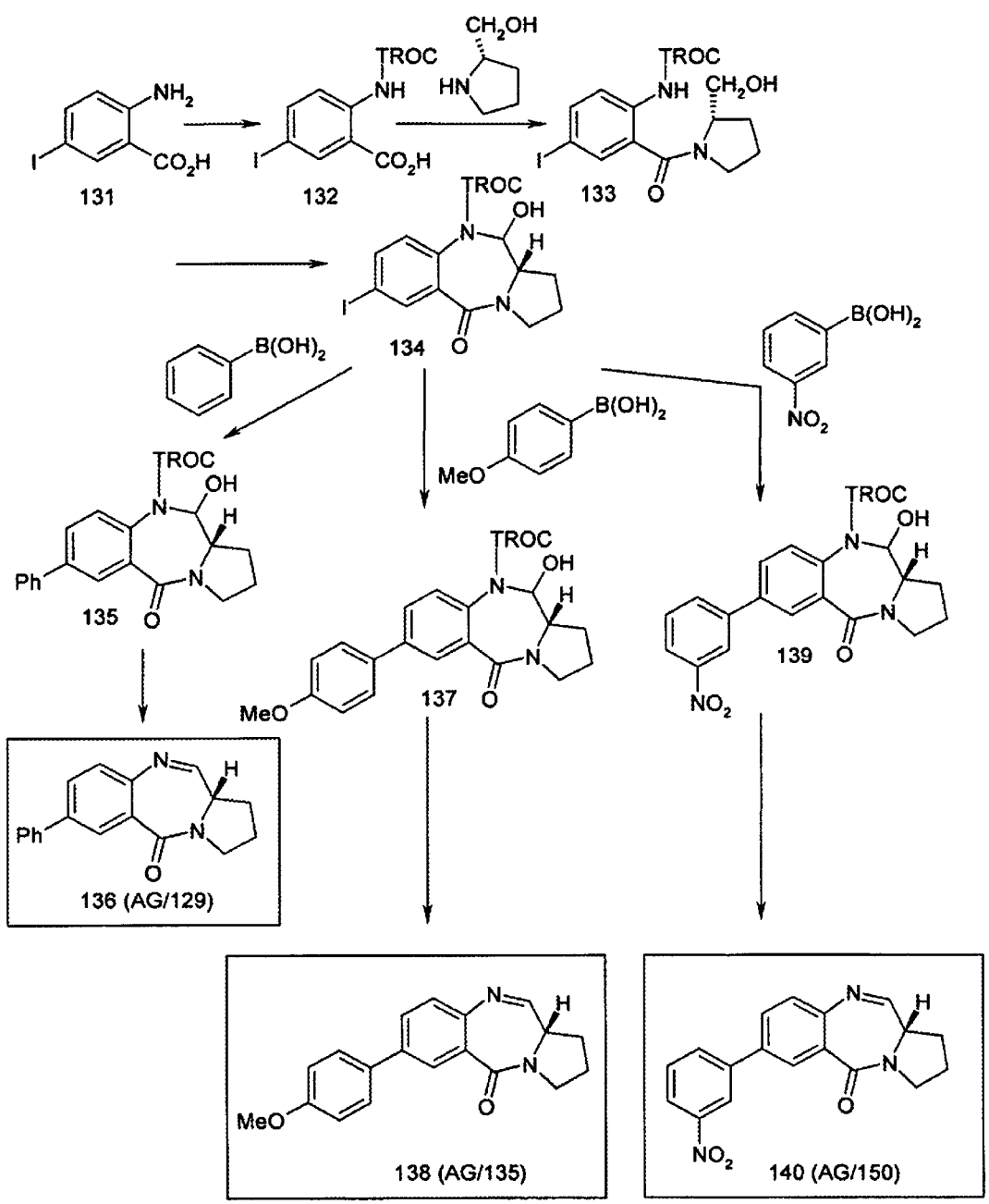

Synthesis of 7-Phenyl PBDs (See FIG. 21)

Synthesis f the 7-Iodo-N10-Troc-PBD Intermediate (134, AG/91)

5-Iodo-2-(2',2',2'-trichloroethoxycarbonylamino)benzoic acid (132)

A solution of Troc-Cl (2.88 mL, 20.9 mmol) in dry dichloromethane (20 mL) was added drop wise to a solution of 5-iodoanthranilic acid 131 (5 g, 19 mmol) and pyridine (3.1 mL, 38 mmol) in dry dichloromethane (30 mL) at 0° C. The solution was stirred for 5 hours at room temperature and then washed with 1N HCl (2×25 mL), water (1×25 mL) and brine (1×25 mL). The organic phase was dried over $MgSO_4$ and evaporated, residue was recrystallized from ethyl acetate to afford the title compound as a yellow solid (6.2 g, 75%): m.p. 248 C (ethyl acetate). $^1$H NMR ($CDCl_3$, DMSO-$d_6$) δ4.83 (s, 2H); 7.78–7.82 (dd, J=9.2, J=2.2 Hz, 1H); 8.18 (d, J=9 Hz, 1H); 8.38 (d, J=2.2 Hz, 1H); 9.0–10.5 (bs, 1H); 11.04 (s, 1H). $^{13}$C NMR ($CDCl_3$, DMSO-$d_6$) δ74.4, 84.6, 95.2, 117.7, 120.7, 140, 140.8, 142.8, 151.5, 169. MS: m/e (relative intensity) 437 (M−1, 60), 289 (55), 272 (37), 245 (100), 218 (27). HRMS Calculated for $C_{10}H_7Cl_3INO_4$: 436.8485. Found: 436.8485.

N-(5-Iodo-(2',2',2'-trichloroethoxycarbonylamino)benzoyl)pyrrolidine-2-methanol (133)

Oxalyl chloride (0.88 mL, 10 mmol) was added to a suspension of 132 (4 g, 9.1 mmol) in dry dichloromethane (50 mL), followed by 3–4 drops of DMF as catalyst. The solution was stirred at room temperature for 12 hours, and then used directly in the next step. The newly formed acid chloride was added drop wise, over 1 hour, to a solution of 2S-(+)-pyrrolidinemethanol (1.01 g, 10 mmol) and triethylamine (3.16 mL, 22.7 mmol) in dry dichloromethane (50 mL) at −20° C. The reaction mixture was allowed to stir for a further hour at −20° C. and was then washed with dilute HCl (1N, 2×50 mL), water (50 mL) and brine (50 mL), dried over $MgSO_4$ and evaporated. The crude product was subjected to flash column chromatography to afford the title compound as a pale yellow oil (3.8 g, 81%): $^1$H NMR ($CDCl_3$, DMSO-$d_6$) δ1.77–2.28 (m, 4H); 3.48 (bs, 2H); 3.7 (dd, J=11.4, J=6.2, 1H); 3.94 (d, J=11.4 Hz, 1H); 4.40 (bs, 1H); 4.75 (d, J=12 Hz, 1H); 4.84 (d, J=12 Hz, 1H); 7.66–7.72 (m, 2H); 7.85 (d, J=8.6 Hz, 1H); 8.91 (bs, 1H). $^{13}$C NMR ($CDCl_3$, DMSO-$d_6$) δ25.0, 28.1, 51.2, 60.7, 65.3, 74.5, 86.1, 95.1, 123.0, 128.0, 135.6, 136.1, 139.8, 151.8, 168.4. IR (Nujol): cm$^{-1}$ 3415, 3215, 1745, 1605, 1527, 1445, 1377, 1221, 1101, 1056, 822, 733. MS: m/e (relative intensity) 522 (M$^{+•}$, 3), 521 (M$^{+•}$, 1), 520 (M$^{+•}$, 3), 491 (3), 490 (1), 489 (3), 372 (7), 341 (28), 272 (80), 245 (14), 216 (14), 83 (15), 70 (100). HRMS Calculated for $C_{15}H_{16}Cl_3IN_2O_4$: 521.9193. Found: 521.9125. $[α]^{25}_D$=+123.4° (c=2.8, $CHCl_3$).

7-Iodo-10-N-(2',2',2'-trichloroethoxycarbonyl)-1,2,3,10,11,11a-hexahydro-5H-pyrrolo[2,1-c][1,4]benzodiazepin-5-one (134)

A solution of DMSO (1.79 mL, 25.67 mmol) in dry dichloromethane (35 mL) was slowly added (30 minutes) to a solution of oxalyl chloride (12.8 mmol) in dry dichloromethane (41.4 mL) at −45° C. The mixture was allowed to stir for 25 minutes and then treated with a solution of 133 (4.78 g, 9.2 mmol), in dry dichloromethane (80 mL), keeping temperature below −40° C. After further 60 minutes at −45° C., a solution of triethylamine (5.1 mL) in of dichloromethane (25 mL) was added, and the reaction mixture allowed to warm to room temperature. The organic phase was washed with water (180 mL), dilute HCl (1N, 2×100 mL) and brine (200 mL). Removal of excess solvent afforded the crude product which was purified by flash chromatography (ethyl acetate/petroleum ether 70/30) to give of a pale yellow oil (3.6 g, 76%): $^1$H NMR (270 MHz, $CDCl_3$) δ2.02–2.15 (m, 4H); 3.37–3.60 (m, 2H); 3.70–3.77 (m, 1H); 4.19 (bs, 1H); 4.28 (d, J=12 Hz, 1H); 5.17 (d, J=12 Hz, 1H); 5.66 (d, J=9.7 Hz, 1H); 7.10 (d, J=8.3 Hz, 1H); 7.79 (dd, J=8.3, J=2.2 Hz, 1H); 8.10 (d, J=2.2 Hz, 1H). $^{13}$C NMR ($CDCl_3$) δ23.0, 28.8, 46.5, 59.6, 75.1, 86.0, 93.2, 94.8, 132.0, 133.6, 135.0, 137.9, 140.1, 154.1, 165.2. IR (Nujol): cm$^{-1}$ 3500–3000, 1716, 1619, 1458, 1376, 1312, 1075, 720. MS: m/e (relative intensity) 520 (M$^{+•}$, 62), 519 (22), 518 (62), 491 (15), 371 (19), 342 (39), 272 (84), 216 (31), 119 (27), 70 (100). HRMS Calculated for $C_{15}H_{14}Cl_3IN_2O_4$: 519.9036. Found: 519.9037. $[α]^{25}_D$=+137.4° (c=1.15, $CHCl_3$).

Example 3(h)
Synthesis of the 7-Phenyl-PBD (136, AG/129)

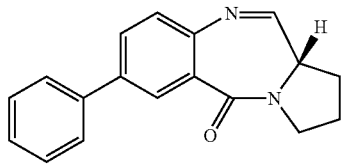

7-Phenyl-10-N-(2',2',2'-trichloroethoxycarbonyl)-1,2,3,10,11,11a-hexahydro-5-H-pyrrolo[2,1-c][1,4]benzodiazepin-5-one (135)

A suspension of 134 (0.5 g, 1.0 mmol), benzeneboronic acid (0.15 g, 1.22 mmol), Pd(PPh$_3$)$_4$ and anhydrous Na$_2$CO$_3$ (0.16 g, 1.48 mmol) in distilled benzene (20 mL), water (2 ml) and ethanol (2 mL) was heated at reflux overnight. The reaction mixture was diluted with ethyl acetate (20 mL) and washed with water (2×20 mL). The organic phase was dried over MgSO$_4$ and evaporated to yield a crude yellow oil. Purification by flash chromatography (ethyl acetate/petroleum ether 30/70 to 70/30) furnished the title compound (0.43 g, 95%): $^1$H NMR (270 MHz, CDCl$_3$) δ1.98–2.09 (m, 2H); 2.12–2.15 (m, 2H); 3.51–3.62 (m, 2H); 3.7–3.79 (m, 1H); 4.28 (d, J=12.1 Hz, 1H); 4.73 (d, J=4.4 Hz, 1H); 5.18 (d, J=12.1 Hz, 1H); 5.66–5.73 (dd, J=4.8, J=9.8 Hz, 1H); 7.33–7.48 (m, 4H); 7.61–7.70 (m, 3H); 8.02 (d, J=2.2 Hz, 1H). $^{13}$C NMR (CDCl$_3$) δ22.9, 28.7, 46.4; 59.8; 75.0; 77.3; 86.0; 94.9; 127.0; 127.3; 128.0; 128.9; 129.6; 130.8; 132.9; 133.5; 139.2; 141.1; 154.4; 166.9. MS: m/e (relative intensity) 468 (M$^+$·, 10), 292 (25), 222 (100), 195 (10), 166 (35), 140 (10), 70 (70). HRMS Calculated for C$_{21}$H$_{19}$C$_{13}$N$_2$O$_4$: 468.0411. Found: 468.0410. [α]$^{25}_D$=+103.80 (c=0.42, CHCl$_3$).

(11aS)-7-Phenyl-1,2,3,11a-tetrahydro-5H-pyrrolo[2,1-c][1,4]benzodiazepin-5-one (136, AG/129)

Cd/Pb (0.47 g) couple was added portion wise to a vigorously stirred solution of 135 (0.33 g, 0.7 mmol) in THF (5 mL) and of aq. ammonium acetate (1M, 5 mL). The suspension was allowed to stir at room temperature for 2 hours, then poured into ethyl acetate (200 mL), dried with MgSO$_4$ and filtered. The filtrate was evaporated and the residue purified by flash column chromatography (ethyl acetate) to afford the title compound as colourless oil (0.19 g, 98%): $^1$H NMR (270 MHz, CDCl$_3$) δ2.0–2.12 (m, 2H); 2.29–2.37 (m, 2H); 3.53–3.63 (m, 1H); 3.76–3.92 (m, 2H); 7.36–7.79 (m, 8H); 8.28 (d, J=2.2 Hz, 1H). $^{13}$C NMR (67.8 MHz, CDCl$_3$) δ24.4; 29.8; 46.9; 53.8; 126.9; 127.3; 127.7; 128.0; 128.2; 128.8; 128.9; 129.1; 130.1; 130.5; 139.5; 145.0; 164.5; 165.1. IR (Nujol): cm$^{-1}$ 3000–2800, 1620, 1455, 1377, 1239, 1239, 1014, 990, 761,728, 697. HRMS Calculated for C$_{18}$H$_{16}$N$_2$O: 276.1261. Found: 276.1262. [α]$^{25}_D$=+131.4° (c=0.19, CHCl$_3$).

Example 3(i)
Synthesis of the 7-(4'-Methoxyphenyl)-PBD (138, AG/135)

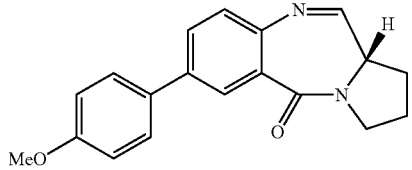

(11S,11aS)-7-(4'-Methoxy)phenyl-11-hydroxy-10-N-(2",2",2"-trichloroethoxycarbonyl)-1,2,3,10,11a-hexahydro-5H-pyrrolo]2,1-c]-[1,4]benzodiazepin-5-one (137)

134 (0.5 g, 1.0 mmol), 4-methoxybenzeneboronic acid (0.19 g, 1.2 mmol), Pd(PPh$_3$)$_4$ (15 mg) and anhydrous Na$_2$CO$_3$ (0.16 g, 1.48 mmol) were heated at reflux, over night, in a mixture of distilled benzene (20 mL), ethanol (2 mL) and water (2 mL). The reaction mixture was diluted with ethyl acetate (20 mL) and washed with water (2×20 mL). The organic phase was dried over MgSO$_4$ and evaporated to yield a crude yellow oil. Purification by flash chromatography (ethyl acetate/petroleum ether 50/50) afforded the pure compound (0.34 g, 71%): $^1$H NMR (CDCl$_3$) δ1.96–2.16 (m, 4H); 3.54–3.63 (m, 2H); 3.71–3.79 (m, 1H); 3.85 (s, 3H); 4.18 (d, J=4.8 Hz, 1H); 4.29 (d, J=12.1 Hz, 1H); 5.20 (d, J=12.1 Hz, 1H); 5.66–5.72 (dd, J=4.5, J=9.8 Hz, 1H); 6.97 (d, J=8.8 Hz, 2H); 7.37 (d, J=8.2 Hz, 1H); 7.57 (d, J=8.8 Hz, 2H); 7.64 (dd, J=2.4, J=8.2 Hz, 1H); 7.97 (d, J=2 Hz, 1H). $^{13}$C NMR (67.8 MHz, CDCl$_3$) δ23.0; 28.7; 46.4; 55.4; 59.6; 75.1; 86.1; 94.9; 114.3; 126.8; 129.1; 130.6; 131.7; 132.0; 132.2; 132.3; 133.5; 140.7; 154.5; 159.6; 166.9. IR (Nujol): cm$^{-1}$ 3000–2800, 1740, 1620, 1462, 1378, 1247, 1082, 816, 721. MS: m/e (relative intensity) 498 (M$^+$·, 15), 350 (20), 321 (15), 252 (100), 196 (22), 182 (5), 126 (7), 70 (28). HRMS Calculated for C$_{22}$H$_{21}$Cl$_3$N$_2$O$_5$: 498.0515. Found: 498.0513. [α]$^{25}_D$=+149.4° (0.25, CHCl$_3$)

(11aS)-7-(4'-Methoxyphenyl)-1,2,3,11a-tetrahydro-5H-pyrrolo[2,1-c]-[1,4]benzodiazepin-5-one (138, AG/135)

Cd/Pb couple (0.51 g) was added portion wise to a, vigorously stirred, solution of 137 (0.34 g, 0.76 mmol) in THF (5 mL) and aq. ammonium acetate (1M, 5 mL). The suspension was allowed to stir at room temperature for 2 hours, then poured into ethyl acetate (200 mL), dried over MgSO$_4$ and filtered. The organic solution was evaporated and the residue purified by flash column chromatography (ethyl acetate), to afford the title compound as colourless oil (0.1 g, 70%): $^1$H NMR (CDCl$_3$, DMSO-d$_6$) δ2.1 (m, 2H); 2.3–2.4 (m, 2H); 3.5–3.62 (m, 1H); 3.85 (m, 5H); 7.0 (d, J=8.8 Hz, 2H); 7.36 (d, J=8.3 Hz, 2H); 7.6 (d, J=8.8 Hz, 2H); 7.72 (dd, J=2.2, J=8.2 Hz 1H); 7.8 (d, J=4.4 Hz, 1H,); 8.2 (d, J=2.2 Hz, 1H). $^{13}$C NMR (270 MHz, CDCl$_3$, DMSO-d$_6$) δ24.1; 29.5; 46.7; 53.6; 55.3; 77.3; 114.1; 114.3; 127.4; 127.6; 127.8; 128.0; 129.3; 131.9; 138.7; 144.3; 159.4; 164.2; 164.8. IR (Nujol): cm$^{-1}$ 3000–2800, 1662, 1607, 1491, 1454, 1245, 1069, 823, 759. MS: m/e (relative intensity) 306 (M$^+$·, 100), 277 (15), 237 (10), 182 (12), 153 (10), 132 (5), 70 (10). HRMS Calculated for C$_{19}$H$_{18}$N$_2$O$_2$: 306.1367. Found: 306.1365. [α]$^{25}_D$=+773.1° (c=0.11, CH$_3$OH).

Example 3(j)
Synthesis of the 7-(3'-Nitrophenyl)-PBD (140, AG/150)

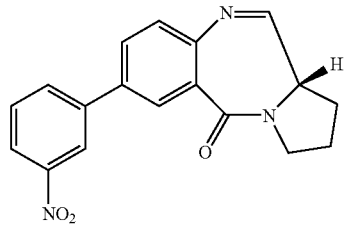

(11S,11aS)-7-(3'-Nitro)phenyl-11-hydroxy-10-N-(2",2",2"-trichloroethoxycarbonyl)-1,2,3,10,11a-hexahydro-5H-pyrrolo[2,1-c]-[1,4]benzodiazepin-5-one (139)

134 (0.5 g, 1.0 mmol), 3-nitrobenzeneboronic acid (0.2 g, 1.2 mmol), Pd(PPh$_3$)$_4$ (25 mg) and anhydrous Na$_2$CO$_3$ (0.16 g, 1.48 mmol) were heated at reflux, over night, in a mixture of distilled benzene (20 mL), ethanol (2 mL) and water (2 mL). The reaction mixture was diluted with ethyl acetate (20 ml) and washed with water (2×20 ml). The organic phase was dried over MgSO$_4$ and evaporated to yield a crude yellow oil. Purification by flash chromatography (ethyl acetate/petroleum ether 50/50) afforded the pure compound (0.45 g, 90%): $^1$H NMR (270 MHz, CDCl$_3$) δ2.0–2.2 (m, 4H); 3.6 (m, 2H); 3.76 (m, 1H); 4.31 (d, J=12 Hz, 1H); 5.19 (d, J=12 Hz, 1H); 5.76 (d, J=10 Hz, 1H); 7.5–8.5 (m, 8H). $^{13}$C NMR (68.7 MHz, CDCl$_3$) δ22.9, 28.7, 46.4, 59.7, 75.0, 86.0, 94.8, 121.7, 122.6, 127.5, 129.4, 129.9, 131.2, 132.0, 132.8, 133.9, 138.3, 140.7, 148.6, 154.1, 166.3. IR (Nujol): cm$^{-1}$ 3000–2800, 1721, 1626, 1530, 1455, 1349, 1062, 821, 759. MS: m/e (relative intensity) 513 (M$^{+·}$), 336 (55), 321 (100), 292 (15), 267 (54), 221 (16), 197 (18), 164 (15), 70 (22). HRMS Calculated for $C_{21}H_{18}C_{13}N_3O_6$: 515.0233. Found: 515.0235. $[\alpha]^{25}_D$=+129.6° (c=0.1, CH$_3$OH)

(11aS)-7-(3'-Nitrophenyl)-1,2,3,11a-tetrahydro-5H-pyrrolo[2,1-c][1,4]benzodiazepin-5-one (140, AG-150)

A solution of TBAF in THF (1M solution, 7.6 mL, 7.6 mmol) was added to a solution 139 (0.39 g, 0.8 mmol) in of THF (20 mL) and the reaction mixture allowed to stir for 2 hours at room temperature. The solution was diluted with ethyl acetate (50 mL) and washed with water (3×50 mL) to remove excess TBAF. The organic phase was dried over MgSO$_4$ and evaporated to dryness. The residue was purified by flash column chromatography (CHCl$_3$), to afford the title compound as a colourless oil (0.15 g, 63%): $^1$H NMR (270 MHz, CDCl$_3$) δ1.8–2.2 (m, 3H); 3.5–4.0 (m, 3H); 7.3–8.5 (m, 7H). IR (Nujol): cm$^{-1}$ 3000–2850, 1624, 1527, 1466, 1349, 1244, 757, 740. MS: m/e (relative intensity) 321 (M$^{+·}$, 100), 292 (8), 265 (5), 224 (5), 197 (7), 151 (5), 70 (5). HRMS Calculated for $C_{18}H_{15}N_3O_3$: 321.1115. Found: 321.1113. $[\alpha]^{25}_D$=+129.6° (c=0.1, CH$_3$OH).

Figure 22:
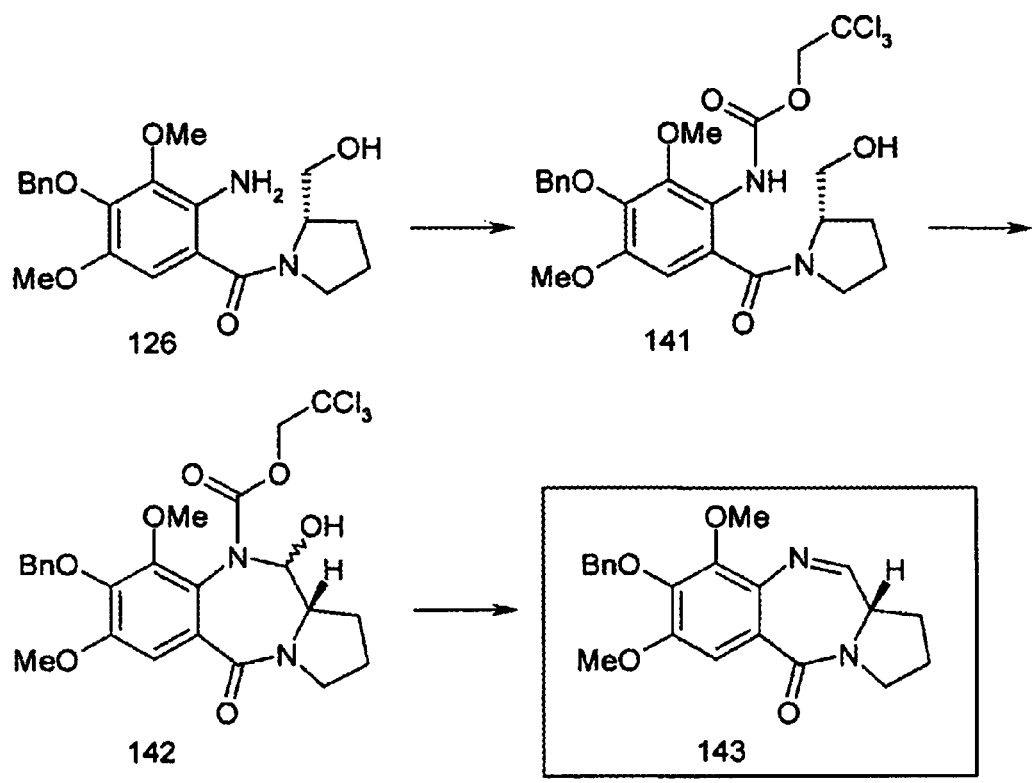

Example 3(k)
8-Benzyloxy-7,9-dimethoxy-1,2,3,11a-tetrahydropyrrolo]2,1-c][1,4]benzodiazepin-5-one (143, DRH-105) (see FIG. 22)

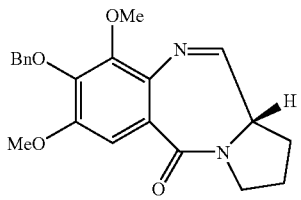

N-(4-Benzyloxy-3,5-dimethoxy-2-[trichloroethyloxycarbonylamino]benzoyl)pyrrolidine-2-methanol (141)

A solution of 2,2,2-trichloroethyl chloroformate (1.08 g, 4.8 mmol) in distilled dichloromethane (10 mL) was added dropwise over 0.5 hours to a solution of anhydrous pyridine (0.80 g, 10.1 mmol) and 126 (Example 3(g))(1.95 g, 5.1 mmol) in distilled dichloromethane (20 mL) at 0° C. After 1 hour the reaction mixture was diluted with anhydrous DCM (100 mL) and washed with 1N HCl (2×100 mL), H$_2$O (100 mL), brine (100 mL) and dried over anhydrous MgSO$_4$. Evaporation of the solvent yielded a brown oil which was purified by flash column chromatography (silica gel, EtOAc) to afford the product as a yellow glass (2.65 g, 4.7 mmol, 94%); $^1$H NMR (270 MHz, CDCl$_3$) δ1.6–2.2 (m, 4H); 3.3–3.6 (m, 2H), 3.6–3.9 (m, 2H), 3.8 (s, 3H), 3.9 (s, 3H), 4.2–4.3 (m, 1H), 4.8 (s, 2H), 5.1 (s, 2H), 6.6 (s, 1H), 7.2 (br s, 1H), 7.3–7.5 (m, 5H); $^{13}$C NMR (67.8 MHZ, CDCl$_3$) δ171.5, 153.1, 142.0, 137.023, 128.3, 128.3, 128.2, 120.1, 105.3, 95.4, 75.3, 74.6, 66.5, 61.4, 61.3, 56.3, 50.7, 28.7, 24.6.

(11S,11aS)-8-benzyloxy-7,9-dimethoxy-11-hydroxy-10-N-(2',2',2'-trichloroethoxylcarbonyl)-1,2,3,10,11,11a-hexahydro-5H-pyrrolo[2,1-c][1,4]benzodiazepin-5-one (142)

Anhydrous DMSO (0.97 g, 12.5 mmol) in dry DCM (10 mL) was added dropwise over 30 minutes to a stirred solution of oxalyl chloride (3.08 mL of a 2N solution in DCM, 6.2 mmol) in dry DCM (10 mL) under a nitrogen atmosphere at −45° C. After stirring for 15 minutes, the substrate (2.46 g, 4.38 mmol) in dry DCM (25 mL) was added dropwise over 45 minutes to the reaction mixture, which was then stirred for a further 45 minutes at −45° C. TEA (1.77 g; 17.5 mmol) was added dropwise to the mixture over 0.5 hours and stirred for a further 15 minutes. The reaction mixture was left to warm to room temperature, diluted with H$_2$O (100 mL)and the phases allowed to separate. The organic phase was washed with 1N HCl (2×50 mL), water (2×50 mL), brine (2×50 mL) and dried over MgSO$_4$. The solvent was evaporated to afford the product as an off-white glass (3.92 g, 11.7 mmol; 97%); $^1$H NMR (270 MHz, CDCl$_3$) δ2.01–2.17 (m, 4H), 3.44–3.77 (m, 2H), 3.87–3.90 (m, 1H), 3.88 (s, 3H), 3.91 (s, 3H), 4.68 (dd, 2H), 5.01 (s, 2H), 5.62 (d, 1H), 7.08 (s, 1H), 7.27–7.48 (m, 5H); $^{13}$C NMR (67.8 MHz, CDCl$_3$) δ166.7, 155.2, 153.6, 150.5, 143.6, 137.1, 129.8, 129.3, 128.4, 128.3, 128.2, 128.1, 121.8, 106.5, 106.3, 94.7, 86.2, 85.9, 75.6, 75.4, 75.2, 75.0, 61.8, 61.5, 60.2, 59.870, 56.1, 56.0, 46.5, 46.3, 45.8, 28.7, 28.6, 23.0.

8-Benzyloxy-7,9-dimethoxy-1,2,3,11a-tetrahydropyrrolo[2,1-c][1,4]benzodiazepin-5-one (143)

10% Cd/Pb couple (1.2 g; 10 mmol Cd) was added to a rapidly stirring solution of 142 (1.08 g; 1.9 mmol) in a mixture of THF (15 mL) and 1N NH$_4$OAc (15 mL). After 3.5 h, TLC revealed that reaction was still incomplete and more 10% Cd/Pb couple (500 mg) was added. After a further 1 hour the reaction mixture was diluted with EtOAc (150 mL). The solution was dried over anhydrous MgSO$_4$ and the solids were filtered and rinsed with EtOAc (50 mL). Removal of excess solvent yielded the product as a yellow glass (0.48 g, 1.3 mmol, 68%). H$^1$ NMR (270 MHz, CDCl$_3$) δ7.73 (d, 1H, J=4.4 Hz), 7.36 (s, 2H), 7.31 (s, 2H), 7.11 (s, 1H), 7.08 (s, 1H), 5.12 (br s, 2H), 3.98–3.42 (m, 9H), 2.38–2.29 (m, 2H), 2.23–1.83 (m, 2H).

Figure 23:
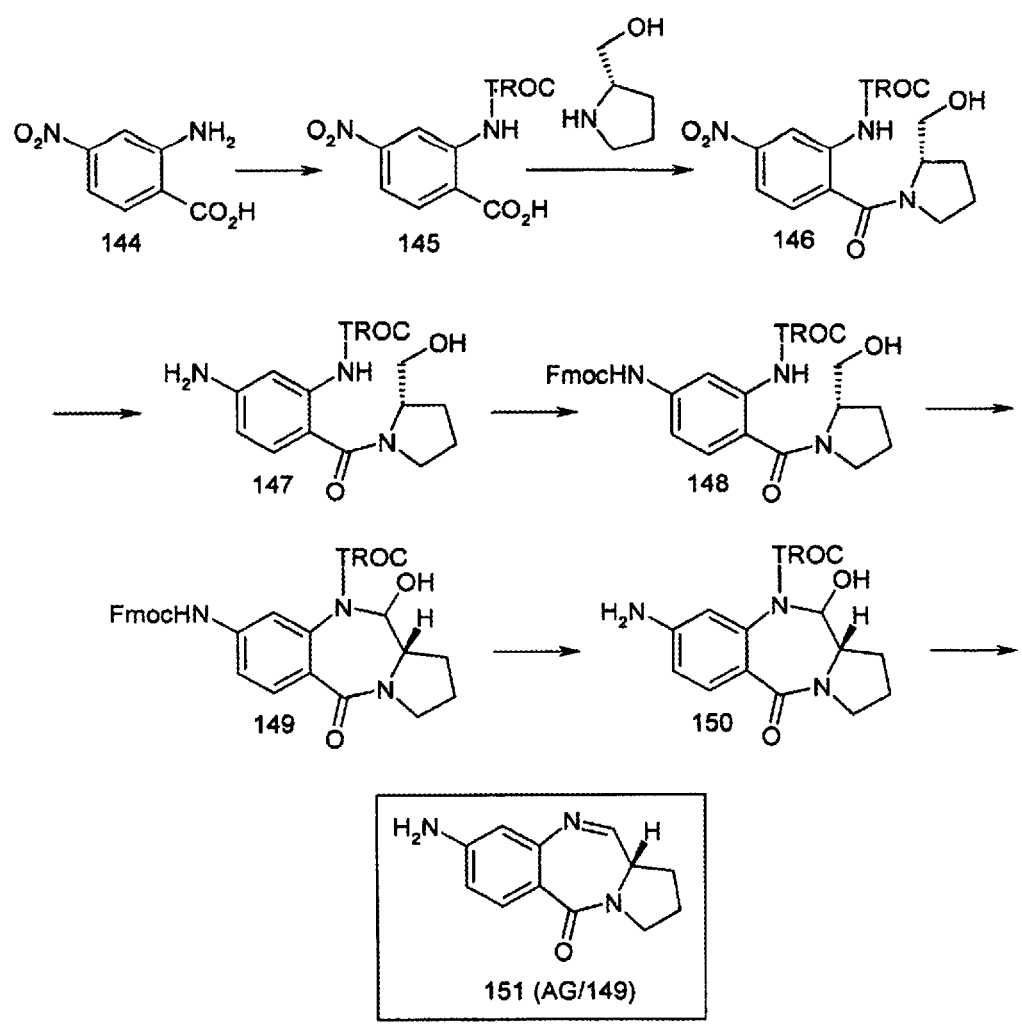

Example 3(l)
Synthesis of the C8-NH$_2$ PBD (151, AG/149) (see FIG. 23)

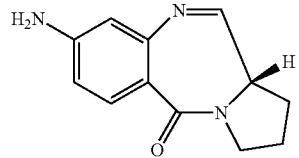

4-Nitro-2-(2',2',2'-trichloroethoxycarbonylamino)benzoic acid (145)

A solution of 2,2,2-trichloroethylchloroformate (Troc-Cl) (1.66 mL, 12.1 mmol) in dry dichloromethane (25 mL) was added drop wise to a solution of 4-nitroanthranilic acid 144 (2 g, 11 mmol) and pyridine (1.78 mL, 22 mmol) in dichloromethane (25 ml) at 0° C. The solution was allowed to stir at 25° C. for 5 hours. The reaction mixture was washed with dilute HCl (1N, 2×50 mL), water (1×50 mL), brine (1×25 mL) and dried over MgSO$_4$. Removal of excess solvent by rotary evaporation under reduced pressure afforded the crude product which was used in the subsequent reaction without further purification.

N-[4-nitro-(2',2',2'-trichloroethoxycarbonylamino)benzoyl]pyrrolidine-2-methanol (146)

Oxalyl chloride (1 mL, 12.1 mmol) and a catalytic amount of dry DMF were added to a suspension of the crude product from the previous reaction in of dry dichloromethane (50 mL) and the reaction mixture was allowed to stir at room temperature for 12 hours. The newly formed acid chloride was added drop wise, over 1 hour, to a solution of 2S-(+)-pyrrolidinemethanol (1.22 g, 12.1 mmol) and triethylamine (3.8 mL, 27.5 mmol) in dichloromethane (50 mL) at −20° C. ($CCl_4$-dry ice). The reaction mixture was stirred for a further hour at −20° C. and was then allowed to warm to room temperature. The reaction mixture was washed with dilute HCl (1N, 2×50 mL), water (50 mL) and brine (50 mL), dried over $MgSO_4$ and evaporated under reduced pressure. The residue was purified by flash chromatography (EtOAc/petroleum ether 50/50), removal of excess eluent afforded of a yellow oil (1.34 g, 30%, over two steps): $^1$H NMR (270 MHz, $CDCl_3$) δ1.7–2.3 (m, 4H); 3.45 (m, 2H); 3.71 (dd, J=5.5, J=11, 1H); 4.06 (m, 2H); 4.43 (bs, 1H); 4.85 (d, J=13, 1H); 4.89 (d, J=13 Hz, 1H); 7.56 (d, J=8.4 Hz, 1H); 7.96 (dd, J=2.2, J=8.4 Hz, 1H); 8.94 (d, J=2.2 Hz, 1H); 9.2 (bs, 1H). $^{13}$C NMR (67.8 MHz, $CDCl_3$) δ24.9; 27.9; 50.8; 60.5; 64.3; 74.6; 94.9; 115.9; 117.9; 128.6; 130.5; 136.9; 149.0; 151.8; 167.7. MS: m/e (relative intensity) 441 ([M+1], 1), 291 (10), 260 (12), 191 (30), 164 (15), 154 (8), 113 (20), 77 (20), 70 (100). HRMS Calculated for $C_{15}H_{16}C_{13}N_3O_6$: 439.0104. Found: 439.0105. $[\alpha]^{25}_D$=−110.6° (c=0.13, $CHCl_3$).

N-[4-amino(2',2',2'-trichloroethoxycarbonylamino)benzoyl]pyrrolidine-2-methanol (147)

A solution of 146 (1 g, 2.3 mmol) and $SnCl_2 \cdot 2H_2O$ (2.56 g, 11.4 mmol) in methanol (20 mL) was heated at reflux for 6 hours (the reaction was monitored by TLC (3% methanol, ethyl acetate). The reaction mixture was reduced to ⅓ of it's original volume and the pH adjusted to 8–9 with satd. aqueous $NaHCO_3$. Ethyl acetate (100 mL) was added and the mixture was vigorously stirred for 12 hours, then filtered through Celite to remove tin salts. The organic phase was dried over $MgSO_4$ and evaporated to afford the product as a yellow oil (0.94 g, 97%) which was used in the next reaction without further purification: $^1$H NMR (270 MHz, $CDCl_3$) δ1.6–1.8 (m, 2H); 1.9 (m, 1H); 2.17 (m, 1H); 3.48–3.58 (m, 1H); 3.62–3.72 (m, 3H); 3.84 (m, 1H); 4.44 (m, 1H); 4.77 (d, J=12.1 Hz , 1H); 4.83 (d, J=12.1 Hz, 1H); 6.32 (dd, J=2.2, J=8.43 Hz, 1H); 7.18 (d, J=8.43 Hz, 1H); 7.52 (d, J=2.2 Hz, 1H); 9.62 (bs, 1H). $^{13}$C NMR (67.8 MHz, $CDCl_3$) δ21.1; 25.2; 28.2; 51.9; 60.9; 65.4; 74.3; 95.3; 105.5; 108.3; 112.6; 130.1; 138.9; 149.7; 151.8; 171.5. IR (Nujol): $cm^{-1}$ 3346, 3000–2800, 1738, 1620, 1463, 1196, 1046, 963, 820 760. MS: m/e (relative intensity) 409 ([M−1], 15), 309 (20), 179 (25), 161 (100), 134 (8), 113 (25), 77 (35), 70 (85). HRMS Calculated for $C_{15}H_{18}Cl_{13}N_3O_4$: 409.0362. Found: 409.0363. $[\alpha]^{25}_D$=−60.1° (c=0.3, $CHCl_3$).

N-[4-(Fmoc)amino(2',2', 2'-trichloroethoxycarbonylamino)benzoyl]pyrrolidine-2-methanol (148)

An aqueous solution of $NaHCO_3$ (0.6 g, 5.67=mol, in 20 mL of $H_2O$) was added to a solution of 147 (0.94 g, 2.3 mmol) in THF (20 mL). The reaction mixture was cooled to 0° C. and Fmoc-Cl (0.65 g, 2.5 mmol) was added in small portions. After addition the reaction mixture was allowed to stir for 2 hours at room temperature. (TLC: ethyl acetate/petroleum ether 50/50). The reaction mixture was acidified with dilute HCl (1N) and extracted with ethyl acetate (2×20 mL). The organic phase was dried ($MgSO_4$) and evaporated and the resulting yellow oil thus obtained was purified by flash chromatography to afford the product (1.03 g, 72%): $^1$H NMR (270 MHz, $CDCl_3$) δ1.68 (m, 2H); 1.84 (m, 1H); 2.11 (m, 1H); 3.48 (m, 2H); 3.71 (m, 1H); 3.87 (m, 1H); 4.19 (t, J=6.8 Hz, 1H); 4.40 (m, 2H); 4.45 (d, J=6.78 Hz, 2H); 4.73 (d, J=12.1, 1H); 4.78 (d, J=12.1 Hz, 1H); 7.2–7.8 (m, 11H); 8.04 (bs, 1H). $^{13}$C NMR (67.8 MHz, $CDCl_3$) δ25.1; 28.1; 46.8; 51.6; 60.8; 65.7; 67.1; 74.3; 95.2; 109.9; 112.3; 118.3; 120.0; 124.9; 127.1; 127.8; 129.3; 137.5; 140.9; 141.2; 143.6; 151.8; 153.2; 170.3. IR (Nujol): $cm^{-1}$ 3301, 3000–2800, 1738, 1599, 1525, 1451, 1224, 1056, 985, 758, 740, 667. MS: m/e (relative intensity) 632 ($M^{+\cdot}$), 409 (15), 309 (20), 179 (25), 161 (100), 134 (8), 113 (25), 77 (35), 70 (85). $[\alpha]^{25}_D$=−70.3° (c=0.25, $CHCl_3$).

(11S,11aS)-8-(Fmoc)amino-11-hydroxy-10-N-(2',2',2'-trichloroethoxycarbonyl)-1,2,3,10,11,11a-hexahydro-5H-pyrrolo[2,1-c][1,4]benzodiazepin-5-one (149)

A solution of DMSO (0.31 ml, 4.4 mmol) in of dry dichloromethane (10 mL) was slowly added (over 30 minutes) to a solution of oxalyl chloride (2.2 mmol) in dry dichloromethane (11.1 mL) at −45° C. The mixture was allowed to stir for 15 minutes followed by the addition of a solution of 148 (1 g, 1.58 mmol) in of dry dichloromethane (15 ml), keeping the temperature below −40° C. After further 60 minutes at −45° C., a solution of triethylamine (0.88 ml 6.32 mmol) in dichloromethane (6 mL) was added and the reaction mixture allowed to warm to room temperature. The reaction mixture was washed with water (50 mL), dilute HCl (1N, 50 mL) and brine (50 mL). Evaporation of solvent afforded the crude product which was purified by flash chromatography (ethyl acetate/petroleum ether 50/50). Removal of excess eluent furnished the product as a pale yellow oil (0.81 g, 82%): $^1$H NMR ($CDCl_3$) δ1.96–2.16 (m, 4H); 3.47–3.56 (m, 3H); 3.6 (m, 1H); 4.1–4.28 (m, 3H); 4.46 (d, J=6.15 Hz, 2H); 5.01 (d, J=12.1 Hz, 1H); 5.64 (d, J=12.1 Hz 1H); 7.22–7.76 (m, 11H). $^{13}$C NMR (67.8 MHz, $CDCl_3$) δ22.9; 28.7; 46.4; 46.9; 59.9; 67.0; 75.1; 86.0; 94.8; 117.7; 119.6; 120.1; 124.9; 127.9; 129.8; 134.9; 140.8; 141.3; 143.5; 153.0; 154.1; 166.7. IR (Nujol): $cm^{-1}$ 3282, 3000–2800, 1713, 1610, 1533, 1451, 1220, 1058, 908, 735, 647 MS: m/e (relative intensity) 631 ([M+2], 1), 196 (5), 178 (100), 152 (5), 89 (7), 70 (10). HRMS Calculated for $C_{30}H_{26}Cl_3N_3O_6$: 629.0887. Found: 629.0887. $[\alpha]^{25}_D$=+58.7° (c=0.5, $CHCl_3$).

(11S,11aS)-8-amino-11-hydroxy-10-N-(2',2',2'-trichloroethoxycarbonyl)-1,2,3,10,11,11a-hexahydro-5H-pyrrolo[2,1-c][1,4]benzodiazepin-5-one (150)

The protected carbinolamine 149 (0.8 g, 1.3 mmol) was added to a 5% solution of piperidine in $CH_3CN$ (12 mL, 5 eq. of piperidine). The mixture was allowed to stir for 12 hours, extracted with water (2×50 mL) and the organic phase was evaporated under reduced pressure to yield a pale yellow oil (0.24 g, 50%): $^1$H NMR (270 MHz, $CDCl_3$) δ1.9–2.2 (m, 4H); 3.45–3.7 (m, 3H); 4.26 (d, J=12.1 Hz, 1H); 4.55 (m, 3H); 5.18 (d, J=12.1 Hz, 1H); 5.61 (d, J=10.3 Hz, 1H); 6.61 (s, 1H); 6.69 (d, J=7.3 Hz, 1H); 7.56 (d, J=8.2 Hz, 1H). $^{13}$C NMR (67.8 MHz, $CDCl_3$) δ23.0; 28.7; 46.3; 59.8; 74.9; 95.1; 114.8; 116.5; 130.4; 135.3; 154.4; 167.3. IR (Nujol): $cm^{-1}$ 3340, 3224, 3000–2800, 1714, 1602, 1460, 1311, 1208, 1141, 1061, 826, 759, 665. MS: m/e (relative intensity) 407 ($M^{+\cdot}$, 40), 381 (5), 340 (10), 309 (25), 161 (100), 134 (15), 105 (15), 70 (80). HRMS Calculated for $C_{15}H_{16}C_{13}N_3O_4$. 407.0206. Found: 407.0206. $[\alpha]^{25}_D$=+47.8° (c=0.5, $CHCl_3$).

Synthesis of (11aS)-8-amino-1,2,3,11a-tetrahydro-5H-pyrrolo[2,1-c][1,4]benzodiazepin-5-one (151)

Cd/Pb couple (5 eq, 0.34 g) was added portion wise to a vigorously stirred solution of 150 (0.2 g, 0.5 mmol) in THF (10 mL) and aqueous ammonium acetate (10 mL). Stirring was allowed to continue for a further 2 hours at room temperature and the reaction mixture was poured into ethyl acetate (100 mL). The organic phase was dried over MgSO$_4$, filtered and evaporated to yield the crude product which was subjected to flash chromatography (silica gel, 5% MeOH, 95% CHCl$_3$). Removal of excess eluent afforded the product as a white solid (26 mg, 53% yield); $^1$H NMR (270 MHz, CDCl$_3$, CD$_3$OD) δ1.6–2.2 (m, 4H); 3.2–3.4 (m, 2H); 3.5 (m, 1H); 5.0 (m, 2H); 6.05 (m, 1H); 6.25 (m, 1H); 7.43 (m, 1H); 7.75 (m, 1H). IR (Nujol): cm$^{-1}$ 3304, 3000–2800, 1613, 1457, 1377, 1244, 1202, 1122, 1072, 825, 759, 721. MS: m/e (relative intensity) 215 (M$^{+\cdot}$, 100), 186 (15), 178 (10), 146 (10), 119 (25), 91 (15), 70 (30), 65 (5). HRMS Calculated for C$_{12}$H$_{13}$N$_3$O: 215.1058. Found: 215.1059. [α]$^{25}_D$=+163.3° (c=0.2, CHCl$_3$).

Example 3(m)

Figure 24:
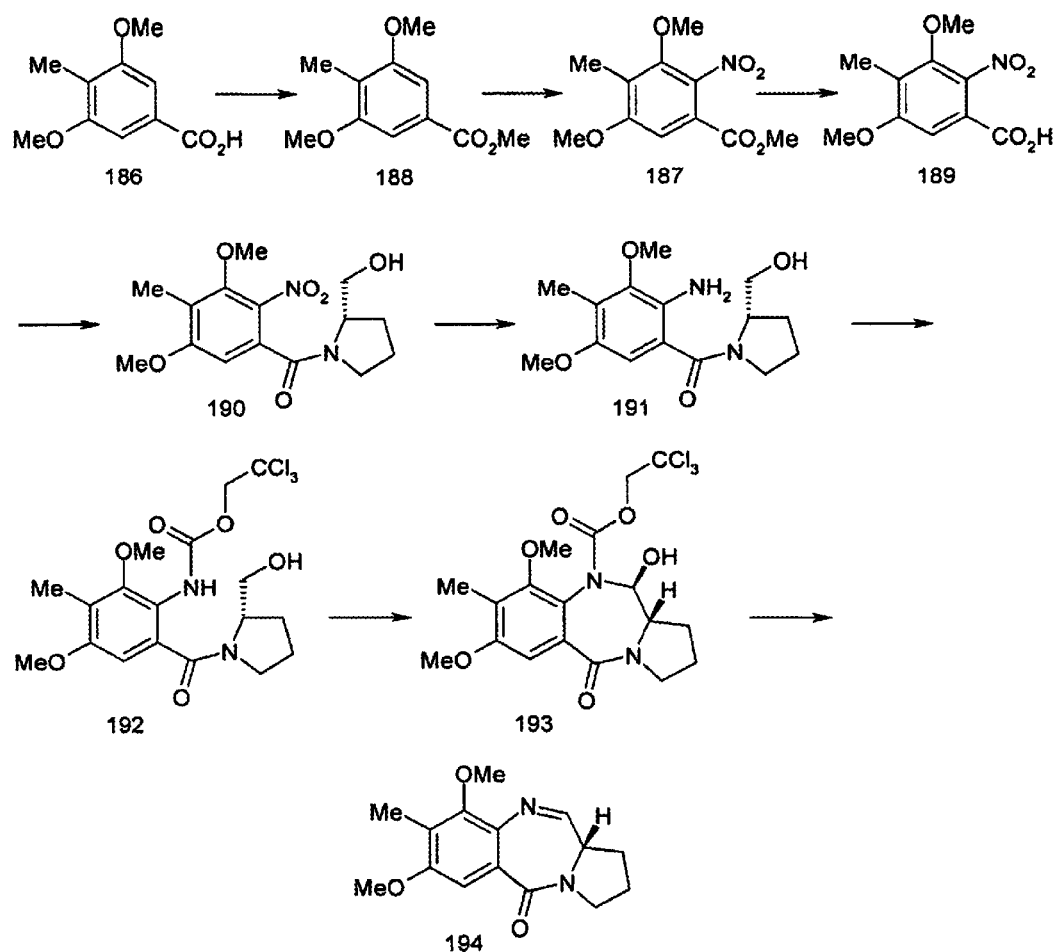

Synthesis of (11aS)-8-methyl-7,9-dimethoxy-1,2,3,11a-tetrahydro-5H-pyrrolo[2,1-c][1,4]benzodiazepin-5-one (194) (see FIG. 24)

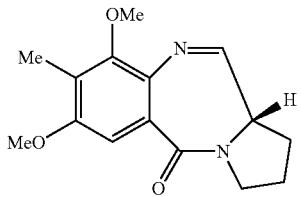

Methyl 4-methyl-3,5-dimethoxybenzoate (187)

Concentrated sulphuric acid (1 mL), was added dropwise to a solution of 4-methyl-3,5-dimethoxybenzoic acid (186) (5.01 g, 25.56 mmol) in refluxing methanol (20 mL). The reaction mixture was heated at reflux for a further 5 hours and then cooled to room temperature and concentrated to a third of its original volume. The concentrate was poured onto crushed ice (c. 150 mL) and allowed to stand for 30 minutes. The aqueous mixture was extracted with ethyl acetate (3×100 mL) and the combined organic phase washed with distilled water (3×100 mL), brine (2×100 mL) and dried over anhydrous MgSO$_4$. Removal of excess solvent under reduced pressure afforded the product as a beige solid (187) (4.865 g, 23.17 mmol, 91%); $^1$H NMR (270 MHz, CDCl$_3$) δ7.21 (s, 2H), 3.91 (s, 3H), 3.86 (s, 6H), 2.13 (s, 3H); $^{13}$C NMR (67.8 MHz, CDCl$_3$) δ171.57, 167.28, 158.16, 158.10, 128.23, 120.39, 105.20, 104.70, 55.85, 52.13, 8.77, 8.66.

Methyl 2-nitro-4-methyl-3,5-dimethoxybenzoate (188)

Finely ground copper nitrate (Cu(NO$_2$)$_3$, 5.37 g, 28.57 mmol) was added portionwise to a vigorously stirred solution of 187 (4.8 g, 22.86 mmol) in acetic anhydride (30 mL), whilst keeping the reaction temperature below 40° C. The reaction mixture was stirred for 2 hours and then poured onto crushed ice (800 mL). The aqueous mixture was left to stir for 1 hour and the product collected by filtration to afford a yellow solid (188) (4.88 g, 18.945 mmol); $^1$H NMR (270 MHz, CDCl$_3$) δ7.20 (br s, 1H), 3.92 (s, 3H), 3.89 (s, 3H), 3.84 (s, 3H), 2.21 (s, 3H); $^{13}$C NMR (67.8 MHz, CDCl$_3$) δ163.70, 159.01, 150.89, 140.08, 127.06, 121.54, 106.98, 62.88, 56.21, 52.98, 9.82.

2-Nitro-4-methyl-3,5-dimethoxybenzoic acid (189)

Potassium hydroxide (3.71 g, 66.31 mmol) was added to a stirred solution of 188 (4.83 g, 18.95 mmol) in anhydrous methanol (80 mL) and the reaction mixture heated at reflux for 3 h. The reaction mixture was allowed to cool and acidified to pH2 with 1 N HCl and the solid precipitate was filtered and washed with water (50 mL) and left to air dry to afford the product as a yellow-beige solid (189) (3.69 g, 15.31 mmol, 81%); $^1$H NMR (270 MHz, CDCl$_3$) δ13.88 (br s, 1H), 7.23 (s, 1H), 3.90 (s, 3H), 3.75 (s, 3H), 2.14 (s, 3H); $^{13}$C NMR (67.8 MHz, CDCl$_3$) δ164.09, 158.65, 150.09, 139.38, 125.70, 122.50, 107.24, 62.78, 56.34, 9.62.

N-(4-Methyl-3,5-dimethoxy-2-nitrobenzoyl)pyrrolidine-2-methanol (190)

A catalytic amount of DMF (2 drops) was added to a stirred solution of 189 (3.96 g, 15.32 mmol) and oxalyl chloride (2.14 g, 16.85 mmol) in dry CH$_2$Cl$_2$ (50 mL) under a nitrogen atmosphere. The reaction mixture was allowed to stir overnight and the resulting acid chloride used directly in the next stage of the procedure. 4-methyl-3,5-dimethoxy-2-nitro-benzoyl chloride in anhydrous DCM (50 mL) was added dropwise over 0.5 hours to a stirring solution of pyrrolidine methanol (1.55 g, 15.32 mmol, 1.1 eq) and TEA (3.87 g, 38.3 mmol, 2.5 eq) in anhydrous DCM (50 mL) at 0° C. under a nitrogen atmosphere and the reaction mixture was allowed to stir overnight at room temperature. The reaction mixture was washed with 1 N HCl (2×100 mL), and the organic layer was washed with distilled H$_2$O (2×100 mL), brine (2×100 mL) and dried over anhydrous MgSO$_4$. Evaporation of excess solvent yielded a yellow glass (190) (2.13 g, 6.56 mmol, 43% -2 steps); $^1$H NMR (270 MHz, CDCl$_3$) δ6.61 (s, 1H), 4.30–4.28 (m, 1H), 3.91 (s, 3H), 3.89 (s, 3H), 3.83–3.68 (m, 2H), 3.46–3.26 (m, 2H), 2.19 (s, 3H), 1.94–1.68 (m, 4H); $^{13}$C NMR (67.8 MHz, CDCl$_3$) δ167.85, 161.15, 152.62, 135.70, 132.32, 123.17, 103.70, 65.87, 62.61, 61.37, 56.36, 50.20, 28.41, 24.50, 9.34.

N-(2-Amino-4-methyl-3,5-dimethoxybenzoyl) pyrrolidine-2-methanol (191)

Hydrazine hydrate (1.26 g, 39.37 mmol) was added dropwise to a solution of 190 (2.13 g, 6.56 mmol) in methanol (50 mL) gently refluxing over Raney nickel (1 g, slurry). The resulting vigorous evolution of hydrogen gas subsided after approximately 10 minutes and the reaction was deemed to be complete by TLC after 2 h. The reaction mixture was filtered through celite and the solvent evaporated. Distilled water (100 mL) was added to the residue, and the aqueous mixture was extracted with EtOAc (3×100 mL) and the combined organic phase washed with H$_2$O (3×100 mL) and brine (3×100 mL) and dried over anhydrous MgSO$_4$. Evaporation of the solvent afforded the product as a brown glass (191) (1.91 g, 6.50 mmol) which was protected directly as the troc-carbamate.

N-(4-Methyl-3,5-dimethoxy-2-[trichloroethyloxycarbonylamino]-benzoyl)pyrrolidine-2-methanol (192)

A solution of 2,2,2-trichloroethyl chloroformate (1.38 g, 6.5 mmol) in distilled DCM (25 mL) was added dropwise over 0.5 hours to a solution of anhydrous pyridine (1.03 g, 13 mmol) and 191 (1.91 g, 6.5 mmol) in distilled DCM (25 mL) at 0° C. After 6 hours at room temperature, the reaction mixture was diluted with anhydrous DCM (100 mL) and washed with 1 N HCl (2×100 mL), H$_2$O (100 mL), brine (100 mL) and dried over anhydrous MgSO$_4$. Evaporation of the solvent yielded a brown oil which was purified by flash column chromatography (silica gel, EtOAc) to afford the product (192) as a yellow glass (2.13 g, 4.53 mmol, 70%); $^1$H NMR (270 MHz, CDCl$_3$) δ7.59 (br s, 1H), 6.56 (s, 1H), 4.78 (br s, 2H), 4.25–4.23 (m, 1H), 3.82–3.79 (m, 3H+1H), 3.69–3.63 (m, 3H+1H), 3.52 (m, 1H), 3.42–3.33 (m, 1H), 2.13–2.06 (m, 3H+1H), 1.88–1.64 (m, 3H); $^{13}$C NMR (67.8 MHZ, CDCl$_3$) δ169.95, 156.82, 156.67, 154.02, 153.34, 131.92, 121.74, 119.33, 103.94, 95.43, 74.42, 66.04, 61.01, 60.60, 60.27, 55.73, 50.46, 28.53, 24.47, 9.13.

(11S,11aS)-8-Methyl-7,9-dimethoxy-11-hydroxy-10-N-(2',2',2'-tri-chloroethoxylcarbonyl)-1,2,3,10,11,11a-hexahydro-5H-pyrrolo[2,1-c][1,4]benzodiazepin-5-one (193)

Anhydrous DMSO (1.006 g, 12.87 mmol) in dry DCM (10 mL) was added dropwise over 5 minutes to a stirred solution of oxalyl chloride (3.19 mL of a 2 N solution in DCM, 6.373 mmol) under a nitrogen atmosphere at −50° C. After stirring for 5 minutes, a solution of 192 (2.13 g, 4.53 mmol) in dry DCM (10 mL) was added dropwise over 45 minutes to the reaction mixture, which was then stirred for a further 45 minutes at −50°=0 C. TEA (1.83 g; 18.13 mmol) was added dropwise to the mixture over 0.5 hours and stirred for a further 15 minutes. The reaction mixture was left to warm to room temperature, diluted with $H_2O$ (100 mL)and the phases allowed to separate. The organic phase was washed with 1 N HCl (2×50 mL), water (2×50 mL), brine (2×50 mL) and dried over $MgSO_4$. The solvent was evaporated to afford the product (193) as an off-white glass (1.84 g, 3.93 mmol; 87%). $^1H$ NMR (270 MHz, $CDCl_3$) δ7.05 (s, 1H) (minor rotamer 1:4, visible at d 7.06), 5.58 (dd, J=3.84 Hz, J=9.89, 1H) (minor rotamer 1:4, visible at d 5.68, J=4.21 Hz, J=9.53), 4.71 (d, J=11.72 Hz, 1H), 4.56 (d, J=11.73 Hz, 1H), 4.11 (d, J=3.85 Hz, 1H), 3.88 (s, 3H), 3.76 (s, 3H), 3.79–3.47 (m, 2H), 2.21–1.99 (m, 4H), 2.16 (s, 3H); $^{13}C$ NMR (67.8 MHz, $CDCl_3$) rotamers δ166.82, 158.31, 157.92, 155.65, 155.43, 131.52, 124.17, 123.99, 121.62, 105.90, 105.64, 105.38, 94.53, 86.17, 85.93, 75.80, 75.23, 61.77, 61.65, 59.98, 59.58, 59.40, 55.88, 55.79, 46.56, 46.38, 28.70, 28.62, 22.94, 10.14, 9.75.

8-Methyl-7,9-dimethoxy-1,2,3,11a-tetrahydropyrrolo[2,1-c][1,4]benzodiazepin-5-one (194)

10% Cd/Pb couple (1.34 g; 10.7 mmol Cd) was added to a rapidly stirring solution of 193 (1 g; 2.14 mmol) in a mixture of THF (15 mL) and 1 N $NH_4OAc$ (15 mL). After 3.5 hours the reaction was diluted with EtOAc (150 mL). The solution was dried over anhydrous $MgSO_4$ and the solids were filtered and rinsed with EtOAc (50 mL). Removal of excess solvent yielded the product (194) as a white glass (554 mg, 2.021 mmol, 94%). $^1H$ NMR (270 MHz, $CDCl_3$) (mixture of imine and methyl ether forms) δ7.72 (imine, d, J=4.39, 1H), 7.29 (s, 1H), 3.90 (s, 3H), 3.88–3.51 (m, 3H+2H+1H), 2.37–2.04 (m, 4H), 2.22 (s, 3H); $^{13}C$ NMR (67.8 MHz, $CDCl_3$) δ164.65, 161.41, 156.79, 153.47, 133.87, 126.29, 124.27, 105.71, 60.98, 55.80, 55.70, 53.71, 46.70, 29.52, 29.34, 24.13, 9.33.

Figure 26:
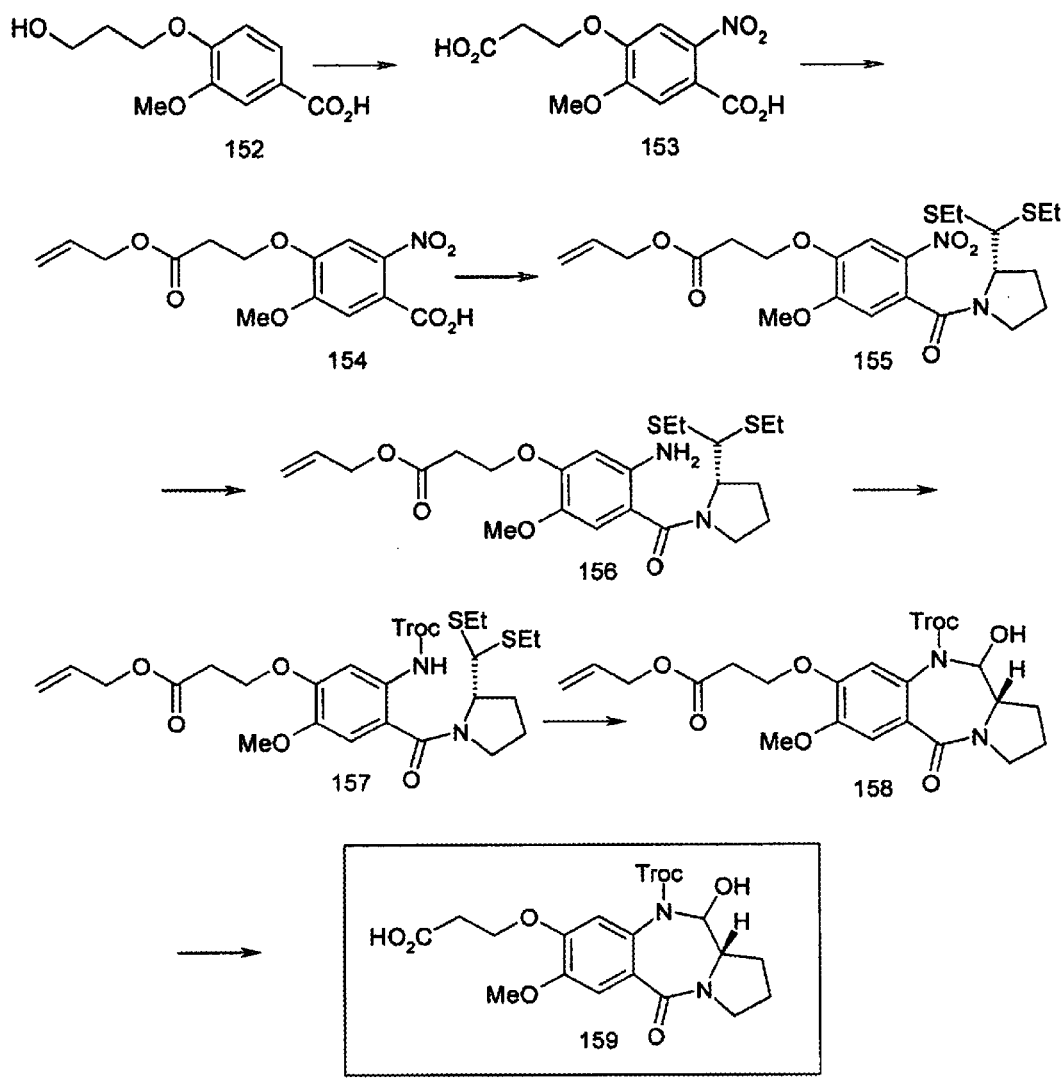
FIG. 26 is a synthesis of an intermediate in the preparation of compounds of formula IV of the present invention.

Example 4
Synthesis of the C8-Amines Synthesis of 3-(11-Hydroxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-2-propenylpropanoate (159) (see FIG. 26)

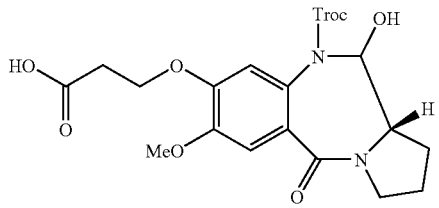

Nitro Di-acid (153)

14.63 g of (4-carboxy-2-methoxy-5hydroxy-phenoxy) propanoic acid 152 (61 mmol) was added portionwise to 70% nitric acid (100 mL ) stirred at 0° C. The reaction was stirred for 1 hour at 0° C. then allowed to return to rt. The reaction mixture was then poured onto ice and allowed to stir for 18 h. The solids were then collected by filtration and washed with water. The aqueous layer was then extracted with ethyl acetate (3×150 mL). The organics were then washed with water and brine and dried with sodium sulphate. The solvent was then removed in vacuo to give 153 as a yellow solid, yield=14.01 g (83%) mp 141° C. $^1H$ NMR ($CDCl_3$): δ8.51 (bs, 2H, COOH), 7.57 (s, 1H, $CHCNO_2$), 7.15 (s, 1H, $CH_3OCCH$), 4.35 (t, 2H, J=6.41 Hz, $CH_2CH_2O$), 3.99 (s, 1H, $OCH_3$), 2.86 (t, 2H, J=6.41 Hz, $CH_2CH_2O$). $^{13}C$-NMR ($CDCl_3$): δ33.93 ($CH_2CH_2O$), 56.42 ($OCH_3$), 65.20 ($CH_2CH_2O$), 108.27 ($NO_2CCH$), 111.26 ($CH_3OCCH$), 122.50 (CCOOH), 141.14($CNO_2$), 149.21 ($CH_2CH_2OC.$), 152.40 ($CH_3OC.$), 166.93 (arom. COOH), 172.24 (aliph. COOH). IR (Nujol) v 2860, 2620, 1740, 1720, 1590, 1540, 1480, 1390, 1350, 1290, 1230, 1250, 1200, 1060 $cm^{-1}$. EIMS m/e (relative intensity): 286 ($M^+$, 20), 241 (10), 213 (100), 169 (20), 152 (5), 111 (20), 96 (5), 79 (5), 73 (15), 55 (10). HRMS Calcd. for $C_{11}H_{14}NO_8$= 285.0511 found=285.0538.

2-Propene 3-(4-carboxy-2-methoxy-5-nitrophenoxy) propanoate (154)

A mixture of 3-(4-carboxy-2-methoxy-5-nitrophenoxy) propanoic acid (153) (20 g, 74.3 mmol) and p-toluene sulphonic acid monohydrate (2.3 g, 7.4 mmol) in allyl alcohol (240 mL, 3.5 mol) was refluxed for 7 hours then allowed to cool. The allyl alcohol was then removed in vacuo, and the residue triturated with dilute HCl acid and collected by filtration. This solid was taken up in EtOAc, and the resulting solution washed with water and brine and dried over sodium sulphate. Evaporation in vacuo afforded 154 as a white solid (19.27 g, 84%): mp 128–130° C.; $^1H$-NMR ($CDCl_3$): δ2.92 (t, 2H, J=6.35 Hz); 3.94 (s, 3H); 4.38 (t, 2H, J=6.41 Hz); 4.65 (d, 2H, J=5.61 Hz); 5.27 (dd, 1H, $J_1$=1.28 Hz, $J_2$=19.42 Hz); 5.33 (dd, 1H, $J_1$=1.28 Hz, $J_2$=17.04 Hz); 5.92 (m, 1H); 7.15 (s, 1H); 7.45 (s, 1H); $^{13}C$ NMR (67.8 MHz, $CDCl_3$): δ34.1, 56.5, 65.0, 65.4, 108.5, 111.3, 118.3, 122.9, 131.8, 141.1, 149.1, 152.6, 167.1, 170.0; IR (Nujol); v 1730, 1630, 1550, 1430, 1390, 1290, 1230, 1190, 1170, 1070, 1030, 1010 $cm^{-1}$; MS (EI) m/z (relative intensity): 325 ($M^+$, 19), 251 (3), 213 (2), 196 (3), 211 (3), 113 (19), 91 (4), 71 (9), 55 (6); HRMS: calcd. for $C_{14}H_{15}NO_8$ 325.0798, found 232.0773.

Prop-2-enyl 4-(N-2S-Diethylthiomethylpyrrolidine-carboxy)-2-methoxy-5-nitrophenoxy)propanoate (155)

2-Propene 3-(4-carboxy-2-methoxy-5-nitrophenyloxy) propanoate (154): 5 g, 15.34 mmol), oxalyl chloride (2 mL, 23 mmol) and 5 drops of DMF were stirred in dry THF (100 mL) for 18 h. The solvent was then removed in vacuo and the residue dissolved in dry THF (50 mL). This was added dropwise to a vigorously stirred mixture of (2s)-pyrrolidone-2-caroxaldehyde diethyl thioacetate(3.15 g, 15.34 mmol) and triethylamine (1.86 g, 18.41 mmol). The stirring was continued for 18 h. The solvent was then removed in vacuo and the product purified by flash chromatography eluting with ethyl acetate to give 155 (7.48 g, 95%) as a yellow oil. $^1H$ NMR ($CDCl_3$): δ7.74 (s, 1H, OCCHC), 6.83 (s, 1H, MeOCCHC), 5.98–5.86 (m, 1H, $CH_2CHCH_2$, 5.33 (d, 1H, J=26.56 Hz, $OCH_2CHCH_2$), 5.28 (d, 1H, J=20.24 Hz, $OCH_2CHCH_2$), 4.88 (d, 1H, J=3.85 Hz, NCHCH), 4.74–4.65 (m, 2H, $OCH_2CHCH_2$) 4.42 (t, 2H, J=7.69 Hz, $CH_2CH_2OC.$), 3.94 (s, 3H, $OCH_3$), 3.29–3.21 (m, 2H, $NCH_2$), 2.96 (p, 2H, J=3.12 Hz, $CH_2CH_2O$), 2.87–2.67 (m, 4H, $SCH_2CH_3$), 2.32–1.78 (m, 4H, $NCH_2CH_2CH_2$) 1.38–1.31 (m, 6H, $SCH_2CH_3$). $^{13}C$-NMR ($CDCl_3$): δ15.00, 15.13 ($SCH_2CH_3$), 24.63 ($NCH_2CH_2CH_2$), 26.28, 26.59, 27.22 ($NCH_2CH_2CH_2$), 34.13 ($CH_2CH_2O$), 50.19 ($NCH_2$), 52.80 (NCHCH), 56.60 ($OCH_3$), 61.08 (NCH), 65.13

(CH$_2$CH$_2$O), 65.64 (OCH$_2$CHCH$_2$), 108.70 (arom. CH), 109.47 (arom. CH), 118.55 (OCH$_2$CHCH$_2$), 128.58 (CCON), 131.73 (OCH$_2$CHCH$_2$), 137.17 (CNO$_2$), 147.98 (CH$_2$CH$_2$OC.), 154.57 (COCH$_3$), 166.61 (CON), 170.14 (COO). IR (Nujol) ν=3550–2720, 3000, 2630, 2200, 1740, 1640, 1580, 1530, 1340, 1280, 1220, 1180, 1050 cm$^{-1}$. MS (EI): m/e (relative intensity): 527 (M$^+$, 1), 377 (10), 310 (12), 309 (72), 308 (94), 268 (20), 142 (4). HRMS calcd. for C$_{24}$H$_{35}$O$_7$N$_2$S$_2$=527.1875, found=527.1885.

5-Amino-3-(4-(2-diethylthiomethyl-(2S)-perhydro-1-pyrroloylcarbonyl)-2-methoxyphenyloxy)$_2$-propenylpropanoate (156)

8 (7.21 g, 14.05 mmol) and Tin(II) chloride (15.85 g, 76 mmol) was refluxed for 40 minutes in ethyl acetate (100 mL) then allowed to cool. The solvent was then removed in vacuo and the residue was triturated with saturated bicarbonate solution at 0° C. EtOAc (50 mL) was added and the reaction stirred overnight. The reaction mixture was then filtered through Celite and the filter cake washed with ethyl acetate. The combined organics were then washed with water and brine, dried with sodium sulphate and the solvent removed in vacuo. The product was purified using flash chromatography eluting with 5% MeOH in dichloromethane to give a yellow oil, yield=5.87 g (86%). $^1$H NMR (CDCl$_3$): δ6.82 (s, 1H, arom. CH), 6.28 (s, 1H, arom.CH), 5.99–5.85 (m, 1H, OCH$_2$CHCH$_2$), 5.31 (dd, 1H, J=1.28 Hz, 27.66 Hz, OCH$_2$CHCH$_2$), 5.26 (dd, 1H, J=1.28 Hz, 20.70 Hz, OCH$_2$CHCH$_2$), 4.71–4.62 (m, 5H, including doublet at 4.62, 2H, J=5.49 Hz, NH$_2$+NCHCH, OCH$_2$CHCH$_2$), 4.27 (t, 2H, J=6.59 Hz, CH$_2$CH$_2$O), 3.92, (m, 1H, NCH), 3.74 (s, 3H, OCH$_3$), 3.66–3.57 (m, 2H, NCH$_2$) 2.89 (t, 2H, J=6.6 Hz, CH$_2$CH$_2$O), 2.83–2.64 (m, 4H, SCH$_2$CH$_3$), 2.28–1.80 (m, 4H, NCH$_2$CH$_2$CH$_2$), 1.25 (m, 6H, SCH$_2$CH$_3$); $^{13}$C NMR (CDCl$_3$) δ14.20 (SCH$_2$CH$_3$), 26.55, 27.23 (NCH$_2$CH$_2$CH$_2$), 34.27 (CH$_2$CH$_2$O), 53.20 (NCHCH), 56.08 (OCH$_3$), 60.10 (NCH), 60.39 (NCH$_2$), 64.20 (CH$_2$CH$_2$O), 64.41 (OCH$_2$CHCH$_2$), 102.26 (arom. CH), 113.71 (arom. CH), 118.40 (OCH$_2$CHCH$_2$), 131.93 (OCH$_2$CHCH$_2$), 141.03 (CNH$_2$), 141.74 (CH$_2$CH$_2$OC.), 154.56 (COCH$_3$), 169.69 (CON), 170.53 (COO). IR (neat liquid film) 3500–3000, 3460, 3400, 2970, 1740, 1650, 1535, 1470, 1345, 1290, 1225, 1190 cm$^{-1}$; MS (EI): m/e (relative intensity): 482 (M$^+$, 4), 347 (2), 278 (31), 137 (1), 70 (3); HRMS calcd. for C$_{23}$H$_{34}$O$_5$N$_2$S$_2$=482.1909, found=482.1925.

3-(4-(2-Diethylthiomethyl-(2S)-perhydro-1-pyrrolylcarbonyl)-2-methoxy-5-(2,2,2-trichloroethyloxycarbonylamino)phenyloxy)$_2$-propenylpropanoate (157)

To a solution of 156 (5.67 g, 11.74 mmol) in dichloromethane (200 mL) was added pyridine (2.02 mL, 23.48 mmol). To this was added dropwise at 0° C. a solution of trichloroethyl chloroformate (1.616 mL, 11.74 mmol). The solution was stirred for a further 1 hour at 0° C. The organics were washed with 1 N HCl (3×100 mL), water (3×100 mL) brine (100 mL), dried over magnesium sulphate and the solvent removed in vacuo to give a brown oil (6.8 g, 88%) $^1$H NMR (CDCl$_3$): δ9.14 (bs, 1H, NH), 7.88 (bs, 1H, CHCNH), 6.93 (s, 1H, MeOCCHC), 5.99–5.86 (m, 1H, OCH$_2$CHCH$_2$), 5.31 (dt, 1H, J=1.47 Hz, 27.84 Hz OCH$_2$CHCH$_2$), 5.25 (dt, 1H, J=1.29 Hz, 21.61 Hz, CH$_2$CHCH$_2$),4.89–4.77 (m, 4H, including doublet 1H, J=1.28 Hz, CHCHSEt, NH, CH$_2$-TrOC), 4.62 (d, 2H, J=1.28 Hz, OCH$_2$CHCH$_2$), 3.81 (s, 3H, OCH$_3$), 3.60 (m, 2H, NCH$_2$), 2.91 (d, 2H, J=6.42 Hz, CH$_2$CH$_2$O), 2.84–2.61 (m, 4H, SCH$_2$CH$_3$), 1.37–1.23 (m, 6H, SCH$_2$CH$_3$); $^{13}$C NMR (CDCl$_3$): δ170.33 (ester CO), 168.50 (CON), 151.94 (OCO), 150.29 (COCH$_3$), 144.52 (COCH$_2$CH$_2$), 131.93 (OCH$_2$CHCH$_2$), 131.35 (CNH), 118.29 (OCH$_2$CHCH$_2$), 112.21 (arom. CH), 105.51 (arom. CH), 95.27 (CCl$_3$), 76.24 (CH$_2$TrOC), 74.39 (CH$_2$TrOC), 65.42 (CH$_2$CH$_2$O), 61.14 (NCH), 56.30 (OCH$_3$), 53.00 (NCHCHSEt), 34.27 (CH$_2$CH$_2$O), 27.30, 26.71, 26.43, 25.24 (NCH$_2$CH$_2$CH$_2$), 15.27, 14.87, 14.18 (SCH$_2$CH$_3$). MS (EI): m/e (relative intensity): 658, 656 (M$^+$, 1), 508 (1), 373 (6), 305 (5), 304 (27), 192 (5), 70 (12).

3-(11-Hydroxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-2-propenylpropanoate (158)

A solution of 157 (6.8 g, 10.34 mmol) in acetonitrile/water (4:1, 200 mL) was treated with calcium carbonate (2.585 g, 25.85 mmol) and mercuric(II) chloride (7.00 g, 25.85 mmol) and the solution was stirred for 18 h. The reaction was then filtered through Celite and the filter pad washed with ethyl acetate. The organics were collected and washed with water (3×50 mL), brine (100 mL) and dried over magnesium sulphate. The solvent was removed in vacuo and the resulting product was purified by flash chromatography eluting with ethyl acetate to give the product as a yellow oil (3.67 g, 64%) $^1$H NMR (CDCl$_3$): δ7.25 (arom. CH), 6.86 (s, 1H, arom. CH), 6.00–5.85 (m, 1H, CH$_2$CHCH$_2$), 5.67 (d, 1H, J=9.71 Hz, TrOC—CH$_2$) 5.37–5.20 (m, 3H, TrOC—CH$_2$+OCH$_2$CHCH$_2$), 4.65 (d, 2H, J=5.67 Hz, CH$_2$CHCH$_2$O), 4.36–4.22 (m, 3H, CH$_2$CH$_2$O+NCHOH), 3.90 (s, 3H, OCH$_3$), 3.72–3.47 (m, 3H, NCH+NCH$_2$), 2.91 (t, J=6.41 Hz, CH$_2$CH$_2$O) 2.29–2.00 (m, 4H, NCH$_2$CH$_2$CH$_2$) $^{13}$C NMR (CDCl$_3$): δ170.33 (ester carbonyl CO), 166.17 (CON), 154.4 (OCO), 149.88 (COCH$_3$), 148.93 (COCH$_2$CH$_2$), 131.86 (CH$_2$CHCH$_2$), 127.48 (arom. CN), 126.24 (CCON), 118.42 (OCH$_2$CHCH$_2$), 114.48 (arom. CH), 110.82 (arom. CH), 95.09 (CCl$_3$), 86.42 (NCHOH), 74.96 (TrOC—CH$_2$), 65.47 (OCH$_2$CHCH$_2$), 64.43 (CH$_2$CH$_2$O), 60.13 (NCH), 56.14 (OCH$_3$), 46.44 (NCH$_2$), 34.26 (CH$_2$CH$_2$O), 28.64 (NCH$_2$CH$_2$CH$_2$),MS (EI) m/z (relative intensity): =552 (M$^+$10), 550 (10), 374 (2), 368 (5), 304 (15), 192 (8), 70 (24), 55(24). HRMS calcd. for C$_{22}$H$_{25}$N$_2$O$_8$Cl$_3$=552.0651, found 3 peaks due to chlorine 552.0646, 550.676, 554.0617.

3-(11-Hydroxy-5-oxo-7-methoxy-10-(2,2,2-trichloroethyloxocarbonylamino)-(11aS)-2,3,5,10,11,11a-hexahydro-1H-benzo[e]pyrrolo[2,1-a][1,4]diazepin-8-yloxypropanoic acid (159)

A solution of 158 (3.5 g, 6.35 mmol) was dissolved in ethanol (100 mL). To this was added Tetrakis (triphenylphospine)palladium(0) (350 mg, 0.303 mmol) and the solution refluxed for 30 minutes until the reaction was complete by TLC monitoring. The reaction was then allowed to cool and the filtered through Celite. The EtOH was then removed in vacuo to give the crude material as a yellow solid which was used directly in the next steps. $^1$H-NMR (CDCl$_3$): δ7.22 (s, 1H, OCCHCN), 7.01 (s, 1H, MeOCCHC), 6.27 (bs, COOH), 5.67 (d, 1H, J=9.5 Hz, TrOC—CH$_2$), 5.06 (d, 1H, J=12.09 Hz, TrOC—CH$_2$), 4.29–4.11 (m, 2H, CHOH), 3.85 (s, 3H, OCH$_3$), 3.71 (t, 2H, J=6.97 Hz, CH$_2$CH$_2$O), 3.51 (m, 1H, NCH), 2.80 (m, 2H, NCH$_2$), 2.12–1.99 (m, 4H, NCH$_2$CH$_2$CH$_2$), 1.21 (t, 2H, J=6.96 Hz, CH$_2$CH$_2$O) $^{13}$C NMR (CDCl$_3$): δ=174.27 (acid CH), 167.34 (CON), 154.20 (OCO), 149.78 (COCH$_3$), 148.74 (COCH2CH2), 133.79 (arom. CH), 132.16 (arom. CH), 128.66 (arom. CN), 125.87 (CCON), 95.06 (CCl$_3$), 86.53 (NCHCHOH), 74.95 (CH$_2$–TrOC), 60.67 (NCH), 58.24 (CH,CH$_2$O), 56.04 (OCH$_3$), 46.44 (NCH$_2$), 35.24 (NCH$_2$CH$_2$CH$_2$), 28.59 (NCH$_2$CH$_2$CH$_2$), 23.08 (CH$_2$CH$_2$O)

Figure 27:
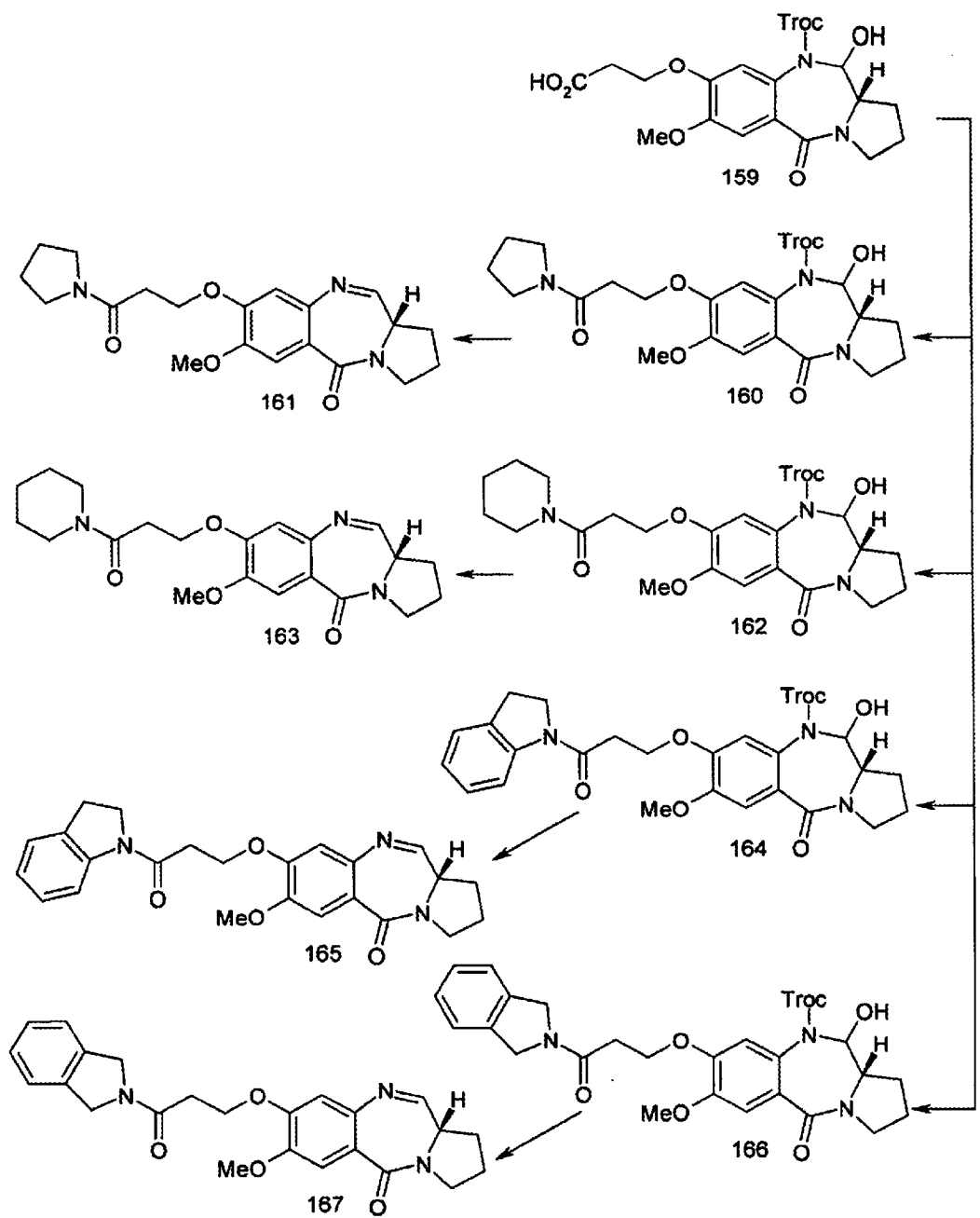
FIG. 27 is a synthesis routes for compounds of formula IV of the present invention.

Example 4(a)
3-(7-methoxy-5-oxy(11aS)-2,3,5,11a-tetrahydro-1H-benzo[e]pyrro[1,2-a[]1,4]diazepin-8-yloxy)-1-perhydro-1-pyrrolyl-1-propanone (161)(see FIG. 27)

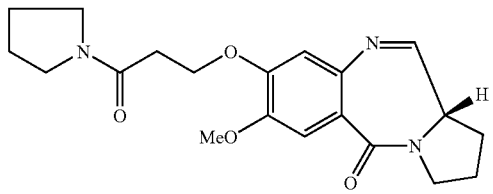

3-(11-Hydroxy-7-methoxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-1-perhydro-1-pyrrolyl-1-propanone (160)

To a solution of 159 (100 mg, 0.196 mmol) in dichloromethane was added 1-(3-dimethylaminopropyl)-3-ethylcarbodiimide hydrochloride (44 mg, 0.23 mmol) and 4-(dimethylamino)pyridine (5 mg, 0.04 mmol) and the solution stirred for 1 h. To the reaction was added pyrrolidine (16.36 mg, 0.23 mmol) and the reaction stirred for a further 2 h. The solvent was then removed in vacuo and the compound purified by flash chromatography eluting with 5% methanol in dichloromethane to give the product as a yellow oil, yield=56 mg, 51%. $^1$H NMR (CDCl$_3$) δ7.25 (OCCH), 6.90 (s, 1H, MeOCCHC), 5.66 (d, 1H, J=5.49 Hz, TrOC—CH$_2$), 5.16 (d, 1H, J=12.09 Hz, TrOC—CH$_2$), 4.84–4.74 (m, 2H, CHOH, C11aH), 4.35–4.23 (m, 2H, CH$_2$CH$_2$O), 3.90 (s, 3H, OCH$_3$), ), 3.73–3.67 (m, 1H, NCH), 3.53–3.44 (m, 6H C-ring NCH$_2$, pyrrolidine-N(CH$_2$)$_2$), 2.92–2.76 (m, 2H CH$_2$CH$_2$O), 2.11–1.85 (8H, C-ring NCH$_2$CH$_2$CH$_2$+pyrrolidine-NCH$_2$CH$_2$CH$_2$); $^{13}$C-NMR (CDCl$_3$): δ168.62 (amide CO), 167.05 (CON), 154.31 (OCO), 149.94 (COCH$_3$), 148.56 (COCH$_2$CH$_2$), 127.76 (arom. CN), 125.95 (CCON), 114.14 (arom. CH), 110.49 (arom. CH), 95.04 (CCl$_3$), 86.48 (NCHCHOH), 74.98 (CH$_2$—TROC), 65.15 (CH$_2$CH$_2$O), 60.20 (NCH), 56.13 (OCH$_3$), 46.85, 46.44, 45.76, 34.47, 28.60, 26.02, 24.42 (various N—(X)CH$_2$), 23.04 (CH$_2$CH$_2$O); FABMS m/z (relative intensity) 564 (M$^+$1), 550(3), 549 (2), 548 (8), 547 (2), 546 (8), 279 (2), 192 (4), 126 (18), 98 (6).

3-(7-methoxy-5-oxy(11aS)-2,3,5,11a-tetrahydro-1H-benzo[e]pyrrolo[1,2-a][1,4]diazepin-8-yloxy)-1-perhydro-1-pyrrolyl-1-propanone (161)

Method A: To a solution of 160 (100 mg, 0.164 mmol) in dichloromethane (5 mL) was added 1-(3-dimethylaminopropyl)-3-ethylcarbodiimide hydrochloride (38 mg, 0.2 mmol) and pyrrolidine (14 mg, 0.2 mmol) and the reaction stirred for 18 h. The mixture was then dilute with dichloromethane (100 mL) and washed with water (3×50 mL), saturated sodium bicarbonate solution (3×50 mL) and brine (50 mL). The solvent was removed in vacuo and the product purified by flash chromatography eluting with 5% methanol in dichloromethane to give the product 161 as a white solid (yield 26.3 mg, 40%)

Method B: To a solution of 160 (100 mg, 0.164 mmol) in dichloromethane (5 mL) was added 1-(3-dimethylaminopropyl)-3-ethylcarbodiimide hydrochloride (38 mg, 0.2 mmol) and the reaction stirred for 3 hours. The reaction was then treated with tetrabutylammonium fluoride (200 µL of a 1.0 M solution in THF, 0.2 mmol) and stirred for 30 minutes. The reaction was then treated with pyrrolidine (14 mg, 0.2 mmol) and stirred for 18 h. The mixture was then dilute with dichloromethane (100 mL) and washed with water (3×50 mL), saturated sodium bicarbonate solution (3×50 mL) and brine (50 mL). The solvent was removed in vacuo and the product purified by flash chromatography eluting with 5% methanol in dichloromethane to give the product 161 as a white solid (yield 54.2 mg, 82%)

Method C: To a solution of 160 (56 mg, 0.1 mmol) in THF (3 mL) was added 1 N ammonium acetate solution (2 mL) and the reaction mixture stirred. To the solution was added 10% Cd/Pb couple (0.5 mmol, 62.4 mg) and the reaction was stirred for 90 minutes. The reaction was filtered and diluted with ethyl acetate (20 mL). The solution was dried with magnesium sulphate and the solvent removed in vacuo. the product as then purified by flash chromatography eluting with 5% methanol in dichloromethane to give the compound as a white solid (yield =21 mg, 56%). $^1$H NMR (CDCl$_3$): δ7.66 (m, 1H, J=4.39 Hz, N=CH), 7.50 (s, 1H, arom. CH), 6.88 (s, 1H arom. CH), 4.42 (t, 2H, J=6.96 Hz, OOCCH$_2$CH$_2$), 3.92 (s, 3H, OCH$_3$), 3.90–3.44 (m, 5H, pyrrolidine CH$_2$+NCH), 2.87 (t, 2H, 5.96 Hz, OOCCH$_2$CH$_2$), 2.28–2.33 (m, 2H, NCH$_2$CH$_2$), 2.10–1.87 (m, 8H, C-ring+pyrrolidine CH$_2$). 168.58 (amide CO), 164.65 (CON), 162.43 (imine CH), 150.52 (COCH$_3$), 147.61 (COCH$_2$CH$_2$), 140.76 (arom. CN), 120.33 (CCON), 111.54 (arom. CH), 110.61 (arom. CH), 65.20 (COCH$_2$CH$_2$), 56.21 (COCH$_3$), 53.7 (NCH), 46.77, 46.67, 45.69, 34.40, 29.62, 26.06, 24.54, (CH$_2$), 24.19 (COCH$_2$CH$_2$) MS (EI): m/e (relative intensity): 371 (M$^+$, 10), 246 (10), 245 (5), 231 (3), 126 (18), 98 (2), 70 (5), 55 (3); HRMS calcd. for C$_{20}$H$_{15}$O$_4$N$_3$=371.1845, found 371.1788.

Example 4(b)
3-(7-methoxy-5-oxy(11aS)-2,3,5,11a-tetrahydro-1H-benzo[e]pyrrolo[1,2-a][1,4diazepin-8-yloxy)-1-piperidino-1-propanone (163) (see FIG. 27)

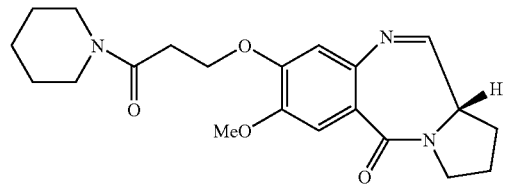

3-(11-Hydroxy-7-methoxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-1-perhydro-1-piperidino-1-propanone (162)

To a solution of 159 (100 mg, 0.196 mmol) in dichloromethane was added 1-(3-dimethylaminopropyl)-3-ethylcarbodiimide hydrochloride (44 mg, 0.23 mmol) and 4-(dimethylamino)pyridine (5 mg, 0.04 mmol) and the solution stirred for 1 h. To the reaction was added piperidine (25 µL, 0.23 mmol) and the reaction stirred for a further 2 h. The solvent was then removed in vacuo and the compound purified by flash chromatography eluting with 5% methanol in dichloromethane to give the product as a yellow oil, yield=94 mg, 84%). $^1$H-NMR (CDCl$_3$): δ7.25 (s, 1H, OCCHCN), 6.90 (s, 1H, MeOCCHC), 5.65 (d, 1H, J=9.71 Hz, TrOC—CH$_2$), 5.17 (d, 1H, J=11.94 Hz, TrOC—CH$_2$), 4.37–4.24 (m, 4H, CHOH+CH$_2$CH$_2$O), 3.91 (s, 3H, OCH$_3$), 3.73–3.67 (m, 1H, NCH), 3.54–3.45 (m, 6H, NCH$_2$, piperidine-N(CH$_2$)$_2$), 2.99–2.83 (m, 2H, CH$_2$CH$_2$O), 2.13–2.00 (m, 4H, NCH$_2$CH$_2$) 1.67–1.56 (m, 6H, piperidine-CH$_2$); $^{13}$C NMR (CDCl$_3$): δ168.22 (amide CO), 167.11 (CON), 154.38 (OCO), 149.96 (COCH$_3$), 148.57 (COCH$_2$CH$_2$), 127.74 (arom. CN), 125.94 (CCON), 114.19 (arom. CH), 110.44 (arom. CH), 95.02 (CCl$_3$), 86.38

(NCHCHOH), 74.96 (CH₂—TROC), 65.38 (CH₂CH₂O), 60.33 (NCH), 56.08 (OCH₃), 46.77 , 46.44, 42.75, 32.73, 28.60, 26.33, 25.48, 24.44 (various N—(X)CH₂), 23.05 (CH₂CH₂O); MS (EI) m/z (relative intensity): =579 (1), 577 (1), 331 (1), 278 (1), 246 (1), 192 (4), 140 (32), 113 (2), 112 (2), 97 (1), 84 (3), 77 (3), 70 (7), 69 (4), 55 (4), HRMS calcd. for $C_{24}H_{30}N_3O_7Cl_3$=579.1120 found 579.1066
3-(7-methoxy-5-oxy(11aS)-2,3,5,11a-tetrahydro-1H-benzo[e]pyrrolo[1,2-a][1,4]diazepin-8-yloxy)-1-piperidino-1-propanone (163)

To a solution of 162 (94 mg, 0.162 mmol) in THF (3 mL) was added 1 M ammonium acetate solution (2 mL) and the reaction mixture stirred. To the solution was added 10% Cd/Pb couple (0.81 mmol, 100 mg) and the reaction was stirred for 90 minutes. The reaction was filtered and diluted with ethyl acetate (20 mL). The solution was dried with magnesium sulphate and the solvent removed in vacuo. the product as then purified by flash chromatography eluting with 5% methanol in dichloromethane to give the compound as a white solid (yield 25 mg, 39%). ¹H NMR (CDCl₃): δ7.67 (d, 1H, J=4.4 Hz, N=CH), 7.51 (s, 1H, OCCHCN), 6.89 (s, 1H, MeOCCHC), 4.42 (t, 2H, J=7.14 Hz, CH₂CH₂O), 3.93 (s, 3H, OCH₃), 3.90–3.44 (m, 5H, NCH, NCH₂, piperidine-N(CH₂)₂), 2.73 (t, 2H, J=7.32 Hz CH₂CH₂O), 2.33–2.29 (m, 2H, C-ring CH₂), 2.11–2.02 (m, 2H, C-ring CH₂), 1.62–1.59 (m, 6H, piperidine CH₂), ¹³C NMR (CDCl₃): δ168.19 (amide CO), 164.66 (imine CH), 162.43 (CON), 150.52 (COCH₃), 147.61 (COCH₂CH₂), 140.70 (arom. CN), 120.31 (CCON), 111.51 (arom. CH), 110.58 (arom. CH), 65.44 (CH₂CH₂O), 56.11 (OCH₃), 53.73 (NCH), 46.70, 46.39, 42.69, 32.72, 29.62, 26.38, 25.52, 24.40 (various N—(X)CH₂), 24.19 (CH₂CH₂O); MS (EI): m/e (relative intensity): 385 (M⁺·, 6), 246 (8), 245 (3), 231 (3), 140 (15), 138 (5), 97 (5). 84 (3); HRMS calcd. for $C_{21}H_{27}O_4N_3$=385.2002, found 385.2058.

Example 4(c)
1,(2,3-dihydro-1H-indolyl)-3-(7-methoxy-5-oxy(11aS)-2,3,5,11a-tetrahydro-1H-benzo[e]pyrrolo[1,2-a][1,4]diazepin-8-yloxy)-1-propanone (165) (see FIG. 27)

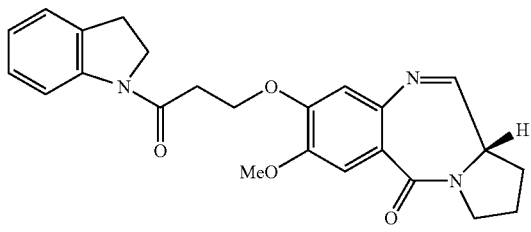

1-(2,3-Dihydro-1H-1-indolyl)-3-(11-hydroxy-7-methoxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-1-propanone (164)

To a solution of 159 (100 mg, 0.196 mmol) in DMF was added 1-(3-dimethylaminopropyl)-3-ethylcarbodiimide hydrochloride (44 mg, 0.23 mmol) and 4-(dimethylamino)pyridine (5 mg, 0.04 mmol) and the solution stirred for 1 h. To the reaction was added indoline (27.4 mg, 0.23 mmol) and the reaction stirred for a further 8 h. The solvent was then removed in vacuo and the compound purified by flash chromatography eluting with 5% methanol in dichloromethane to give the product as a yellow oil (yield=71 mg, 61%). ¹H-NMR (CDCl₃): δ1.99–2.12 (m, 4H, NCH₂CH₂CH₂), 3.20 (t, J=8.42 Hz, CH₂CH₂O), 3.71–5.00 (m, 4H, NCH₂, NCH, CHOH), 3.89 (s, 3H, OCH₃), 4.18–4.09 (m, 2H, indole-CH₂), 4.27 (d, 2H, J=11.90 Hz, indole-CH₂), 4.43 (t, J=6.23 Hz, CH₂CH₂O), 5.16 (d, 1H, J=11.91 Hz, TrOC—CH₂), 5.30 (s, 1H, OH), 5.66 (d, 1H, J=9.89 Hz, TrOC—CH₂), 7.20–6.93 (m, 5H, indole-CH, arom CH), 8.18 (d, 1H, J=8.25 Hz, indole-CH); ¹³C-NMR (CDCl₃): δ168.24 (CON), 166.97 (CON), 154.36 (OCO), 149.91, COCH₃), 148.65 (COCH₂CH₂), 132.14, 131.99 (indolyl ring junction), 128.61, 128.43 (indole-CH), 127.52, (arom. CN), 124.61 (CCON), 114.20 (arom. CH), 110.58 (arom. CH) 95.02 (CCl₃), 86.43 (NCHCHOH), 75.01 ((TrOC—CH), 64.89 (CH₂CH₂O), 60.13 (NCH), 56.11 (OCH₃), 48.11 (indole-CH₂), 46.43 (NCH₂), 35.64, 28.64, 27.97, (CH₂), 23.03 (CH₂CH₂O); MS (EI) m/z (relative intensity): =595 (M⁺1), 415 (1), 365 (1), 246 (2), 192 (13), 174 (11), 173 (7), 119 (17), 118 (10), 70 (13).

Iso-indoline (2,3,-dihydro-1H-isoindole)
¹H NMR (CDCl₃): δ7.22 (m, 4H, arom CH), 4.26 (s, 4H, CH₂), 4.08 (bs, 1H, NH), ¹³C NMR (CDCl₃): δ140.37, 140.36 (ring junctions), 127.15, 126.90, 122.60, 122.51, 122.33 (arom. CH), 52.31 (CH₂).

1,(2,3-dihydro-1H-indolyl)-3-(7-methoxy-5-oxy(11aS)-2,3,5,11a-tetrahydro-1H-benzo]pyrrolo[1,2-a][1,4]diazepin-8-yloxy)-1-propanone (165)

To a solution of 164 (71 mg, 0.116 mmol) in THF (3 mL) was added 1 M ammonium acetate solution (2 mL) and the reaction mixture stirred. To the solution was added 10% Cd/Pb couple (0.58 mmol, 72 mg) and the reaction was stirred for 90 minutes. The reaction was filtered and diluted with ethyl acetate (20 mL). The solution was dried with magnesium sulphate and the solvent removed in vacuo. The product as then purified by flash chromatography eluting with 5% methanol in dichloromethane to give the compound as a white solid (yield=26 mg, 54%). ¹H NMR (CDCl₃): δ7.66 (d, 1H, J=4.58 Hz, CH=N), 7.50 (s, arom. CH), 7.19 (m, 4H indolyl arom. CH), 6.91 (s, 1H, arom. CH), 4.48 (m, 2H, CH₂CH₂O), 4.18–4.19 (m, 2H, indolyl CH₂), 3.91 (s, 3H, OCH₃), 3.88–3.44 (m, 3H, NCH, +indolyl CH₂), 3.02 (t, 2H, J=6.6 Hz, CH₂CH₂O), 2.30–2.28 (m, 2H, NCH₂), 2.17–2.05 (m, 4H, NCH₂CH₂CH₂); ¹³C NMR (CDCl₃): δ168.31 (amide CO), 164.61 (CON), 162.47, (imine CH), 147.59 (COCH₂CH₂), 140.70 (arom. CN), 127.53, 124.59, 123.87, (indolyl arom. CH), 120.44 (CCON), 117.03 (indolyl arom. CH), 11.56 (arom. CH), 110.61 (arom. CH), 64.80 (COCH₂CH₂), 56.14 (COCH₃), 53.70 (NCH), 48.11, 46.69, 35.50, 29.60, 28.67, 28.00 (CH₂), 24.19 (COCH₂CH₂).

Example 4(d)
1,(2,3-dihydro-1H-2-isoindolyl)-3-(7-methoxy-5-oxy(11aS)-2,3,5,11a-tetrahydro-1H-benzo[e]pyrrolo[1,2-a][1,4]diazepin-8-yloxy)-1-propanone (167) (see FIG. 27)

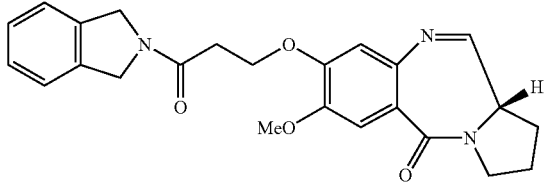

1-(2,3-dihydro-1H-2-isoindolyl)-3-(11-hydroxy-7-methoxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-1-propanone (166)

To a solution of 159 (100 mg, 0.196 mmol) in DMF was added 1-(3-dimethylaminopropyl)-3-ethylcarbodiimide hydrochloride (44 mg, 0.23 mmol) and 4-(dimethylamino)

pyridine (5 mg, 0.04 mmol) and the solution stirred for 1 h. To the reaction was added indoline (27.4 mg, 0.23 mmol) and the reaction stirred for a further 8 h. The solvent was then removed in vacuo and the compound purified by flash chromatography eluting with 5% methanol in dichloromethane to give the product as a yellow oil (yield =75 mg, 64%). $^1$H-NMR (CDCl$_3$): δ7.29–7.20 (m, 5H, isoindole arom.+arom.CH), 6.91 (s, 1H, arom CH), 5.66 (d, 1H, J=9.7 Hz, TrOC—CH$_2$) 5.30 (s, 1H, OH), 5.19 (d, 1H, J=9.7 Hz, TrOC—CH$_2$), 4.94 (m, 2H, isoindolyl CH$_2$), 4.79 (s, 2H, isoindolyl CH$_2$), 4.38 (t, 2H, J=6.42 Hz, CH$_2$CH$_2$O), 4.25, (d, 1H, J=11.91 Hz, C11-H), 3.81–3.40 (2H, NCH$_2$), 3.03–2.85 (m, 2H, CH$_2$CH$_2$O), 2.11–1.98 (m, 4H, NCH$_2$CH$_2$CH$_2$); $^{13}$C-NMR (CDCl$_3$): δ169.17 (CON), 167.02 (CON), 154.27 (OCO), 149.91 (COCH$_3$), 148.64 (COCH$_2$CH$_2$), 136.19, 136.11 (isoindolyl ring junction), 128.61, 127.88 (isoindolyl CH), 127.78 (arom. CN), 127.58, (CCON), 114.28 (arom. CH), 110.54 (arom. CH), 95.09 (CCl$_3$), 86.51 (NCHCHOH), 74.98 (TrOC—CH$_2$), 65.21 (CH$_2$CH$_2$O), 60.23 (NCH), 56.05 (OCH$_3$), 52.14, 52.81 (isoindolyl CH$_2$), 46.43, (NCH$_2$), 34.31, 29.68, 28.60 (NxCH$_2$), 23.03 (CH$_2$CH$_2$O); FABMS m/z (relative intensity): =612 (1), 596 (1), 594 (1), 279 (1), 192 (1), 174 (8), 146 (5), 118 (13), 91 (2), 55 (3). FABHRMS found compound minus OH i.e. C$_{27}$H$_{27}$N$_3$O$_6$Cl$_3$=595.1044
1,(2,3-dihydro-1H-2-isoindolyl)-3-(7-methoxy-5-oxy (11aS)-2,3,5,11a-tetrahydro-1H-benzo]pyrrolo[1,2-a][1,4] diazepin-8-yloxy)-1-propanone (167)

To a solution of 166 (75 mg, 0.122 mmol) in THF (3 mL) was added 1 M ammonium acetate solution (2 mL) and the reaction mixture stirred. To the solution was added 10% Cd/Pb couple (0.61 mmol, 76 mg) and the reaction was stirred for 90 minutes. The reaction was filtered and diluted with ethyl acetate (20 mL). The solution was dried with magnesium sulphate and the solvent removed in vacuo. The product was then purified by flash chromatography eluting with 5% methanol in dichloromethane to give the compound as a white solid (yield=42.6 mg, 83%). $^1$H NMR (CDCl$_3$): δ7.66 (d, 2H, J=4.39 Hz, N═CH), 7.48 (s, 1H, arom. CH), 7.30 (s, 4H, indolyl arom. CH), 6.89 (s, 1H, arom. CH), 4.48 (t, 3H, J=6.59 Hz, COCH$_2$CH$_2$), 3.84 (s, 3H, OCH$_3$), 3.81–3.69 (m, 2H, indolyl CH$_2$), 3.61–3.51 (m, 1H, NCH), 2.97 (p, 5H, J=6.9 Hz, CH$_2$CH$_2$O), 2.32–2.28 (m, 2H, NCH$_2$), 2.30–2.01 (m, 4H, NCH$_2$CH$_2$CH$_2$); $^{13}$C NMR (CDCl$_3$): δ169.29 (amide CO), 164.66 (imine CH), 162.52 (CON), 150.45 (COCH$_3$), 147.63 (COCH$_2$CH$_2$), 140.57, (arom. CN), 127.86, 127.56, 123.04, 122.62 (indolyl arom. CH), 120.38 (CCON), 111.52 (arom. CH), 110.53 (arom. CH), 65.16 (COCH$_2$CH$_2$), 56.06 (COCH$_3$), 53.73 (NCH), 52.16, 50.64, 46.70, 34.22, 29.57 (CH$_2$), 24.18 (COCH$_2$CH$_2$); MS (EI): m/e (relative intensity): 419 (M$^{+\cdot}$, 21), 416 (2), 415 (2), 246 (10), 245 (3), 231 (3), 174 (4); HRMS calcd. for C$_{24}$H$_{25}$O$_4$N$_3$=419.1845, found 419.1821.

Example 4(e)

Figure 25:
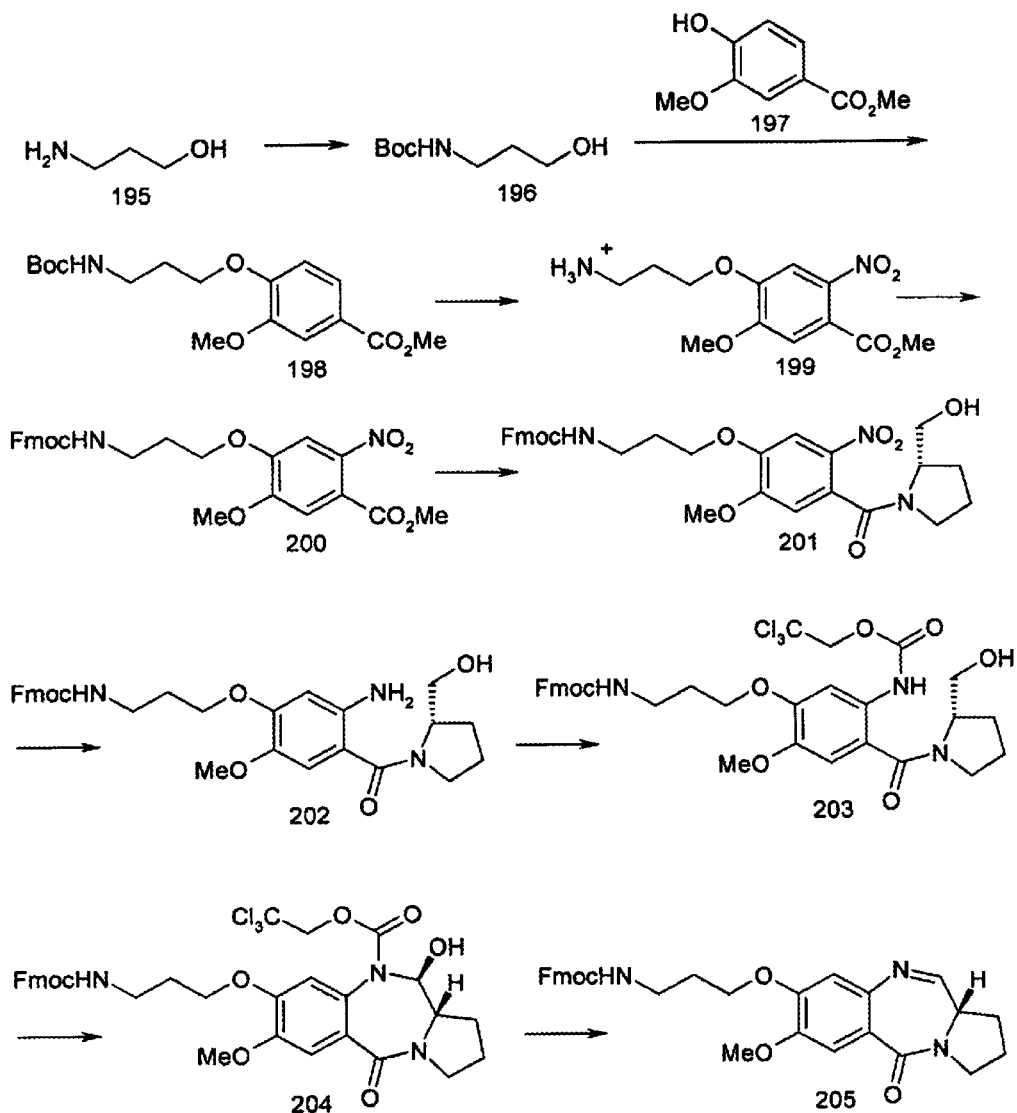
FIG. 25 is a synthesis route for a compound of formula IV.

Synthesis of (11aS) 8-(N-9-fluorenylmethoxycarbonyl) aminopropyloxy-7-methoxy-1,2,3,11a-tetrahydro-5H-pyrrolo[2,1-c][1,4]benzodiazepine-5-one (205) (See FIG. 25)

Synthesis of N-(tert-butoxycarbonyl)-3-hydroxypropylamine (196)

A solution of (Boc)$_2$O (25.0 g, 114.5 mmol) in anhydrous DCM (50 mL) was added dropwise to a stirred solution of 3-amino-1-propanol (195) (7.8 g, 104.5 mmol) in anhydrous DCM (100 mL), under a nitrogen atmosphere. The reaction mixture was allowed to stir for 12 hours, after which time TLC (50% pet-ether/EtOAc) revealed complete loss of starting material. The solution was diluted with Et$_2$O (150 mL) and washed with phosphate buffer 0.5 M, pH5.4 (2×70 mL), sat. aqueous NaHCO$_3$ (70 mL), brine (2×70 mL) and dried over MgSO$_4$. Excess solvent was removed by evaporation under reduced pressure to give a viscous colourless oil (196) (18.3 g, 100%). $^1$H NMR (270 MHz, CDCl$_3$): δ1.44 (s, 9H, CH$_3$), 1.67 (m, 2H, H2'), 3.26 (q, 2H, J=6.23 Hz, H3'), 3.65 (dd, 2H, J=5.86, 5.68 Hz, H1'), 3.78 (dt, 1H, J=6.04, 5.87 Hz, OH), 5.18 (br, 1H, NH); $^{13}$C NMR (67.8 MHz, CDCl$_3$): δ28.4 (CH$_3$), 32.6 (C2'), 37.1 (C3'), 59.3 (C1'), 79.4 (C$_{quater}$), 157.1 (C═O); MS (E/I) m/z (relative intensity): 176 (M$^{+\cdot}$, 30), 120 (100), 119 (31), 102 (49), 83 (33), 76 (67), 74 (36); HRMS (E/I) exact mass calcd for C$_8$H$_{17}$O$_3$N: m/e 175.1200, obsd m/e 175.1208; IR (Nujol$^\circ$) n: (cm$^{-1}$) 3355, 2976, 2936, 2878, 1810, 1694, 1531, 1455, 1392, 1366, 1278, 1253, 1173, 1072, 996, 914, 870, 781, 752, 638.

Synthesis of Methyl 4-[N-(tert-butoxycarbonyl)] aminopropyloxy-3-methoxybenzoate (198)

A solution of DEAD (18.3 g, 105.3 mmol) in freshly distilled THF (50 mL) was added dropwise to a mechanically stirred solution of triphenylphosphine (27.6 g, 105.3 mmol), methyl vanillate 197 (19.2 g, 105.3 mmol), and Boc-amino-1-propanol (196) (18.4 g, 105.3 mmol) in freshly distilled THF (250 mL), at 0° C. under a nitrogen atmosphere. After the DEAD was added the reaction mixture was allowed to stir at room temperature overnight and the progress of the reaction was monitored by TLC (50% EtOAc/pet-ether). The solvent was removed by evaporation under reduced pressure and the residue was triturated with Et$_2$O (300 mL) to precipitate some of TPO and diethyl hydrazinedicarboxylate, which were removed by filtration. The filtrate was washed with 1 N aqueous NaOH (150 mL), H$_2$O (2×150 mL), brine (2×150 mL) and dried over MgSO$_4$. Excess solvent was removed by evaporation under reduced pressure and the crude product (198) was purified by column chromatography (80% pet-ether/EtOAc) to afford a beige solid (30 g, 85%). mp=79–82° C.; $^1$H-NMR (CDCl$_3$, 270 MHz): δ1.46 (s, 9H, CH$_3$), 2.0–2.08 (m, 2H, H2'), 3.38 (dd, 2H, J=5.68, 6.04 Hz H3'), 3.90 (s, 3H, OCH$_{3ester}$), 3.93 (s, 3H, OCH$_{3ether}$), 4.14 (t, 2H, J=5.95 Hz, H3'), 5.58 (br, 1H, NH), 6.86 (d, 1H, J=8.42 Hz, H5), 7.55 (d, 1H, J=1.83 Hz, H2), 7.65 (dd, 1H, J=2.02, 8.42 Hz, H6); $^{13}$C-NMR (CDCl$_3$, 68.7 MHz): δ28.5 (C$_{prima}$), 29.2 (C2'), 38.9 (C3')) 52.0 (OCH$_{3ester}$), 55–8 (OCH$_{3ether}$), 68.1 (C1'), 78.9 (C$_{quater}$), 111.3 (C5), 112.0 (C2), 122.84 (C$_{arom}$), 123.5 (C6), 148.8 (C$_{arom}$), 152.1 (C$_{arom}$), 156.1 (NC═O), 166.8 (C═O); MS (E/I) m/z (relative intensity): 339 (M$^{+\cdot}$, 11), 266 (13), 182 (42), 151 (27), 102 (100); HRMS (E/I) exact mass calcd for C$_{17}$H$_{25}$NO$_6$: m/e 339.1682, obsd m/e 339.1733; IR (Nujol$^\circ$) n: (cm$^{-1}$) 3362, 2923, 2854, 1712, 1684, 1599, 1520, 1464, 1377, 1272, 1217, 1132, 1045, 1022, 872, 780, 762, 722.

Synthesis of Methyl 4-Aminopropyloxy-5-methoxy-2-nitrobenzoate (199)

The ester 198 (4.0 g, 11.8 mmol) was added in small portions to a stirred solution of 70% HNO$_3$ (2 mL acid/g of substrate) at room temperature and the reaction mixture was allowed to stir overnight. After 16 hours TLC (CHCl$_3$) revealed the complete loss of starting material. The reaction mixture was cooled in an ice bath, and 15 g of iced water was added, precipitating the product. The precipitate was collected by vacuum filtration and washed with small amount of iced water. The filtrate was cooled and a second crop of precipitate was collected by vacuum filtration and washed with iced water. The combined precipitate was dried in vacuo to provide compound 199 as a yellow solid, which was not purified further, but used directly in the subsequent reaction (2.3 g, 70%). mp=101–103° C.; $^1$H-NMR (CDCl$_3$/DMSO-d$_6$, 270 MHz): δ2.31 (m, 2H, H2'), 3.20 (br, 2H, H3'), 3.95 (s, 3H, OCH$_{3ether}$), 3.98 (s, 3H, OCH$_{3ester}$), 4.24 (t, 2H, J=5.95 Hz, H1'), 7.11 (s, 1H, H6), 7.49 (s, 1H, H3), 8.21 (s, 3H, NH); $^{13}$C-NMR (CDCl$_3$, 68.7 MHz): δ26.5 (C2'), 37.0 (C3'), 53.0 (OCH$_{3ester}$), 56.0 (OCH$_{3ether}$), 66.7 (C1'), 108.3 (C3), 111.0 (C6), 121.6 (C$_{arom}$), 140.9 (C2), 149.3 (C$_{arom}$), 152.6 (C$_{arom}$), 166.8 (C=O); MS (E/I) m/z (relative intensity): 284 (M$^+$·, 90), 237 (70), 227 (93), 196 (47), 181 (38), 137 (100), 122 (81), 93 (52), 79 (44); HRMS (E/I) exact mass calcd for C$_{12}$H$_{17}$N$_2$O$_6$: m/e 284.1008, obsd m/e 284.1018; IR (Nujol°) n: (cm$^{-1}$) 3472, 2937, 2911, 2855, 1733, 1532, 1516, 1462, 1377, 1292, 1224, 1143, 1052, 884, 812, 792, 773, 756, 724, 646.

Synthesis of Methyl 4-(N-9-fluorenylmethoxycarbonyl) aminopropyloxy-5-methoxy-2-nitrobenzoic acid (200)

A solution of 199 (3.9 g, 11.2 mmol) and KOH (1.9 g, 33.4 mmol) in aqueous methanol (77 mL, MeOH; 15 mL, H$_2$O) was heated at reflux for 90 minutes. At which time TLC (EtOAc/MeOH/TEA 100:10:1) revealed complete consumption of starting material. Excess MeOH was removed by evaporation under reduced pressure and the concentrate diluted with H$_2$O (20 mL). The aqueous solution was neutralised with conc. HCl, diluted with THF (100 mL) and sodium carbonate (2.9 g, 27.9 mmol) was added to adjust the solution to pH9. Fluorenylmethyl chloroformate (3.0 g, 11.6 mmol) was added portionwise over 30 minutes to the basic solution and the reaction mixture was allowed to stir for 12 hours. Excess THF was removed by evaporation under reduced pressure and the aqueous fraction was extracted with EtOAc (3×100 mL) to remove excess fluorenylmethyl chloroformate and related by-products. The aqueous layer was then acidified with conc. HCl and extracted again with EtOAc (3×100 mL). The organic phase was washed with H$_2$O (2×100 mL), brine (100 mL), dried over MgSO$_4$, and excess solvent was removed by evaporation under reduced pressure to afford 200 as a beige solid which was not purified further, but used directly in the subsequent reaction (4.7 g, 86%). mp=145–146° C.; $^1$H-NMR (CDCl$_3$, 270 MHz): δ1.81 (m, 2H, H2'), 3.43 (m, 2H, H3'), 3.78 (s, 3H, OCH$_3$), 4.08–4.23 (m, 3H, H1'+Fmoc CH), 4.49 (d, 2H, J=6.41, Fmoc CH$_2$), 5.70 (br, 1H, NH), 7.14 (s, 1H, H6), 7.26–7.41 (m, 5H, Fmoc$_{aryl}$+H3), 7.59 (d, 2H, J=7.51 Hz, Fmoc$_{aryl}$), 7.74 (d, 2H, J=7.15 Hz, Fmoc$_{aryl}$), 9.62 (s, 1H, CO$_2$H); $^{13}$C-NMR (CDCl$_3$, 68.7 MHz): δ28.8 (C2'), 39.1 (C3'), 47.2 (CH Fmoc), 56.4 (OCH$_3$), 66.3 (CH$_2$Fmoc), 68.5 (C1'), 107.9 (C3), 111.1 (C6), 120.0, 124.9, 127.1 and 127.7 (CH Fmoc$_{aryl}$), 128.0 (C$_{arom}$), 137.0 (C$_{arom}$), 141.3 (C Fmoc$_{aryl}$), 143.8 (C Fmoc$_{aryl}$), 148.2 (C$_{arom}$), 154.7 (C$_{arom}$), 156.8 (NC=O) 171.5 (CO$_2$H); MS (FAB) m/z (relative intensity): 493 (M$^+$· +1, 3), 297 (6), 271 (4), 191 (18), 180 (21), 179 (100), 178 (67), 165 (30), 102 (17), 93 (13); HRMS (FAB) exact mass calcd for C$_{26}$H$_{25}$N$_2$O$_8$ (M+H): m/e 493.1532, obsd m/e 493.1536; IR (Nujol°) n: (cm$^{-1}$) 1712, 1535, 1463, 1377, 1277, 1219, 1081, 970, 762, 722, 656.

Synthesis of (2S)-N-[4-(N-9-fluorenylmethoxycarbonyl) aminopropyloxy-5-methoxy-2-nitrobenzoyl)]pyrrolidine-2-methanol (201)

A catalytic amount of DMF (2 drops) was added to a solution of the nitrobenzoic acid 200 (8.0 g, 16.3 mmol) and oxalyl chloride (2.3 g, 17.9 mmol) in anhydrous DCM (120 mL), at room temperature under a nitrogen atmosphere. The reaction mixture was stirred for 16 hours and the resulting solution of acid chloride was cooled to 0° C. (ice/acetone) under a nitrogen atmosphere. A solution of pyrrolidinemethanol (1.8 g, 17.9 mmol) and DIPEA (4.6 g, 35.77 mmol) in anhydrous DCM (40 mL) was added dropwise over 30 minutes. Once the addition was complete, the reaction mixture was allowed to warm to room temperature. Stirring was continued for a further 2 hours, at which time TLC (95% EtOAc/MeOH) revealed complete reaction. The reaction mixture was washed with 1 N aqueous HCl (2×100 mL), H$_2$O (2×100 mL), brine (100 mL), and dried over MgSO$_4$. Excess solvent was removed by evaporation under reduced pressure to afford the crude compound as a brown oil. Purification by flash column chromatography (99% CHCl$_3$/MeOH) afforded 201 as a beige solid (5.6 g, 82%). [α]$^{20}_D$=−53.3° (c=1.03, CHCl$_3$); mp=78–81° C.; $^1$H-NMR (CDCl$_3$, 270 MHz): δ1.69–1.88 (m, 4H, H4+H3), 2.04–2.12 (m, 2H, H2'), 3.16 (m, 2H, H3'), 3.45 (m, 2H, H5), 3.81 (s, 3H, OCH$_3$), 3.86–3.91 (m, 2H, CH$_2$—OH), 4.08–4.24 (m, 3H, H1'+Fmoc CH), 4.38–4.48 (m, 3H, H2+Fmoc CH$_2$), 5.65 (br, 1H, NH), 6.78 (s, 1H, H6$_{arom}$), 7.27–7.42 (m, 5H, H3$_{arom}$+Fmoc$_{aryl}$), 7.61 (d, 2H, J=7.32 Hz, Fmoc$_{aryl}$), 7.76 (d, 2H, J=7.32 Hz, Fmoc$_{aryl}$); $^{13}$C-NMR (CDCl$_3$, 68.7 MHz): δ24.4 (C4), 28.4 (C3), 28.9 (C2'), 39.1 (C3'), 47.3 (CH Fmoc), 49.5 (C5), 56.6 (OCH$_3$), 60.4 (C2), 61.5 (CH$_2$—OH), 66.2 (CH$_2$ Fmoc), 68.5 (C1'), 108.0 (C3$_{arom}$), 108.9 (C6$_{arom}$), 120.0, 124.9, 127.0 and 127.7 (CH Fmoc$_{aryl}$), 128.0 (C$_{arom}$), 137.0 (C$_{arom}$), 141.3 (C Fmoc$_{aryl}$), 143.9 (C Fmoc$_{aryl}$), 148.2 (C$_{arom}$), 154.7 (C$_{arom}$), 156.5 (NC=O$_{carbamate}$) 171.2 (C=O$_{amide}$); MS (FAB) m/z (relative intensity): 576 (M$^+$· +1, 32), 191 (18), 179 (100), 165 (25), 102 (33); HRMS (FAB) exact mass calcd for C$_{31}$H$_{34}$N$_3$O (M+H): m/e 576.2268 obsd m/e 576.2257; IR (Nujol°) n: (cm$^{-1}$) 2626, 1714, 1615, 1576, 1520, 1452, 1434, 1333, 1276, 1218, 1147, 1059, 869, 818, 759, 742.

Synthesis of (2S)-N-[4-(N-9-fluorenylmethoxycarbonyl) amino propyloxy-5-methoxy-2-aminobenzoyl]pyrrolidine-2-methanol (202)

A mixture of the nitro compound 201 (5.5 g, 9.5 mmol) and SnCl$_2$/2H$_2$O (10.2 g, 45.4 mmol) in MeOH (100 mL) was heated at reflux and the progress of the reaction monitoring by TLC (95% CHCl$_3$/MeOH). After 2 hours excess MeOH was removed by evaporation under reduced pressure, the resulting residue was cooled (ice), and treated carefully with sat. aqueous NaHCO$_3$ (170 mL). The reaction mixture was diluted with EtOAc (170 mL) and after 16 hours stirring at room temperature the inorganic precipitate was removed by filtration through Celite. The organic layer was separated, washed with brine (150 mL), dried over MgSO$_4$, filtered and evaporated in vacuo to give a brown solid. Purification by flash column chromatography (95% CHCl$_3$/MeOH) afforded the pure amine 202 as a greyish-pink solid (4.3 g, 82%). [α]$^{20}_D$=−78.6° (c=1.02, CHCl$_3$); mp =83–86° C.; $^1$-NMR (CDC$_3$, 270 MHz): δ1.68–1.85 (m, 4H, H4+H3), 2.00–2.04 (m, 2H, H2'), 3.43–3.45 (m, 2H, H3'), 3.49–3.58 (m, 2H, H5), 3.67 (s, 3H, OCH$_3$), 3.72–3.78 (m, 2H, CH$_2$—OH), 4.04 (t, 2H, J=5.58 Hz, H1'), 4.22 (t, 1H, J=6.86 Hz, Fmoc CH), 4.41–4.44 (m, 3H, H2+Fmoc CH$_2$), 5.92 (br, 1H, NH), 6.23 (s, 1H, H3$_{arom}$), 6.71 (s, 1H, H6$_{arom}$), 7.27–7.41 (m, 4H, Fmoc$_{aryl}$), 7.62 (d, 2H, J=7.32 Hz, Fmoc$_{aryl}$), 7.75 (d, 2H, J=7.33 Hz, Fmoc$_{aryl}$); $^{13}$C-NMR (CDCl$_3$, 68.7 MHz): δ24.9 (C4), 28.6 (C3), 29.1 (C2'), 39.5 (C3'), 47.3 (CH Fmoc), 51.0 (C5), 56.6 (OCH$_3$), 60.4 (C2), 61.1 (CH$_2$—OH), 66.4 (CH$_2$ Fmoc), 68.0 (C1'), 102.0 (C3$_{arom}$), 111.6 (C6$_{arom}$), 120.0, 125.1, 127.0 and 127.7 (CH Fmoc$_{aryl}$), 128.0 (C$_{arom}$), 137.8 (C$_{arom}$), 141.3 (C Fmoc$_{aryl}$), 144.0 (C Fmoc$_{aryl}$), 148.2 (C$_{arom}$), 150.8 (C$_{arom}$), 156.6 (NC=O$_{carbamate}$), 171.9 (C=O$_{amide}$); MS (FAB) m/z (relative intensity): 546 (M$^+$· +1, 11), 445 (10), 191 (14), 179 (100), 166 (51), 102 (70); HRMS (FAB) exact mass calcd for C$_{31}$H$_{37}$N$_3$O$_6$ (M+H): m/e 546.2526 obsd m/e 546.2532; IR (Nujol°) n: (cm$^{-1}$) 1698, 1622, 1588, 1506, 1476, 1404, 1228, 1173.

Synthesis of (2S)-N-[4-(N-9-fluorenylmethoxycarbonyl)aminopropyloxy-5-methoxy-2-(N-2,2,2-trichloroethyloxycarbonyl)aminobenzoyl]pyrrolidine-2-methanol (203)

A solution of the amine 202 (1.1 g, 2.0 mmol) in DCM (40 mL) was cooled to 0° C. (ice/acetone bath) and treated with pyridine (0.33 mL, 0.3 g, 4.1 mmol). A solution of trichloroethyl chloroformate (0.27 mL, 0.41 g, 1.9 mmol) in DCM (10 mL) was added dropwise over 30 minutes to the stirred mixture. The reaction mixture was allowed to warm to room temperature and stirred for a further 3 hours, at which time TLC (EtOAc) revealed complete loss of starting material. The reaction mixture was washed with 1 N HCl solution (50 mL), $H_2O$ (2×50 mL), brine (50 mL), dried over $MgSO_4$, filtered and evaporated in vacuo. The crude residue was purified by flash column chromatography (98% $CHCl_3$/MeOH) to afford the pure trichloroethyl-carbamate 203 as a brown solid (1.1 g, 74%). $[\alpha]^{20}_D = -35.7°$ (c=0.87, $CHCl_3$); mp=54–57° C.; $^1$H-NMR ($CDCl_3$, 270 MHz): δ1.73–1.89 (m, 2H, H4), 2.00–2.04 (m, 2H, H2'), 2.18 (m, 2H, H3), 3.44–3.54 (m, 4H, H3'+H5), 3.72 (s, 3H, $OCH_3$), 3.81–3.90 (m, 2H, CH213 OH), 4.14–4.25 (m, 3H, H1'+Fmoc CH), 4.43–4.45 (m, 3H, Fmoc $CH_2$+H2), 4.76 (d, 1H, J=12.00 Hz, Troc $CH_2$), 4.83 (d, 1H, J=12.00 Hz, Troc $CH_2$), 5.89 (br, 1H, Fmoc NH), 6.82 (s, 1H, $H6_{arom}$), 7.26–7.41 (m, 4H, $Fmoc_{aryl}$), 7.62 (d, 2H, J=7.33 Hz, $Fmoc_{aryl}$), 7.69 (s, 1H, $H3_{arom}$), 7.75 (d, 2H, J=7.51 Hz, $Fmoc_{aryl}$), 9.06 (br s, 1H, Troc NH); $^{13}$C-NMR ($CDCl_3$, 68.7 MHz): δ25.0 (C4), 28.2 (C3), 28.9 (C2'), 39.5 (C3'), 47.3 (CH Fmoc), 51.4 (C5), 56.1 ($OCH_3$), 60.8 (C2), 66.0 ($CH_2$—OH), 66.3 ($CH_2$ Fmoc), 68.2 (C1'), 74.4 ($CH_2$ Troc), 95.3 ($C_{quat}$), 105.6 ($C3_{arom}$), 110.7 ($C6_{arom}$), 120.0, 125.1, 127.0 and 127.7 (C—$H_{aryl}$ Fmoc), 130.7 ($C_{arom}$), 141.3 ($C_{aryl}$ Fmoc), 144.0 ($C_{aryl}$ Fmoc), 144.5 ($C_{arom}$), 150.0 ($C_{arom}$), 152.1 (NC=$O_{carbamate}$ Troc), 156.5 (NC=$O_{carbamate}$ Fmoc), 170.4 (NC=$O_{amide}$); MS (FAB) m/z (relative intensity): 720 ($M^{+\cdot}$ +1, 2), 275 (4), 192 (29), 179 (100), 166 (13), 102 (48), 70 (10); IR (Nujol°) n: ($cm^{-1}$) 3338, 1742, 1714, 1599, 1520, 1464, 1378, 1215, 1170, 1119, 1024, 817, 759, 740.

Synthesis of (11S,11aS)-10-N-2,2,2-trichloroethyloxycarbonyl-11-hydroxy-8-(N-9-fluorenylmethoxycarbonyl)aminopropyloxy-7-methoxy-1,2,3,6,9,11a-hexahydro-5H-pyrrolo[2,1-c][1,4]benzodiazepin-5-one (204)

All glassware, needles and cannulae used for this procedure had been previously dried overnight in an oven, and were assembled while still warm and the enclosed vessel flooded with nitrogen and evacuated three times. Freshly distilled DCM (6.6 mL) was transferred to the reaction vessel and the temperature lowered to –45° C. (dry ice/$CH_3CN$) under a nitrogen atmosphere. Oxalyl chloride (1.0 mL of a 2 M solution in DCM, 2.0 mmol) was transferred to the reaction vessel, followed by the dropwise addition over 30 minutes of anhydrous DMSO (0.3 mL, 0.3 g, 3.9 mmol) in dry DCM (4.2 mL). After stirring at –45° C. for 30 minutes, a solution of the alcohol 203 (0.79 g, 1.1 mmol) dissolved in dry DCM (6.6 mL) was added dropwise over 50 minutes. The reaction mixture was allowed to stir at –45° C. for 45 minutes, the mixture was then treated dropwise with DIPEA (1.9 mL, 1.4 g, 10.8 mmol) in dry DCM (4.2 mL) over 30 minutes at –45° C. After 35 minutes, TLC (97% $CHCl_3$/MeOH) revealed complete consumption of starting material. The reaction mixture was allowed to warm to room temperature, diluted with DCM (30 mL), washed with 1 N HCl solution (30 mL), $H_2O$ (30 mL), brine (40 mL), dried over $MgSO_4$, filtered and evaporated in vacuo. Purification by flash column chromatography (97% $CHCl_3$/MeOH) furnished the protected carbinolamine 204 as a brown solid (0.48 g, 78%). $[\alpha]^{20}_D = +62.3°$ (c=0.83, $CHCl_3$); mp=76–79° C.; $^1$H-NMR ($CDCl_3$, 270 MHz) δ2.00–2.17 (m, 6H, H2+H2'+H1), 3.43–3.60 (m, 3H, H3'+H11a), 3.66–3.73 (m, 2H, H3), 3.78 (s, 3H, $OCH_3$), 4.20–4.32 (m, 4H, H1'+Fmoc CH+1H Troc $CH_2$), 4.44 (d, 2H, J=6.78 Hz, Fmoc $CH_2$), 5.25 (d, 1H, J=12.00 Hz, Troc $CH_2$), 5.65 (d, 1H, J=9.71 Hz, H11), 5.87 (br, 1H, NH), 6.82 (s, 1H, H6), 7.23–7.41 (m, 5H, H9+$Fmoc_{aryl}$), 7.61 (d, 2H, J=7.32 Hz, $Fmoc_{aryl}$), 7.75 (d, 2H, J=7.51 Hz, $Fmoc_{aryl}$); $^{13}$C-NMR ($CDCl_3$, 68.7 MHz) δ23.0 (C2), 28.6 (C1), 29.0 (C2'), 39.5 (C3, ), 46.4 (C3), 47.3 (CH Fmoc), 56.0 ($OCH_3$), 60.0 (C11a), 66.4 ($CH_2$ Fmoc), 68.3 (C1'), 74.9 ($CH_2$ Troc), 86.4 (C1), 95.1 ($C_{quat}$), 110.5 (C16), 113.8 (C9), 120.0, 125.1, 127.0 and 127.7 (C-$H_{aryl}$ Fmoc), 128.8 ($C_{arom}$) 130.9 ($C_{arom}$), 141.3 ($C_{aryl}$ Fmoc), 143.9 ($C_{aryl}$ Fmoc), 148.8 ($C_{arom}$), 149.9 ($C_{arom}$), 154.4 (NC=$O_{carbamate}$ Troc), 156.6 (NC=$O_{carbamate}$ Fmoc), 167.0 ($C4_{amide}$); MS (FAB) m/z (relative intensity): 702 (6), 275 (3), 192 (16), 179 (100), 165 (18), 102 (21), 70 (15); IR (Nujol°) n: ($cm^{-1}$) 3383, 2970, 2946, 2880, 2844, 1713, 1602, 1513, 1464, 1377, 1218, 1034, 908, 723, 645.

Synthesis of (11aS) 8-(N-9-fluorenylmethoxycarbonyl)aminopropyloxy-7-methoxy-1,2,3,11a-tetrahydro-5H-pyrrolo[2,1-c][1,4]benzodiazepin-5-one (205)

Yellow lead (II) oxide (500 mg, 2.24 mmol) was dissolved in 50% aqueous acetic acid (5 mL) and the solution added slowly to a vigorously stirred suspension of cadmium dust (2.5 g, 22.4 mmol) in de-ionised $H_2O$ (10 mL). The cadmium darkened as lead deposited on the surface and the clumps were broken up carefully. After 20 minutes, the solid couple was filtered under vacuum, washed with $H_2O$ and acetone and dried in vacuo. The lumps were crushed and stored in a closed vial.

The cadmium/lead couple (0.62 g, equiv. 0.56 g, 4.94 mmol Cd) was added in one portion to a solution of the Troc protected carbinolamine 204 (0.71 g, 0.99 mmol) and ammonium acetate (1.0 M, 9 mL) in THF (9 mL) at room temperature. The reaction mixture was stirred for 4 hours, during which time the reaction mixture became cloudy and opaque with a fluffy white precipitate. When reaction was complete as indicated by TLC (95% $CHCl_3$/MeOH), the solids were removed by filtration through Celite, and the THF removed by evaporation under reduced pressure. The filter cake was washed with several aliquots of EtOAc. The aqueous layer was extracted with EtOAc (3×15 mL), and the organic phase was dried over $MgSO_4$, filtered and evaporated in vacuo. Purification by flash column chromatography (97% $CHCl_3$/MeOH) furnished the target compound 205 as a brown solid (0.47 g, 90%) which was repeatedly evaporated in vacuo with $CHCl_3$ in order to obtain the N10—C11 imine form of the compound. $[\alpha]^{20}_D + 385.1°$ (c=0.47, $CHCl_3$); mp=73–76° C; $^1$H-NMR ($CDCl_3$, 270 MHz): δ2.04–2.06 (m, 4H, H2 +H1), 2.27–2.29 (m, 2H, H2'), 3.45–3.47 (m, 2H, H3'), 3.67–3.73 (m, 2H, H3), 3.80 (s, 3H, $OCH_3$), ), 3.84–4.23 (m, 4H, H11a+H1'+Fmoc CH), 4.43–4.46 (m, 2H, Fmoc $CH_2$), 5.92 (br, 1H, NH), 6.82 (s, 1H, H6), 7.29–7.41 (m, 4H, $Fmoc_{aryl}$), 7.5 (s, 1H, H9), 7.61 (d, 2H, J=7.14 Hz, $Fmoc_{aryl}$), 7.67 (d, 1H, J=4.40 Hz, $H11_{imine}$), 7.75 (d, 2H, J=7.33 Hz, $Fmoc_{aryl}$); $^{13}$C-NMR ($CDCl_3$, 68.7 MHz): δ22.3 (C2), 29.3 (C1), 29.6 (C2'), 39.6 (C3'), 46.7 (C3), 47.4 (CH Fmoc), 53.7 ($OCH_3$), 56.0 (C11a), 66.3 ($CH_2$ Fmoc), 68.3 (C1'), 110.2 (C6), 111.4 (C9), 120.0 (C—$H_{aryl}$ Fmoc), 120.5 ($C_{arom}$), 125.1, 127.0, and 127.7 (C—$H_{aryl}$ Fmoc), 140.6 ($C_{arom}$), 141.3 ($C_{aryl}$ Fmoc), 144.0 ($C_{aryl}$ Fmoc), 147.7 ($C_{arom}$), 150.3 ($C_{arom}$), 156.6 (NC=$O_{carbamate}$), 162.5 (C11), 164.5 ($C4_{amide}$); MS (FAB) m/z (relative intensity): 526 ($M^{+\cdot}$ 1, 15), 348 (7), 330

(4), 304 (4), 247 (12), 191 (15), 179 (100), 165 (17), 102 (40), 91 (10), 70 (13); HRMS (FAB) exact mass calcd for $C_{31}H_{32}N_3O$, (M+H): m/e 526.2264 obsd m/e 526.2198; IR (Nujol°) n: (cm$^{-1}$) 3327, 1729, 1690, 1601, 1509, 1427, 1261, 1217, 1023, 759, 740, 699.

Examples 5 to 8
Cytotoxicity Data
NCI In vitro Cytotoxicity Studies

The National Cancer Institute (NCI), Bethesda, Md., USA has available an in vitro cytotoxicity screen which consists of approximately 60 human tumour cell lines against which compounds are tested at a minimum of five concentrations each differing 10-fold. A 48 hour continuous exposure protocol is used, where cell viability or growth is estimated with an SRB protein assay.

Method

The test compounds were evaluated against approximately 60 human tumour cell lines. The NCI screening procedures were described in detail by Monks and co-workers (Monks, A et al., Journal of the National Cancer Institute, 1991, 83, 757). Briefly, cell suspensions were diluted according to the particular cell type and the expected target cell density (5000–40,000 cells per well based on cell growth characteristics), and added by pipette (100 μL) into 96-well microtitre plates. The cells were allowed a preincubation period of 24 hours at 37° C. for stabilisation. Dilutions at twice the intended test concentration were added at time zero in 100 μL aliquots to the wells. The test compounds were evaluated at five 10-fold dilutions ($10^{-4}$, $10^{-5}$, $10^{-6}$, $10^{-7}$ and $10^{-8}$ μM). The test compounds were incubated for 48 hours in 5% $CO_2$ atmosphere and 100% humidity. The cells were then assayed using the sulphorhodamine B assay. A plate reader was used to read the optical densities and a microcomputer processed the readings into $LC_{50}$ values, which is the dosage required to kill half of the cells.

The results presented in examples 5 to 8 are $LC_{50}$ values which are below 10 μM, which is taken to be the dividing line between cytotoxicity and non-cytotoxicity.

NCI Hollow Fibre Assay for Preliminary in vivo Testing

The Biological testing Branch of the Developmental Therapeutics Program of the NCI has adopted a preliminary in vivo screening tool for assessing the potential anticancer activity of compounds identified by the large scale in vitro cell screen. For these assays, human tumour cells are cultivated in polyvinylidene (PVDF) hollow fibres, and a sample of each cell line is implanted into each of two physiologic compartments (intraperitoneal and subcutaneaous) in mice. Each test mouse received a total of 6 fibres (3 intraperitoneally and 3 subcutaneously) representing 3 distinct cancer cell lines. These mice are treated with potential antitumour compounds at each of 2 test doses by the intraperitoneal route using a QD×4 treatment schedule. Vehicle controls consist of 6 mice receiving the compound diluent only. The fibre cultures are collected on the day following the last day of treatment. To assess anticancer effects, the viable cell mass is determined for each of the cell lines using a formazyn dye (MTT) conversion assay. From this, the % T/C can be calculated using the average optical density of compound treated samples divided by the average optical; density of the vehicle controls. In addition, the net increase in cell mass can be determined for each sample, as a sample of fibre cultures are assessed for viable cell mass on the day of implantation into mice. Thus, the cytostatic and cytocidal capacities of the test compound can be assessed.

Generally, each compound is tested against a minimum of 12 human cancer cell lines. This represents a total of 4 experiments since each experiment contains 3 cell lines. The data are reported as % T/C for each of the 2 compound doses against each of the cell lines with separate values calculated for the intraperitoneal and subcutaneous samples.

Compounds are selected for further in vivo testing in standard subcutaneous xenograft models on the basis of several hollow fibre assay criteria. These include: (1) a % T/C of 50 or less in 10 of the 48 possible test combinations (12 cell lines×2 sites×2 compound doses); (2) activity at a distance (intraperitoneal drug/subcutaneous culture) in a minimum of 4 of the 24 possible combinations; and/or (3) a net cell kill of 1 or more of the cell lines in either implant site. To simplify evaluation, a points system has been adopted which allows rapid evaluation of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score of 20, a SC score of 8 or a net cell kill of one or more cell lines are referred for xenograft testing. This comparison indicated that there was a very low probability of missing an active compound f the hollow fibre assay was used as the initial in vivo screening tool. In addition to these criteria, other factors (e.g. unique structure, mechanism of action) may result in referral of a compound for xenograft testing without the compound meeting these criteria.

NCI Human Xenograft Studies

These are carried out on nude athymic mice with a disabled immune system. The human tumour tissue to be tested is implanted in their flanks, and whilst the control mouse receives no treatment, the others are subjected to varying doses of the test compound, which is administered intraperitoneally. The results are expressed as the toxicity of the compound, the amount of tumour growth, and the inhibition of growth.

Example 5
In vitro Cytotoxicity of Compounds of Formula I

Figure 28:
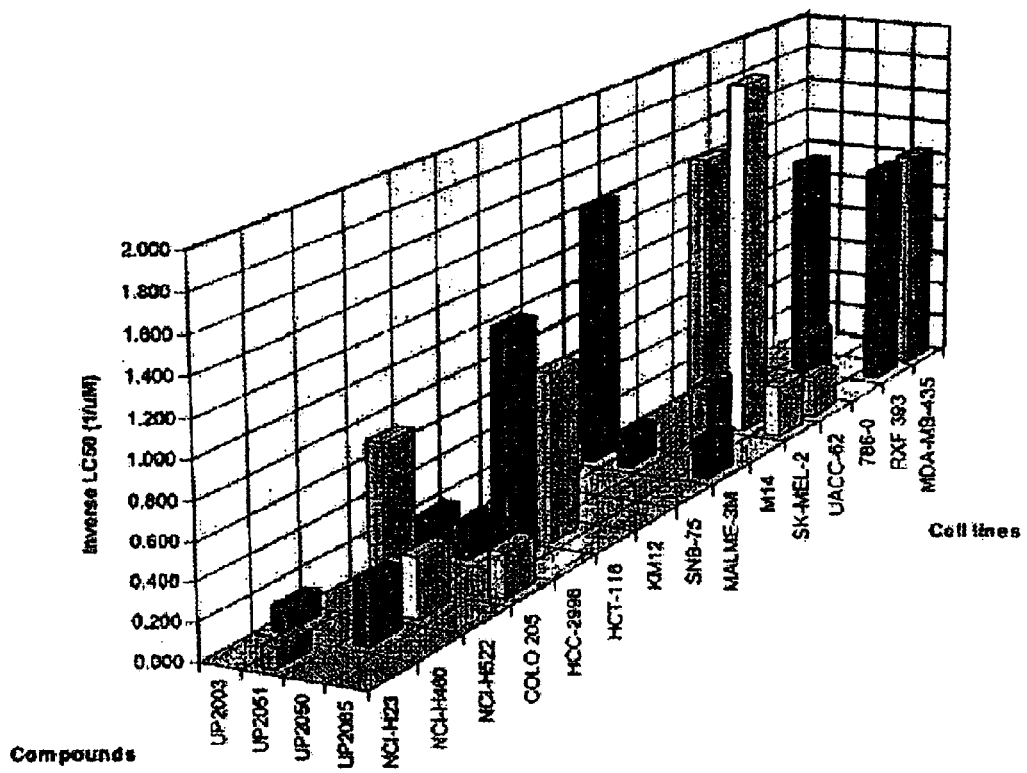
FIGS. 28 to 31 are graphs illustrating the cytotoxicity results of examples 5 to 8 respectively.

Some of the compounds synthesised in example 1, were subjected to the NCI In Vitro Cytotoxicity study. The results ($LC_{50}$; μM) are set out below, and are illustrated in FIG. 28.

| TUMOUR TYPE | CELL-LINE DESIGNATION | UP2003 (24) | UP2051 (31) | UP2052 (33) | UP2065 (42) |
|---|---|---|---|---|---|
| | | $LC_{50}$(μM) | | | |
| Lung | NCI-H23 | | 9.3 | | |
| | NCI-H460 | 7.6 | | 3.0 | |
| | NCI-H522 | | | 3.1 | |
| Colon | COLO 205 | 1.4 | | | 4.0 |
| | HCC-2998 | 5.2 | 5.2 | 0.8 | |
| | HCT-116 | | | 1.1 | |
| | KM12 | 9.5 | | | |
| CNS | SNB-75 | 6.0 | | | |
| Melanoma | MALME-3M | 0.7 | 5.1 | | 4.7 |
| | M14 | | | 2.7 | |
| | SK-MEL-2 | | 7.6 | 0.5 | 3.5 |
| | UACC-62 | 0.7 | | | |
| Renal | 786-0 | | | 3.0 | |
| | RXF 393 | | 0.8 | | 0.8 |
| Breast | MDA-MB-435 | | | | 0.8 |

Of the compounds tested, the above showed cytotoxicity against human lung, colon, CNS, melanoma, renal and breast cancer cell lines. Replacing the C-8 benzyloxy group in UP2003 (24) with a methoxy substituent (UP2065, 42) significantly changed the cytotoxicity profile, activity was lost against lung, CNS, and colon cancer cell lines (only reduced activity against Colo 205 remained). However, additional cytotoxic activity was gained against the melanoma cell lines SKMEL-2 and MALME-3M, the renal cell line RXF-393 and the breast cell line MDA-MB-435. Reduction of the ester moiety in UP2003 (24) to afford the alcohol UP2052 (33) resulted in increased activity in the lung cancer cell line NCI-460 and the colon cell line HCC-2998. Additional activity was registered against the lung cell line NC1—H522, the colon cell line HCT-116, the melanoma cell line M14 and the renal cancer cell line 786–0. Interestingly, the acetylated analogue UP2051 (31) exhibited attenuated or abolished activity in these cell lines (e.g. 7.6 µM verses 0.5 µM for UP2052 in the melanoma SK-MEL-2 cell line.

Example 6(a)

In vitro Cytotoxicity of Compounds of Formula II

Figure 29:
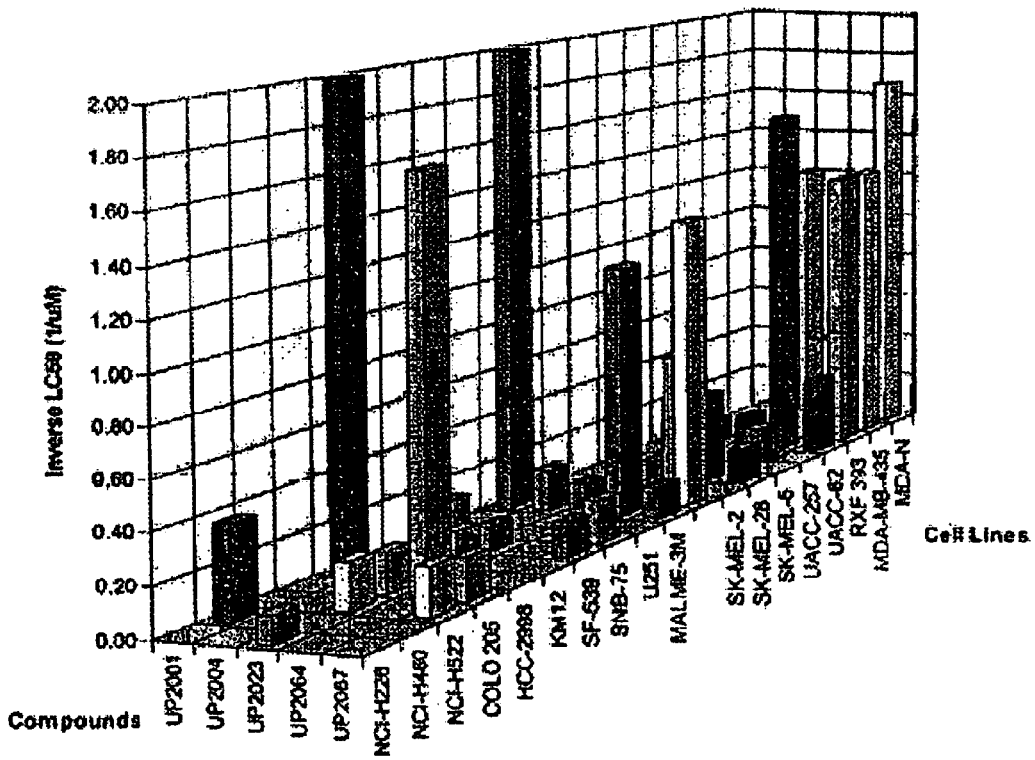

Some of the compounds synthesised in example 2, were subjected to the NCI In Vitro Cytotoxicity study. The results ($LC_{50}$; µM) are set out below, and are illustrated in FIG. 29.

| TUMOUR TYPE | CELL-LINE DESIG-NATION | UP2064 (74) | UP2001 (80) | UP2004 (70) | UP2023 (64) | UP2067 (172) |
|---|---|---|---|---|---|---|
| | | | $LC_{50}(\mu M)$ | | | |
| Lung | NCI-H23 | | | 7.6 | | |
| | NCI-H226 | | | | 9.1 | |
| | NCI-H460 | 2.7 | | | | |
| | NCI-H522 | | | | 5.2 | 5.0 |
| Colon | COLO 205 | 0.6 | | 3.9 | 5.8 | 5.8 |
| | HCC-2998 | | 0.099 | 5.5 | 7.0 | |
| | KM12 | | | | 7.1 | |
| CNS | SF-539 | | | | 9.4 | 6.8 |
| | SNB-75 | | 7.5 | | | 5.4 |
| Melanoma | MALME-3M | 0.9 | 0.073 | | 7.8 | 7.4 |
| | M14 | | | | | 0.8 |
| | SK-MEL-2 | 1.7 | | | 7.4 | |
| | SK-MEL-28 | 2.6 | | | 8.4 | 6.6 |
| | SK-MEL-5 | | | 7.8 | 6.0 | |
| | UACC-257 | 7.4 | | 7.3 | | |
| | UACC-62 | 0.6 | 0.077 | 5.3 | 7.2 | 3.0 |
| Renal | RXF 393 | 0.8 | | | 6.1 | 0.8 |
| Breast | MDA-MB-435 | 2.3 | | | 7.6 | 0.8 |
| | MDA-N | | | 9.0 | 6.6 | 0.6 |

Of the compounds tested, the above listed exert their cytotoxic effect ($LC_{50}$) most strongly in the Lung, Colon, CNS. Melanoma, Renal and Breast cell line panels. Within the group, it is apparent that exchanging a C-8 benzyloxy substituent (UP2004, 70) for a methoxy group (UP2064, 74) results in increased activity in the Melanoma panel. The methoxy analogue is more potent and acts against a greater number of cell lines. The methoxy analogue also exhibits improved activity against the colon cancer cell line Colo 205 and, in addition, the methoxy analogue exhibits activity against the renal cell line RXF-393 which is not observed with the benzyloxy compound. Replacing the electron rich dimethoxy A-ring with an iodo substituted aromatic ring (UP2023, 64) resulted in slight attenuation of activity in some cell lines, but the analogue showed activity against a wider spread of cell lines (i.e. 5 melanoma cell lines against only 3 for the benzyloxy analogue). Changing the nature of the C-ring ex-unsaturation from an alkene to a ketone (UP2067, 172) lead to additional activity against the breast cancer cell line MDA-MB-435, renal cell line RXF-393, the melanomas MALME-3M, M14, SKMEL-28, the CNS cancers SF-539 and SNB-75 and against the lung cell line NCI-H522.

The PBD dimer UP2001 (80) exhibited potent and selective cytotoxicity activity against the lung cancer cell line NCI-H460, the colon cell line HCC-2998, the CNS cancer cell line SNB-75 and the melanoma cell lines MALME-3M (very potent, 0.08 µM) and UACC-62 (very potent, 0.07 µM), which may be attributable to its ability to cross link DNA.

Example 6(b)

Hollow Fibre Assay on Compounds of Formula II

Two of the compounds tested underwent the NCI Hollow Fibre Assay, and the results are presented below.

| | UP2001 (80) | UP2004 (70) |
|---|---|---|
| IP score | 40 | 8 |
| SC score | 14 | 10 |
| Total score | 54 | 18 |
| Cell Kill | Y | N |

UP2001 (80) and UP2004 (70) were subjected to the NCI Hollow Fibre assay described above. UP2001 has been selected for xenograft studies based on its combined IP+SC score (54) which was greatly in excess of 20, and its SC score which was higher than 8. UP2004 has been selected on the basis of its SC score, it being higher than 8.

Example 6(c)

Human Xenograft Studies on Compound 80 (UP 2001)

Human tumour xenograft studies on UP2001 were performed by the Biological Testing Branch of the NCI as described above.

Athymic nude mice bearing MDA-MB-435 xenografts (human mammary tumour), Ovcar-3 (human ovarian tumour), UACC-62 (human melanoma) or OVCAR-5 (human ovarian tumour) were treated at doses of 0.67 (high), 0.45 (middle) and 0.3 (low) mg/kg/injection given once every 4th day for a total of 3 doses (6 mice per dose level with 20 controls).

UP2001 (80) was evaluated by measuring the toxicity of the drug and its ability to retard tumour growth.

| | Toxicity | | | % T/C | | | % Growth Delay | | |
|---|---|---|---|---|---|---|---|---|---|
| Tumour | High | Mid | Low | High | Mid | Low | High | Mid | Low |
| MDA-MB-435 | 3/6 | 1/6 | 2/6 | toxic | 3 | 3 | 41 | 41 | 41 |
| OV-CAR-3 | 0/6 | 0/6 | 0/6 | 7 | 20 | 46 | 73 | 73 | 9 |
| UACC-62 | 0/6 | 0/6 | 0/6 | 22 | 28 | 67 | 43 | 43 | 43 |
| OV-CAR-5 | 0 | 0/6 | 0/6 | 52 | 45 | 38 | 16 | 28 | 32 |

Toxicity represents the number of mice which died as a result of treatment. % T/C represents the width of the tumours in the "test" mice (T) (as measured with calipers) compared to control untreated mice (C) and presented as a percentage. % Growth Delay represents the increase in the amount of time taken for the tumors to reach an arbitrary size of 250 mg.

In the MDA-MB-435 xenografts UP2001 restricted tumour growth in treated mice to only 3% of the tumour growth observed in the control population. In addition, a 41% delay in the time taken to reach tumour mass of 250 mg was also observed. Some toxicity towards the hosts was observed even at low dose.

A good dose response was observed for UP2001 (80) in the Ovcar-3 xenografts. At the high dose, tumour growth in treated subjects was only 7% of that observed in the control population. At the medium dose the value was 20% and at the low dose the tumours in the treated mice were 46% of the size of the control tumours.

At the high dose a 73% growth delay in reaching a tumour mass of 250 mg was observed. No mice died as a result of exposure to UP2001 (80).

A similar dose response for tumour growth was observed in the UACC-62 xenografts for UP2001 (80). At the high dose treated tumours were 22% of the size of the control tumours. At the medium dose treated tumours were 28% of the size of the control tumours and at the low dose treated tumours were 67% of the size of the control tumours. Again no mice died as a result of exposure to UP2001 (80).

Results for the human ovrian tumour OVAR-5 were less clear cut; approximately 50% tumour size reduction was observed and growth delay was observed but activity appeared to be higher at lower concentrations. However, again, no mice died as a result of exposure to UP2001 (80).

UP2001 (80) was also evaluated against the human CNS tumour SF-295. Athymic nude mice bearing SF-295 were treated at doses of 0.40, 0.27 and 0.18 mg/Kg by injection given intravenously once daily for a total of 5 doses.

| Toxicity | | | % T/C | | | Tumour Free | | |
|---|---|---|---|---|---|---|---|---|
| High | Med | Low | High | Med | Low | High | Med | Low |
| 2/6 | 1/6 | 2/6 | 0% | 0% | 0% | 4/4 | 5/5 | 3/4 |

UP2001 (80) displayed curative properties against SF-295 xenografts. At high and medium doses all the surviving mice were tumour free on day 27 of the experiment. At the lower dose 3 out of 4 mice were tumour free on day 27. Some toxicity was associated with the treatment, 2 mice dying at the high dose, 1 at the medium dose and two at the low dose. The higher intensities of the injection schedule may be reflected in the higher mortality observed.

Example 7
In vitro Cytotoxicity of Compounds of Formula III

Figure 30:
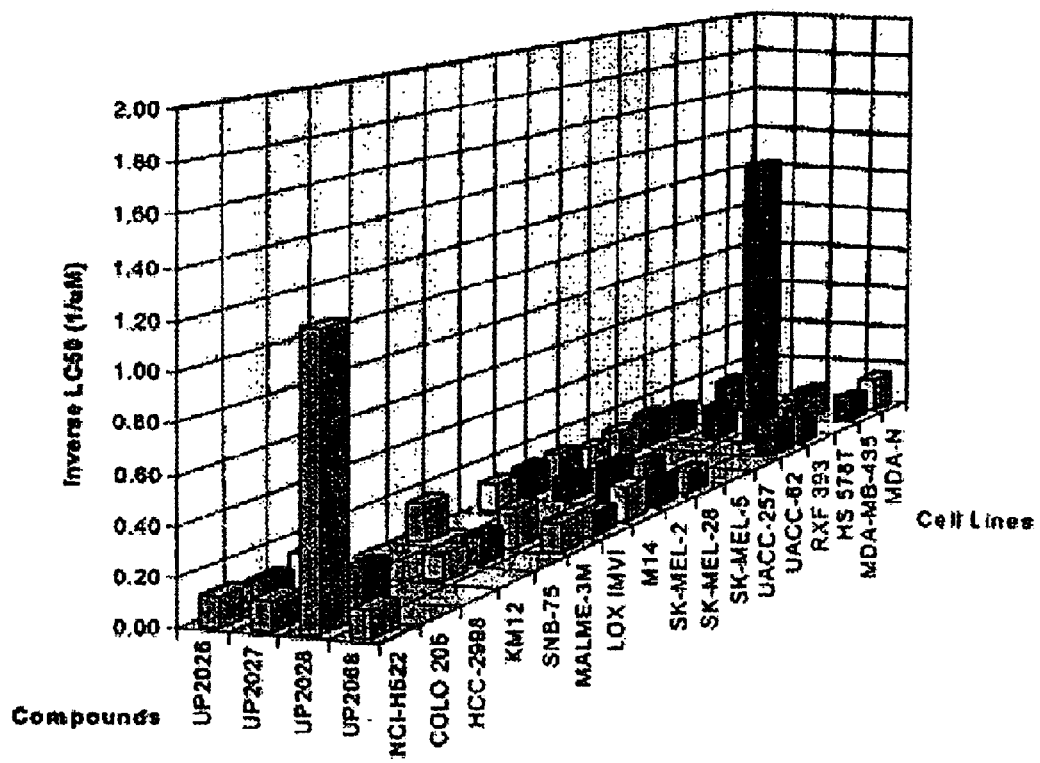
Figure 31:
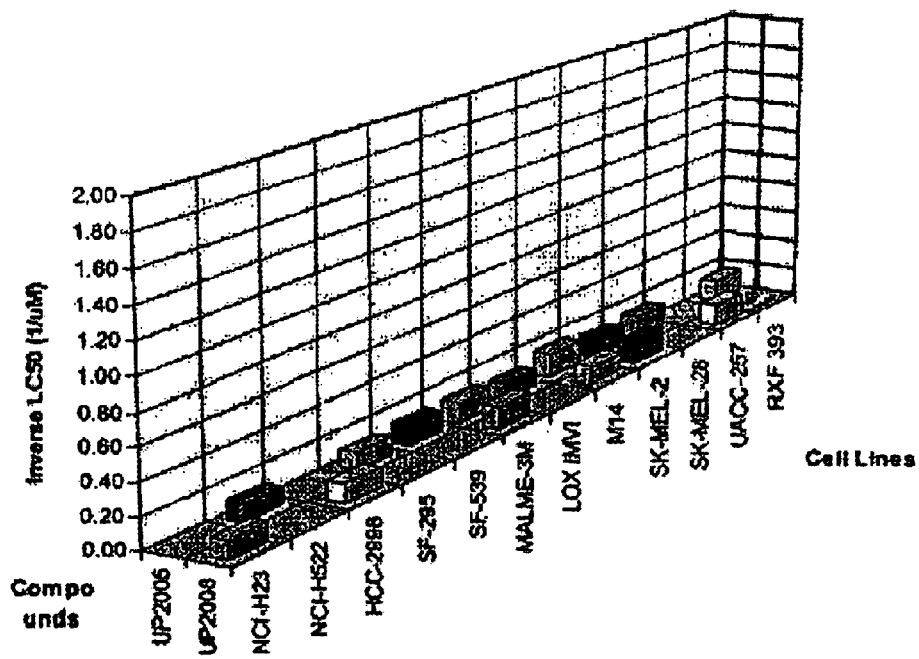

All of the compounds synthesised in example 3, were subjected to the NCI In Vitro Cytotoxicity screen. The results (LC50;μM) are set out below, and are illustrated in FIG. 30.

| TUMOUR TYPE | CELL-LINE DESIGNATION | UP2026 (136) | UP2027 (138) | UP2028 (151) | UP2068 (96) |
|---|---|---|---|---|---|
| | | LC$_{50}$(μM) | | | |
| Lung | NCI-H522 | 7.8 | 8.0 | 0.8 | 8.5 |
| Colon | COLO 205 | 8.8 | | 5.0 | |
| | HCC-2998 | 6.4 | | | |
| | KM12 | | | 8.8 | |
| CNS | SNB-75 | | | 8.2 | |
| Melanoma | MALME-3M | 6.1 | | 5.7 | 8.3 |
| | LOX IMVI | | | | 9.7 |
| | M14 | 7.8 | | | 6.5 |
| | SK-MEL-2 | 7.4 | 9.5 | 5.4 | 8.1 |
| | SK-MEL-28 | 7.1 | | 8.1 | 9.6 |
| | SK-MEL-5 | 9.0 | | | |
| | UACC-257 | 7.7 | | | |
| | UACC-62 | 6.6 | | | |

-continued

| TUMOUR TYPE | CELL-LINE DESIGNATION | UP2026 (136) | UP2027 (138) | UP2028 (151) | UP2068 (96) |
|---|---|---|---|---|---|
| Renal | RXF 393 | 7.6 | 6.6 | 0.7 | 6.3 |
| Breast | HS 578T | | | 9.2 | |
| | MDA-MB-435 | 6.3 | | 7.2 | 8.3 |
| | MDA-N | | | | 6.3 |

The C-7-phenyl substituted compound UP2026 (136) showed cytotoxicity against cell lines in the human lung, colon, melanoma, renal and breast cancer panels. Interestingly, unlike other PBDs the molecule was inactive in the CNS cell line panel. However, UP2026 (136) was active against nearly all the members of the melanoma panel. Inclusion of a methoxy group in the C7 aryl moiety (138) resulted in increased selectivity as cytoxicity was only observed in the lung cell line NCI-H522, the melanoma cell line SKMEL-2 and the renal cell line RXF-393. Introduction of a nitro group at C7 completely abolished cytotoxic activity, however, it seems likely that activity would be restored once the nitro group is reduced to an amine; in this way UP2029 (140) might prove to be a useful prodrug with potential use in treating large hypoxic tumours. The C8 amino substituted PBD (UP2028, 151) showed good activity in the lung, colon, CNS, melanoma, renal and breast cell line panels. On the other hand the trimethoxy PBD (UP2068, 96) was only active in the lung, melanoma, renal and breast cell line panels.

Example 7
In vitro Cytotoxicity of Compounds of Formula III

All of the compounds synthesised in example 3, were subjected to the NCI In Vitro Cytotoxicity screen. The results (LC50; μM) are set out below, and are illustrated in FIG. 30.

| TUMOUR TYPE | CELL-LINE DESIGNATION | UP2005 (161) | UP2008 (167) |
|---|---|---|---|
| | | LC$_{50}$(μM) | |
| Lung | NCI-H23 | | 8.9 |
| | NCI-H522 | 8.7 | |
| Colon | HCC-2998 | | 8.1 |
| CNS | SF-295 | 8.8 | |
| | SF-539 | 7.7 | |
| Melanoma | MALME-3M | 7.5 | 6.8 |
| | LOX IMVI | 9.2 | |
| | M14 | 6.2 | 8.4 |
| | SK-MEL-2 | 7.6 | 6.5 |
| | SK-MEL-28 | 6.5 | |
| | UACC-257 | | 7.1 |
| Renal | RXF 393 | 6.8 | |

Two of the four C8 PBD amides, UP2005 (161) and UP2008 (167), demonstrated cytotoxicity (LC$_{50}$) in the NCI assay. UP2005 (161) showed selectivity for the lung, CNS, melanoma and renal cancer in panels. The compound was particularly active in the melanoma panel exhibiting cytotoxicity against 5 out of the 8 melanoma cell lines. UP2008 (167) revealed a slightly different profile being active in the lung, colon, and melanoma panels. Again the molecule was particularly active in the melanoma panel.

Example 9
Further Results for PBD dimer SJG-136 (UP2001, 80)

The compound synthesized in example 2(d) (SJG-136, 80) underwent some further assays.

The first assay, which is described in G. B. Jones, et al., *Anti-Cancer Drug Des.*, 1990, 5, 249, which is incorporated herein by reference, determines the effect of the test compound on the helix melting temperature of DNA. This assay is designed to give an indication of the strength and extent of cross-linking of the DNA strands by the test compound (i.e. a measure of the stabilisation of the DNA upon ligand binding).

The melting temperature was determined for a 1:5 molar ratio of [ligand] [DNA], where the calf thymus DNA concentration is 100 mM in aqueous sodium phosphate buffer (10 mM sodium phosphate +1 mM EDTA, pH7.00±0.01). For calf thymus DNA at pH7.00±0.01, the melting temperature is 67.83±0.06° C. (mean value from 30 separate determinations).

For a 1:5 molar ratio of [PBD]:[DNA], the PBD dimer 80 elevates the helix melting temperature ($\Delta T_m$) of calf thymus DNA by an unprecedented 33.60C after incubation for 18 hours at 37° C. Under identical conditions, the C-ring-unsubstituted dimer DSB-120:

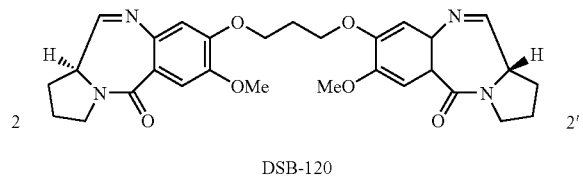

DSB-120 provides a $\Delta T_m$ of 15.1° C., demonstrating the extraordinary effect of introducing C2/C2'-unsaturation. In common with other PBD dimers, 80 exerts most of its effect upon the GC-rich or high temperature regions of the DNA melting curves. In a similar fashion to DSB-120, it provides some 60–80% of its stabilising effect without prior incubation, suggesting a kinetic effect in the PBD reactivity profile. However, the comparative $\Delta T_m$ curves show that, on a concentration basis alone, SJG-136 is $\geq$10-fold more effective than DSB-120. Even at a [PBD]:[DNA] molar ratio of 1:100, SJG-136 still exhibits significantly better DNA binding affinity than the monomer tomaymycin at a 1:5 [PBD] [DNA] molar ratio.

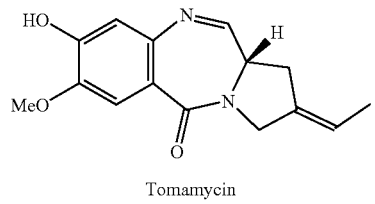

Tomamycin

The results for a [PBD]:[DNA] ratio of 1:5 are summarised in the table below (All $\Delta Tm$ values ±0.1–0.2° C.)

| Compound | Induced $\Delta T_m$ (° C.) after incubation at 37° C. for | | |
|---|---|---|---|
| | 0 h | 4 h | 18 h |
| SJG-136 (80) | 25.7 | 31.9 | 33.6 |
| DSB-120 | 10.2 | 13.1 | 15.1 |
| Tomamycin | 0.97 | 2.38 | 2.56 |

The data presented in the above table show that SJG-136 (80) is the most potent DNA-stabilising agent known to date according to this particular assay.

The second assay determined the cytotoxicity of SJG-136 (80) in the human ovarian carcinoma cell line A2780 and its cisplatin-resistant subline A2780cis R, and compared this data with the cytotoxicity of the related dimer DSB-120 (see above) and Cisplatin. Relative to the parental line, the A2780cis R subline is known to have elevated GSH levels, an increased level of repair of DNA-cisplatin adducts, and a decreased ability to uptake cisplatin (M. Smellie, et al., *Br. J. Cancer*, 1994, 70, 48).

The results, which were obtained by incubating the cells with the compounds for 96 hours at 37° C., and assessing the cell number using Sulforhodamine B, are presented in the table below:

| | $IC_{50}$[a] (µM) for | | |
|---|---|---|---|
| | A2780 | A2780cis[R] | RF[b] |
| SJG-136 (80) | 0.000023 | 0.000024 | 1.1 |
| DSB-120 | 0.0072 | 0.21 | 29.2 |
| Cisplatin | 0.265 | 8.4 | 32 |

[a]Dose of compounds required to inhibit cell growth by 50% compared with control
[b]RF is the resistance factor ($IC_{50}$ resistant/parent)

The $IC_{50}$ value for 80 in the A2780 cell line is only 23 pM, representing a 320-fold increase in cytotoxicity compared to DSB-120 ($IC_{50}$=7.2 nM). More interestingly, whereas DSB-120 has a reduced potency in the cisplatin-resistant A2780cis R ($IC_{50}$=0.21 mM), SJG-136 is almost 9,000-fold more potent in this cell line with a similar $IC_{50}$ value (24 pM) to that in the normal A2780, giving a Resistance Factor of 1.1. The fact that both DSB-120 and cisplatin give Resistance Factors of 29.2 and 32, respectively, across this pair of cell lines suggests that SJG-136 may have potential in the treatment of cisplatin-refractory disease.

Example 10
Ovarian Carcinoma Cytotoxicity Assay

Compounds of the invention (and Anthramycin as a comparison) were evaluated for their cytotoxic activity in ovarian cell lines by Dr Lloyd R. Kelland's group at The Institute of Cancer Research, Sutton, UK. The five cell lines investigated were SKOV-3, A2780/A2780cisR and CH1/CH1cisR (cisR denotes that the cell line is resistant to cisplatin).

Single viable cells were seeded in growth medium (160 L) in 96-well microtitre plates and allowed to attach overnight. The PBDs were then dissolved in DMSO (to give 20 mM drug concentrations) immediately prior to adding to the cells in quadruplicate wells. The final drug concentrations in the wells ranged from 100 µM to 2.5 nM as follows: 100, 25, 10, 2.5, 1 µM, 250, 100, 25, 10, 2.5 nM (drugs were diluted in growth medium and then 40 µL added to the existing well volume of 160 µL to give final concentrations as above). After 96 hours, the medium was removed and the remaining cells fixed by exposure to 10% trichloroacetic acid on ice for 30 minutes. The wells were then washed 3–4 times with tap water, air dried overnight and treated with 100 µL of sulphorhodamine B (0.4%) dissolved in 1% acetic acid. Staining was allowed to continue for 10–15 minutes, then the wells were washed 3–4 times with 1% acetic acid, air dried and then added to Tris base (100 µL of 10 mM). Plates were then shaken and absorbance readings at 540 nm were determined using a plate reader. By using the Quattro-Pro software package, the $IC_{50}$ values were calculated from plots of concentration versus percentage absorbance (compared with 8 untreated wells).

(a) Compounds of Formula I

| Compound | IC$_{50}$ (μM) | | | | |
|---|---|---|---|---|---|
| | A2780 | A2780cisR | CH1 | CH1cisR | Skov3 |
| Anthramycin | 0.155 | 0.16 | 0.062 | 0.05 | 0.16 |
| UP2003 (24) | 0.0145 | 0.12 | 0.016 | 0.04 | 0.012 |
| UP2051 (31) | 0.1 | 0.27 | 0.105 | 0.16 | 0.46 |
| UP2052 (33) | 0.07 | 0.105 | 0.09 | 0.037 | 0.105 |
| UP2053 (56) | 0.0054 | 0.058 | 0.0115 | 0.011 | 0.1 |
| UP2065 (42) | 0.36 | 0.46 | 0.115 | 0.15 | 0.45 |
| UP2074 (10) | 0.155 | 0.43 | 0.105 | 0.27 | 0.52 |
| UP2089 (177) | 0.0022 | 0.0042 | <0.0025 | 0.0023 | 0.0054 |
| UP2092 (179) | 0.004 | 0.007 | 0.0016 | 0.0082 | 0.0098 |
| UP2095 (181) | <0.05 | <0.05 | <0.05 | <0.05 | <0.05 |

The most potent members of this group of compounds are those PBDs that possess aryl or vinyl substitution at the 2 position of the PBD: UP2089 (177), UP2092 (179) and UP2095 (181). Without wishing to be bound by theory, the potent activity of these molecules can probably be ascribed to the presence of conjugated endo-exo unsaturation in these molecules. Endo-exo unsaturation may improve the fit of the molecule in the minor groove of DNA, although the conjugated system may also indirectly affect the potency of the molecules through electronic and conformational effects. UP2089 (177) and UP2092 (181) are up to 100 times more potent than the natural product anthramycin, which also possesses conjugated endo exo unsaturation.

PBD dimers are able to cross-link DNA and block tumour cell replication and thus generally show high cytotoxicity. The PBD dimer UP2053, which possesses only endo unsaturation, exhibits potent activity in these ovarian cell lines. The dimer is markedly more cytotoxic than anthramycin but not as potent as the monomers UP2089 and 2092.

The remaining molecules of Formula I are monomers possessing only endo unsaturation, these molecules are broadly comparable with anthramycin. However, the ester UP2003 and the alcohol UP2053 are more potent than anthramycin against these ovarian tumour cell lines.

(b) Compounds of Formula II

| UP No. | IC$_{50}$/μM | | | | |
|---|---|---|---|---|---|
| | A2780 | A2780cisR | CH1 | CH1cisR | Skov3 |
| Anthramycin | 0.155 | 0.16 | 0.062 | 0.05 | 0.16 |
| UP2001 (80) | 0.000023 | 0.000024 | 0.00012 | 0.0006 | 0.0091 |
| UP2004 (70) | 0.029 | 0.2 | 0.017 | 0.082 | 0.35 |
| UP2023 (64) | 0.49 | 1.45 | 0.37 | 0.43 | 16 |
| UP2064 (74) | 0.15 | 0.36 | 0.066 | 0.084 | 0.39 |
| UP2067 (172) | 0.115 | 0.39 | 0.165 | 0.18 | 0.54 |
| UP2100 (207) | <0.05 | 0.066 | <0.05 | <0.05 | 0.081 |

Compound UP2100 (207) has the sructural; formula:

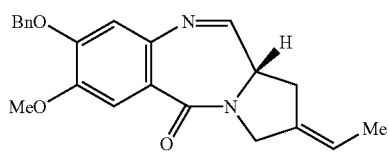

207 and was synthesised by the same route as compound 70.

UP2001 (80) exhibits cytotoxicity at picomolar/sub nanomolar levels across the ovarian tumour cell line panel. The potency of the molecule is probably due to its cross-linking properties coupled with the effect of exo saturation. UP2001 is markedly more potent than UP2053.

The monomers UP2004 (70) and UP2100 (206) exhibit good activity against the ovarian tumour cell lines comparable to tjat for anthramycin. UP2023 (64), which possesses a 7-iodo substituent is significantly less active than UP2004 (70), which contains two alkoxy groups at the 7 and 8 positions.

(c) Compounds of Formula III

| Compound | IC$_{50}$/μM | | | | |
|---|---|---|---|---|---|
| | A2780 | A2780cisR | CH1 | CH1cisR | Skov3 |
| UP2020 (90) | 10 | 7.2 | 1.7 | 2.8 | 1.6 |
| UP2021 (130) | >100 | >100 | 51 | 47 | >100 |
| UP2022 (143) | | 16.5 | 14 | 11 | 33 |
| UP2024 (101) | 1.4 | 1.8 | 1.45 | 1.25 | 2.35 |
| UP2025 (106) | 0.064 | 0.155 | 0.082 | 0.11 | 1.7 |
| UP2026 (136) | 1.15 | 3.7 | 1.5 | 1.45 | 4.9 |
| UP2027 (138) | 0.56 | 1.55 | 1.35 | 1.15 | 1.7 |
| UP2029 (140) | 34.5 | 32 | 22.5 | 14 | 1.4 |
| UP2066 (113) | 11 | 12 | 3.8 | 7.4 | 15 |
| UP2068 (96) | 0.47 | 0.66 | 0.52 | 0.42 | 0.76 |
| UP2086 (120) | 0.84 | 0.45 | 1.6 | 2.2 | 2.5 |

UP2025 is the most potent monomer with two methoxy groups donating electrons to the A-ring, however some compounds with 3 electron donating groups appear to be less cytotoxic (eg. UP2020–2022 and UP2066).

The simple phenyl substituted PBD (UP2026, 136) shows micromolar activity in the ovarian tumour cell lines. Introducing an electron donating methoxy group into the phenyl substituent increases cytotoxicity (138) but the presence of an electron withdrawing nitro group reduces cytotoxic activity (140).

(d) Compounds of Formula IV

| Compound | IC$_{50}$/μM | | | | |
|---|---|---|---|---|---|
| | A2780 | A2780cisR | CH1 | CH1cisR | Skov3 |
| UP2005 (161) | 1.5 | 4.3 | 1.4 | 1.85 | 5.4 |
| UP2006 (163) | 3.2 | 14.5 | 4.9 | 7.9 | 23.5 |
| UP2007 (165) | 1.55 | 4.9 | 1.5 | 3.0 | 5.8 |
| UP2008 (167) | 0.23 | 0.94 | 0.24 | 0.42 | 1.45 |
| UP2088 (205) | 11 | 8.5 | 12 | 16 | 14 |

What is claimed is:

1. A compound of the formula:

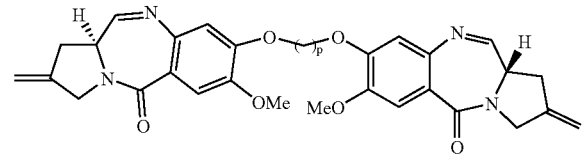

wherein p is 3.

2. A method of treatment of lung, colon, CNS, ovarian or breast carcinomas or melanomas of the human or animal body comprising administering to such a subject a therapeutically effective amount of a compound according to claim 1.

3. A method of treatment of a cisplatin-refractory ovarian carcinoma of the human or animal body comprising administering to such a subject a therapeutically effective amount of a compound according to claim 1.

4. A method of inhibiting the growth of human ovarian cisplatin-refactory cells which method comprises treating said cells with a compound according to claim 1.

5. A pharmaceutical composition comprising a compound of formula:

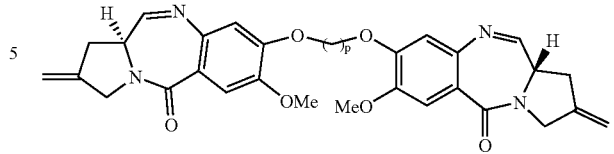

wherein p is 3 and a pharmaceutically acceptable excipient, carrier, buffer or stabilizer.

* * * * *